(12) United States Patent
Boyd et al.

(10) Patent No.: US 7,226,923 B2
(45) Date of Patent: Jun. 5, 2007

(54) PHTHALAZINONE DERIVATIVES

(75) Inventors: Edward Boyd, Reading (GB);
Frederick Brookfield, Benson (GB);
Guy Georges, Habach (DE); Bernhard Goller, Penzberg (DE); Sabine Huensch, Penzberg (DE); Petra Rueger, Penzberg (DE); Matthias Rueth, Penzberg (DE); Stefan Scheiblich, Penzberg (DE); Christine Schuell, Penzberg (DE); Wolfgang von der Saal, Murnau (DE); Justin Warne, London (GB); Stefan Weigand, Penzberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 70 days.

(21) Appl. No.: 11/233,311

(22) Filed: Sep. 23, 2005

(65) Prior Publication Data
US 2006/0089359 A1   Apr. 27, 2006

(30) Foreign Application Priority Data
Sep. 24, 2004   (EP)   .................. 04022755

(51) Int. Cl.
*C07D 403/12* (2006.01)
*C07D 403/14* (2006.01)
*A61K 31/502* (2006.01)

(52) U.S. Cl. .................. 514/248; 544/116; 544/237; 514/234.5

(58) Field of Classification Search .............. 544/237, 544/116; 514/248, 234.5
See application file for complete search history.

(56) References Cited

U.S. PATENT DOCUMENTS

| | | | |
|---|---|---|---|
| 6,207,401 B1 | 3/2001 | Plowman et al. | |

FOREIGN PATENT DOCUMENTS

| | | |
|---|---|---|
| EP | 1 051 500 | 11/2000 |
| WO | WO 95/19169 | 7/1995 |
| WO | WO 95/23141 | 8/1995 |
| WO | WO 97/022702 | 6/1997 |
| WO | WO 97/42187 | 11/1997 |
| WO | WO 99/06396 | 2/1999 |
| WO | WO 00/05219 | 2/2000 |
| WO | WO 00/44728 | 8/2000 |
| WO | WO 00/47212 | 8/2000 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 01/55116 | 8/2001 |
| WO | WO 01/77085 | 10/2001 |
| WO | WO 02/22601 | 3/2002 |
| WO | WO 02/22602 | 3/2002 |
| WO | WO 02/22603 | 3/2002 |
| WO | WO 02/22604 | 3/2002 |
| WO | WO 02/22605 | 3/2002 |
| WO | WO 02/22606 | 3/2002 |
| WO | WO 02/22607 | 3/2002 |
| WO | WO 02/22608 | 6/2002 |
| WO | WO 02/50065 | 6/2002 |
| WO | WO 02/50066 | 6/2002 |
| WO | WO 02/057259 | 7/2002 |
| WO | WO 02/059111 | 8/2002 |
| WO | WO 02/059112 | 8/2002 |
| WO | WO 02/062789 | 8/2002 |
| WO | WO 02/066461 | 8/2002 |
| WO | WO 02/068415 | 9/2002 |
| WO | WO 02/96905 | 12/2002 |
| WO | WO 03/015785 | 2/2003 |
| WO | WO 03/055491 | 7/2003 |
| WO | WO 03/077921 | 9/2003 |
| WO | WO 03/078423 | 9/2003 |
| WO | WO 03/078426 | 9/2003 |
| WO | WO 03/078427 | 9/2003 |
| WO | WO 04/000833 | 12/2003 |

(Continued)

OTHER PUBLICATIONS

Adams, R.R., et al, Trends Cell Biol. 11 (2001) 49-54.

(Continued)

*Primary Examiner*—Kahsay Habte
(74) *Attorney, Agent, or Firm*—George W. Johnson; Patricia S. Rocha-Tramaloni

(57) ABSTRACT

Compounds of formula I

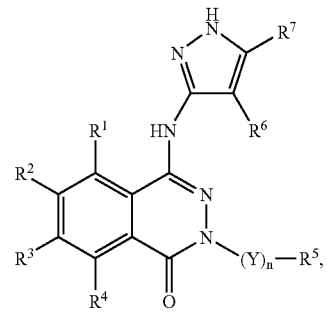

formula I their pharmaceutically acceptable salts, enantiomeric forms, diastereoisomers and racemates are disclosed. Also disclosed are methods for the preparation of the above-mentioned compounds, pharmaceutical compositions containing them, as well as the use of the above-mentioned compounds in the treatment, control or prevention of illnesses such as cancer.

49 Claims, No Drawings

FOREIGN PATENT DOCUMENTS

WO  WO 04/005283  1/2004

OTHER PUBLICATIONS

Bischoff, J.R. and Plowman, G.D., Trends Cell Biol. 9 (1999) 454-459.

Giet, R., and Prigent, C., J. Cell Sci. 112 (1999) 3591-3601.

Harrington, E.A. et al, Nat. Med. 10 (2004) 262-267.

Hunter, T., Cell 50 (1987) 823-829.

Isola, J.J. et al., Am. J. Pathol. 147 (1995) 905-911.

Nigg, E.A., Nat. Rev. Mol. cell Biol. 2 (2001) 21-32.

Sen, S. et al, J. Natl. Cancer Inst. 94 (2002) 1320-1329.

PHTHALAZINONE DERIVATIVES

FIELD OF THE INVENTION

The present invention relates to novel phthalazinone derivatives, to a process for their manufacture, pharmaceutical compositions containing them, the manufacture of the compounds as well as the use of these compounds for the treatment of cancer.

BACKGROUND OF THE INVENTION

Protein kinases regulate many different signaling processes by adding phosphate groups to proteins (Hunter, T., Cell 50 (1987) 823–829); particularly serine/threonine kinases phosphorylate proteins on the alcohol moiety of serine or threonine residues. The serine/threonine kinase family includes members that control cell growth, migration, differentiation, gene expression, muscle contraction, glucose metabolism, cellular protein synthesis, and regulation of the cell cycle.

The Aurora kinases are a family of serine/threonine kinases that are believed to play a key role in the protein phosphorylation events that are essential for the completion of essential mitotic events. The Aurora kinase family is made up of three key members: Aurora A, B and C (also known as Aurora-2, Aurora-1 and Aurora-3 respectively). Aurora-1 and Aurora-2 are described in U.S. Pat. No. 6,207,401 of Sugen and in related patents and patent applications, e.g. EP 0 868 519 and EP 1 051 500.

For Aurora A there is increasing evidence that it is a novel proto-oncogene. Aurora A gene is amplified and transcript/protein is highly expressed in a majority of human tumor cell lines and primary colorectal, breast and other tumors. It has been shown that Aurora A overexpression leads to genetic instability shown by amplified centrosomes and significant increase in aneuploidy and transforms Rat1 fibroblasts and mouse NIH3T3 cells in vitro. Aurora A-transformed NIH3T3 cells grow as tumors in nude mice (Bischoff, J. R., and Plowman, G. D., Trends Cell Biol. 9 (1999) 454; Giet, R., and Prigent, C., J. Cell Sci. 112 (1999) 3591–3601; Nigg, E. A., Nat. Rev. Mol. Cell Biol. 2 (2001) 21–32; Adams, R. R., et al., Trends Cell Biol. 11 (2001) 49–54). Moreover, amplification of Aurora A is associated with aneuploidy and aggressive clinical behavior (Sen, S., et al., J. Natl. Cancer Inst. 94 (2002) 1320–1329) and amplification of its locus correlates with poor prognosis for patients with node-negative breast cancer (Isola, J. J., et al., Am. J. Pathol. 147 (1995) 905–911). For these reasons it is proposed that Aurora A overexpression contributes to cancer phenotype by being involved in chromosome segregation and mitotic checkpoint control.

Human tumor cell lines depleted of Aurora A transcripts arrest in mitosis. Accordingly, the specific inhibition of Aurora kinase by selective inhibitors is recognized to stop uncontrolled proliferation, re-establish mitotic checkpoint control and lead to apoptosis of tumor cells. In a xenograft model, an Aurora inhibitor therefore slows tumor growth and induces regression (Harrington, E. A., et al., Nat. Med. 10 (2004) 262–267).

Low molecular weight inhibitors for protein kinases are widely known in the state of the art: For Aurora inhibition such inhibitors are based on i.e. quinazoline derivatives as claimed in the following patents and patent applications: WO 00/44728; WO 00/47212; WO 01/21594; WO 01/21595; WO 01/21596; WO 01/21597; WO 01/77085; WO 01/55116; WO 95/19169; WO 95/23141; WO 97/42187; WO 99/06396; pyrazole and triazole derivatives as claimed in the following patents and patent applications: WO 02/22601; WO 02/22602; WO 02/22603; WO 02/22604; WO 02/22605; WO 02/22606; WO 02/22607; WO 02/22608; WO 02/50065; WO 02/50066; WO 02/057259; WO 02/059112; WO 02/059111; WO 02/062789; WO 02/066461; WO 02/068415; pyrimidine derivatives: WO 03/077921; WO 03/078423; WO 03/078426; WO 03/078427; WO 04/000833 or imidazole, oxazole and thiazole derivatives: WO 02/96905; WO 04/005283.

Some phthalazinones or related compounds are known as polymerase or phosphodiesterase inhibitors from WO 03/015785 and WO 00/05219.

However there remains a need for structural new compounds with improved therapeutic properties, such as enhanced activity, decreased toxicity, better solubility and improved pharmacokinetic profile, to name only a few.

SUMMARY OF THE INVENTION

The present invention relates to the compounds of the general formula I,

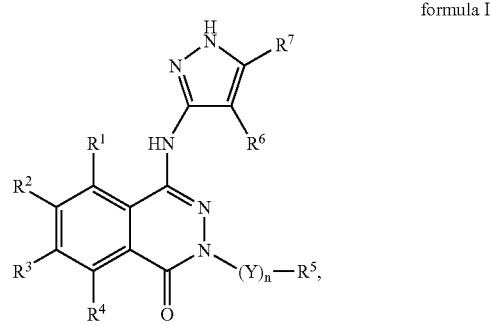

formula I wherein
$R^1$, $R^2$, $R^3$ and $R^4$ independently represent $R^8$—X—, cycloalkyl-$T^1$-, heterocyclyl-$T^2$-, hydrogen, halogen, nitro, cyano,
—OH, —NH$_2$, —NH—C(O)H, —C(O)OH, —C(O)NH$_2$, —S(O)$_2$NH$_2$,
—NHC(O)NH$_2$, —C(O)NH—O-alkyl,
—C(O)N(alkyl)-O-alkyl, —NHC(O)NH—O-alkyl,
—NHC(O)N(alkyl)-O-alkyl, —S(O)$_2$NH—O-alkyl,
—S(O)$_2$N(alkyl)-O-alkyl, or alkyl optionally substituted one or several times by halogen, hydroxy or alkoxy;
$R^8$ is cycloalkyl-$T^1$-,
heterocyclyl-$T^2$-,
aryl-$T^3$-,
heteroaryl-$T^4$-, or
alkyl optionally substituted one or several times by halogen;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—NHS(O)$_2$—, —S(O)$_2$NH—, —S(O)$_2$N(alkyl)-,
—S(O)$_2$—, —S(O)—, —C(O)O—, —OC(O)—, —C(O)—,
—NH—,
—N(alkyl)-, —O— or —S—; and
$T^1$, $T^2$, $T^3$ and $T^4$ independently represent a single bond or alkylene optionally substituted one or two times by hydroxy;
$R^5$ is hydrogen, alkyl being optionally substituted one or several times by halogen or alkoxy, heteroaryl, or phenyl, which is optionally substituted one or two times by halogen, —NO$_2$, —OH, —C(O)OH,
—C(O)NH-aryl, —C(O)NH$_2$,
—C(O)NH-alkyl, —C(O)N(alkyl)$_2$,
—C(O)-heterocyclyl, —NH$_2$, —NHC(O)-aryl, —NHC(O)-cycloalkyl, —NHC(O)-alkyl,
—N(alkyl)C(O)-alkyl, —NHC(O)O-alkyl, —N(alkyl)C(O)O-alkyl,
—NHC(O)-alkoxyalkyl, —NH—S(O)$_2$-aryl,
—NH—S(O)$_2$-alkyl, —C(O)NH—S(O)$_2$-aryl,
—C(O)NH—S(O)$_2$-alkyl, —S(O)$_2$-alkyl,
—NH-aryl, —O-aryl, —S(O)-aryl, aryl, heterocyclyl, cycloalkyl, alkyl, alkoxy or alkylsulfanyl, said alkyl, alkoxy and alkylsulfanyl groups being optionally substituted one or several times by halogen;

naphtyl,
1,3-Dihydro-isobenzofuranyl,
benzo[1,3]dioxol-5-yl,
cycloalkyl or
alkenyl;

Y is alkylene, alkylene-C(O)— or alkylene-CH(OH)—;

n is 0 or 1;

R$^6$ is hydrogen, alkyl, cyano or halogen;

R$^7$ is hydrogen, alkyl or cycloalkyl;

and all pharmaceutically acceptable salts thereof.

The compounds according to this invention show activity as protein kinase inhibitors. Many diseases are associated with abnormal cellular responses triggered by protein kinase mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds according to this invention in particular show activity as Aurora A kinase inhibitors, and may therefore be useful for the treatment of diseases mediated by said kinase. Aurora A inhibition leads to cell cycle arrest in the G2 phase of the cell cycle and exerts an antiproliferative effect in tumor cell lines. This indicates that Aurora A inhibitors may be useful in the treatment of i.e. hyperproliferative diseases such as cancer and in particular colorectal, breast, lung, prostate, pancreatic, gastric, bladder, ovarian, melanoma, neuroblastoma, cervical, kidney or renal cancers, leukemias or lymphomas. Treatment of acute-myelogenous leukemia (AML, acute lymphocytic leukemia (ALL) and gastrointestinal stromal tumor (GIST) is included.

Objects of the present invention are of the compounds of formula I and their tautomers, pharmaceutically acceptable salts, enantiomeric forms, diastereoisomers and racemates, their use as Aurora A kinase inhibitors, the preparation of the above-mentioned compounds, medicaments containing them and their manufacture, and pharmaceutical compositions and salts of same, as well as the use of the above-mentioned compounds in the treatment, control or prevention of illnesses, especially of illnesses and disorders as mentioned above or in the manufacture of corresponding medicaments.

DETAILED DESCRIPTION OF THE INVENTION

The present invention relates to the compounds of the general formula I,

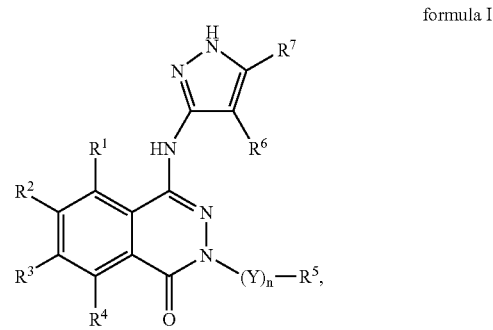

formula I wherein

R$^1$, R$^2$, R$^3$ and R$^4$ independently represent R$^8$—X—, cycloalkyl-T$^1$-, heterocyclyl-T$^2$-, hydrogen, halogen, nitro, cyano,
—OH, —NH$_2$, —NH—C(O)H, —C(O)OH, —C(O)NH$_2$, —S(O)$_2$NH$_2$,
—NHC(O)NH$_2$, —C(O)NH—O-alkyl,
—C(O)N(alkyl)-O-alkyl, —NHC(O)NH—O-alkyl,
—NHC(O)N(alkyl)-O-alkyl, —S(O)$_2$NH—O-alkyl,
—S(O)$_2$N(alkyl)-O-alkyl, or alkyl optionally substituted one or several times by halogen, hydroxy or alkoxy;

R$^8$ is cycloalkyl-T$^1$-,
heterocyclyl-T$^2$-,
aryl-T$^3$-,
heteroaryl-T$^4$-, or
alkyl optionally substituted one or several times by halogen;

X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—NHS(O)$_2$—, —S(O)$_2$NH—, —S(O)$_2$N(alkyl)-,
—S(O)$_2$—, —S(O)—, —C(O)O—, —OC(O)—, —C(O)—, —NH—,
—N(alkyl)-, —O— or —S—; and T$^1$, T$^2$, T$^3$ and T$^4$ independently represent a single bond or alkylene optionally substituted one or two times by hydroxy;

R$^5$ is hydrogen, alkyl being optionally substituted one or several times by halogen or alkoxy, heteroaryl, or phenyl, which is optionally substituted one or two times by halogen, —NO$_2$, —OH, —C(O)OH,
—C(O)NH-aryl, —C(O)NH$_2$,
—C(O)NH-alkyl, —C(O)N(alkyl)$_2$,
—C(O)-heterocyclyl, —NH$_2$, —NHC(O)-aryl, —NHC(O)-cycloalkyl, —NHC(O)-alkyl,
—N(alkyl)C(O)-alkyl, —NHC(O)O-alkyl, —N(alkyl)C(O)O-alkyl,
—NHC(O)-alkoxyalkyl, —NH—S(O)$_2$-aryl,
—NH—S(O)$_2$-alkyl, —C(O)NH—S(O)$_2$-aryl,
—C(O)NH—S(O)$_2$-alkyl, —S(O)$_2$-alkyl,
—NH-aryl, —O-aryl, —S(O)-aryl, aryl, heterocyclyl, cycloalkyl, alkyl, alkoxy or alkylsulfanyl, said alkyl, alkoxy and alkylsulfanyl groups being optionally substituted one or several times by halogen;
naphtyl,
1,3-Dihydro-isobenzofuranyl,
benzo[1,3]dioxol-5-yl,
cycloalkyl or
alkenyl;
Y is alkylene, alkylene-C(O)— or alkylene-CH(OH)—;
n is 0 or 1;
$R^6$ is hydrogen, alkyl, cyano or halogen;
$R^7$ is hydrogen, alkyl or cycloalkyl;
and all pharmaceutically acceptable salts thereof.

The compounds according to this invention show activity as protein kinase inhibitors. Many diseases are associated with abnormal cellular responses triggered by protein kinase mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

The compounds according to this invention in particular show activity as Aurora A kinase inhibitors, and may therefore be useful for the treatment of diseases mediated by said kinase. Aurora A inhibition leads to cell cycle arrest in the G2 phase of the cell cycle and exerts an antiproliferative effect in tumor cell lines. This indicates that Aurora A inhibitors may be useful in the treatment of i.e. hyperproliferative diseases such as cancer and in particular colorectal, breast, lung, prostate, pancreatic, gastric, bladder, ovarian, melanoma, neuroblastoma, cervical, kidney or renal cancers, leukemias or lymphomas. Treatment of acute-myelogenous leukemia (AML, acute lymphocytic leukemia (ALL) and gastrointestinal stromal tumor (GIST) is included.

Objects of the present invention are of the compounds of formula I and their tautomers, pharmaceutically acceptable salts, enantiomeric forms, diastereoisomers and racemates, their use as Aurora A kinase inhibitors, the preparation of the above-mentioned compounds, medicaments containing them and their manufacture, and pharmaceutical compositions of same, as well as the use of the above-mentioned compounds in the treatment, control or prevention of illnesses, especially of illnesses and disorders as mentioned above or in the manufacture of corresponding medicaments.

DEFINITIONS

As used herein, the term "alkyl" means a saturated, straight-chain or branched-chain hydrocarbon containing from 1 to 6, preferably from 1 to 4, more preferred 1 or 2, carbon atoms, such as methyl, ethyl, n-propyl, isopropyl, n-butyl, 2-butyl, t-butyl.

As used herein, the term "alkoxy" means an alkyl group as defined above which is connected via an oxygen atom.

As used herein, the term "alkylsulfanyl" means an alkyl group as defined above which is connected via a sulfur atom.

If said alkyl, alkoxy or alkylsulfanyl group is substituted one or several times by halogen, it is substituted one to five, preferably one to three times by chlorine or fluorine, preferably by fluorine. Examples are difluoromethyl, trifluoromethyl, 2,2,2-trifluoroethyl, perfluorethyl, 2,2,2-trichloroethyl, 2-chloro-ethyl, 3-chloro-propyland the like, preferably difluoromethyl, trifluoromethyl, 2,2,2-trifluoroethyl or perfluorethyl.

If said alkyl is substituted one or several times by hydroxy or alkoxy it is substituted one to three, preferably one to two times by hydroxy or alkoxy. Examples are e.g. hydroxymethyl, 2-hydroxy-butyl, 2-hydroxy-ethyl, 1-hydroxy-ethyl, 2-hydroxy-propyl, 3-hydroxy-butyl, 2,3-dihydroxy-propyl, 2,3-dihydroxy-butyl, 1,2,3-trihydroxy-propyl, 2-hydroxy-pentyl, methoxy-methyl, ethoxy-methyl, 2-methoxy-ethyl, 2-ethoxy-ethyl, 4-methoxy-butyl, 2-methoxy-butyl, 2-ethoxy-propyl, 3-propoxy-butyl, 2,3-dimethoxy-propyl, 2-ethoxy-3-methoxy-propyl, 2,3-diethoxy-butyl, 1,2,3-trimethoxy-propyl, 2-methoxy-pentyl and the like.

As used herein, the term "alkylene" means a saturated, straight-chain or branched-chain, preferably straight-chain hydrocarbon containing from 1 to 5, preferably from 1 to 3, carbon atoms, such as methylene, ethylene, trimethylene(1,3-propylene); tetramethylene(butylene), pentamethylene, methyl-methylene, methyl-ethylene(1,2-propylene), ethyl-ethylene, propyl-ethylene, 1-methyl-trimethylene, 2-methyl-trimethylene, 1-ethyl-trimethylene, 2-ethyl-trimethylene.

Preferably Y represents methylene or ethylene and more preferred methylene.

As used herein, the term "alkenyl" means a unsaturated, straight-chain or branched-chain, preferably straight-chain hydrocarbon containing from 2 to 6, preferably from 2 to 4, carbon atoms. Examples of such "alkenyl" are vinyl(ethenyl), allyl, isopropenyl, 2-butenyl, 3-butenylene, 3-methyl-2-butenyl, 2-pentenyl, 3-pentenyl, 4-pentenyl, 4-methyl-3-pentenyl, 2-hexenyl, 3-hexenyl, 4-hexenyl and 5-hexenylene, preferably allyl.

The term "halogen" as used herein means fluorine, chlorine, bromine and iodine, preferably fluorine, chlorine or bromine and more preferred fluorine and chlorine.

The term "aryl" as used herein means a phenyl or naphthyl, e.g. 1-naphthyl, 2-naphthyl or 3-naphthyl and preferably a phenyl group. Such aryl group can be optionally substituted one to three, preferably one or two times by a) alkyl b) halogenated alkyl c) halogen, preferably by chlorine or fluorine, d) cyano, e) alkoxy, f) halogenated alkoxy g) —C(O)-alkyl, preferably acetyl, h) alkylsulfonyl, i) hydroxy, j) amino or k) nitro. Preferably the aryl is optionally substituted by a) alkyl b) halogenated alkyl c) halogen d) cyano, e) alkoxy, f) halogenated alkoxy or i) hydroxy. More preferred the aryl is optionally substituted by a) alkyl b) halogenated alkyl c) halogen d) cyano, e) alkoxy, f) halogenated alkoxy or i) hydroxy. In one embodiment of the invention the aryl group as defined in $R^8$ is optionally substituted one to three times as described above while the aryl groups in $R^5$ are unsubstituted. Even more preferred all aryl groups are unsubstituted. Examples of substituted aryl groups are e.g. 4-methyl-phenyl, 3-methyl-phenyl, 2-methyl-phenyl, 4-chloro-phenyl, 3-chloro-phenyl, 2-chloro-phenyl, 4-fluoro-phenyl, 2-fluoro-phenyl, 4-trifluoromethyl-phenyl, 4-trifluoromethyl-2-fluoro-phenyl, 3-trifluoromethyl-phenyl, 4-trifluoromethoxy-phenyl, 3-trifluoromethoxy-phenyl, 4-cyano-phenyl, 3-cyano-phenyl, 4-amino-phenyl, 3-hydroxy-phenyl, 4-acetyl-phenyl, 4-acetyl-2-methyl-phenyl and the like.

The term "heteroaryl" means a mono- or bicyclic aromatic ring with 5 to 10 ring atoms, which contains up to 3, preferably 1 or 2 heteroatoms selected independently from N, O or S and the remaining ring atoms being carbon atoms. Such heteroaryl group can be optionally substituted one to three, preferably one or two times by a) alkyl, which is defined as above, preferably by methyl, b) halogenated alkyl c) halogen, preferably by chlorine or fluorine d) cyano, e) alkoxy, f) halogenated. Preferably the heteroaryl is optionally substituted by a) alkyl b) halogenated alkyl c) halogen d) cyano, e) alkoxy, f) halogenated alkoxy or i) hydroxy. More preferred the heteroaryl is optionally substituted by a) alkyl b) halogenated alkyl c) halogen d) cyano, e) alkoxy, f) halogenated alkoxy or i) hydroxy. Even more preferred the heteroaryl is optionally substituted by alkyl. Examples of such heteroaryl groups are thiophenyl, methylthiophenyl, pyrazolyl, dimethylisoxazolyl, pyridyl, benzothiophenyl, indolyl, furyl, pyrrolyl, imidazolyl, pyrimidyl, pyrazinyl, pyridazinyl, triazinyl, oxazolyl, isoxazolyl, thiazolyl, methylthiazolyl, isothiazolyl, thiadiazolyl, oxadiazolyl, triazolyl, quinolyl, isoquinolyl, benzofuranyl and the like, preferably thiazolyl, methylthiazolyl, pyridyl, methylpyridyl, trifluoromethyl-pyridyl, pyrimidyl, triazolyl, methyltriazolyl or thiadiazolyl, more preferred pyridyl or methylthiazolyl.

The term "cycloalkyl" means a monocyclic saturated hydrocarbon ring with 3 to 7, preferably 3 to 5, ring atoms. Such monocyclic saturated hydrocarbon ring can be optionally substituted one to three, preferably one or two times by alkyl, preferably by methyl. Preferably the cycloalkyl is unsubstituted. Examples of such saturated carbocyclic groups are cyclopropyl, 1-methyl-cycloprop-1-yl, cyclobutyl, cyclopentyl, cyclohexyl, 3,3-dimethyl-cyclohex-1-yl, and cycloheptyl, preferably cyclopropyl, preferably cyclopropyl, cyclobutyl, and cycloheptyl, more preferred cyclopropyl.

The term "heterocyclyl" means a saturated, monocyclic ring with 5 to 6 ring atoms which contains up to 3, preferably 1 or 2 heteroatoms selected independently from N, O or S and the remaining ring atoms being carbon atoms. Such saturated heterocyclic group can be optionally substituted one to three, preferably one or two times by a) alkyl, which is defined as above, preferably by methyl, b) —C(O)-alkyl, preferably acetyl, c) oxo or d) —S(O)$_2$-alkyl. Preferably the heterocyclic group can be optionally substituted by alkyl. Examples of such saturated heterocyclic groups are pyrrolidinyl, morpholinyl, thiomorpholinyl, 1,1-Dioxo-1lambda*6*-thiomorpholin-4-yl (or 1,1-Dioxido-thiomorpholin-4-yl), piperazinyl, N-methyl-piperazinyl, N-acetyl-piperazinyl, 3-oxo-piperazin-1-yl, 2-oxo-piperazin-1-yl piperidyl, oxazolidinyl, thiazolidinyl and the like, preferably morpholinyl, piperazinyl, N-methyl-piperazinyl or N-acetyl-piperazinyl, and especially morpholinyl, N-methyl-piperazinyl or piperidyl.

As used herein, in relation to mass spectrometry (MS) the term "ESI+" refers to positive electrospray ionization mode.

The term "pharmaceutically acceptable salt" is as used on page 103.

The term "therapeutically effective" or "therapeutically effective amount" as used herein means an amount of at least one compound of Formula 1, or a pharmaceutically acceptable salt thereof, that significantly inhibits proliferation and/or prevents differentiation of a human tumor cell, including human tumor cell lines.

As used herein, in relation to nuclear magnetic resonance (NMR) the term "D$_6$-DMSO" refers to deuterated dimethylsulfoxide; the term "CDCl$_3$" refers to deuterated chloroform; the term "C$_6$D$_6$" refers to deuterated benzene; and the term "CD$_3$OD" refers to deuterated methanol.

DETAILED DESCRIPTION OF THE INVENTION

The compounds of formula I can exist in different tautomeric forms and in variable mixtures thereof. All tautomeric forms of the compounds of formula I and mixtures thereof are an objective of the invention. For example, the pyrazole ring of formula I can exist in two tautomeric forms as shown here below:

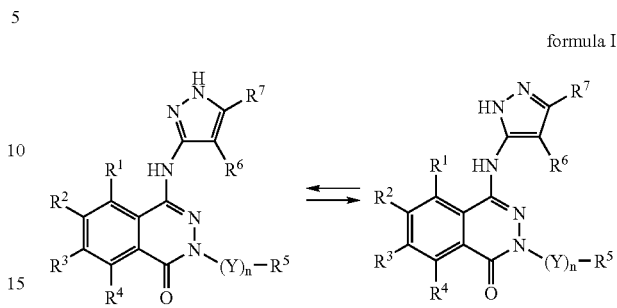

formula I

An embodiment of the invention are the compounds according to formula I, wherein
$R^1$, $R^2$, $R^3$ and $R^4$ independently represent $R^8$—X—, cycloalkyl-$T^1$-, heterocyclyl-$T^2$-, hydrogen,
halogen, nitro, cyano,
—OH, —NH$_2$, —C(O)OH, —C(O)NH$_2$, —S(O)$_2$NH$_2$,
—NHC(O)NH$_2$, —C(O)NH—O-alkyl,
—C(O)N(alkyl)-O-alkyl, —NHC(O)NH—O-alkyl,
—NHC(O)N(alkyl)-O-alkyl, —S(O)$_2$NH—O-alkyl,
—S(O)$_2$N(alkyl)-O-alkyl, or alkyl optionally substituted one or several times by halogen, hydroxy or alkoxy;
$R^8$ is cycloalkyl-$T^1$-,
heterocyclyl-$T^2$-,
aryl-$T^3$-,
heteroaryl-$T^4$-, or
alkyl optionally substituted one or several times by halogen;
X is —C(O)NH—, —C(O)N(alkyl)-,
—N(alkyl)C(O)—, —NHC(O)—,
—NHC(O)NH—, —NHC(O)N(alkyl)-,
—NHS(O)$_2$—, —S(O)$_2$NH—, —S(O)$_2$N(alkyl)-,
—S(O)$_2$—, —S(O)—, —C(O)O—, —OC(O)—, —C(O)—,
—NH—,
—N(alkyl)-, —O— or —S—;
$T^1$, $T^2$, $T^3$ and $T^4$ independently represent a single bond or alkylene optionally substituted one or two times by hydroxy;
$R^5$ is hydrogen,
alkyl being optionally substituted one or several times by halogen,
heteroaryl, or
phenyl, which is optionally substituted one or two times by halogen, —NO$_2$, —OH,
—C(O)NH-aryl, —C(O)NH$_2$,
—C(O)NH-alkyl, —C(O)N(alkyl)$_2$,
—C(O)-heterocyclyl, —NH$_2$, —NHC(O)-aryl, —NHC(O)-cycloalkyl, —NHC(O)-alkyl,
—NHC(O)-alkoxyalkyl, —NH—S(O)$_2$-aryl,
—NH—S(O)$_2$-alkyl, —C(O)NH—S(O)$_2$-aryl,
—C(O)NH—S(O)$_2$-alkyl, —S(O)$_2$-alkyl, alkyl, alkoxy or alkylsulfanyl, said alkyl, alkoxy and alkylsulfanyl groups being optionally substituted one or several times by halogen;
or 1,3-Dihydro-isobenzofuranyl;
Y is alkylene;
n is 0 or 1;
$R^6$ is hydrogen, alkyl, cyano or halogen; and
$R^7$ is hydrogen, alkyl or cycloalkyl;

Another embodiment of the invention are the compounds according to formula I, wherein n is 0.

Another embodiment of the invention are the compounds according to formula I, wherein
X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;
R$^5$ is hydrogen,
alkyl being optionally substituted one or several times by halogen,
heteroaryl, or
phenyl, which is optionally substituted one or two times by halogen, —NO$_2$, —OH,
—C(O)NH-aryl, —C(O)NH$_2$,
—C(O)NH-alkyl, —C(O)N(alkyl)$_2$,
—C(O)-heterocyclyl, —NH$_2$, —NHC(O)-aryl, —NHC(O)-cycloalkyl, —NHC(O)-alkyl,
—NHC(O)-alkoxyalkyl, —NH—S(O)$_2$-aryl,
—NH—S(O)$_2$-alkyl, —C(O)NH—S(O)$_2$-aryl,
—C(O)NH—S(O)$_2$-alkyl, —S(O)$_2$-alkyl, alkyl, alkoxy or alkylsulfanyl, said alkyl, alkoxy and alkylsulfanyl groups being optionally substituted one or several times by halogen;
or 1,3-Dihydro-isobenzofuranyl;
Y is alkylene; and
n is 0.

Another embodiment of the invention are the compounds according to formula I, wherein n is 1.

Another embodiment of the invention are the compounds according to formula I, wherein
X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;
R$^5$ is hydrogen,
alkyl being optionally substituted one or several times by halogen,
heteroaryl, or
phenyl, which is optionally substituted one or two times by halogen, —NO$_2$, —OH,
—C(O)NH-aryl, —C(O)NH$_2$,
—C(O)NH-alkyl, —C(O)N(alkyl)$_2$,
—C(O)-heterocyclyl, —NH$_2$, —NHC(O)-aryl, —NHC(O)-cycloalkyl, —NHC(O)-alkyl,
—NHC(O)-alkoxyalkyl, —NH—S(O)$_2$-aryl,
—NH—S(O)$_2$-alkyl, —C(O)NH—S(O)$_2$-aryl,
—C(O)NH—S(O)$_2$-alkyl, —S(O)$_2$-alkyl, alkyl, alkoxy or alkylsulfanyl, said alkyl, alkoxy and alkylsulfanyl groups being optionally substituted one or several times by halogen;
or 1,3-Dihydro-isobenzofuranyl;
Y is alkylene; and
n is 1.

Still another embodiment of the invention are the compounds according to formula I, wherein R$^5$ is hydrogen or alkyl optionally substituted one or several times by halogen.

Still another embodiment of the invention are the compounds according to formula I, wherein
X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;
R$^5$ is hydrogen or alkyl optionally substituted one or several times by halogen;
Y is alkylene; and
n is 0.

Such compounds are for example:
2-Methyl-4-(5-methyl-1H-pyrazol-3-ylamino)-2H-phthalazin-1-one;
2-Isobutyl-4-(5-methyl-1H-pyrazol-3-ylamino)-2H-phthalazin-1-one;
4-(5-Methyl-1H-pyrazol-3-ylamino)-2-(2,2,2-trifluoroethyl)-2H-phthalazin-1-one; and
2-Isopropyl-4-(5-methyl-1H-pyrazol-3-ylamino)-2H-phthalazin-1-one.

Still another embodiment of the invention are the compounds according to formula I, wherein R$^5$ is heteroaryl; and n is 1.

Still another embodiment of the invention are the compounds according to formula I, wherein
X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;
R$^5$ is heteroaryl;
Y is alkylene; and
n is 1.

Still another embodiment of the invention are the compounds according to formula I, wherein
R$^5$ phenyl, which is optionally substituted one or two times by halogen, —NO$_2$, —OH, —S(O)$_2$-alkyl, alkyl, alkoxy or alkylsulfanyl, said alkyl, alkoxy and alkylsulfanyl groups being optionally substituted one or several times by halogen;
or 1,3-Dihydro-isobenzofuran; and
n is 0.

Another embodiment of the invention are the compounds according to formula I, wherein
X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;
R$^5$ phenyl, which is optionally substituted one or two times by halogen, —NO$_2$, —OH, —S(O)$_2$-alkyl, alkyl, alkoxy or alkylsulfanyl, said alkyl, alkoxy and alkylsulfanyl groups being optionally substituted one or several times by halogen;
or 1,3-Dihydro-isobenzofuran;
Y is alkylene; and
n is 0.

Such compounds are for example:
4-(5-Methyl-1H-pyrazol-3-ylamino)-2-phenyl-2H-phthalazin-1-one;
4-(5-Methyl-1H-pyrazol-3-ylamino)-2-p-tolyl-2H-phthalazin-1-one;
2-(4-Fluoro-phenyl)-4-(5-methyl-1H-pyrazol-3-ylamino)-2H-phthalazin-1-one;
2-(4-tert-Butyl-phenyl)-4-(5-methyl-1H-pyrazol-3-ylamino)-2H-phthalazin-1-one;

2-(4-Methoxy-phenyl)-4-(5-methyl-1H-pyrazol-3-ylamino)-2H-phthalazin-1-one;
4-(1H-Pyrazol-3-ylamino)-2-p-tolyl-2H-phthalazin-1-one;
2-(4-Chloro-phenyl)-4-(5-methyl-1H-pyrazol-3-ylamino)-2H-phthalazin-1-one; and
4-(5-Methyl-1H-pyrazol-3-ylamino)-2-m-tolyl-2H-phthalazin-1-one.

Still another embodiment of the invention are the compounds according to formula I, wherein
$R^5$ phenyl, which is optionally substituted one or two times by halogen, —$NO_2$, —OH, —$S(O)_2$-alkyl, alkyl, alkoxy or alkylsulfanyl, said alkyl, alkoxy and alkylsulfanyl groups being optionally substituted one or several times by halogen;
or 1,3-Dihydro-isobenzofuran; and
n is 1.

Still another embodiment of the invention are the compounds according to formula I, wherein
X is —C(O)NH—, —C(O)N(alkyl)-,
—N(alkyl)C(O)—, —NHC(O)—,
NHC(O)NH—, —NHC(O)N(alkyl)-,
—NHS(O)$_2$—, —S(O)$_2$NH—, —S(O)$_2$N(alkyl)-,
—S(O)$_2$—, —S(O)—, —C(O)O—, —OC(O)—, —C(O)—, —NH—,
—N(alkyl)-, —O— or —S—;
$R^5$ phenyl, which is optionally substituted one or two times by halogen, —$NO_2$, —OH, —$S(O)_2$-alkyl, alkyl, alkoxy or alkylsulfanyl, said alkyl, alkoxy and alkylsulfanyl groups being optionally substituted one or several times by halogen;
or 1,3-Dihydro-isobenzofuran; and
Y is alkylene; and
n is 1.

Such compounds are for example:
2-Benzyl-4-(5-methyl-1H-pyrazol-3-ylamino)-2H-phthalazin-1-one; and
4-(5-Methyl-1H-pyrazol-3-ylamino)-2-(4-nitro-benzyl)-2H-phthalazin-1-one.

Still another embodiment of the invention are the compounds according to formula I, wherein
$R^5$ phenyl, which is substituted one or two times by
—$NH_2$, —NHC(O)-aryl,
—NHC(O)-cycloalkyl, —NHC(O)-alkyl, —NHC(O)-alkoxyalkyl, —NH—S(O)$_2$-aryl, —NH—S(O)$_2$-alkyl; and
n is 1.

Still another embodiment of the invention are the compounds according to formula I, wherein
X is —C(O)NH—, —C(O)N(alkyl)-,
—N(alkyl)C(O)—, —NHC(O)—,
—NHC(O)NH—, —NHC(O)N(alkyl)-,
—NHS(O)$_2$—, —S(O)$_2$NH—, —S(O)$_2$N(alkyl)-,
—S(O)$_2$—, —S(O)—, —C(O)O—, —OC(O)—, —C(O)—, —NH—,
—N(alkyl)-, —O— or —S—;
$R^5$ phenyl, which is substituted one or two times by
—$NH_2$, —NHC(O)-aryl,
—NHC(O)-cycloalkyl, —NHC(O)-alkyl, —NHC(O)-alkoxyalkyl, —NH—S(O)$_2$-aryl, —NH—S(O)$_2$-alkyl;
Y is alkylene; and
n is 1.

Such compounds are for example:
2-(4-Amino-benzyl)-4-(5-methyl-1H-pyrazol-3-ylamino)-2H-phthalazin-1-one;
N-{4-[4-(5-Methyl-1H-pyrazol-3-ylamino)-1-oxo-1H-phthalazin-2-ylmethyl]-phenyl}-acetamide; and
N-{4-[1-Oxo-4-(1H-pyrazol-3-ylamino)-1H-phthalazin-2-ylmethyl]-phenyl}-acetamide.

Another embodiment of the invention are the compounds according to formula I, wherein
$R^1$, $R^2$, $R^3$ and $R^4$ independently represent hydrogen, halogen, nitro, cyano, —OH, —$NH_2$, —C(O)OH, —C(O)NH$_2$, —S(O)$_2$NH$_2$, —NHC(O)NH$_2$,
—C(O)NH—O-alkyl, —C(O)N(alkyl)-O-alkyl,
—NHC(O)NH—O-alkyl, —NHC(O)N(alkyl)-O-alkyl,
—S(O)$_2$NH—O-alkyl, —S(O)$_2$N(alkyl)-O-alkyl,
alkyl optionally substituted one or several times by halogen, hydroxy or alkoxy; and
$R^5$ is hydrogen or alkyl optionally substituted one or several times by halogen.

Another embodiment of the invention are the compounds according to formula I, wherein
$R^1$, $R^2$, $R^3$ and $R^4$ independently represent hydrogen, halogen, nitro, cyano, —OH, —$NH_2$, —C(O)OH, —C(O)NH$_2$, —S(O)$_2$NH$_2$, —NHC(O)NH$_2$,
—C(O)NH—O-alkyl, —C(O)N(alkyl)-O-alkyl,
—NHC(O)NH—O-alkyl, —NHC(O)N(alkyl)-O-alkyl,
—S(O)$_2$NH—O-alkyl, —S(O)$_2$N(alkyl)-O-alkyl,
alkyl optionally substituted one or several times by halogen, hydroxy or alkoxy;
X is —C(O)NH—, —C(O)N(alkyl)-,
—N(alkyl)C(O)—, —NHC(O)—,
—NHC(O)NH—, —NHC(O)N(alkyl)-,
—NHS(O)$_2$—, —S(O)$_2$NH—, —S(O)$_2$N(alkyl)-,
—S(O)$_2$—, —S(O)—, —C(O)O—, —OC(O)—, —C(O)—, —NH—,
—N(alkyl)-, —O— or —S—;
$R^5$ is hydrogen or alkyl optionally substituted one or several times by halogen;
Y is alkylene; and
n is 0.

Another embodiment of the invention are the compounds according to formula I, wherein $R^1$, $R^2$, $R^3$ and $R^4$ independently represent hydrogen, cycloalkyl-$T^1$- or heterocyclyl-$T^2$-.

Another embodiment of the invention are the compounds according to formula I, wherein
$R^1$, $R^2$, $R^3$ and $R^4$ independently represent hydrogen, cycloalkyl-$T^1$- or heterocyclyl-$T^2$-; and
n is 0.

Still another embodiment of the invention are the compounds according to formula I, wherein
$R^1$, $R^2$, $R^3$ and $R^4$ independently represent hydrogen, cycloalkyl-$T^1$- or heterocyclyl-$T^2$-;
X is —C(O)NH—, —C(O)N(alkyl)-,
—N(alkyl)C(O)—, —NHC(O)—,
—NHC(O)NH—, —NHC(O)N(alkyl)-,
—NHS(O)$_2$—, —S(O)$_2$NH—, —S(O)$_2$N(alkyl)-,
—S(O)$_2$—, —S(O)—, —C(O)O—, —OC(O)—, —C(O)—, —NH—,
—N(alkyl)-, —O— or —S—;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen, cycloalkyl-$T^1$- or heterocyclyl-$T^2$-; and
n is 1.

Another embodiment of the invention are the compounds according to formula I, wherein $R^1$, $R^2$, $R^3$ and $R^4$ independently represent hydrogen, cycloalkyl-$T^1$- or heterocyclyl-$T^2$-;

X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;

$R^5$ is hydrogen or alkyl optionally substituted one or several times by halogen;

Y is alkylene; and n is 1.

Still another embodiment of the invention are the compounds according to formula I, wherein $R^1$, $R^2$, $R^3$ and $R^4$ independently represent hydrogen, cycloalkyl-$T^1$- or heterocyclyl-$T^2$-;

$R^5$ phenyl, which is optionally substituted one or two times by halogen, —NO$_2$, —OH, —S(O)$_2$-alkyl, alkyl, alkoxy or alkylsulfanyl, said alkyl, alkoxy and alkylsulfanyl groups being optionally substituted one or several times by halogen;

or 1,3-Dihydro-isobenzofuran; and n is 1.

Still another embodiment of the invention are the compounds according to formula I, wherein $R^1$, $R^2$, $R^3$ and $R^4$ independently represent hydrogen, cycloalkyl-$T^1$- or heterocyclyl-$T^2$-;

X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;

$R^5$ phenyl, which is optionally substituted one or two times by halogen, —NO$_2$, —OH, —S(O)$_2$-alkyl, alkyl, alkoxy or alkylsulfanyl, said alkyl, alkoxy and alkylsulfanyl groups being optionally substituted one or several times by halogen;

or 1,3-Dihydro-isobenzofuran;

Y is alkylene; and n is 1.

Another embodiment of the invention are the compounds according to formula I, wherein $R^1$, $R^2$, $R^3$ and $R^4$ independently represent hydrogen or $R^8$—X—.

Another embodiment of the invention are the compounds according to formula I, wherein $R^1$, $R^2$, $R^3$ and $R^4$ independently represent hydrogen or $R^8$—X—.

X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;

$R^5$ is hydrogen, alkyl being optionally substituted one or several times by halogen, heteroaryl, or phenyl, which is optionally substituted one or two times by halogen, —NO$_2$, —OH, —C(O)NH-aryl, —C(O)NH$_2$, —C(O)NH-alkyl, —C(O)N(alkyl)$_2$, —C(O)-heterocyclyl, —NH$_2$, —NHC(O)-aryl, —NHC(O)-cycloalkyl, —NHC(O)-alkyl, —NHC(O)-alkoxyalkyl, —NH—S(O)$_2$-aryl, —NH—S(O)$_2$-alkyl, —C(O)NH—S(O)$_2$-aryl, —C(O)NH—S(O)$_2$-alkyl, —S(O)$_2$-alkyl, alkyl, alkoxy or alkylsulfanyl, said alkyl, alkoxy and alkylsulfanyl groups being optionally substituted one or several times by halogen;

or 1,3-Dihydro-isobenzofuranyl; and

Y is alkylene.

Another embodiment of the invention are the compounds according to formula I, wherein $R^1$, $R^2$, $R^3$ and $R^4$ independently represent hydrogen or $R^8$—X—; and n is 0.

Another embodiment of the invention are the compounds according to formula I, wherein $R^1$, $R^2$, $R^3$ and $R^4$ independently represent hydrogen or $R^8$—X—.

X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;

$R^5$ is hydrogen, alkyl being optionally substituted one or several times by halogen, heteroaryl, or phenyl, which is optionally substituted one or two times by halogen, —NO$_2$, —OH, —C(O)NH-aryl, —C(O)NH$_2$, —C(O)NH-alkyl, —C(O)N(alkyl)$_2$, —C(O)-heterocyclyl, —NH$_2$, —NHC(O)-aryl, —NHC(O)-cycloalkyl, —NHC(O)-alkyl, —NHC(O)-alkoxyalkyl, —NH—S(O)$_2$-aryl, —NH—S(O)$_2$-alkyl, —C(O)NH—S(O)$_2$-aryl, —C(O)NH—S(O)$_2$-alkyl, —S(O)$_2$-alkyl, alkyl, alkoxy or alkylsulfanyl, said alkyl, alkoxy and alkylsulfanyl groups being optionally substituted one or several times by halogen;

or 1,3-Dihydro-isobenzofuranyl;

Y is alkylene; and n is 0.

Still another embodiment of the invention are the compounds according to formula I, wherein $R^1$, $R^2$, $R^3$ and $R^4$ independently represent hydrogen or $R^8$—X—;

$R^5$ is hydrogen or alkyl optionally substituted one or several times by halogen; and n is 0.

Still another embodiment of the invention are the compounds according to formula I, wherein $R^1$, $R^2$, $R^3$ and $R^4$ independently represent hydrogen or $R^8$—X—;

X is —C(O)NH—, —C(O)N(alkyl)-, —N(alkyl)C(O)—, —NHC(O)—, —NHC(O)NH—, —NHC(O)N(alkyl)-, —NHS(O)$_2$—, —S(O)$_2$NH—, —S(O)$_2$N(alkyl)-, —S(O)$_2$—, —S(O)—, —C(O)O—, —OC(O)—, —C(O)—, —NH—, —N(alkyl)-, —O— or —S—;

$R^5$ is hydrogen or alkyl optionally substituted one or several times by halogen;

Y is alkylene; and n is 0.

Another embodiment of the invention are the compounds according to formula I, wherein
$R^1$, $R^2$, $R^3$ and $R^4$ independently represent hydrogen or $R^8$—X—;
$R^5$ is hydrogen or alkyl optionally substituted one or several times by halogen; and
n is 1.

Another embodiment of the invention are the compounds according to formula I, wherein
$R^1$, $R^2$, $R^3$ and $R^4$ independently represent hydrogen or $R^8$—X—; and
X is —NHC(O)—, —N(alkyl)C(O)—, —NHC(O)NH—, —NHC(O)N(alkyl)- or —NHS(O)$_2$—;

Another embodiment of the invention are the compounds according to formula I, wherein
$R^1$, $R^2$, $R^3$ and $R^4$ independently represent hydrogen or $R^8$—X—;
X is —NHC(O)—, —N(alkyl)C(O)—, —NHC(O)NH—, —NHC(O)N(alkyl)- or —NHS(O)$_2$—; and
n is 0.

Another embodiment of the invention are the compounds according to formula I, wherein
$R^1$, $R^2$, $R^3$ and $R^4$ independently represent hydrogen or $R^8$—X—;
X is —NHC(O)—, —N(alkyl)C(O)—, —NHC(O)NH—, —NHC(O)N(alkyl)- or —NHS(O)$_2$—;
$R^5$ is hydrogen,
alkyl being optionally substituted one or several times by halogen, heteroaryl, or
phenyl, which is optionally substituted one or two times by halogen, —NO$_2$, —OH,
—C(O)NH-aryl, —C(O)NH$_2$,
—C(O)NH-alkyl, —C(O)N(alkyl)$_2$,
—C(O)-heterocyclyl, —NH$_2$, —NHC(O)-aryl, —NHC(O)-cycloalkyl, —NHC(O)-alkyl,
—NHC(O)-alkoxyalkyl, —NH—S(O)$_2$-aryl,
—NH—S(O)$_2$-alkyl, —C(O)NH—S(O)$_2$-aryl,
—C(O)NH—S(O)$_2$-alkyl, —S(O)$_2$-alkyl, alkyl, alkoxy or alkylsulfanyl, said alkyl, alkoxy and alkylsulfanyl groups being optionally substituted one or several times by halogen;
or 1,3-Dihydro-isobenzofuranyl;
Y is alkylene; and
n is 0.

Another embodiment of the invention are the compounds according to formula I, wherein
$R^1$, $R^2$, $R^3$ and $R^4$ independently represent hydrogen or $R^8$—X—;
X is —NHC(O)—, —N(alkyl)C(O)—, —NHC(O)NH—, —NHC(O)N(alkyl)- or —NHS(O)$_2$—; and
n is 1.

Still another embodiment of the invention are the compounds according to formula I, wherein
$R^1$, $R^2$, $R^3$ and $R^4$ independently represent hydrogen or $R^8$—X—;
X is —NHC(O)—, —N(alkyl)C(O)—, —NHC(O)NH—, —NHC(O)N(alkyl)- or —NHS(O)$_2$—;
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
X is —NHC(O)—, —N(alkyl)C(O)—, —NHC(O)NH—, —NHC(O)N(alkyl)- or —NHS(O)$_2$—;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
X is —NHC(O)—, —N(alkyl)C(O)—, —NHC(O)NH—, —NHC(O)N(alkyl)- or —NHS(O)$_2$—;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—; and
X is —C(O)NH—, —C(O)N(alkyl)-, —C(O)O— or —OC(O)—.

Another embodiment of the invention are the compounds according to formula I, wherein
$R^1$, $R^2$, $R^3$ and $R^4$ independently represent hydrogen or $R^8$—X—;
X is —C(O)NH—, —C(O)N(alkyl)-, —C(O)O— or —OC(O)—; and
n is 0.

Another embodiment of the invention are the compounds according to formula I, wherein
$R^1$, $R^2$, $R^3$ and $R^4$ independently represent hydrogen or $R^8$—X—;
X is —C(O)NH—, —C(O)N(alkyl)-, —C(O)O— or —OC(O)—; and
n is 1.

Still another embodiment of the invention are the compounds according to formula I, wherein
$R^1$, $R^2$, $R^3$ and $R^4$ independently represent hydrogen or $R^8$—X—;
X is —C(O)NH—, —C(O)N(alkyl)-, —C(O)O— or —OC(O)—; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
X is —C(O)NH—, —C(O)N(alkyl)-, —C(O)O— or —OC(O)—;
$R^5$ is hydrogen or alkyl optionally substituted one or several times by halogen; and
Y is alkylene.

Still another embodiment of the invention are the compounds according to formula I, wherein
$R^1$, $R^2$, $R^3$ and $R^4$ independently represent hydrogen or $R^8$—X—;
X is —C(O)NH—, —C(O)N(alkyl)-, —C(O)O— or —OC(O)—;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
X is —C(O)NH—, —C(O)N(alkyl)-, —C(O)O— or —OC(O)—;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—; and
X is —S(O)$_2$NH—, —S(O)$_2$N(alkyl)-, —S(O)$_2$— or —S(O)—.

Another embodiment of the invention are the compounds according to formula I, wherein
$R^1$, $R^2$, $R^3$ and $R^4$ independently represent hydrogen or $R^8$—X—;
X is —S(O)$_2$NH—, —S(O)$_2$N(alkyl)-, —S(O)$_2$— or —S(O)—; and
n is 0.

Another embodiment of the invention are the compounds according to formula I, wherein
$R^1$, $R^2$, $R^3$ and $R^4$ independently represent hydrogen or $R^8$—X—;
X is —S(O)$_2$NH—, —S(O)$_2$N(alkyl)-, —S(O)$_2$— or —S(O)—; and
n is 1.

Still another embodiment of the invention are the compounds according to formula I, wherein
$R^1$, $R^2$, $R^3$ and $R^4$ independently represent hydrogen or $R^8$—X—;
X is —S(O)$_2$NH—, —S(O)$_2$N(alkyl)-, —S(O)$_2$— or —S(O)—; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
X is —S(O)$_2$NH—, —S(O)$_2$N(alkyl)-, —S(O)$_2$— or —S(O)—;
$R^5$ is hydrogen or alkyl optionally substituted one or several times by halogen; and
Y is alkylene.

Still another embodiment of the invention are the compounds according to formula I, wherein
$R^1$, $R^2$, $R^3$ and $R^4$ independently represent hydrogen or $R^8$—X—;
X is —S(O)$_2$NH—, —S(O)$_2$N(alkyl)-, —S(O)$_2$— or —S(O)—;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
X is —S(O)$_2$NH—, —S(O)$_2$N(alkyl)-, —S(O)$_2$— or —S(O)—;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—; and
X is —NH—, —N(alkyl)-, —O— or —S—.

Another embodiment of the invention are the compounds according to formula I, wherein
$R^1$, $R^2$, $R^3$ and $R^4$ independently represent hydrogen or $R^8$—X—;
X is —NH—, —N(alkyl)-, —O— or —S—; and
n is 0.

Another embodiment of the invention are the compounds according to formula I, wherein
$R^1$, $R^2$, $R^3$ and $R^4$ independently represent hydrogen or $R^8$—X—;
X is —NH—, —N(alkyl)-, —O— or —S—; and
n is 1.

Still another embodiment of the invention are the compounds according to formula I, wherein
$R^1$, $R^2$, $R^3$ and $R^4$ independently represent hydrogen or $R^8$—X—;
X is —NH—, —N(alkyl)-, —O— or —S—; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
X is —NH—, —N(alkyl)-, —O— or —S—;
$R^5$ is hydrogen or alkyl optionally substituted one or several times by halogen; and
Y is alkylene.

Still another embodiment of the invention are the compounds according to formula I, wherein
$R^1$, $R^2$, $R^3$ and $R^4$ independently represent hydrogen or $R^8$—X—;
X is —NH—, —N(alkyl)-, —O— or —S—;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
X is —NH—, —N(alkyl)-, —O— or —S—;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —C(O)NH—, —C(O)N(alkyl)-, —C(O)O— or —OC(O)—; and
$T^1$ represents a single bond or alkylene.

Another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —C(O)NH—, —C(O)N(alkyl)-, —C(O)O— or —OC(O)—;
$T^1$ represents a single bond or alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —C(O)NH—, —C(O)N(alkyl)-, —C(O)O— or —OC(O)—;
$T^1$ represents a single bond or alkylene; and
n is 1.

Still another embodiment of the invention are the compounds according to formula I, wherein $R^1$, $R^2$, $R^3$ and $R^4$ independently represent hydrogen or $R^8$—X—;
$R^8$ is cycloalkyl-$T^1$-;
X is —C(O)NH—, —C(O)N(alkyl)-, —C(O)O— or —OC(O)—;
$T^1$ represents a single bond or alkylene; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —C(O)NH—, —C(O)N(alkyl)-, —C(O)O— or —OC(O)—;
$T^1$ represents a single bond or alkylene;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —C(O)NH—, —C(O)N(alkyl)-, —C(O)O— or —OC(O)—;
$T^1$ represents a single bond or alkylene;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —NH—, —N(alkyl)-, —O— or —S—; and
$T^1$ represents a single bond or alkylene.

Another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —NH—, —N(alkyl)-, —O— or —S—;
$T^1$ represents a single bond or alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —NH—, —N(alkyl)-, —O— or —S—;
$T^1$ represents a single bond or alkylene; and
n is 1.

Still another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —NH—, —N(alkyl)-, —O— or —S—;
$T^1$ represents a single bond or alkylene; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —NH—, —N(alkyl)-, —O— or —S—;
$T^1$ represents a single bond or alkylene;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is cycloalkyl-$T^1$-;
X is —NH—, —N(alkyl)-, —O— or —S—;
$T^1$ represents a single bond or alkylene;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-; and
X is —NHC(O)—, —N(alkyl)C(O)—, —NHC(O)NH—, —NHC(O)N(alkyl)- or —NHS(O)$_2$—;

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —NHC(O)—, —N(alkyl)C(O)—, —NHC(O)NH—, —NHC(O)N(alkyl)- or —NHS(O)$_2$—; and
n is 0.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —NHC(O)—, —N(alkyl)C(O)—, —NHC(O)NH—, —NHC(O)N(alkyl)- or —NHS(O)$_2$—; and
n is 1.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —NHC(O)—, —N(alkyl)C(O)—, —NHC(O)NH—, —NHC(O)N(alkyl)- or —NHS(O)$_2$—; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —NHC(O)—, —N(alkyl)C(O)—, —NHC(O)NH—, —NHC(O)N(alkyl)- or —NHS(O)$_2$—;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —NHC(O)—, —N(alkyl)C(O)—, —NHC(O)NH—, —NHC(O)N(alkyl)- or —NHS(O)$_2$—;

$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-; and
X is —C(O)NH—, —C(O)N(alkyl)-, —C(O)O— or —OC(O)—.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —C(O)NH—, —C(O)N(alkyl)-, —C(O)O— or —OC(O)—; and
n is 0.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —C(O)NH—, —C(O)N(alkyl)-, —C(O)O— or —OC(O)—; and
n is 1.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —C(O)NH—, —C(O)N(alkyl)-, —C(O)O— or —OC(O)—; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —C(O)NH—, —C(O)N(alkyl)-, —C(O)O— or —OC(O)—;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —C(O)NH—, —C(O)N(alkyl)-, —C(O)O— or —OC(O)—;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-; and
X is —S(O)$_2$NH—, —S(O)$_2$N(alkyl)-, —S(O)$_2$— or —S(O)—.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —S(O)$_2$NH—, —S(O)$_2$N(alkyl)-, —S(O)$_2$— or —S(O)—; and
n is 0.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —S(O)$_2$NH—, —S(O)$_2$N(alkyl)-, —S(O)$_2$— or —S(O)—; and
n is 1.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —S(O)$_2$NH—, —S(O)$_2$N(alkyl)-, —S(O)$_2$— or —S(O)—; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —S(O)$_2$NH—, —S(O)$_2$N(alkyl)-, —S(O)$_2$— or —S(O)—;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —S(O)$_2$NH—, —S(O)$_2$N(alkyl)-, —S(O)$_2$— or —S(O)—;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-; and
X is —NH—, —N(alkyl)-, —O— or —S—.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —NH—, —N(alkyl)-, —O— or —S—; and
n is 0.

Another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —NH—, —N(alkyl)-, —O— or —S—; and
n is 1.

Still another embodiment of the invention are the compounds according to formula I, wherein $R^1$, $R^2$, $R^3$ and $R^4$ independently represent hydrogen or $R^8$—X—;
$R^8$ is heterocyclyl-$T^2$-;
X is —NH—, —N(alkyl)-, —O— or —S—; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —NH—, —N(alkyl)-, —O— or —S—;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —NH—, —N(alkyl)-, —O— or —S—;
$R^5$ is hydrogen or alkyl optionally substituted one or several times by halogen;
Y is alkylene; and
n is 0.

Still another embodiment of the invention are the compounds according to formula I, wherein
$R^1$, $R^2$, $R^3$ and $R^4$ independently represent hydrogen or $R^8$—X—;
$R^8$ is heterocyclyl-$T^2$-;
X is —C(O)—,
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is aryl-$T^3$-;
X is —NHC(O)—, —N(alkyl)C(O)—, —NHC(O)NH—, —NHC(O)N(alkyl)- or —NHS(O)$_2$—; and
$T^3$ represents a single bond or alkylene.

Another embodiment of the invention are the compounds according to formula I, wherein
$R^1$, $R^2$, $R^3$ and $R^4$ independently represent hydrogen or $R^8$—X—; $R^8$ is aryl-$T^3$-;
X is —NHC(O)—, —N(alkyl)C(O)—, —NHC(O)NH—, —NHC(O)N(alkyl)- or —NHS(O)$_2$—;
$T^3$ represents a single bond or alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is aryl-$T^3$-;
X is —NHC(O)—, —N(alkyl)C(O)—, —NHC(O)NH—, —NHC(O)N(alkyl)- or —NHS(O)$_2$—;
$T^3$ represents a single bond or alkylene; and
n is 1.

Still another embodiment of the invention are the compounds according to formula I, wherein
$R^1$, $R^2$, $R^3$ and $R^4$ independently represent hydrogen or $R^8$—X—;
$R^8$ is aryl-$T^3$-;
X is —NHC(O)—, —N(alkyl)C(O)—, —NHC(O)NH—, —NHC(O)N(alkyl)- or —NHS(O)$_2$—;

$T^3$ represents a single bond or alkylene; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is aryl-$T^3$-;
X is —NHC(O)—, —N(alkyl)C(O)—, —NHC(O)NH—, —NHC(O)N(alkyl)- or —NHS(O)$_2$—;
$T^3$ represents a single bond or alkylene;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is aryl-$T^3$-;
X is —NHC(O)—, —N(alkyl)C(O)—, —NHC(O)NH—, —NHC(O)N(alkyl)- or —NHS(O)$_2$—;
$T^3$ represents a single bond or alkylene;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is aryl-$T^3$-;
X is —C(O)NH—, —C(O)N(alkyl)-, —C(O)O— or —OC(O)—; and
$T^3$ represents a single bond or alkylene.

Another embodiment of the invention are the compounds according to formula I, wherein
$R^1$, $R^2$, $R^3$ and $R^4$ independently represent hydrogen or $R^8$—X—;
$R^8$ is aryl-$T^3$-;
X is —C(O)NH—, —C(O)N(alkyl)-, —C(O)O— or —OC(O)—;
$T^3$ represents a single bond or alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is aryl-$T^3$-;
X is —C(O)NH—, —C(O)N(alkyl)-, —C(O)O— or —OC(O)—;
$T^3$ represents a single bond or alkylene; and
n is 1.

Still another embodiment of the invention are the compounds according to formula I, wherein
$R^1$, $R^2$, $R^3$ and $R^4$ independently represent hydrogen or $R^8$—X—;
$R^8$ is aryl-$T^3$-;
X is —C(O)NH—, —C(O)N(alkyl)-, —C(O)O— or —OC(O)—;
$T^3$ represents a single bond or alkylene; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is aryl-$T^3$-;

X is —C(O)NH—, —C(O)N(alkyl)-, —C(O)O— or —OC(O)—;
T³ represents a single bond or alkylene;
R⁵ is hydrogen or alkyl optionally substituted one or several times by halogen; and
n is 0.

Still another embodiment of the invention are the compounds according to formula I, wherein
R¹, R², R³ and R⁴ independently represent hydrogen or R⁸—X—;
R⁸ is aryl-T³-;
X is —C(O)NH—, —C(O)N(alkyl)-, —C(O)O— or —OC(O)—;
T³ represents a single bond or alkylene;
R⁵ is hydrogen or alkyl optionally substituted one or several times by halogen;
Y is alkylene; and
n is 0.

Another embodiment of the invention are the compounds according to formula I, wherein
R¹, R², R³ and R⁴ independently represent hydrogen or R⁸—X—; and
R⁸ is aryl-T³-;
X is —S(O)₂NH—, —S(O)₂N(alkyl)-, —S(O)₂— or —S(O)—; and
T³ represents a single bond or alkylene.

Another embodiment of the invention are the compounds according to formula I, wherein
R¹, R², R³ and R⁴ independently represent hydrogen or R⁸—X—;
R⁸ is aryl-T³-;
X is —S(O)₂NH—, —S(O)₂N(alkyl)-, —S(O)₂— or —S(O)—;
T³ represents a single bond or alkylene; and
n is 0.

Another embodiment of the invention are the compounds according to formula I, wherein
R¹, R², R³ and R⁴ independently represent hydrogen or R⁸—X—;
R⁸ is aryl-T³-;
X is —S(O)₂NH—, —S(O)₂N(alkyl)-, —S(O)₂— or —S(O)—;
T³ represents a single bond or alkylene; and
n is 1.

Still another embodiment of the invention are the compounds according to formula I, wherein
R¹, R², R³ and R⁴ independently represent hydrogen or R⁸—X—;
R⁸ is aryl-T³-;
X is —S(O)₂NH—, —S(O)₂N(alkyl)-, —S(O)₂— or —S(O)—;
T³ represents a single bond or alkylene; and
R⁵ is hydrogen or alkyl optionally substituted one or several times by halogen.

Still another embodiment of the invention are the compounds according to formula I, wherein
R¹, R², R³ and R⁴ independently represent hydrogen or R⁸—X—;
R⁸ is aryl-T³-;
X is —S(O)₂NH—, —S(O)₂N(alkyl)-, —S(O)₂— or —S(O)—;
T³ represents a single bond or alkylene;
R⁵ is hydrogen or alkyl optionally substituted one or several times by halogen; and
n is 0.

Still another embodiment of the invention are the compounds according to formula I, wherein
R¹, R², R³ and R⁴ independently represent hydrogen or R⁸—X—;
R⁸ is aryl-T³-;
X is —S(O)₂NH—, —S(O)₂N(alkyl)-, —S(O)₂— or —S(O)—;
T³ represents a single bond or alkylene;
R⁵ is hydrogen or alkyl optionally substituted one or several times by halogen;
Y is alkylene; and
n is 0.

Another embodiment of the invention are the compounds according to formula I, wherein
R¹, R², R³ and R⁴ independently represent hydrogen or R⁸—X—;
R⁸ is aryl-T³-;
X is —NH—, —N(alkyl)-, —O— or —S—; and
T³ represents a single bond or alkylene.

Another embodiment of the invention are the compounds according to formula I, wherein
R¹, R², R³ and R⁴ independently represent hydrogen or R⁸—X—;
R⁸ is aryl-T³-;
X is —NH—, —N(alkyl)-, —O— or —S—;
T³ represents a single bond or alkylene; and
n is 0.

Another embodiment of the invention are the compounds according to formula I, wherein
R¹, R², R³ and R⁴ independently represent hydrogen or R⁸—X—;
R⁸ is aryl-T³-;
X is —NH—, —N(alkyl)-, —O— or —S—;
T³ represents a single bond or alkylene; and
n is 1.

Still another embodiment of the invention are the compounds according to formula I, wherein
R¹, R², R³ and R⁴ independently represent hydrogen or R⁸—X—;
R⁸ is aryl-T³-;
X is —NH—, —N(alkyl)-, —O— or —S—;
T³ represents a single bond or alkylene; and
R⁵ is hydrogen or alkyl optionally substituted one or several times by halogen.

Still another embodiment of the invention are the compounds according to formula I, wherein
R¹, R², R³ and R⁴ independently represent hydrogen or R⁸—X—;
R⁸ is aryl-T³-;
X is —NH—, —N(alkyl)-, —O— or —S—;
T³ represents a single bond or alkylene;
R⁵ is hydrogen or alkyl optionally substituted one or several times by halogen; and
n is 0.

Still another embodiment of the invention are the compounds according to formula I, wherein
R¹, R², R³ and R⁴ independently represent hydrogen or R⁸—X—;
R⁸ is aryl-T³-;
X is —NH—, —N(alkyl)-, —O— or —S—;
T³ represents a single bond or alkylene;
R⁵ is hydrogen or alkyl optionally substituted one or several times by halogen; and
Y is alkylene; and
n is 0.

Another embodiment of the invention are the compounds according to formula I, wherein
R¹, R², R³ and R⁴ independently represent hydrogen or R⁸—X—;

$R^8$ is heteroaryl-$T^4$-;
X is —NHC(O)—, —N(alkyl)C(O)—, —NHC(O)NH—, —NHC(O)N(alkyl)- or —NHS(O)$_2$—; and
$T^4$ represents a single bond or alkylene.

Another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NHC(O)—, —N(alkyl)C(O)—, —NHC(O)NH—, —NHC(O)N(alkyl)- or —NHS(O)$_2$—;
$T^4$ represents a single bond or alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NHC(O)—, —N(alkyl)C(O)—, —NHC(O)NH—, —NHC(O)N(alkyl)- or —NHS(O)$_2$—;
$T^4$ represents a single bond or alkylene; and
n is 1.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NHC(O)—, —N(alkyl)C(O)—, —NHC(O)NH—, —NHC(O)N(alkyl)- or —NHS(O)$_2$—;
$T^4$ represents a single bond or alkylene; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NHC(O)—, —N(alkyl)C(O)—, —NHC(O)NH—, —NHC(O)N(alkyl)- or —NHS(O)$_2$—;
$T^4$ represents a single bond or alkylene;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NHC(O)—, —N(alkyl)C(O)—, —NHC(O)NH—, —NHC(O)N(alkyl)- or —NHS(O)$_2$—;
$T^4$ represents a single bond or alkylene;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —C(O)NH—, —C(O)N(alkyl)-, —C(O)O— or —OC(O)—; and
$T^4$ represents a single bond or alkylene.

Another embodiment of the invention are the compounds according to formula I, wherein
$R^1$, $R^2$, $R^3$ and $R^4$ independently represent hydrogen or $R^8$—X—;

$R^8$ is heteroaryl-$T^4$-;
X is —C(O)NH—, —C(O)N(alkyl)-, —C(O)O— or —OC(O)—;
$T^4$ represents a single bond or alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —C(O)NH—, —C(O)N(alkyl)-, —C(O)O— or —OC(O)—;
$T^4$ represents a single bond or alkylene; and
n is 1.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —C(O)NH—, —C(O)N(alkyl)-, —C(O)O— or —OC(O)—;
$T^4$ represents a single bond or alkylene; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —C(O)NH—, —C(O)N(alkyl)-, —C(O)O— or —OC(O)—;
$T^4$ represents a single bond or alkylene;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —C(O)NH—, —C(O)N(alkyl)-, —C(O)O— or —OC(O)—;
$T^4$ represents a single bond or alkylene;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—; and
$R^8$ is heteroaryl-$T^4$-;
X is —S(O)$_2$NH—, —S(O)$_2$N(alkyl)-, —S(O)$_2$— or —S(O)—; and
$T^4$ represents a single bond or alkylene.

Another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —S(O)$_2$NH—, —S(O)$_2$N(alkyl)-, —S(O)$_2$— or —S(O)—;
$T^4$ represents a single bond or alkylene; and
n is 0.

Another embodiment of the invention are the compounds according to formula I, wherein $R^1$, $R^2$, $R^3$ and $R^4$ independently represent hydrogen or $R^8$—X—;
$R^8$ is heteroaryl-$T^4$-;
X is —S(O)$_2$NH—, —S(O)$_2$N(alkyl)-, —S(O)$_2$— or —S(O)—;
$T^4$ represents a single bond or alkylene; and
n is 1.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —S(O)$_2$NH—, —S(O)$_2$N(alkyl)-, —S(O)$_2$— or —S(O)—;
$T^4$ represents a single bond or alkylene; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —S(O)$_2$NH—, —S(O)$_2$N(alkyl)-, —S(O)$_2$— or —S(O)—;
$T^4$ represents a single bond or alkylene;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —S(O)$_2$NH—, —S(O)$_2$N(alkyl)-, —S(O)$_2$— or —S(O)—;
$T^4$ represents a single bond or alkylene;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NH—, —N(alkyl)-, —O— or —S—; and
$T^4$ represents a single bond or alkylene.

Another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NH—, —N(alkyl)-, —O— or —S—;
$T^4$ represents a single bond or alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NH—, —N(alkyl)-, —O— or —S—;
$T^4$ represents a single bond or alkylene; and
n is 1.

Still another embodiment of the invention are the compounds according to formula I, wherein
$R^1$, $R^2$, $R^3$ and $R^4$ independently represent hydrogen or $R^8$—X—;

$R^8$ is heteroaryl-$T^4$-;
X is —NH—, —N(alkyl)-, —O— or —S—;
$T^4$ represents a single bond or alkylene; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NH—, —N(alkyl)-, —O— or —S—;
$T^4$ represents a single bond or alkylene;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is heteroaryl-$T^4$-;
X is —NH—, —N(alkyl)-, —O— or —S—;
$T^4$ represents a single bond or alkylene;
$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—;
$R^8$ is alkyl optionally substituted one or several times by halogen; and
X is —NHC(O)—, —N(alkyl)C(O)—, —NHC(O)NH—, —NHC(O)N(alkyl)- or —NHS(O)$_2$—;

Another embodiment of the invention are the compounds according to formula I, wherein
$R^1$, $R^2$, $R^3$ and $R^4$ independently represent hydrogen or $R^8$—X—;
$R^8$ is alkyl optionally substituted one or several times by halogen;
X is —NHC(O)—, —N(alkyl)C(O)—, —NHC(O)NH—, —NHC(O)N(alkyl)- or —NHS(O)$_2$—; and
n is 0.

Another embodiment of the invention are the compounds according to formula I, wherein
$R^1$, $R^2$, $R^3$ and $R^4$ independently represent hydrogen or $R^8$—X—;
$R^8$ is alkyl optionally substituted one or several times by halogen;
X is —NHC(O)—, —N(alkyl)C(O)—, —NHC(O)NH—, —NHC(O)N(alkyl)- or —NHS(O)$_2$—; and
n is 1.

Still another embodiment of the invention are the compounds according to formula I, wherein
$R^1$, $R^2$, $R^3$ and $R^4$ independently represent hydrogen or $R^8$—X—;
$R^8$ is alkyl optionally substituted one or several times by halogen;
X is —NHC(O)—, —N(alkyl)C(O)—, —NHC(O)NH—, —NHC(O)N(alkyl)- or —NHS(O)$_2$—; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;

$R^8$ is alkyl optionally substituted one or several times by halogen;

X is —NHC(O)—, —N(alkyl)C(O)—, —NHC(O)NH—, —NHC(O)N(alkyl)- or —NHS(O)$_2$—;

$R^5$ is hydrogen or alkyl optionally substituted one or several times by halogen; and n is 0.

Still another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —NHC(O)—, —N(alkyl)C(O)—, —NHC(O)NH—, —NHC(O)N(alkyl)- or —NHS(O)$_2$—;

$R^5$ is hydrogen or alkyl optionally substituted one or several times by halogen;

Y is alkylene; and n is 0.

Another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen; and

X is —C(O)NH—, —C(O)N(alkyl)-, —C(O)O— or —OC(O)—.

Another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —C(O)NH—, —C(O)N(alkyl)-, —C(O)O— or —OC(O)—; and n is 0.

Another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —C(O)NH—, —C(O)N(alkyl)-, —C(O)O— or —OC(O)—; and n is 1.

Still another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —C(O)NH—, —C(O)N(alkyl)-, —C(O)O— or —OC(O)—; and $R^5$ is hydrogen or alkyl optionally substituted one or several times by halogen.

Still another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —C(O)NH—, —C(O)N(alkyl)-, —C(O)O— or —OC(O)—;

$R^5$ is hydrogen or alkyl optionally substituted one or several times by halogen; and n is 0.

Still another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —C(O)NH—, —C(O)N(alkyl)-, —C(O)O— or —OC(O)—;

$R^5$ is hydrogen or alkyl optionally substituted one or several times by halogen;

Y is alkylene; and n is 0.

Another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen; and

X is —S(O)$_2$NH—, —S(O)$_2$N(alkyl)-, —S(O)$_2$— or —S(O)—.

Another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —S(O)$_2$NH—, —S(O)$_2$N(alkyl)-, —S(O)$_2$— or —S(O)—; and n is 0.

Another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —S(O)$_2$NH—, —S(O)$_2$N(alkyl)-, —S(O)$_2$— or —S(O)—; and n is 1.

Still another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —S(O)$_2$NH—, —S(O)$_2$N(alkyl)-, —S(O)$_2$— or —S(O)—; and $R^5$ is hydrogen or alkyl optionally substituted one or several times by halogen.

Still another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —S(O)$_2$NH—, —S(O)$_2$N(alkyl)-, —S(O)$_2$— or —S(O)—;

$R^5$ is hydrogen or alkyl optionally substituted one or several times by halogen; and n is 0.

Still another embodiment of the invention are the compounds according to formula I, wherein $R^1$, $R^2$, $R^3$ and $R^4$ independently represent hydrogen or $R^8$—X—;

$R^8$ is alkyl optionally substituted one or several times by halogen;

X is —S(O)$_2$NH—, —S(O)$_2$N(alkyl)-, —S(O)$_2$— or —S(O)—;

$R^5$ is hydrogen or alkyl optionally substituted one or several times by halogen;
Y is alkylene; and
n is 0.

Another embodiment of the invention are the compounds according to formula I, wherein
$R^1$, $R^2$, $R^3$ and $R^4$ independently represent hydrogen or $R^8$—X—; and
$R^8$ is alkyl optionally substituted one or several times by halogen;
X is —NH—, —N(alkyl)-, —O— or —S—.

Another embodiment of the invention are the compounds according to formula I, wherein
$R^1$, $R^2$, $R^3$ and $R^4$ independently represent hydrogen or $R^8$—X—;
$R^8$ is alkyl optionally substituted one or several times by halogen;
X is —NH—, —N(alkyl)-, —O— or —S—; and
n is 0.

Another embodiment of the invention are the compounds according to formula I, wherein
$R^1$, $R^2$, $R^3$ and $R^4$ independently represent hydrogen or $R^8$—X—;
$R^8$ is alkyl optionally substituted one or several times by halogen;
X is —NH—, —N(alkyl)-, —O— or —S—; and
n is 1.

Still another embodiment of the invention are the compounds according to formula I, wherein
$R^1$, $R^2$, $R^3$ and $R^4$ independently represent hydrogen or $R^8$—X—;
$R^8$ is alkyl optionally substituted one or several times by halogen;
X is —NH—, —N(alkyl)-, —O— or —S—; and
$R^5$ is hydrogen or alkyl optionally substituted one or several times by halogen.

Still another embodiment of the invention are the compounds according to formula I, wherein
$R^1$, $R^2$, $R^3$ and $R^4$ independently represent hydrogen or $R^8$—X—;
$R^8$ is alkyl optionally substituted one or several times by halogen;
X is —NH—, —N(alkyl)-, —O— or —S—;
$R^5$ is hydrogen or alkyl optionally substituted one or several times by halogen; and
n is 0.

Still another embodiment of the invention are the compounds according to formula I, wherein
$R^1$, $R^2$, $R^3$ and $R^4$ independently represent hydrogen or $R^8$—X—;
$R^8$ is alkyl optionally substituted one or several times by halogen;
X is —NH—, —N(alkyl)-, —O— or —S—;
$R^5$ is hydrogen or alkyl optionally substituted one or several times by halogen;
Y is alkylene; and
n is 0.

Preferred are all compounds of the invention, wherein $R^1$ represents hydrogen. Still preferred are all compounds of the invention, wherein $R^1$ and $R^4$ represent hydrogen. Still preferred are all compounds of the invention, wherein $R^1$ and $R^2$ represent hydrogen. Still preferred are all compounds of the invention, wherein $R^1$ and $R^3$ represent hydrogen. Further preferred are all compounds of the invention, wherein $R^1$, $R^2$ and $R^4$ represent hydrogen. And still further preferred are all compounds of the invention, wherein $R^1$, $R^3$ and $R^4$ represent hydrogen.

Another embodiment of the invention are the compounds according to formula I, wherein only one of $R^1$, $R^2$, $R^3$ and $R^4$ can represent $R^8$—O—.

Another embodiment of the invention are the compounds according to formula I, wherein at least three of $R^1$, $R^2$, $R^3$ and $R^4$ can represent $R^8$—O—.

Another embodiment of the invention are the compounds according to formula I, wherein only one at least three one of $R^1$, $R^2$, $R^3$ and $R^4$ can represent $R^8$—O—.

Another embodiment of the invention are the compounds according to formula I, wherein
$R^1$, $R^2$, $R^3$ and $R^4$ independently represent $R^8$—X—, heterocyclyl-$T^2$-, hydrogen, halogen, nitro, —OH, —NH$_2$, —NH—C(O)H, —C(O)OH, —C(O)NH$_2$, —C(O)NH—O-alkyl, or alkyl optionally substituted one or several times by hydroxy or alkoxy;
$R^8$ is cycloalkyl-$T^1$-,
heterocyclyl-$T^2$-,
aryl-$T^3$-,
heteroaryl-$T^4$-, or
alkyl optionally substituted one or several times by halogen;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;
$T^1$, $T^2$, $T^3$ and $T^4$ independently represent a single bond or alkylene;
$R^5$ is hydrogen,
alkyl being optionally substituted one or several times by halogen or alkoxy,
heteroaryl, or
phenyl, which is optionally substituted one or two times by halogen, —NO$_2$, —C(O)OH,
—C(O)NH-alkyl, —NH$_2$, —NHC(O)-alkyl, —NHC(O)-alkoxyalkyl, —N(alkyl)C(O)-alkyl,
—NHC(O)O-alkyl, —N(alkyl)C(O)O-alkyl, —NH—S(O)$_2$-alkyl, —S(O)$_2$-alkyl, —NHC(O)-aryl,
—NH-aryl, —O-aryl, —S(O)-aryl, aryl, heterocyclyl, cycloalkyl, alkyl, alkoxy or alkylsulfanyl, said alkyl, alkoxy and alkylsulfanyl groups being optionally substituted one or several times by halogen;
naphtyl,
benzo[1,3]dioxol-5-yl,
cycloalkyl or
alkenyl;
Y is alkylene, alkylene-C(O)— or alkylene-CH(OH)—;
n is 0 or 1;
$R^6$ is hydrogen; and
$R^7$ is hydrogen, alkyl or cycloalkyl.

Another embodiment of the invention are the compounds according to formula I, wherein
$R^1$ is hydrogen;
$R^2$, $R^3$ and $R^4$ independently represent $R^8$—X—, heterocyclyl-$T^2$-, hydrogen, halogen, nitro, —OH, —NH$_2$, —NH—C(O)H, —C(O)OH, —C(O)NH$_2$, —C(O)NH—O-alkyl, or alkyl optionally substituted one or several times by hydroxy or alkoxy;
$R^8$ is cycloalkyl-$T^1$-,
heterocyclyl-$T^2$-,
aryl-$T^3$,
heteroaryl-$T^4$-, or
alkyl optionally substituted one or several times by halogen;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-, —S(O)$_2$NH—, —S(O)$_2$N(alkyl)-,
—S(O)$_2$—, —OC(O)—, —C(O)—, —NH—,
—N(alkyl)-, —O— or —S—;
T$^1$, T$^2$, T$^3$ and T$^4$ independently represent a single bond or alkylene;
R$^5$ is hydrogen,
alkyl being optionally substituted one or several times by halogen or alkoxy,
heteroaryl, or
phenyl, which is optionally substituted one or two times by halogen, —NO$_2$, —C(O)OH,
—C(O)NH-alkyl, —NH$_2$, —NHC(O)-alkyl, —NHC(O)-alkoxyalkyl, —N(alkyl)C(O)-alkyl,
—NHC(O)O-alkyl, —N(alkyl)C(O)O-alkyl, —NH—S(O)$_2$-alkyl, —S(O)$_2$-alkyl, —NHC(O)-aryl,
—NH-aryl, —O-aryl, —S(O)-aryl, aryl, heterocyclyl, cycloalkyl, alkyl, alkoxy or alkylsulfanyl, said alkyl, alkoxy and alkylsulfanyl groups being optionally substituted one or several times by halogen;
naphtyl,
benzo[1,3]dioxol-5-yl,
cycloalkyl or
alkenyl;
Y is alkylene, alkylene-C(O)— or alkylene-CH(OH)—;
n is 0 or 1;
R$^6$ is hydrogen; and
R$^7$ is hydrogen, alkyl or cycloalkyl.

Another embodiment of the invention are the compounds according to formula I, wherein
R$^1$ is hydrogen;
one of R$^2$, R$^3$ and R$^4$ represents R$^8$—X—, heterocyclyl-T$^2$-, hydrogen, halogen, nitro, —OH, —NH$_2$,
—NH—C(O)H, —C(O)OH,
—C(O)NH$_2$, —C(O)NH—O-alkyl, or alkyl optionally substituted one or several times by hydroxy or alkoxy;
and the remaining two of R$^2$, R$^3$ and R$^4$ are hydrogen;
R$^8$ is cycloalkyl-T$^1$-,
heterocyclyl-T$^2$-,
aryl-T$^3$-,
heteroaryl-T$^4$-, or
alkyl optionally substituted one or several times by halogen;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;
T$^1$, T$^2$, T$^3$ and T$^4$ independently represent a single bond or alkylene;
R$^5$ is hydrogen,
alkyl being optionally substituted one or several times by halogen or alkoxy,
heteroaryl, or
phenyl, which is optionally substituted one or two times by halogen, —NO$_2$, —C(O)OH,
—C(O)NH-alkyl, —NH$_2$, —NHC(O)-alkyl, —NHC(O)-alkoxyalkyl, —N(alkyl)C(O)-alkyl,
—NHC(O)O-alkyl, —N(alkyl)C(O)O-alkyl, —NH—S(O)$_2$-alkyl, —S(O)$_2$-alkyl, —NHC(O)-aryl,
—NH-aryl, —O-aryl, —S(O)-aryl, aryl, heterocyclyl, cycloalkyl, alkyl, alkoxy or alkylsulfanyl, said alkyl, alkoxy and alkylsulfanyl groups being optionally substituted one or several times by halogen;
naphtyl,
benzo[1,3]dioxol-5-yl,
cycloalkyl or
alkenyl;
Y is alkylene, alkylene-C(O)— or alkylene-CH(OH)—;
n is 0 or 1;
R$^6$ is hydrogen; and
R$^7$ is hydrogen, alkyl or cycloalkyl.

Another embodiment of the invention are the compounds according to formula I, wherein
R$^1$ is hydrogen;
one of R$^2$, R$^3$ and R$^4$ represents R$^8$—X—, heterocyclyl-T$^2$-, halogen, nitro, —OH, —NH$_2$, —C(O)OH,
—C(O)NH$_2$, —C(O)NH—O-alkyl, or alkyl optionally substituted one or several times by hydroxy or alkoxy;
and the remaining two of R$^2$, R$^3$ and R$^4$ are hydrogen;
R$^8$ is cycloalkyl-T$^1$-,
heterocyclyl-T$^2$-,
aryl-T$^3$-,
heteroaryl-T$^4$-, or
alkyl optionally substituted one or several times by halogen;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;
T$^1$, T$^2$, T$^3$ and T$^4$ independently represent a single bond or alkylene;
R$^5$ is alkyl or phenyl;
Y is alkylene;
n is 0 or 1;
R$^6$ is hydrogen; and
R$^7$ is hydrogen, alkyl or cycloalkyl.

Another embodiment of the invention are the compounds according to formula I, wherein
R$^1$ and R$^2$ are hydrogen;
one of R$^3$ and R$^4$ represents R$^8$—X—, heterocyclyl-T$^2$-, halogen, nitro, —OH, —NH$_2$, —C(O)OH,
—C(O)NH$_2$, —C(O)NH—O-alkyl, or alkyl optionally substituted one or several times by hydroxy or alkoxy;
and the remaining one of R$^3$ and R$^4$ is hydrogen;
R$^8$ is cycloalkyl-T$^1$-,
heterocyclyl-T$^2$-,
aryl-T$^3$-,
heteroaryl-T$^4$-, or
alkyl optionally substituted one or several times by halogen;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;
T$^1$, T$^2$, T$^3$ and T$^4$ independently represent a single bond or alkylene;
R$^5$ is alkyl;
n is 0;
R$^6$ is hydrogen; and
R$^7$ is hydrogen, alkyl or cycloalkyl.

Another embodiment of the invention are the compounds according to formula I, wherein
R$^1$, R$^2$ and R$^4$ are hydrogen;
R$^3$ represents R$^8$—X—, heterocyclyl-T$^2$-, halogen, nitro, —OH, —NH$_2$, —C(O)OH,
—C(O)NH$_2$, —C(O)NH—O-alkyl, or alkyl optionally substituted one or several times by hydroxy or alkoxy;
R$^8$ is cycloalkyl-T$^1$-,
heterocyclyl-T$^2$-,
aryl-T$^3$-,
heteroaryl-T$^4$-, or alkyl optionally substituted one or several times by halogen;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;

$T^1$, $T^2$, $T^3$ and $T^4$ independently represent a single bond or alkylene;

$R^5$ is alkyl or phenyl;

Y is alkylene;

n is 0 or 1;

$R^6$ is hydrogen; and $R^7$ is hydrogen, alkyl or cycloalkyl.

Such compounds are for example:

7-Fluoro-2-isopropyl-4-(5-methyl-1H-pyrazol-3-ylamino)-2H-phthalazin-1-one;

2-Isopropyl-4-(5-methyl-1H-pyrazol-3-ylamino)-7-morpholino-2H-phthalazin-1-one;

2-Benzyl-4-(5-methyl-1H-pyrazol-3-ylamino)-7-morpholino-2H-phthalazin-1-one;

2-Isopropyl-7-(4-methyl-piperazin-1-yl)-4-(5-methyl-2H-pyrazol-3-ylamino)-2H-phthalazin-1-one;

2-Isopropyl-4-(5-methyl-1H-pyrazol-3-ylamino)-7-dimethylamino-2H-phthalazin-1-one;

[3-Isopropyl-1-(5-methyl-2H-pyrazol-3-ylamino)-4-oxo-3,4-dihydro-phthalazin-6-yl]-methyl-carbamic acid tert-butyl ester;

2-Isopropyl-4-(5-methyl-1H-pyrazol-3-ylamino)-7-methoxy-2H-phthalazin-1-one;

2-Isopropyl-4-(5-methyl-1H-pyrazol-3-ylamino)-7-(pyridin-2-ylmethoxy)-2H-phthalazin-1-one;

2-Isopropyl-4-(5-methyl-1H-pyrazol-3-ylamino)-7-(pyridin-3-ylmethoxy)-2H-phthalazin-1-one;

2-Isopropyl-4-(5-methyl-1H-pyrazol-3-ylamino)-7-(pyridin-4-ylmethoxy)-2H-phthalazin-1-one;

2-Isopropyl-4-(5-methyl-1H-pyrazol-3-ylamino)-7-(2-morpholin-4-yl-ethoxy)-2H-phthalazin-1-one;

7-Hydroxy-2-isopropyl-4-(5-methyl-1H-pyrazol-3-ylamino)-2H-phthalazin-1-one;

7-Difluoromethoxy-2-isopropyl-4-(5-methyl-1H-pyrazol-3-ylamino)-2H-phthalazin-1-one;

2-Benzyl-7-methoxy-4-(5-methyl-1H-pyrazol-3-ylamino)-2H-phthalazin-1-one;

2-Isopropyl-4-(5-methyl-1H-pyrazol-3-ylamino)-7-methylsulfanyl-2H-phthalazin-1-one;

2-Isopropyl-7-methanesulfonyl-4-(5-methyl-1H-pyrazol-3-ylamino)-2H-phthalazin-1-one;

2-Isopropyl-4-(5-methyl-1H-pyrazol-3-ylamino)-7-(2-morpholin-4-yl-ethylsulfanyl)-2H-phthalazin-1-one;

2-Isopropyl-7-[methyl-(2-morpholin-4-yl-ethyl)-amino]-4-(5-methyl-1H-pyrazol-3-ylamino)-2H-phthalazin-1-one;

2-Isopropyl-4-(5-methyl-1H-pyrazol-3-ylamino)-7-(methyl-pyridin-4-ylmethyl-amino)-2H-phthalazin-1-one;

2-Isopropyl-4-(5-methyl-1H-pyrazol-3-ylamino)-7-(methyl-pyridin-3-ylmethyl-amino)-2H-phthalazin-1-one;

2-Isopropyl-4-(5-methyl-1H-pyrazol-3-ylamino)-7-(methyl-pyridin-2-ylmethyl-amino)-2H-phthalazin-1-one;

N-[3-Isopropyl-1-(5-methyl-1H-pyrazol-3-ylamino)-4-oxo-3,4-dihydro-phthalazin-6-yl]-N-methyl-acetamide;

3-Isopropyl-1-[3-isopropyl-1-(5-methyl-1H-pyrazol-3-ylamino)-4-oxo-3,4-dihydro-phthalazin-6-yl]-1-methyl-urea;

[3-Isopropyl-1-(5-methyl-1H-pyrazol-3-ylamino)-4-oxo-3,4-dihydro-phthalazin-6-yl]-methyl-carbamic acid ethyl ester;

N-[3-Isopropyl-1-(5-methyl-1H-pyrazol-3-ylamino)-4-oxo-3,4-dihydro-phthalazin-6-yl]-acetamide;

7-[(4-Fluoro-benzyl)-methyl-amino]-2-isopropyl-4-(5-methyl-1H-pyrazol-3-ylamino)-2H-phthalazin-1-one;

N-[3-Isopropyl-1-(5-methyl-1H-pyrazol-3-ylamino)-4-oxo-3,4-dihydro-phthalazin-6-yl]-N-methyl-methanesulfonamide;

2-Isopropyl-4-(5-methyl-1H-pyrazol-3-ylamino)-7-(2-morpholin-4-yl-ethylamino)-2H-phthalazin-1-one;

2-Isopropyl-7-methylamino-4-(5-methyl-1H-pyrazol-3-ylamino)-2H-phthalazin-1-one;

1-[3-Isopropyl-1-(5-methyl-1H-pyrazol-3-ylamino)-4-oxo-3,4-dihydro-phthalazin-6-yl]-3-methyl-urea;

4-(5-Cyclopropyl-2H-pyrazol-3-ylamino)-7-dimethylamino-2-isopropyl-2H-phthalazin-1-one; N-[3-Isopropyl-1-(5-methyl-1H-pyrazol-3-ylamino)-4-oxo-3,4-dihydro-phthalazin-6-yl]-methanesulfonamide;

2-Isopropyl-7-methoxymethyl-4-(5-methyl-1H-pyrazol-3-ylamino)-2H-phthalazin-1-one;

2-Benzyl-7-methoxymethyl-4-(5-methyl-1H-pyrazol-3-ylamino)-2H-phthalazin-1-one;

2-Isopropyl-7-(4-methyl-piperazin-1-ylmethyl)-4-(5-methyl-1H-pyrazol-3-ylamino)-2H-phthalazin-1-one;

2-Isopropyl-4-(5-methyl-1H-pyrazol-3-ylamino)-7-morpholin-4-ylmethyl-2H-phthalazin-1-one;

3-Isopropyl-1-(5-methyl-1H-pyrazol-3-ylamino)-4-oxo-3,4-dihydro-phthalazine-6-carboxylic acid;

2-Isopropyl-4-(5-methyl-1H-pyrazol-3-ylamino)-7-(morpholine-4-carbonyl)-2H-phthalazin-1-one;

3-Isopropyl-1-(5-methyl-1H-pyrazol-3-ylamino)-4-oxo-3,4-dihydro-phthalazine-6-carboxylic acid diethylamide;

3-Isopropyl-1-(5-methyl-1H-pyrazol-3-ylamino)-4-oxo-3,4-dihydro-phthalazine-6-carboxylic acid methoxy-amide;

3-Isopropyl-1-(5-methyl-1H-pyrazol-3-ylamino)-4-oxo-3,4-dihydro-phthalazine-6-carboxylic acid isopropylamide;

3-Isopropyl-1-(5-methyl-1H-pyrazol-3-ylamino)-4-oxo-3,4-dihydro-phthalazine-6-carboxylic acid cyclopropylmethyl ester;

7-(4-Acetyl-piperazine-1-carbonyl)-2-isopropyl-4-(5-methyl-1H-pyrazol-3-ylamino)-2H-phthalazin-1-one;

3-Isopropyl-1-(5-methyl-1H-pyrazol-3-ylamino)-4-oxo-3,4-dihydro-phthalazine-6-carboxylic acid methyl ester;

7-Hydroxymethyl-2-isopropyl-4-(5-methyl-1H-pyrazol-3-ylamino)-2H-phthalazin-1-one;

6-Hydroxymethyl-2-isopropyl-4-(5-methyl-1H-pyrazol-3-ylamino)-2H-phthalazin-1-one;

3-Isopropyl-1-(5-methyl-1H-pyrazol-3-ylamino)-4-oxo-3,4-dihydro-phthalazine-6-carboxylic acid amide;

2-Isopropyl-4-(5-methyl-1H-pyrazol-3-ylamino)-7-piperidin-1-yl-2H-phthalazin-1-one; and 2-Isopropyl-4-(5-methyl-1H-pyrazol-3-ylamino)-7-pyrrolidin-1-yl-2H-phthalazin-1-one.

Another embodiment of the invention are the compounds according to formula I, wherein $R^1$, $R^2$ and $R^3$ are hydrogen;

$R^4$ represents $R^8$—X—, heterocyclyl-$T^2$-;

$R^8$ is alkyl;

X is —NH— or —N(alkyl)-;

$T^2$ represents a single bond or alkylene;

$R^5$ is alkyl;

n is 0;

$R^6$ is hydrogen; and $R^7$ is hydrogen, alkyl or cycloalkyl.

Such compounds are for example:

2-Isopropyl-4-(5-methyl-1H-pyrazol-3-ylamino)-8-morpholino-2H-phthalazin-1-one; and 2-Isopropyl-4-(5-methyl-1H-pyrazol-3-ylamino)-8-dimethylamino-2H-phthalazin-1-one.

Another embodiment of the invention are the compounds according to formula I, wherein
$R^1$, $R^3$ and $R^4$ are hydrogen;
$R^2$ represents $R^8$—X—, heterocyclyl-$T^2$-, halogen, nitro, —$NH_2$, or alkyl optionally substituted one or several times by hydroxy or alkoxy;
$R^8$ is alkyl;
X is —NH—, —N(alkyl)- or —O—;
$T^2$ represent a single bond or alkylene;
$R^5$ is alkyl or phenyl;
n is 0;
$R^6$ is hydrogen; and
$R^7$ is hydrogen, alkyl or cycloalkyl.
Such compounds are for example:
6-Fluoro-2-isopropyl-4-(5-methyl-1H-pyrazol-3-ylamino)-2H-phthalazin-1-one;
2-Isopropyl-4-(5-methyl-1H-pyrazol-3-ylamino)-6-morpholino-2H-phthalazin-1-one;
2-Isopropyl-4-(5-methyl-1H-pyrazol-3-ylamino)-6-dimethylamino-2H-phthalazin-1-one;
2-Isopropyl-6-methoxy-4-(5-methyl-1H-pyrazol-3-ylamino)-2H-phthalazin-1-one;
2-Isopropyl-6-methoxymethyl-4-(5-methyl-2H-pyrazol-3-ylamino)-2H-phthalazin-1-one;
6-Hydroxymethyl-2-isopropyl-4-(5-methyl-1H-pyrazol-3-ylamino)-2H-phthalazin-1-one; and
6-Amino-4-(5-methyl-1H-pyrazol-3-ylamino)-2-phenyl-2H-phthalazin-1-one.

Another embodiment of the invention are the compounds according to formula I, wherein
$R^1$, $R^2$ and $R^4$ are hydrogen;
$R^3$ represents $R^8$—X—, heterocyclyl-$T^2$-, hydrogen, halogen, nitro, —OH, —$NH_2$, —NH—C(O)H, —C(O)OH, —C(O)$NH_2$, —C(O)NH—O-alkyl, or alkyl optionally substituted one or several times by hydroxy or alkoxy;
$R^8$ is cycloalkyl-$T^1$-,
heterocyclyl-$T^2$-,
aryl-$T^3$-,
heteroaryl-$T^4$-, or
alkyl optionally substituted one or several times by halogen;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;
$T^1$, $T^2$, $T^3$ and $T^4$ independently represent a single bond or alkylene;
$R^5$ is hydrogen,
alkyl being optionally substituted one or several times by halogen,
heteroaryl, or
phenyl, which is optionally substituted one or two times by halogen, —$NO_2$, —C(O)OH, —$NH_2$, —NHC(O)-alkyl, —S(O)$_2$-alkyl, alkyl, alkoxy or alkylsulfanyl, said alkyl, alkoxy and alkylsulfanyl groups being optionally substituted one or several times by halogen;
benzo[1,3]dioxol-5-yl,
cycloalkyl or
alkenyl;
Y is alkylene, alkylene-C(O)— or alkylene-CH(OH)—;
n is 0 or 1;
$R^6$ is hydrogen; and
$R^7$ is hydrogen, alkyl or cycloalkyl.

Another embodiment of the invention are the compounds according to formula I, wherein
$R^1$, $R^2$, $R^3$ and $R^4$ represent hydrogen;
$R^5$ is hydrogen,
alkyl being optionally substituted one or several times by halogen or alkoxy,
heteroaryl, or
phenyl, which is optionally substituted one or two times by halogen, —$NO_2$, —C(O)OH, —C(O)NH-alkyl, —$NH_2$, —NHC(O)-alkyl, —N(alkyl)C(O)-alkyl, —NHC(O)-alkoxyalkyl, —NHC(O)O-alkyl, —N(alkyl)C(O)O-alkyl, —NH—S(O)$_2$-alkyl, —S(O)$_2$-alkyl, —NHC(O)-aryl, —NH-aryl, —O-aryl, —S(O)-aryl, aryl, heterocyclyl, cycloalkyl, alkyl, alkoxy or alkylsulfanyl, said alkyl, alkoxy and alkylsulfanyl groups being optionally substituted one or several times by halogen;
naphtyl,
benzo[1,3]dioxol-5-yl,
cycloalkyl or
alkenyl;
Y is alkylene, alkylene-C(O)— or alkylene-CH(OH)—;
n is 0 or 1;
$R^6$ is hydrogen; and
$R^7$ is hydrogen, alkyl or cycloalkyl.
Such compounds are for example:
4-(5-Methyl-1H-pyrazol-3-ylamino)-2-phenyl-2H-phthalazin-1-one;
2-Benzyl-4-(5-methyl-1H-pyrazol-3-ylamino)-2H-phthalazin-1-one;
2-Methyl-4-(5-methyl-1H-pyrazol-3-ylamino)-2H-phthalazin-1-one;
2-Isobutyl-4-(5-methyl-1H-pyrazol-3-ylamino)-2H-phthalazin-1-one;
4-(5-Methyl-1H-pyrazol-3-ylamino)-2-(2,2,2-trifluoro-ethyl)-2H-phthalazin-1-one;
4-(5-Methyl-1H-pyrazol-3-ylamino)-2-p-tolyl-2H-phthalazin-1-one;
2-(4-Fluoro-phenyl)-4-(5-methyl-1H-pyrazol-3-ylamino)-2H-phthalazin-1-one;
2-(4-tert-Butyl-phenyl)-4-(5-methyl-1H-pyrazol-3-ylamino)-2H-phthalazin-1-one;
2-(4-Methoxy-phenyl)-4-(5-methyl-1H-pyrazol-3-ylamino)-2H-phthalazin-1-one;
4-(1H-Pyrazol-3-ylamino)-2-p-tolyl-2H-phthalazin-1-one;
2-(4-Methoxy-benzyl)-4-(5-methyl-1H-pyrazol-3-ylamino)-2H-phthalazin-1-one;
2-(3-Methoxy-benzyl)-4-(5-methyl-1H-pyrazol-3-ylamino)-2H-phthalazin-1-one;
2-(2,5-Difluoro-benzyl)-4-(5-methyl-1H-pyrazol-3-ylamino)-2H-phthalazin-1-one;
2-(4-Methanesulfonyl-benzyl)-4-(5-methyl-2H-pyrazol-3-ylamino)-2H-phthalazin-1-one;
2-(3,4-Difluoro-benzyl)-4-(5-methyl-1H-pyrazol-3-ylamino)-2H-phthalazin-1-one;
4-(5-Methyl-1H-pyrazol-3-ylamino)-2-(2-methyl-thiazol-4-ylmethyl)-2H-phthalazin-1-one;
4-(5-Methyl-2H-pyrazol-3-ylamino)-2-pyridin-4-ylmethyl-2H-phthalazin-1-one;
4-(5-Methyl-2H-pyrazol-3-ylamino)-2-pyridin-3-ylmethyl-2H-phthalazin-1-one;
2-(2-Fluoro-benzyl)-4-(5-methyl-1H-pyrazol-3-ylamino)-2H-phthalazin-1-one;
2-(4-Fluoro-benzyl)-4-(5-methyl-1H-pyrazol-3-ylamino)-2H-phthalazin-1-one;

2-(3,5-Difluoro-benzyl)-4-(5-methyl-1H-pyrazol-3-ylamino)-2H-phthalazin-1-one;
4-(5-Methyl-2H-pyrazol-3-ylamino)-2-pyridin-2-ylmethyl-2H-phthalazin-1-one;
2-Isopropyl-4-(5-methyl-1H-pyrazol-3-ylamino)-2H-phthalazin-1-one;
3-[4-(5-Methyl-1H-pyrazol-3-ylamino)-1-oxo-1H-phthalazin-2-ylmethyl]-benzoic acid;
4-(5-Methyl-1H-pyrazol-3-ylamino)-2-(4-trifluoromethyl-phenyl)-2H-phthalazin-1-one;
2-(4-Chloro-phenyl)-4-(5-methyl-1H-pyrazol-3-ylamino)-2H-phthalazin-1-one;
4-(5-Methyl-1H-pyrazol-3-ylamino)-2-m-tolyl-2H-phthalazin-1-one;
4-(5-Methyl-1H-pyrazol-3-ylamino)-2-(4-nitro-benzyl)-2H-phthalazin-1-one;
2-(4-Amino-benzyl)-4-(5-methyl-1H-pyrazol-3-ylamino)-2H-phthalazin-1-one;
N-{4-[4-(5-Methyl-1H-pyrazol-3-ylamino)-1-oxo-1H-phthalazin-2-ylmethyl]-phenyl}-acetamide;
N-{4-[1-Oxo-4-(1H-pyrazol-3-ylamino)-1H-phthalazin-2-ylmethyl]-phenyl}-acetamide;
2-[2-(4-Methoxy-phenyl)-2-oxo-ethyl]-4-(5-methyl-1H-pyrazol-3-ylamino)-2H-phthalazin-1-one;
2-[2-(3-Methoxy-phenyl)-2-oxo-ethyl]-4-(5-methyl-1H-pyrazol-3-ylamino)-2H-phthalazin-1-one;
4-(5-Methyl-1H-pyrazol-3-ylamino)-2-[2-oxo-2-(4-trifluoromethoxy-phenyl)-ethyl]-2H-phthalazin-1-one;
2-(2-Benzo[1,3]dioxol-5-yl-2-oxo-ethyl)-4-(5-methyl-1H-pyrazol-3-ylamino)-2-phthalazin-1-one;
4-(5-Methyl-1H-pyrazol-3-ylamino)-2-[2-oxo-2-(4-trifluoromethyl-phenyl)-ethyl]-2H-phthalazin-1-one;
4-(5-Methyl-1H-pyrazol-3-ylamino)-2-(2-oxo-2-phenyl-ethyl)-2H-phthalazin-1-one;
2-Allyl-4-(5-methyl-1H-pyrazol-3-ylamino)-2H-phthalazin-1-one;
2-Cyclopropylmethyl-4-(5-methyl-1H-pyrazol-3-ylamino)-2H-phthalazin-1-one;
4-(5-Methyl-1H-pyrazol-3-ylamino)-2-(4-methylsulfanyl-benzyl)-2H-phthalazin-1-one;
2-(2-Hydroxy-2-phenyl-ethyl)-4-(5-methyl-1H-pyrazol-3-ylamino)-2H-phthalazin-1-one;
2-(4-tert-Butyl-2-chloro-phenyl)-4-(5-methyl-1H-pyrazol-3-ylamino)-2H-phthalazin-1-one;
2-[4-(2-Methyl-propane-2-sulfonyl)-phenyl]-4-(5-methyl-1H-pyrazol-3-ylamino)-2H-phthalazin-1-one;
2-(4-Benzenesulfinyl-phenyl)-4-(5-methyl-1H-pyrazol-3-ylamino)-2H-phthalazin-1-one;
N-Ethyl-N-{4-[4-(5-methyl-1H-pyrazol-3-ylamino)-1-oxo-1H-phthalazin-2-yl]-phenyl}-acetamide;
{4-[4-(5-Methyl-1H-pyrazol-3-ylamino)-1-oxo-1H-phthalazin-2-yl]-phenyl}-carbamic acid ethyl ester;
Methyl-{4-[4-(5-methyl-1H-pyrazol-3-ylamino)-1-oxo-1H-phthalazin-2-yl]-phenyl}-carbamic acid ethyl ester;
Methyl-{4-[4-(5-methyl-1H-pyrazol-3-ylamino)-1-oxo-1H-phthalazin-2-yl]-phenyl}-carbamic acid isopropyl ester;
{4-[4-(5-Methyl-1H-pyrazol-3-ylamino)-1-oxo-1H-phthalazin-2-yl]-phenyl}-carbamic acid isopropyl ester;
4-(5-Methyl-1H-pyrazol-3-ylamino)-2-(4-nitro-phenyl)-2H-phthalazin-1-one;
2-(4-Cyclohexyl-phenyl)-4-(5-methyl-1H-pyrazol-3-ylamino)-2H-phthalazin-1-one;
4-(5-Methyl-1H-pyrazol-3-ylamino)-2-pyridin-4-yl-2H-phthalazin-1-one;
2-(3-tert-Butyl-phenyl)-4-(5-methyl-1H-pyrazol-3-ylamino)-2H-phthalazin-1-one;
2-(2-Methoxy-ethyl)-4-(5-methyl-2H-pyrazol-3-ylamino)-2H-phthalazin-1-one;
2-(2-Methoxy-1-methyl-ethyl)-4-(5-methyl-2H-pyrazol-3-ylamino)-2H-phthalazin-1-one;
2-(4-tert-Butyl-cyclohexyl)-4-(5-methyl-1H-pyrazol-3-ylamino)-2H-phthalazin-1-one;
2-(4-Isopropyl-phenyl)-4-(5-methyl-2H-pyrazol-3-ylamino)-2H-phthalazin-1-one;
2-(4-sec-Butyl-phenyl)-4-(5-methyl-2H-pyrazol-3-ylamino)-2H-phthalazin-1-one
2-Biphenyl-4-yl-4-(5-methyl-1H-pyrazol-3-ylamino)-2H-phthalazin-1-one;
2-(2'-Methyl-biphenyl-4-yl)-4-(5-methyl-1H-pyrazol-3-ylamino)-2H-phthalazin-1-one;
4-(5-Methyl-1H-pyrazol-3-ylamino)-2-(3-trifluoromethyl-phenyl)-2H-phthalazin-1-one;
4-(5-Methyl-1H-pyrazol-3-ylamino)-2-(4-phenoxy-phenyl)-2H-phthalazin-1-one;
4-(5-Methyl-1H-pyrazol-3-ylamino)-2-naphthalen-2-yl-2H-phthalazin-1-one;
2-(2-Chloro-phenyl)-4-(5-methyl-1H-pyrazol-3-ylamino)-2H-phthalazin-1-one;
N-Methyl-4-[4-(5-methyl-1H-pyrazol-3-ylamino)-1-oxo-1H-phthalazin-2-yl]-benzamide;
N-{4-[4-(5-Methyl-1H-pyrazol-3-ylamino)-1-oxo-1H-phthalazin-2-yl]-phenyl}-acetami
2-Methoxy-N-{4-[4-(5-methyl-1H-pyrazol-3-ylamino)-1-oxo-1H-phthalazin-2-yl]-phenyl}-acetamide;
2,2-Dimethyl-N-{4-[4-(5-methyl-1H-pyrazol-3-ylamino)-1-oxo-1H-phthalazin-2-yl]-phenyl}-propionamide;
N-{4-[4-(5-Methyl-1H-pyrazol-3-ylamino)-1-oxo-1H-phthalazin-2-yl]-phenyl}-benzamide;
N-{4-[4-(5-Methyl-1H-pyrazol-3-ylamino)-1-oxo-1H-phthalazin-2-yl]-phenyl}-methanesulfonamide;
4-(5-Methyl-1H-pyrazol-3-ylamino)-2-(4-phenylamino-phenyl)-2H-phthalazin-1-one;
4-(5-Methyl-1H-pyrazol-3-ylamino)-2-(4-morpholin-4-yl-phenyl)-2H-phthalazin-1-one;
4-(5-Methyl-1H-pyrazol-3-ylamino)-2-(4-pyrrolidin-1-yl-phenyl)-2H-phthalazin-1-one;
4-(5-Methyl-2H-pyrazol-3-ylamino)-2-(4-piperidin-1-yl-phenyl)-2H-phthalazin-1-one;
2-(2-Chloro-4-trifluoromethyl-phenyl)-4-(5-methyl-1H-pyrazol-3-ylamino)-2H-phthalazin-1-one; and
2-(4-Amino-phenyl)-4-(5-methyl-1H-pyrazol-3-ylamino)-2H-phthalazin-1-one.

Another embodiment of the invention are the compounds according to formula I, wherein
$R^1$ and $R^4$ are hydrogen;
$R^2$ and $R^3$ independently represents hydrogen, $R^8$—X—, heterocyclyl-$T^2$-, halogen,
nitro, —OH, —NH$_2$, —NH—C(O)H, —C(O)OH, —C(O)NH$_2$, —C(O)NH—O-alkyl, or alkyl optionally substituted one or several times by hydroxy or alkoxy;
X is —C(O)NH—, —C(O)N(alkyl)-, —N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;

$T^1$, $T^2$, $T^3$ and $T^4$ independently represent a single bond or alkylene;

$R^5$ is phenyl which is substituted by alkyl or alkoxy said alkyl or alkoxy group
being optionally substituted one or several times by halogen;

n is 0;

$R^6$ is hydrogen; and $R^7$ is hydrogen, alkyl or cycloalkyl.

Another embodiment of the invention are the compounds according to formula I, wherein $R^1$ and $R^4$ are hydrogen;

$R^2$ and $R^3$ independently represents hydrogen, halogen, nitro, —NH$_2$, —NH—C(O)H;

$R^5$ is phenyl which is substituted at the para-position by tert-butyl,
trifluoromethyl or trifluoromethoxy;

n is 0;

$R^6$ is hydrogen; and $R^7$ is hydrogen, alkyl or cycloalkyl.

Such compounds are for example:

N-[3-(4-tert-Butyl-phenyl)-1-(5-methyl-2H-pyrazol-3-ylamino)-4-oxo-3,4-dihydro-phthalazin-6-yl]-formamide;

7-Amino-2-(4-tert-butyl-phenyl)-4-(5-methyl-2H-pyrazol-3-ylamino)-2H-phthalazin-1-one;

2-(4-tert-Butyl-phenyl)-4-(5-methyl-2H-pyrazol-3-ylamino)-7-nitro-2H-phthalazin-1-one;

2-(4-tert-Butyl-phenyl)-4-(5-methyl-2H-pyrazol-3-ylamino)-6-nitro-2H-phthalazin-1-one;

6-Amino-2-(4-tert-butyl-phenyl)-4-(5-methyl-2H-pyrazol-3-ylamino)-2H-phthalazin-1-one;

6-Bromo-2-(4-tert-butyl-phenyl)-4-(5-methyl-2H-pyrazol-3-ylamino)-2H-phthalazin-1-one;

2-(4-tert-Butyl-phenyl)-4-(5-cyclopropyl-1H-pyrazol-3-ylamino)-2H-phthalazin-1-one;

2-(4-tert-Butyl-phenyl)-4-(1H-pyrazol-3-ylamino)-2H-phthalazin-1-one; and 4-(5-Methyl-1H-pyrazol-3-ylamino)-2-(4-trifluoromethoxy-phenyl)-2H-phthalazin-1-one.

Still another embodiment of the invention is a process for the manufacture of the compounds of formula I, wherein the compound of formula VII

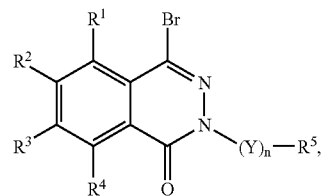

formula VII wherein $R^1$, $R^2$, $R^3$, $R^4$, $R^5$ and Y have the significance as given in formula I above, is reacted with a compound of formula VIII

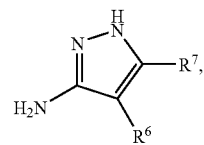

formula VIII wherein $R^6$ and $R^7$ have the significance given in formula I above, to give the respective compound of formula I;

said compound of formula I is isolated from the reaction mixture, and if desired, converted into a pharmaceutically acceptable salt.

The amino pyrazole derivatives of the general formula I, or a pharmaceutically acceptable salt thereof, may be prepared by any process known to be applicable for the preparation of chemically-related compounds by one skilled in the art. Such processes, when used to prepare the amino pyrazole derivatives of formula I, or a pharmaceutically-acceptable salt thereof, are provided as a further feature of the invention and are illustrated by the following schemes 1, 2, 3, 4, 5 and 6 in which, unless otherwise stated, $R^1$, $R^2$, $R^3$, $R^4$, $R^5$, $R^6$, $R^7$, $R^8$, T, X, Y and n, have the significance given herein before. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

Scheme 1

Scheme 1
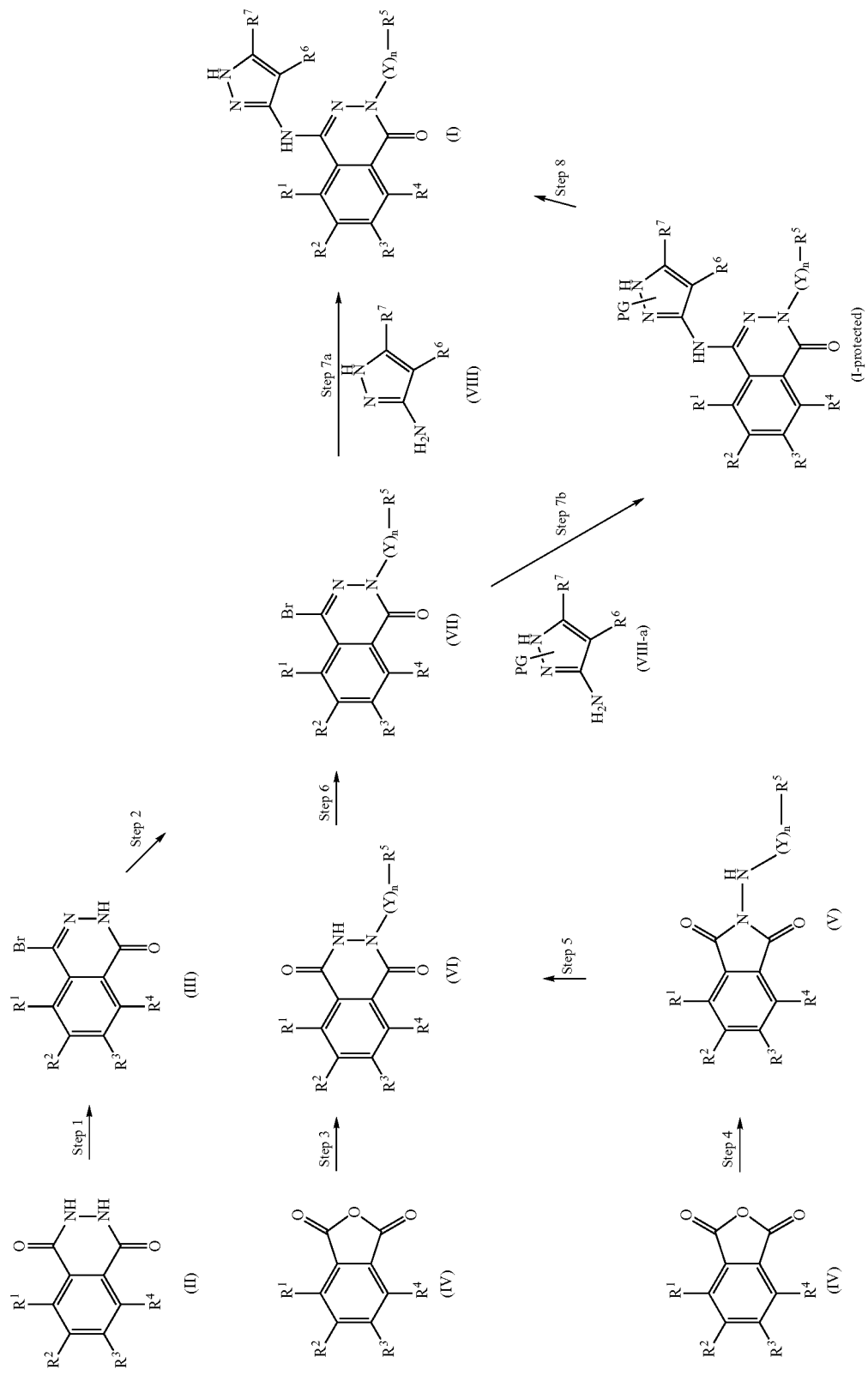

A method for the synthesis of the compounds of formula I starts from the corresponding phthalazine diones of formula II. Step 1 of the reaction sequence (scheme 1) is a two step process in which a dibromination is followed by a monohydrolysis, yielding the 4-bromophthalazinone derivatives of formula III. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 1 the obtained compounds of formula III are converted into their corresponding tertiary amides of formula VII, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 1 the phthalic anhydride derivatives of formula IV are converted with the appropriate hydrazine derivatives into their corresponding phthalazinones of formula VI, using methods well known to someone skilled in the art. The reaction is typically carried out in aprotic solvents such as tetrahydrofuran, N,N-dimethylformamide, N-methylpyrrolidinone or protic solvents such as acetic acid, ethanol, methanol and isopropanol and mixtures thereof at temperatures between 0° C. and 120° C. Typically used hydrazine derivatives are aliphatic hydrazines or aromatic hydrazines, and salts thereof such as phenyl hydrazine hydrochloride, methyl hydrazine hydrochloride, benzyl hydrazine and isopropyl hydrazine hydrochloride which can be prepared readily by someone skilled in the art.

In step 4, scheme 1 the phthalic anhydride derivatives of formula IV are converted with the appropriate hydrazine derivatives into their corresponding N-aminophthalimides of formula V, using methods well known to someone skilled in the art. The reaction is typically carried out in aprotic solvents such as tetrahydrofuran, N,N-dimethylformamide, N-methylpyrrolidinone or protic solvents such as acetic acid, ethanol, methanol and isopropanol and mixtures thereof at temperatures between 0° C. and 120° C. Typically used hydrazine derivatives are aromatic hydrazines, and salts thereof such as 2-chlorophenyl hydrazine, 3-nitrophenyl hydrazine, 4-nitrophenyl hydrazine and 4-carboxyethylphenyl hydrazine which can be prepared readily by someone skilled in the art.

In step 5, scheme 1 the obtained compounds of formula V are converted into their corresponding phthalazinones of formula VI, using methods well known to someone skilled in the art, e.g. ring expansion. The reaction is typically carried out in protic solvents such as glycerol, sulphuric acid and hydrochloric acid at temperatures between 100° C. and 160° C.

In step 6, scheme 1 the obtained compounds of formula VI are converted into their corresponding phthalazinones of formula VII, using methods well known to someone skilled in the art, e.g. imminobromide formation from secondary amides. The reaction is typically carried out without solvent, or in solvents like dichloromethane, dichloroethane and anisole, and mixtures thereof, at temperatures between 30° C. and 150° C. Typically used brominating reagents are phosphorus oxybromide, phosphorus pentabromide and phosphorus tribromide.

In step 7a, scheme 1 the obtained compounds of formula VII are converted into their corresponding aminopyrazole I, using methods well known to someone skilled in the art, e.g. palladium-mediated amination of imminobromides, vinylbromide or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphospine, bis-triphenylphosphinepalladium dichloride in conjunction with phosphine based ligands such as 2,2'-bis(diphenylphosphino)-1.1'-binaphthyl, 4,5-Bis(diphenylphosphino)-9,9 dimethylxanthene and 2-(di-tert-butylphosphino)biphenyl.

Alternatively, Compounds of Formula I are Obtained from Compounds VII in two Step Procedure:

In step 7b, scheme 1, the compounds of formula VII are converted into the corresponding protected aminopyrazoles I-protected, by coupling with an aminopyrazole derivative of formula VIII-a, using the same methods as described for step 7a. In formulas I-protected and VIII-a PG stands for a protecting group like tert.-butyl or para-methoxybenzyl or tert.-butoxycarbonyl, which is attached to the pyrazole ring either via N-1 or N-2.

In step 8, scheme 1, the protecting group PG in compounds of formula I-protected is cleaved to give the aminopyrazole I. This can be done by standard deprotecting methods like heating in the presence of an acid like formic acid or hydrochloric acid. If the protecting group PG is a tert.-butoxycarbonyl group, the cleavage may already occur during the work-up of reaction step 7b.

Scheme 2

A preferred method for the synthesis of the derivatives of formula I, wherein $R^5$ is phenyl which is substituted at the para- or meta-position with —$NH_2$ or —NH—R' and R' is —C(O)-aryl, —C(O)-cycloalkyl, —C(O)-alkyl, —C(O)-alkoxyalkyl, —$S(O)_2$-aryl, —$S(O)_2$-alkyl, is described in scheme 2.

The derivatives of formula I, wherein $R^5$ is phenyl which is substituted at the para- or meta-position with —NH—R' and R' is —C(O)-aryl, —C(O)-cycloalkyl, —C(O)-alkyl, —C(O)—alkoxyalkyl, —$S(O)_2$-aryl, —$S(O)_2$-alkyl, are named I-a in scheme 2.

Scheme 2

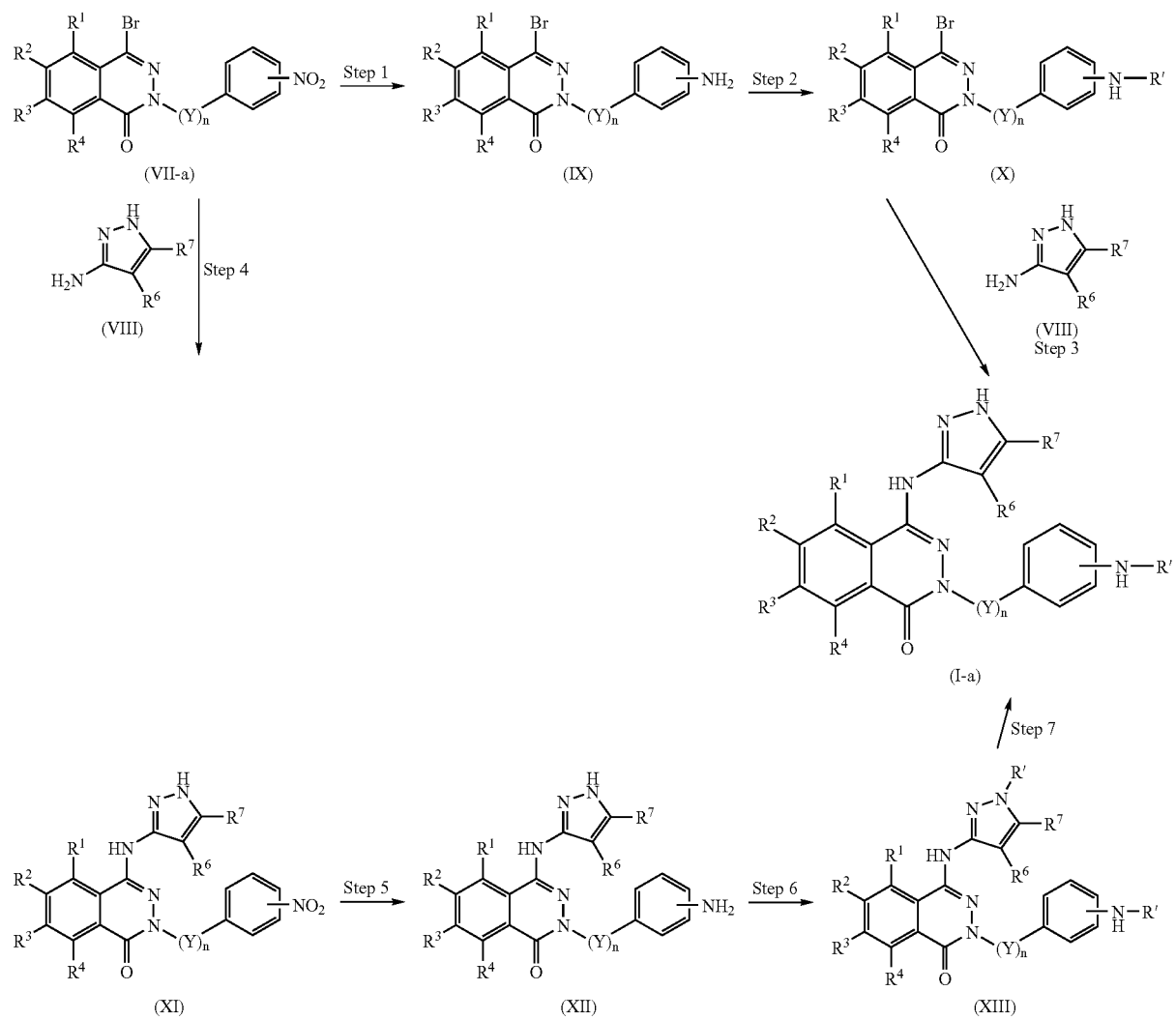

The method for the synthesis of the compounds of formula I-a starts from the corresponding nitrophenyl derivative of formula VII-a. In step 1, scheme 2 the obtained compounds of formula VII-a (see scheme 1) are converted into their corresponding anilines of formula IX, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride.

In step 2, scheme 2 the obtained compounds of formula IX are converted into their corresponding amides, sulfonamides or ureas of formula X, using methods well known to someone skilled in the art, e.g. sulfonylation, acylation or aminocarboxylation of anilines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and 4-(dimethylamino)pyridine.

In step 3, scheme 2 the obtained compounds of formula X are converted into their corresponding aminopyrazole Ia, using methods well known to someone skilled in the art, e.g. palladium-mediated amination of imminobromides, vinylbromide or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphospine, bis-triphenylphosphinepalladium dichloride in conjunction with phosphine based ligands such as 2,2'-bis(diphenylphosphino)-1.1'-binaphthyl, 4,5-Bis(diphenylphosphino)-9,9-dimethylxanthene and 2-(di-tert-butylphosphino)-biphenyl.

In step 4, scheme 2 the bromophthalazinone compounds of formula VII-a are converted into their corresponding aminopyrazole XI, using methods well known to someone skilled in the art, e.g. palladium-mediated amination of imminobromides, vinylbromide or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphosphine, bis-triphenylphosphinepalladium dichloride in conjunction with phosphine based ligands such as 2,2'-bis(diphenylphosphino)-1.1'-binaphthyl, 4,5-Bis(diphenylphosphino)-9,9 dimethylxanthene and 2-(di-tert-butylphosphino)biphenyl.

In step 5, scheme 2 the obtained compounds of formula XI are converted into their corresponding anilines of formula XII, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride.

In step 6, scheme 2 the obtained compounds of formula XII are converted into their corresponding bis-amides, -sulfonamides or -ureas of formula XIII, using methods well known to someone skilled in the art, e.g. sulfonylation, acylation or aminocarboxylation of anilines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and 4-(dimethylamino)pyridine.

In step 7, scheme 2 the obtained compounds of formula XIII are converted into their corresponding amides, sulfonamides or ureas of formula Ia, using methods well known to someone skilled in the art, e.g. hydrolysis of pyrazoloamides, pyrazolosulfonamides and pyrazoloureas. The reaction is typically carried out in protic solvents such as water, methanol and ethanol or aprotic solvents such as acetonitrile, dichloromethane, tetrahydrofuran, N,N-dimethylformamide, N-methylpyrrolidinone and mixtures thereof at temperatures between 0° C. and 80° C. Typically used bases are ammonia, potassium hydroxide, sodium hydroxide and lithium hydroxide.

Scheme 3

A preferred method for the synthesis of the derivatives of formula I, wherein $R^5$ is phenyl which is substituted at the para- or meta-position with —COOH or —C(O)—R" and R" is —NH-aryl, —$NH_2$, —NH-alkyl, —N(alkyl)$_2$, -heterocyclyl, —NH—S(O)$_2$-aryl, —NH—S(O)$_2$-alkyl, is described in scheme 3. The derivatives of formula I, wherein $R^5$ is phenyl which is substituted at the para- or meta-position with —C(O)—R' and R' is —NH-aryl, —$NH_2$, —NH-alkyl, —N(alkyl)$_2$, -heterocyclyl, —NH—S(O)$_2$-aryl, —NH—S(O)$_2$-alkyl, are named I-b in scheme 3.

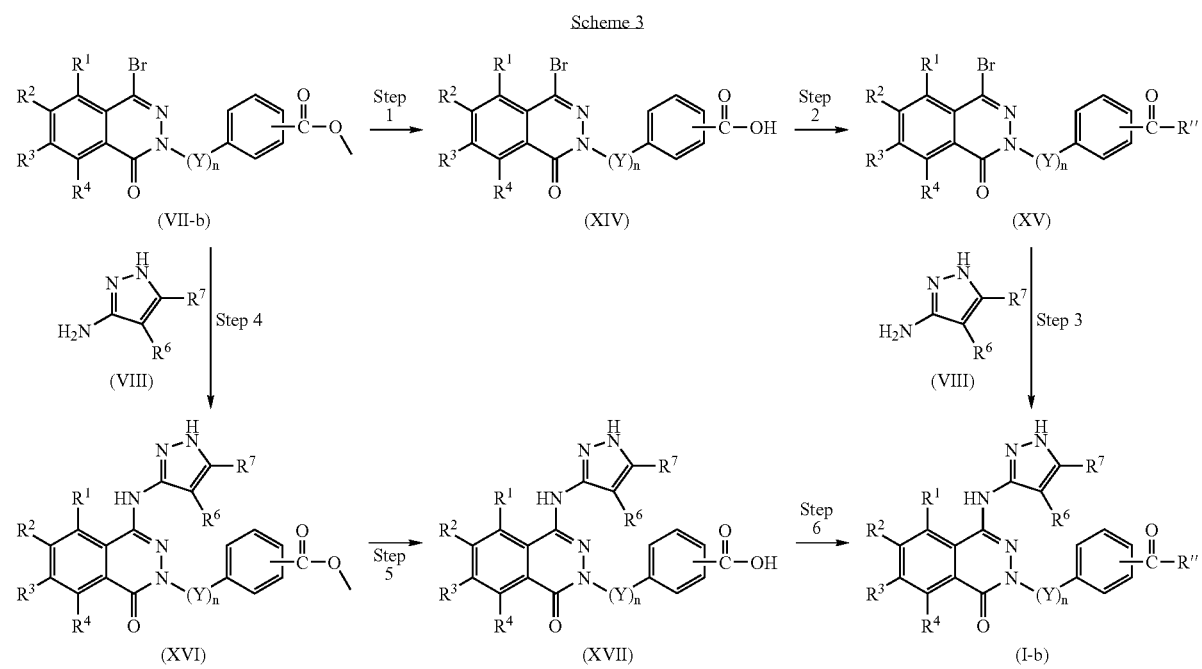

The method for the synthesis of the compounds of formula I-b starts from the corresponding carboxyalkyl derivative of formula VII-b. In step 1, scheme 3 the obtained compounds of formula VII-b (see scheme I) are converted into their corresponding carboxylic acids of formula XIV, using methods well known to someone skilled in the art, e.g. carboxylic acid formation by hydrolysis of alkyl carboxylates. The reaction is typically carried out in solvents like tetrahydrofuran, ethanol and methanol, water and mixtures thereof, at temperatures between 20° C. and 60° C. Typically used hydrolysis reagents are lithium hydroxide, sodium hydroxide and potassium hydroxide.

In step 2, scheme 3 the obtained compounds of formula XIV are converted into their corresponding carboxamide or acylsulfonamides of formula XV, using methods well known to someone skilled in the art, e.g. acylation of amines and sulfonamides. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used coupling agents are N,N'-dicyclohexylcarbodiimide, 1-(3-dimthylaminopropyl)-3-ethylcarbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate. The reaction can be performed in the absence of a base or in the presence of a base. Typically used bases are triethylamine, N,N-diisopropyl ethylamine, pyridine, potassium carbonate and 4-(dimethylamino)pyridine.

In step 3, scheme 3 the obtained compounds of formula XV are converted into their corresponding aminopyrazole Ib, using methods well known to someone skilled in the art, e.g. palladium-mediated amination of imminobromides, vinylbromide or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)-dipalladium, palladium tetrakis-triphenylphospine, bis-triphenylphosphine-palladium dichloride in conjunction with phosphine based ligands such as 2,2'-bis(diphenylphosphino)-1.1'-binaphthyl, 4,5-Bis(diphenylphosphino)-9,9-dimethyl-xanthene and 2-(di-tert-butylphosphino)biphenyl.

In step 4, scheme 3 the bromophthalazinone compounds of formula VIIb are converted into their corresponding aminopyrazole XVI, using methods well known to someone skilled in the art, e.g. palladium-mediated amination of imminobromides, vinylbromide or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphospine, bis-triphenylphosphinepalladium dichloride in conjunction with phosphine based ligands such as 2,2'-bis(diphenylphosphino)-1.1'-binaphthyl, 4,5-Bis(diphenylphosphino)-9,9 dimethylxanthene and 2-(di-tert-butylphosphino)biphenyl.

In step 5, scheme 3 the obtained compounds of formula XVI are converted into their corresponding carboxylic acids of formula XVII, using methods well known to someone skilled in the art, e.g. carboxylic acid formation by hydrolysis of alkyl carboxylates. The reaction is typically carried out in solvents like tetrahydrofuran, ethanol and methanol, water and mixtures thereof, at temperatures between 20° C. and 60° C. Typically used hydrolysis reagents are lithium hydroxide, sodium hydroxide and potassium hydroxide.

In step 6, scheme 3 the obtained compounds of formula XVII are converted into their corresponding carboxamide or acylsulfonamides of formula Ib, using methods well known to someone skilled in the art, e.g. acylation of amines and sulfonamides. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used coupling agents are N,N'-dicyclohexylcarbodiimide, 1-(3-dimthylaminopropyl)-3-ethylcarbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate. The reaction can be performed in the absence of a base or in the presence of a base. Typically used bases are triethylamine, N,N-diisopropyl ethylamine, pyridine, potassium carbonate and 4-(dimethylamino)pyridine.

Scheme 4

A preferred method for the synthesis of the derivatives of formula I, wherein one of $R^1$ to $R^4$ is —$NH_2$ or $R^8$—$X^1$—, with $X^1$ being —NH— or —NH(alkyl)-, one of $R^1$ to $R^4$ is R''', with R''' being defined as $R^1$ to $R^4$ above for formula I and the remaining two of $R^1$ to $R^4$ are hydrogen, is described in scheme 4. The derivatives of formula (I), wherein one of $R^1$ to $R^4$ is $R^8$—$X^1$—, with $X^1$ being —NH— or —NH (alkyl)-, one of $R^1$ to $R^4$ is R''', with R''' being defined as $R^1$ to $R^4$ above for formula I and the remaining two of $R^1$ to $R^4$ are hydrogen, are named I-c in scheme 4.

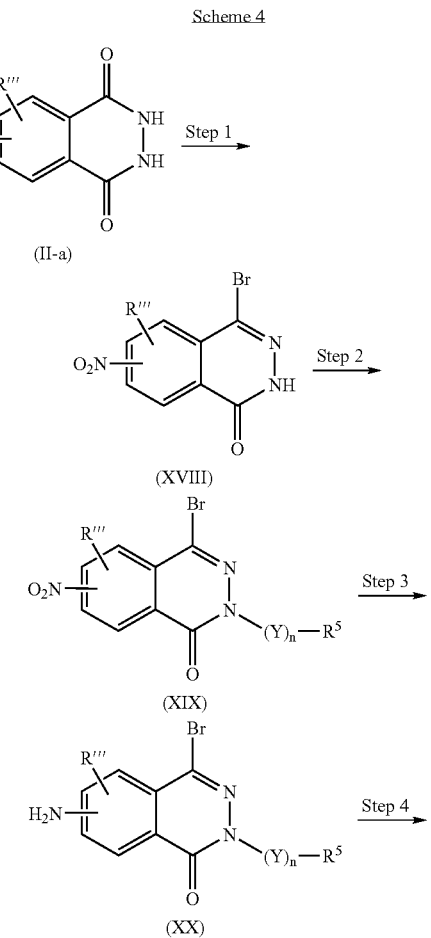

-continued

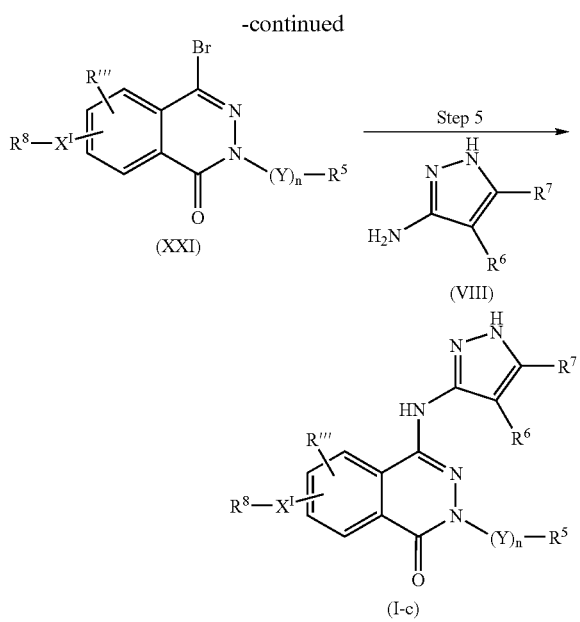

The method for the synthesis of the compounds of formula I-c starts from the corresponding phthalazine diones of formula II-a. Step 1 of the reaction sequence (scheme 4) is a two step process in which a dibromination is followed by a monohydrolysis, yielding the 4-bromo-nitrophthalazinone derivatives of formula XVIII. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 4 the obtained compounds of formula XVIII are converted into their corresponding tertiary amides of formula XIX, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 4 the obtained compounds of formula XIX are converted into their corresponding anilines of formula XX, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride.

In step 4, scheme 4 the obtained compounds of formula XX are converted into their corresponding secondary or tertiary amines of formula XXI, using methods well known to someone skilled in the art, e.g. alkylation of amines. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are potassium carbonate, sodium hydride, potassium hydride, lithium hexamethyldisilazide, sodium hexamethyldisilazide, potassium hexamethyl-disilazide.

Eventually it is necessary to introduce an intermediary N-protecting group like t-butyloxycarbonyl (BOC), which is cleaved after the alkylation step, to obtain the monoalkylated amines. These monoalkylated amines can be used, if desired, as educts for a second alkylation step (for introduction/deprotection of the BOC-group see also schemes 7 and 8).

In step 5, scheme 4 the bromophthalazinone compounds of formula XXI are converted into their corresponding aminopyrazole Ic, using methods well known to someone skilled in the art, e.g. palladium-mediated amination of imminobromides, vinylbromide or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphospine, bis-triphenylphosphinepalladium dichloride in conjunction with phosphine based ligands such as 2,2'-bis (diphenylphosphino)-1.1'-binaphthyl, 4,5-Bis (diphenylphosphino)-9,9 dimethylxanthene and 2-(di-tert-butylphosphino)-biphenyl.

Scheme 5

A method for the synthesis of the derivatives of formula I, wherein one of $R^1$ to $R^4$ is $R^8$—$X^{II}$—, with $X^{II}$ being —C(O)NH—, —NHC(O)NH— or —S(O)$_2$NH—, one of $R^1$ to $R^4$ is R''', with R''' being defined as $R^1$ to $R^4$ above for formula I and the remaining two of $R^1$ to $R^4$ are hydrogen, is described in scheme 5. The derivatives of formula I, wherein one of $R^1$ to $R^4$ is $R^8$—$X^{II}$—, with $X^{II}$ being —C(O)NH—, —NHC(O)NH— or —S(O)$_2$NH—, one of $R^1$ to $R^4$ is R''', with R''' being defined as $R^1$ to $R^4$ above for formula I and the remaining two of $R^1$ to $R^4$ are hydrogen, are named I-d in scheme 5.

Scheme 5

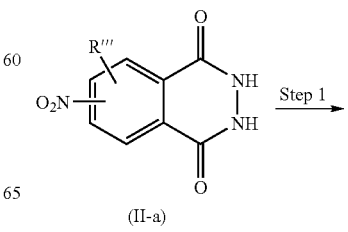

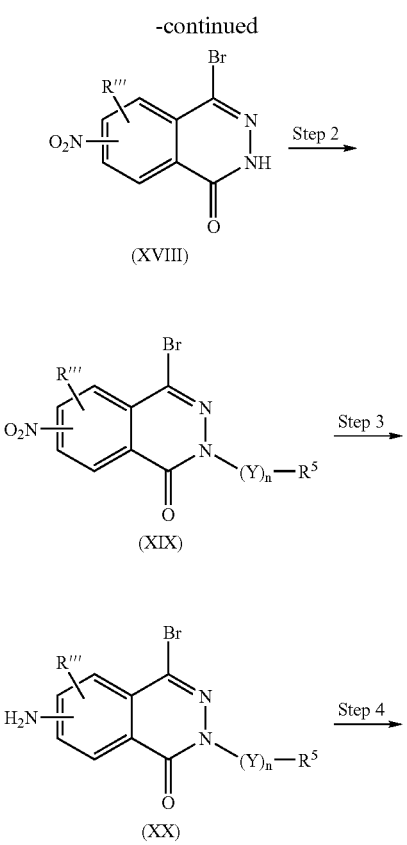

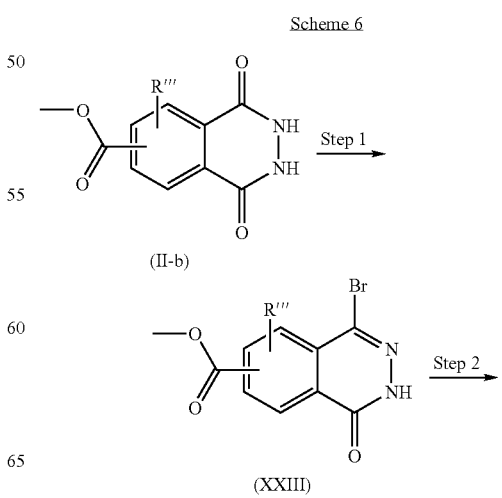

mides or ureas of formula XXII, using methods well known to someone skilled in the art, e.g. sulfonylation, acylation or aminocarboxylation of anilines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and 4-(dimethylamino)pyridine.

In step 5, scheme 5 the bromophthalazinone compounds of formula XXII are converted into their corresponding aminopyrazole Id, using methods well known to someone skilled in the art, e.g. palladium-mediated amination of imminobromides, vinylbromide or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphosphine, bis-triphenylphosphinepalladium dichloride in conjunction with phosphine based ligands such as 2,2'-bis(diphenylphosphino)-1.1'-binaphthyl, 4,5-Bis(diphenylphosphino)-9,9 dimethylxanthene and 2-(di-tert-butylphosphino)biphenyl.

Scheme 6

A preferred method for the synthesis of the derivatives of formula I, wherein one of $R^1$ to $R^4$ is —C(O)OH or $R^8$—X'''—, with X''' being —NHC(O)—, —N(alkyl)C(O)— or —OC(O)—, one of $R^1$ to $R^4$ is R''', with R''' being defined as $R^1$ to $R^4$ above for formula I and the remaining two of $R^1$ to $R^4$ are hydrogen, is described in scheme 6. The derivatives of formula I, wherein one of $R^1$ to $R^4$ is $R^8$—X'''—, with X''' being —NHC(O)—, —N(alkyl)C(O)— or —OC(O)—, one of $R^1$ to $R^4$ is R''', with R''' being defined as $R^1$ to $R^4$ above for formula I and the remaining two of $R^1$ to $R^4$ are hydrogen, are named I-e in scheme 6.

The method for the synthesis of the compounds of formula I-d starts from the corresponding phthalazine diones of formula II-a. Step 1 to step 3 are the same as described for scheme 4 yielding the corresponding amines of formula XX.

In step 4, scheme 5 the obtained compounds of formula XX are converted into their corresponding amides, sulfona- -continued

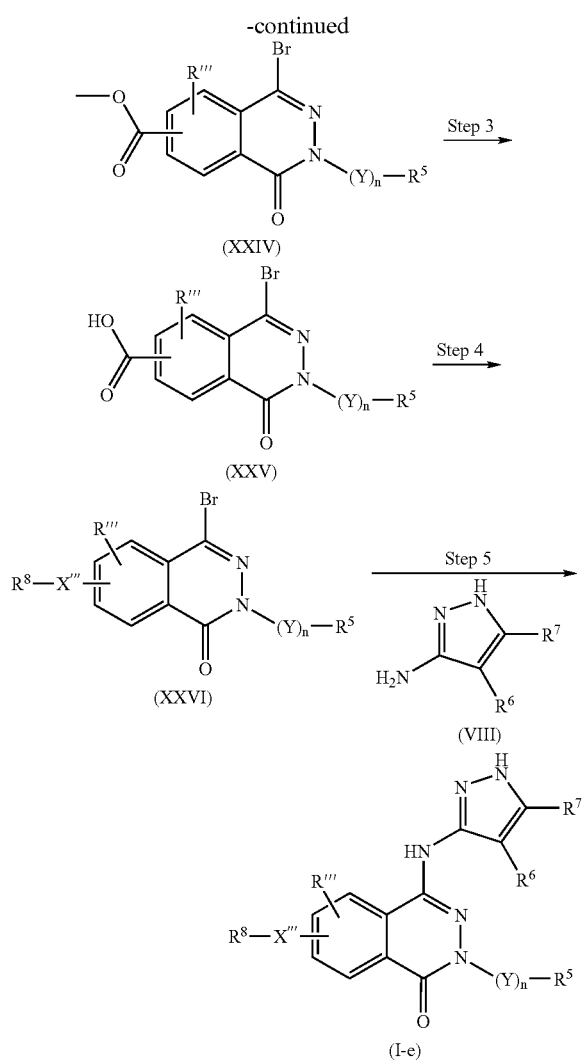

A preferred method for the synthesis of the compounds of formula I-e starts from the corresponding phthalazine diones of formula II-b. Step 1 of the reaction sequence (scheme 6) is a two step process in which a dibromination is followed by a monohydrolysis, yielding the 4-bromo-alkylcarboxyphthalazinone derivatives of formula XXIII. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 6 the obtained compounds of formula XXIII are converted into their corresponding tertiary amides of formula XXIV, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyl-disilazide.

In step 3, scheme 6 the obtained compounds of formula XXIV are converted into their corresponding carboxylic acids of formula XXV, using methods well known to someone skilled in the art, e.g. carboxylic acid formation by hydrolysis of alkyl carboxylates. The reaction is typically carried out in solvents like tetrahydrofuran, ethanol and methanol, water and mixtures thereof, at temperatures between 20° C. and 60° C. Typically used hydrolysis reagents are lithium hydroxide, sodium hydroxide and potassium hydroxide.

In step 4, scheme 6 the obtained compounds of formula XXV are converted into their corresponding carboxamide, acylsulfonamides or carboxylic acid esters of formula XXVI, using methods well known to someone skilled in the art, e.g. acylation of amines, sulfonamides and alcohols. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used coupling agents are N,N'-dicyclohexylcarbodiimide, 1-(3-dimthylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate. The reaction can be performed in the absence of a base or in the presence of a base. Typically used bases are triethylamine, N,N-diisopropyl ethylamine, pyridine, potassium carbonate and 4-(dimethylamino)pyridine.

In step 5, scheme 6 the bromophthalazinone compounds of formula XXVI are converted into their corresponding aminopyrazole Ie, using methods well known to someone skilled in the art, e.g. palladium-mediated amination of imminobromides, vinylbromide or aryl bromides. The reaction is typically carried out in solvents such as tetrahydrofuran, toluene, alkanols such as methanol, ethanol, isopropanol, and mixtures thereof at temperatures between 40° C. and 110° C.

Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphospine, bis-triphenylphosphinepalladium dichloride in conjunction with phosphine based ligands such as 2,2'-bis(diphenylphosphino)-1.1'-binaphthyl, 4,5-Bis(diphenylphosphino)-9,9 dimethylxanthene and 2-(di-tert-butylphosphino)biphenyl.

Scheme 7

A preferred method for the synthesis of the derivatives of formula I, wherein one of $R^1$ to $R^4$ is $R^8$—$X^{IV}$—, with $X^{IV}$ being —C(O)NH—, —NHC(O)NH— or —S(O)$_2$NH— and —C(O)N(alkyl)-, —NHC(O)N(alkyl)- or —S(O)$_2$N(alkyl)-, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 7. The derivatives of formula I, wherein one of $R^1$ to $R^4$ is $R^8$—$X^{IV}$—, with $X^{IV}$ being —C(O)NH—, —NHC(O)NH— or —S(O)$_2$NH— and —C(O)N(alkyl)-, —NHC(O)N(alkyl)- or —S(O)$_2$N(alkyl)-, one of $R^1$ to $R^4$ is R''', with R''' being defined as $R^1$ to $R^4$ above for formula I and the remaining two of $R^1$ to $R^4$ are hydrogen, $R^6$ is hydrogen and $R^7$ is methyl, are named I-f in scheme 7.

none derivatives of formula XVIII. The first step (dibromination) is typically carried out without solvent, or in solvents like dichloromethane, dichloroethane, anisole, and mixtures

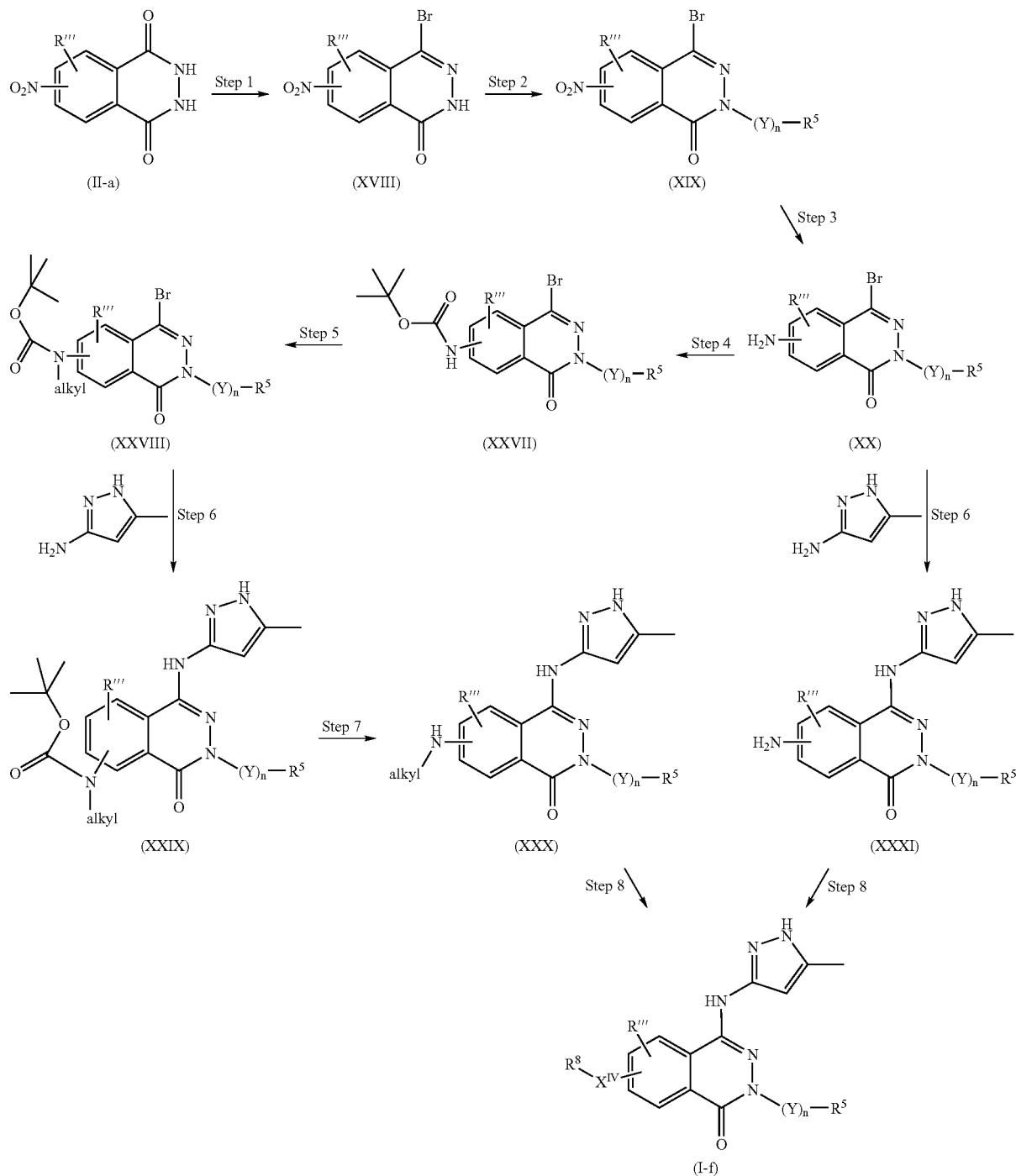

A preferred method for the synthesis of the compounds of formula I-f starts from the corresponding Phthalazine diones of formula II-a. Step 1 of the reaction sequence (scheme 7) is a two step process in which a dibromination is followed by a monohydrolysis, yielding the 4-bromo-nitrophthalazithereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 7 the obtained compounds of formula XVIII are converted into their corresponding tertiary amides of formula XIX, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 7 the obtained compounds of formula XIX are converted into their corresponding anilines of formula XX, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride.

In step 4, scheme 7 the obtained compounds of formula XX are converted into their corresponding secondary carbamates of formula XXVII, using methods well known to someone skilled in the art, e.g. tert-butyloxycarbonylation of amines. The reaction is typically carried out in solvents like N,N-dimethylformamide, N-methylpyrrolidinone, acetonitrile, dichloromethane and dichloroethane, at temperatures between 0° C. and 100° C. Typically used bases are imidazole, triethylamine, N,N-diisopropylethylamine and N,N-dimethylaminopyridine in conjunction with reagents such as di-tert-butyl dicarbonate.

In step 5, scheme 7 the obtained compounds of formula XXVII are converted into their corresponding tertiary carbamates of formula XXVIII, using methods well known to someone skilled in the art, e.g. alkylation of secondary carbamates. The reaction is typically carried out in solvents like N,N-dimethylformamide, N-methylpyrrolidinone, acetonitrile, acetone, dichloromethane and dichloroethane, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 6, scheme 7 the obtained compounds of formula XXVIII (obtained in step 5) or compounds of formula XX (obtained in step 3) are converted into their corresponding amino pyrazoles of formula XXIX or formula XXXI, using methods well known to someone skilled in the art, e.g. palladium-mediated amination of imminobromides, vinylbromides or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphospine, bis-triphenylphosphinepalladium dichloride in conjunction with phosphine based ligands such as 2,2'-bi(phenylphosphino)-1,1'-binaphthyl, 4,5-Bis(diphenylphosphino)-9,9 dimethylxanthene and 2-(di-tert-butylphosphino)biphenyl.

In step 7, scheme 7 the obtained compounds of formula XXIX are converted into their corresponding anilines of formula XXX, using methods well known to someone skilled in the art, e.g. acid mediated de-protection of a boc-protected amine. The reaction is typically carried out in solvents such as dichloromethane, dioxane, diethyl ether, dioxane and alkyl alcohols such as methanol, ethanol and mixtures thereof at temperatures between 0° C. and 40° C. Typically used acids are anhydrous hydrochloric acid, aqueous hydrochloric acid, trifluoroacetic acid, trimethylsilyl bromide and trifluoromethanesulfonic acid.

In step 8, scheme 7 the obtained compounds of formula XXX or formula XXXI are converted into their corresponding amides, sulfonamides or ureas of formula (I-f), using a two step procedure in which a bis acylation (of the amine of formula XXX or formula XXXI and the pyrazole-NH) is followed by a monohydrolysis (of the acylated pyrazole-NH), yielding the aminopyrazole derivatives of formula I-f. The first step (bis acylation) is typically carried out in solvents such as dichloromethane, dioxane, and tetrahydrofuran and mixtures thereof at temperatures between 0° C. and 80° C. using capping reagents such as acid chlorides, acid anhydrides, sulfonyl chlorides and isocyanates. Typically used bases are triethylamine, N,N-diisopropylethylamine and N,N-dimethylaminopyridine, potassium carbonate, sodium hydride, lithium hexamethyldisilazide, sodium hexamethyldisilazide and potassium hexamethyldisilazide at temperatures between 0° C. and 80° C. The second step (monohydrolysis of the diamide, disulfonamide, diurea) is typically carried out in aqueous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate at temperatures between 0° C. and 80° C.

Scheme 8

A preferred method for the synthesis of the derivatives of formula I, wherein one of $R^1$ to $R^4$ is $R^8$—$X^V$—, with $X^V$ being —N(alkyl)- , one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 7. The derivatives of formula I, wherein one of $R^1$ to $R^4$ is $R^8$—$X^{IV}$—, with $X^V$ being —N(alkyl)- , one of $R^1$ to $R^4$ is R''', with R''' being defined as $R^1$ to $R^4$ above for formula I and the remaining two of $R^1$ to $R^4$ are hydrogen, $R^6$ is hydrogen and $R^7$ is methyl, are named I-g in scheme 8.

Scheme 8

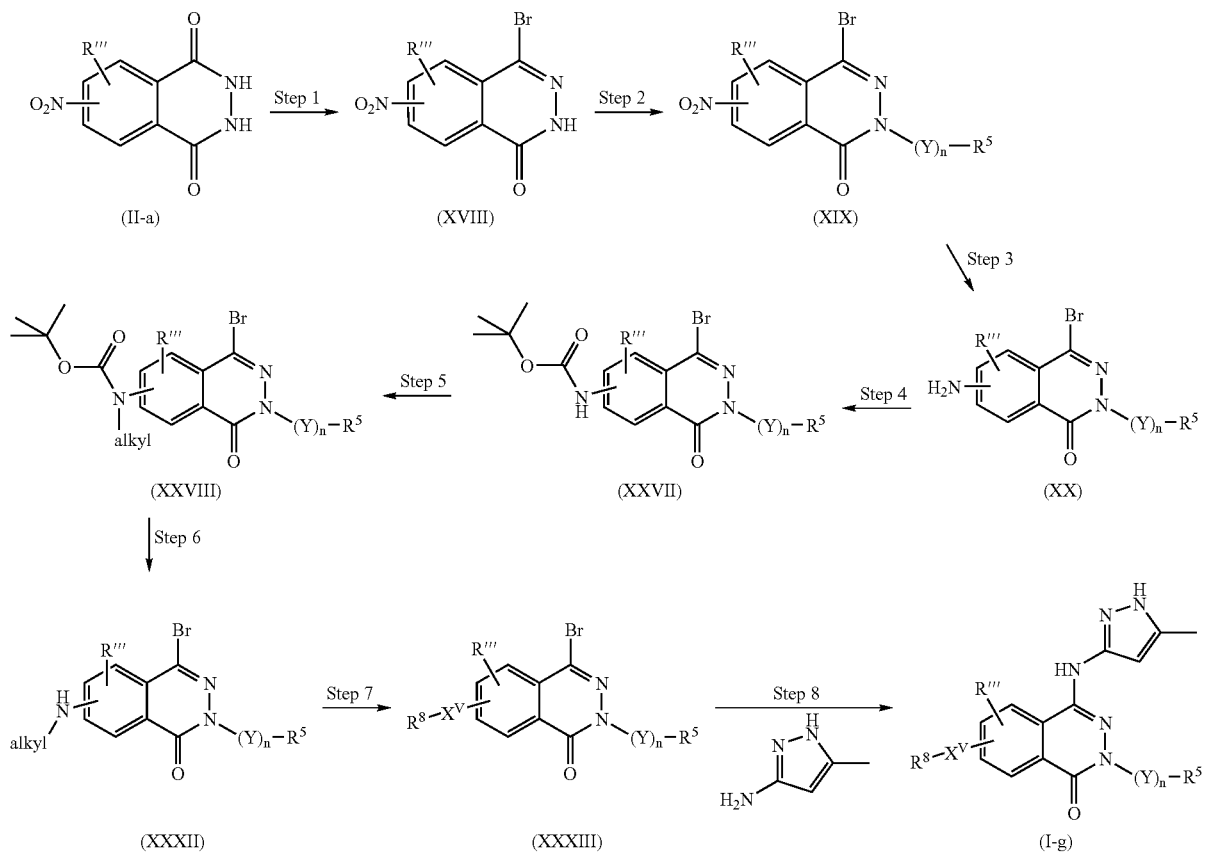

A preferred method for the synthesis of the compounds of formula I-g starts from the corresponding Phthalazine diones of formula II-a. Step 1 of the reaction sequence (scheme 8) is a two step process in which a dibromination is followed by a monohydrolysis, yielding the 4-bromo-nitrophthalazinone derivatives of formula XVIII. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 8 the obtained compounds of formula XVIII are converted into their corresponding tertiary amides of formula XIX, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 8 the obtained compounds of formula XIX are converted into their corresponding anilines of formula XX, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride.

In step 4, scheme 8 the obtained compounds of formula XX are converted into their corresponding secondary carbamates of formula XXVII, using methods well known to someone skilled in the art, e.g. tert-butyloxycarbonylation of amines. The reaction is typically carried out in solvents like N,N-dimethylformamide, N-methylpyrrolidinone, acetonitrile, dichloromethane and dichloroethane, at temperatures between 0° C. and 100° C. Typically used bases are imidazole, triethylamine, N,N-diisopropylethylamine and N,N-dimethylaminopyridine in conjunction with reagents such as di-tert-butyl dicarbonate.

In step 5, scheme 8 the obtained compounds of formula XXVII are converted into their corresponding tertiary carbamates of formula XXVIII, using methods well known to someone skilled in the art, e.g. alkylation of secondary carbamates. The reaction is typically carried out in solvents like N,N-dimethylformamide, N-methylpyrrolidinone, acetonitrile, acetone, dichloromethane and dichloroethane, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 6, scheme 8 the obtained compounds of formula XXVIII are converted into their corresponding secondary amines of formula XXXII, using methods well known to someone skilled in the art, e.g. deprotection of acid labile protecting groups such as a $^{tert}$-butyloxycarbonyl group. The reaction is typically carried out without solvent or in solvents like diethyl ether, dioxane, tetrahydrofuran, dichloromethane and dichloroethane or mixtures thereof, at temperatures between 0° C. and 40° C. Typically used acids are trifluoroacetic acid, trifluoromethane sulfonic acid, aqueous hydrochloric acid, aqueous sulfuric acid or anhydrous hydrogen chloride.

In step 7, scheme 8 the obtained compounds of formula XXXII are converted into their corresponding of formula XXXIII, using methods well known to someone skilled in the art, e.g. alkylation of secondary amines. The reaction is typically carried out in solvents like N,N-dimethylformamide, N-methylpyrrolidinone, acetonitrile, acetone, dichloromethane and dichloroethane, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 8, scheme 8 the obtained compounds of formula (XXXIII) are converted into their corresponding amino pyrazoles of formula I-g, using methods well known to someone skilled in the art, e.g. palladium-mediated amination of imminobromides, vinylbromides or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakistriphenylphospine, bis-triphenylphosphinepalladium dichloride in conjunction with phosphine based ligands such as 2,2'-bi(phenylphosphino)-1,1'-binaphthyl, 4,5-Bis(diphenylphosphino)-9,9 dimethylxanthene and 2-(di-tert-butylphosphino)biphenyl.

Scheme 9

A preferred method for the synthesis of the derivatives of formula I, wherein one of $R^1$ to $R^4$ is —OH or $R^8$—$X^{VI}$—, with $X^{VI}$ being —O— or —C(O)O—, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 9. The derivatives of formula (I), wherein one of $R^1$ to $R^4$ is $R^8$—$X^{IV}$—, with $X^{IV}$ being —O— or —C(O)O—, one of $R^1$ to $R^4$ is R''', with R''' being defined as $R^1$ to $R^4$ above for formula I and the remaining two of $R^1$ to $R^4$ are hydrogen, $R^6$ is hydrogen and $R^7$ is methyl, are named I-h in scheme 9.

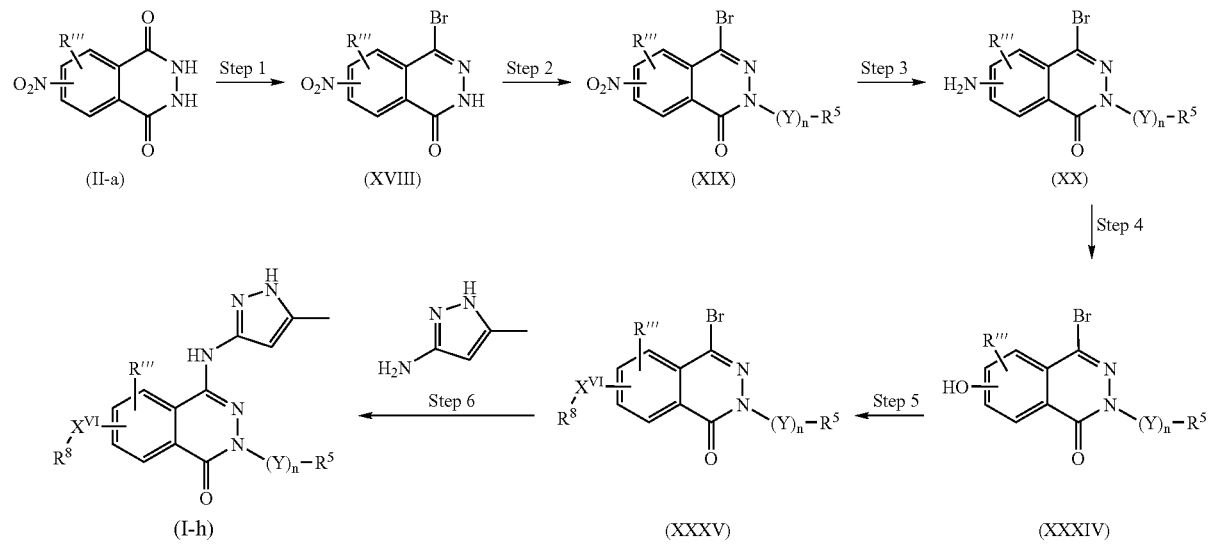

A preferred method for the synthesis of the compounds of formula I-h starts from the corresponding Phthalazine diones of formula II-a. Step 1 of the reaction sequence (scheme 9) is a two step process in which a dibromination is followed by a monohydrolysis, yielding the 4-bromo-nitrophthalazinone derivatives of formula XVIII. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 9 the obtained compounds of formula XVIII are converted into their corresponding tertiary amides of formula XIX, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 9 the obtained compounds of formula XIX are converted into their corresponding anilines of formula XX, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride.

In step 4, scheme 9 the obtained compounds of formula (XX) are converted into their corresponding alcohols of formula XXXIV, using methods well known to someone skilled in the art, e.g. diazotisation of anilines and displacement of the diazonium species with nucleophiles. The reaction is a 2 step process in which step 1 is generation of the diazonium species and step 2 is displacement of the diazonium species is carried out using a nucleophile. Step 1 of the reaction is typically carried out in solvents such as sulfuric acid, hydrochloric acid or acetic acid and mixtures thereof. Typically used reagents are sodium nitrite and isoamylnitrite with additional reagents such as urea. The first step of the reaction is typically carried out at temperatures between −10° C. and 30° C. Step 2 of the reaction is typically carried out in aqueous media such as aqueous hydrochloric acid, aqueous sulfuric acid and aqueous acetic. The second step of the reaction is typically carried out at temperatures between 20° C. and 130° C.

In step 5, scheme 9 the obtained compounds of formula XXXIV are converted into their corresponding ethers of formula XXXV, using methods well known to someone skilled in the art, e.g. alkylation of phenols. The reaction is typically carried out in solvents like N,N-dimethylformamide, tetrahydrofuran, N-methylpyrrolidinone, acetonitrile, acetone, dichloromethane and dichloroethane, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 6, scheme 9 the obtained compounds of formula XXXV are converted into their corresponding amino pyrazoles of formula I-h, using methods well known to someone skilled in the art, e.g. palladium-mediated amination of imminobromides, vinylbromides or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphosphine, bis-triphenylphosphinepalladium dichloride in conjunction with phosphine based ligands such as 2,2'-bi(phenylphosphino)-1,1'-binaphthyl, 4,5-Bis(diphenylphosphino)-9,9 dimethylxanthene and 2-(di-tert-butylphosphino)biphenyl.

Scheme 10

A preferred method for the synthesis of the derivatives of formula I, wherein one of $R^1$ to $R^4$ is $R^8$—S—, or $R^8$—$X^{VII}$—, with $X^{VII}$ being —S(O)— or —S(O)$_2$—, one of $R^1$ to $R^4$ is R'", with R'" being defined as $R^1$ to $R^4$ above for formula I, and the remaining two of $R^1$ to $R^4$ are hydrogen, $R^6$ is hydrogen and $R^7$ is methyl, is described in scheme 10. The derivatives of formula I, wherein one of $R^1$ to $R^4$ is $R^8$—S—, or $R^8$—$X^{VII}$—, with $X^{VII}$ being —S(O)— or —S(O)$_2$—, one of $R^1$ to $R^4$ is R'", R'" being defined as $R^1$ to $R^4$ above for formula I and the remaining two of $R^1$ to $R^4$ are hydrogen, $R^6$ is hydrogen and $R^7$ is methyl, are named I-i (for one of RI to $R^4$ is $R^8$—S—) or I-j (for one of $R^1$ to $R^4$ is $R^8$—$X^{VII}$—) in scheme 10.

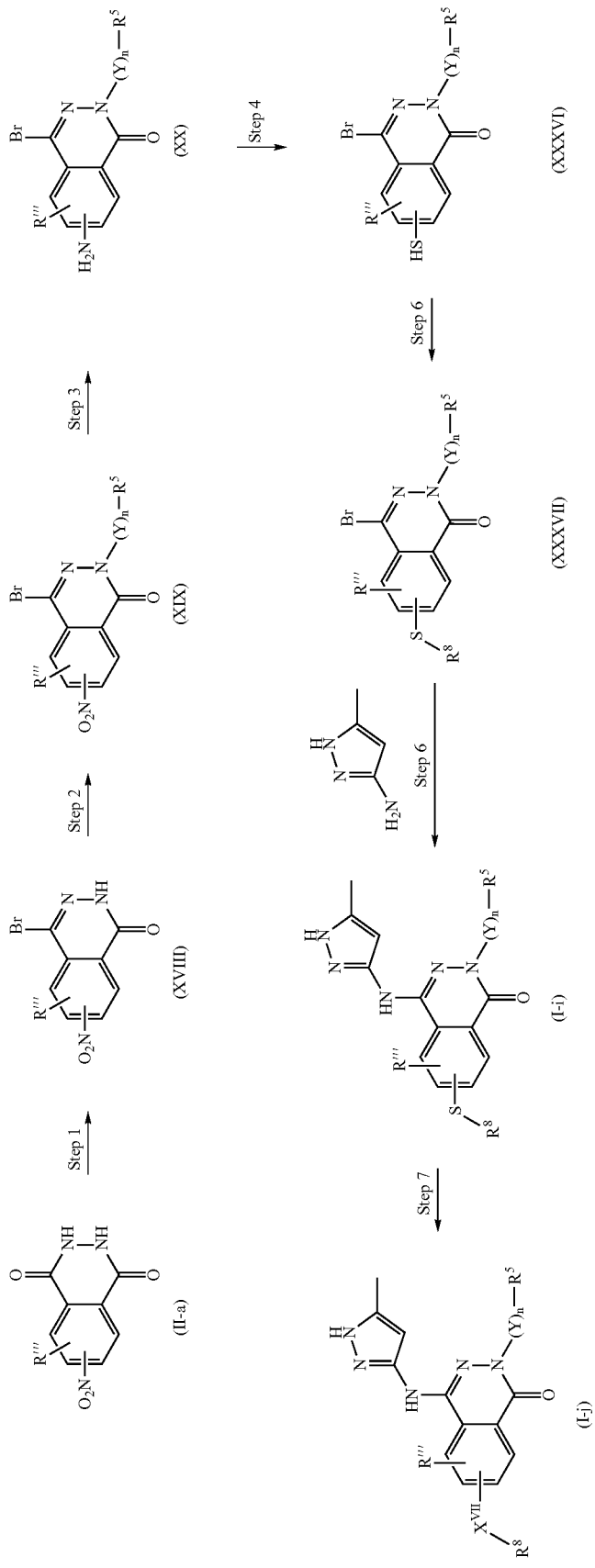

A preferred method for the synthesis of the compounds of formula I-i and I-j starts from the corresponding Phthalazine diones of formula II-a. Step 1 of the reaction sequence (scheme 10) is a two step process in which a dibromination is followed by a monohydrolysis, yielding the 4-bromo-nitrophthalazinone derivatives of formula XVIII. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 10 the obtained compounds of formula XVIII are converted into their corresponding tertiary amides of formula XIX, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 10 the obtained compounds of formula XIX are converted into their corresponding anilines of formula XX, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride.

In step 4, scheme 10 the obtained compounds of formula XX are converted into their corresponding thiols of formula XXXVI, using methods well known to someone skilled in the art, e.g. diazotisation of anilines and displacement of the diazonium species with nucleophiles. The reaction is a 2 step process in which step 1 is generation of the diazonium species and step 2 is displacement of the diazonium species is carried out using a nucleophile. Step 1 of the reaction is typically carried out in solvents such as sulfuric acid, hydrochloric acid or acetic acid and mixtures thereof Typically used reagents are sodium nitrite and isoamylnitrite with additional reagents such as urea. The first step of the reaction is typically carried out at temperatures between −10° C. and 30° C. Step 2 of the reaction is typically carried out in aqueous media such as aqueous hydrochloric acid, aqueous sulfuric acid and aqueous acetic. The second step of the reaction is typically carried out at temperatures between 20° C. and 130° C.

In step 5, scheme 10 the obtained compounds of formula XXXVI are converted into their corresponding ethers of formula XXXVII, using methods well known to someone skilled in the art, e.g. alkylation of thiophenols. The reaction is typically carried out in solvents like N,N-dimethylformamide, tetrahydrofuran, N-methylpyrrolidinone, acetonitrile, acetone, dichloromethane and dichloroethane, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 6, scheme 10 the obtained compounds of formula XXXVII are converted into their corresponding amino pyrazoles of formula I-i, using methods well known to someone skilled in the art, e.g. palladium-mediated amination of imminobromides, vinylbromides or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipanadium, palladium tetrakis-triphenylphospine, bis-triphenylphosphinepalladium dichloride in conjunction with phosphine based ligands such as 2,2'-bi(phenylphosphino)-1,1'-binaphthyl, 4,5-Bis(diphenylphosphino)-9,9 dimethylxanthene and 2-(di-tert-butylphosphino)biphenyl.

In step 7, scheme 10 the obtained compounds of formula I-i are converted into their corresponding sulfoxides or sulfones of formula I-j, using methods well known to someone skilled in the art, e.g. oxidation of thioethers to sulfoxides or sulfones. The reaction is typically carried out in solvents such as tetrahydrofuran, toluene, alkanols such as methanol, ethanol, isopropanol and water and mixtures thereof at temperatures between 0° C. and 110° C. Typically used reagents are OXONE™ and meta-chloroperbenzoic acid.

Scheme 11

A preferred method for the synthesis of the derivatives of formula I, wherein one of $R^1$ to $R^4$ is alkyl, especially methyl, substituted with alkoxy, one of $R^1$ to $R^4$ is $R'''$, with $R'''$ being defined as $R^1$ to $R^4$ above for formula I, and the remaining two of $R^1$ to $R^4$ are hydrogen, is described in scheme 11. The derivatives of formula I, wherein one of $R^1$ to $R^4$ is alkyl, especially methyl, substituted with alkoxy, one of $R^1$ to $R^4$ is $R'''$, with $R'''$ being defined as $R^1$ to $R^4$ above for formula I and the remaining two of $R^1$ to $R^4$ are hydrogen, are named I-k in scheme 11.

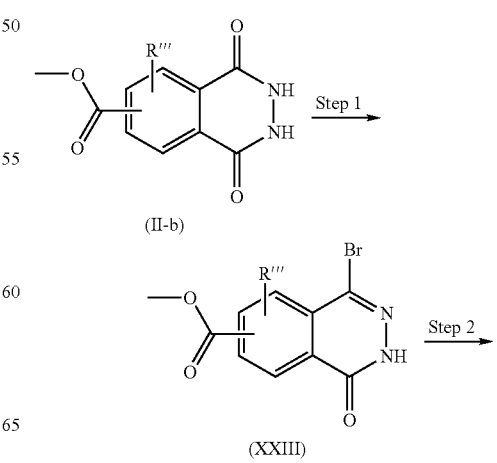

-continued

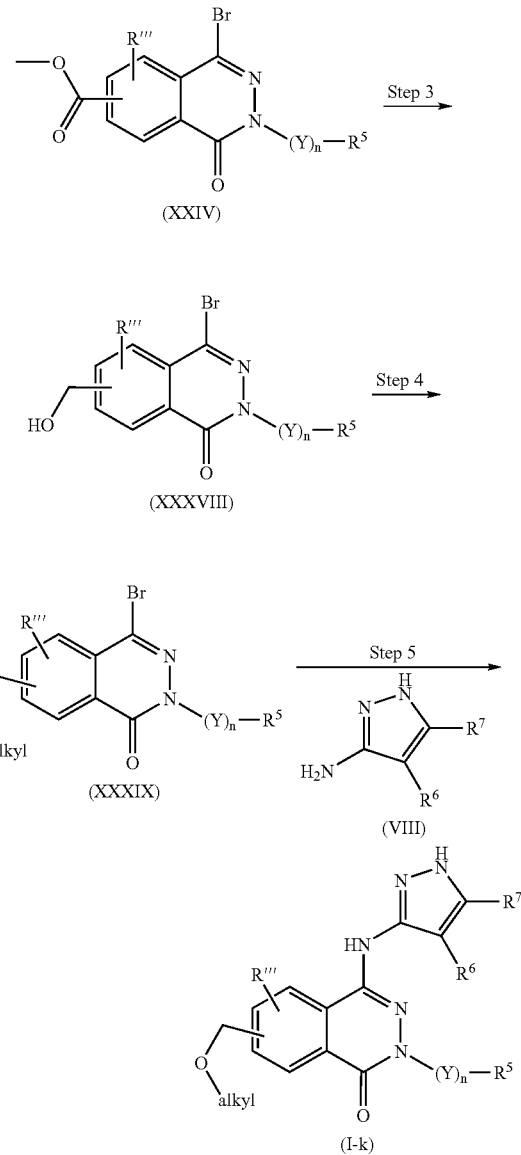

A preferred method for the synthesis of the compounds of formula I-k starts from the corresponding Phthalazine diones of formula I-b. Step 1 of the reaction sequence (scheme 11) is a two step process in which a dibromination is followed by a monohydrolysis, yielding the 4-bromo-alkylcarboxyphthalazinone derivatives of formula XXIII. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 11 the obtained compounds of formula XXIII are converted into their corresponding tertiary amides of formula XXIV, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 11 the obtained compounds of formula XXIV are converted into their corresponding alcohols of formula XXXVIII, using methods well known to someone skilled in the art, e.g. reduction of esters to form alcohols. The reaction is typically carried out in solvents like tetrahydrofuran, dioxane, dichloromethane and mixtures thereof, at temperatures between 0° C. and 100° C. Typically used reducing reagents are lithium borohydride.

In step 4, scheme 11 the obtained compounds of formula XXXVIII are converted into their corresponding ethers of formula XXXIX, using methods well known to someone skilled in the art, e.g. alkylation of alcohols. The reaction is typically carried out in solvents like N,N-dimethylformamide, tetrahydrofuran, N-methylpyrrolidinone, acetonitrile, acetone, dichloromethane and dichloroethane, at temperatures between 0° C. and 100° C. Typically used bases are potassium carbonate, sodium hydride, lithium hexamethyldisilazide, sodium hexamethyldisilazide and potassium hexamethyldisilazide in conjunction with alkylating agents such as alkyl halides, alkyl mesylates and alkyl triflates.

In step 5, scheme 11 the obtained compounds of formula XXXIX are converted into their corresponding amino pyrazoles of formula I-k, using methods well known to someone skilled in the art, e.g. palladium-mediated amination of imminobromides, vinylbromides or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphosphine, bis-triphenylphosphinepalladium dichloride in conjunction with phosphine based ligands such as 2,2'-bi(phenylphosphino)-1,1'-binaphthyl, 4,5-Bis(diphenylphosphino)-9,9 dimethylxanthene and 2-(di-tert-butylphosphino)biphenyl.

Scheme 12

Another preferred method for the synthesis of the derivatives of formula I, wherein one of $R^1$ to $R^4$ is alkyl, especially methyl, substituted with alkoxy, one of $R^1$ to $R^4$ is R''', with R''' being defined as $R^1$ to $R^4$ above for formula I, and the remaining two of $R^1$ to $R^4$ are hydrogen, is described in scheme 12. The derivatives of formula I, wherein one of $R^1$ to $R^4$ is alkyl, especially methyl, substituted with alkoxy, one of $R^1$ to $R^4$ is R''', with R''' being defined as $R^1$ to $R^4$ above for formula I and the remaining two of $R^1$ to $R^4$ are hydrogen, are named I-k in scheme 12.

Scheme 12

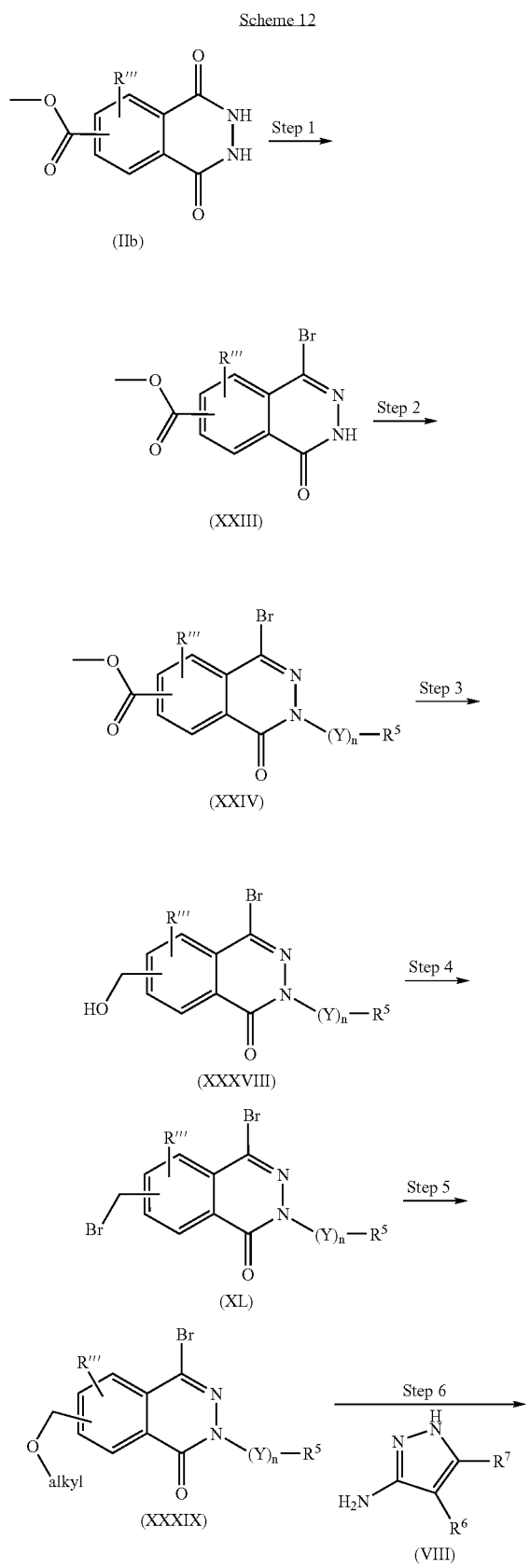

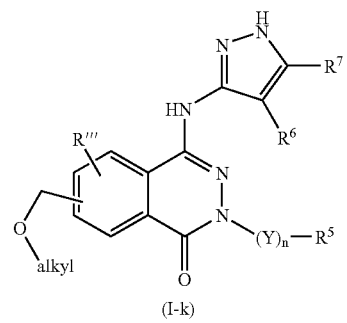

(I-k)

A preferred method for the synthesis of the compounds of formula I-k starts from the corresponding Phthalazine diones of formula II-b. Step 1 of the reaction sequence (scheme 12) is a two step process in which a dibromination is followed by a monohydrolysis, yielding the 4-bromo-alkylcarboxyphthalazinone derivatives of formula XXIII. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 12 the obtained compounds of formula XXIII are converted into their corresponding tertiary amides of formula XXIV, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 12 the obtained compounds of formula XXIV are converted into their corresponding alcohols of formula XXXVIII, using methods well known to someone skilled in the art, e.g. reduction of esters to form alcohols. The reaction is typically carried out in solvents like tetrahydrofuran, dioxane, dichloromethane and mixtures thereof, at temperatures between 0° C. and 100° C. Typically used reducing reagents are lithium borohydride.

In step 4, scheme 12 the obtained compounds of formula XXXVIII are converted into their corresponding alkyl bromides of formula XL, using methods well known to someone skilled in the art, e.g. functional group interconversion of alcohols into bromides. The reaction is typically carried out in solvents like acetonitrile, tetrahydrofuran, dioxane, dichloromethane and mixtures thereof, at temperatures between 0° C. and 100° C. Typically used brominating reagents are trimethylsilyl chloride or trimethylsilyl bromide in conjunction with lithium bromide.

In step 5, scheme 12 the obtained compounds of formula XL are converted into their corresponding ethers of formula XXXIX, using methods well known to someone skilled in the art, e.g. alkylation of alcohols. The reaction is typically carried out in solvents like N,N-dimethylformamide, tetrahydrofuran, N-methylpyrrolidinone, acetonitrile, acetone, dichloromethane and dichloroethane, at temperatures between 0° C. and 100° C. Typically used bases are potassium carbonate, sodium hydride, lithium hexamethyldisilazide, sodium hexamethyldisilazide and potassium hexamethyldisilazide in conjunction with nucleophiles such as alcohols.

In step 6, scheme 12 the obtained compounds of formula XXXIX are converted into their corresponding amino pyrazoles of formula I-k, using methods well known to someone skilled in the art, e.g. palladium-mediated amination of imminobromides, vinylbromides or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphosphine, bis-triphenylphosphinepalladium dichloride in conjunction with phosphine based ligands such as 2,2'-bi(phenylphosphino)-1,1'-binaphthyl, 4,5-Bis(diphenylphosphino)-9,9 dimethylxanthene and 2-(di-tert-butylphosphino)biphenyl.

Alternatively to the routes described scheme 11 and scheme 12, the compounds of formula I-k can be prepared via the N,N'-diprotected intermediate of formula XLV shown in scheme 14.

Scheme 13

A preferred method for the synthesis of the derivatives of formula I, wherein one of $R^1$ to $R^4$ is heterocyclyl-$T^2$, wherein the heterocyclyl contains al least one nitrogen and wherein the heterocyclyl is attached via the nitrogen, and $T^2$ is an alkylene, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 13. The derivatives of formula (I), wherein one of $R^1$ to $R^4$ is heterocyclyl-$T^2$, wherein the heterocyclyl contains al least one nitrogen and wherein the heterocyclyl is attached via the nitrogen, and $T^2$ is an alkylene, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, are named I-l in scheme 13.

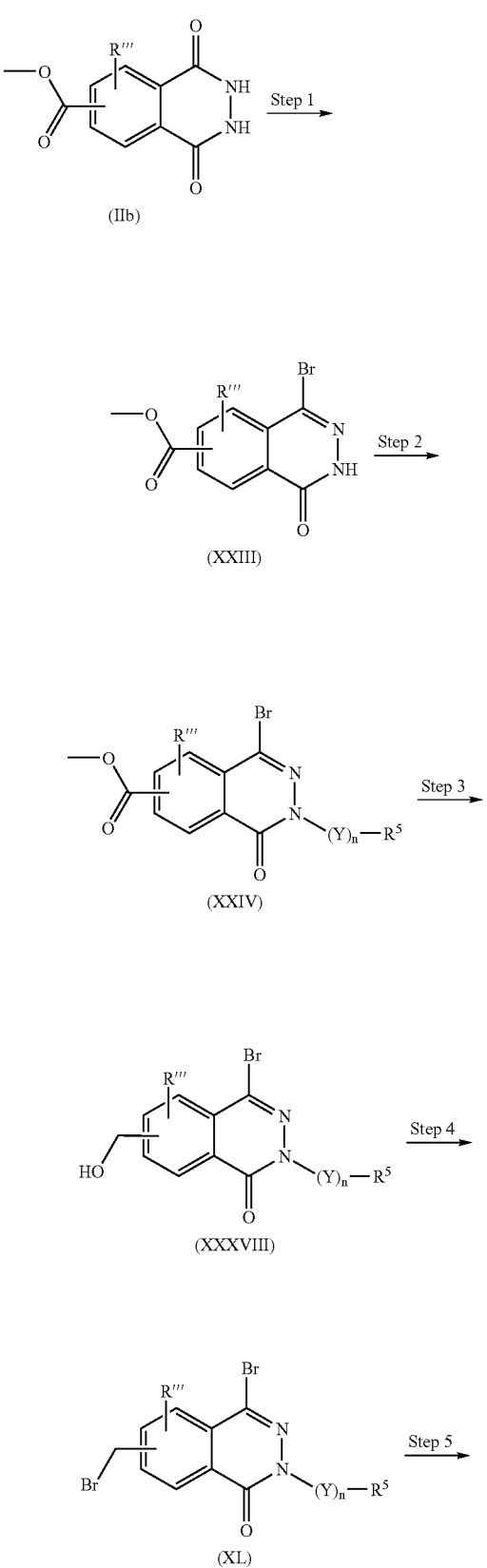

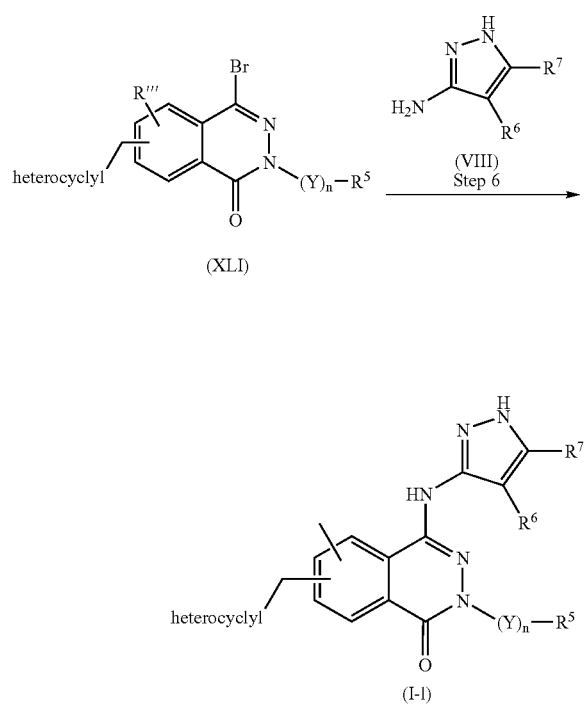

A preferred method for the synthesis of the compounds of formula I-l starts from the corresponding Phthalazine diones of formula II-b. Step 1 of the reaction sequence (scheme 13) is a two step process in which a dibromination is followed by a monohydrolysis, yielding the 4-bromo-alkylcarboxyphthalazinone derivatives of formula XXIII. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 13 the obtained compounds of formula XXIII are converted into their corresponding tertiary amides of formula XXIV, using methods well known to someone skilled in the art, e.g. alkylation under basic conditions. The reaction is typically carried out in aprotic solvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 13 the obtained compounds of formula XXIV are converted into their corresponding alcohols of formula XXXVIII, using methods well known to someone skilled in the art, e.g. reduction of esters to form alcohols. The reaction is typically carried out in solvents like tetrahydrofuran, dioxane, dichloromethane and mixtures thereof, at temperatures between 0° C. and 100° C. Typically used reducing reagents are lithium borohydride.

In step 4, scheme 13 the obtained compounds of formula XXXVIII are converted into their corresponding alkyl bromides of formula XL, using methods well known to someone skilled in the art, e.g. functional group interconversion of alcohols into bromides. The reaction is typically carried out in solvents like acetonitrile, tetrahydrofuran, dioxane, dichloromethane and mixtures thereof, at temperatures between 0° C. and 100° C. Typically used brominating reagents are trimethylsilyl chloride or trimethylsilyl bromide in conjunction with lithium bromide.

In step 5, scheme 13 the obtained compounds of formula XL are converted into their corresponding heterocyclyl alkyl derivatives of formula XLI, using methods well known to someone skilled in the art, e.g. N-alkylation of nitrogen containing heterocycles. The reaction is typically carried out in solvents like N,N-dimethylformamide, tetrahydrofuran, N-methylpyrrolidinone, acetonitrile, acetone, dichloromethane and dichloroethane, at temperatures between 0° C. and 100° C. Typically used bases are potassium carbonate, sodium hydride, lithium hexamethyldisilazide, sodium hexamethyldisilazide and potassium hexamethyldisilazide in conjunction with nucleophiles such as secondary amines.

In step 6, scheme 13 the obtained compounds of formula XLI are converted into their corresponding amino pyrazoles of formula I-l, using methods well known to someone skilled in the art, e.g. palladium-mediated amination of imminobromides, vinylbromides or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphospine, bis-triphenylphosphinepalladium dichloride in conjunction with phosphine based ligands such as 2,2'-bi(phenylphosphino)-1,1'-binaphthyl, 4,5-Bis(diphenylphosphino)-9,9 dimethylxanthene and 2-(di-tert-butylphosphino)biphenyl.

Scheme 14

A preferred method for the synthesis of the derivatives of formula I, wherein one of $R^1$ to $R^4$ is $R^8$—$X^{III}$—, with $X^{III}$ being —NHC(O)—, —N(alkyl)C(O)— or —OC(O)—, one of $R^1$ to $R^4$ is R''', with R''' being defined as $R^1$ to $R^4$ above for formula I, and the remaining two of $R^1$ to $R^4$ are hydrogen, $R^6$ is hydrogen and $R^7$ is methyl, is described in scheme 14. The derivatives of formula I, wherein one of $R^1$ to $R^4$ is $R^8$—$X^{III}$—, with $X^{III}$ being —NHC(O)—, —N(alkyl)C(O)— or —OC(O)—, one of $R^1$ to $R^4$ is R''', with R''' being defined as $R^1$ to $R^4$ above for formula I and the remaining two of $R^1$ to $R^4$ are hydrogen, are named I-m in scheme 14.

Scheme 14
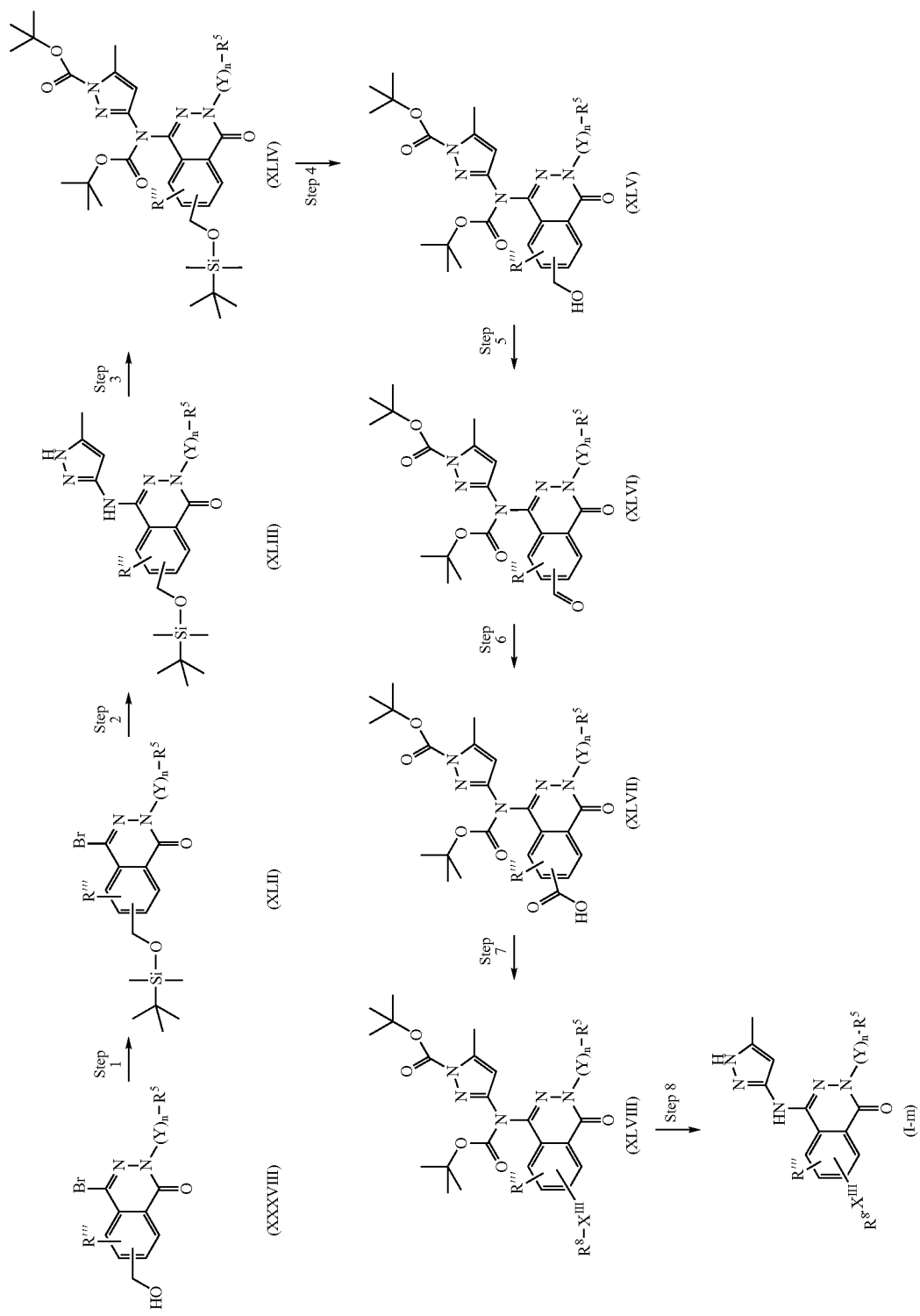

A preferred method for the synthesis of the compounds of formula I-m starts from the corresponding hydroxymethyl bromophthalazinones of formula XXXVIII (for preparation see schemes 11 and 12). In step 1, scheme 14 the obtained compounds of formula XXXVIII are converted into their corresponding silyl ethers of formula XLII, using methods well known to someone skilled in the art, e.g. silyl protection of an alcohol. The reaction is typically carried out in aprotic solvents such as dichloromethane, tetrahydrofuran, N,N-dimethylformamide, dimethyl sulfoxide, N-methylpyrrolidinone and mixtures thereof at temperatures between 0° C. and 40° C. Typically used reagents are silyl chlorides or silyl triflates such as tert-butyldimethylsilyl chloride and tert-butyldimethylsilyl triflates. Typically used bases are imidazole, triethylamine, pyridine and N,N-4-dimethylaminopyridine.

In step 2, scheme 14 the obtained compounds of formula XLII are converted into their corresponding amino pyrazoles of formula XLIII, using methods well known to someone skilled in the art, e.g. palladium-mediated amination of imminobromides, vinylbromides or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphospine, bis-triphenylphosphinepalladium dichloride in conjunction with phosphine based ligands such as 2,2'-bi(phenylphosphino)-1,1'-binaphthyl, 4,5-Bis(diphenylphosphino)-9,9 dimethylxanthene and 2-(di-tert-butylphosphino)biphenyl.

In step 3, scheme 14 the obtained compounds of formula XLIII are converted into their corresponding protected amino pyrazoles of formula XLIV, using methods well known to someone skilled in the art, e.g. carbamate protection of amines. The reaction is typically carried out in solvents such as tetrahydrofuran, dioxane, dichloromethane, N,N-dimethylformamide or N-methylpyrrolidinone. Typically used bases are triethylamine, sodium hydride, N,N-4-dimethylaminopyridine at temperatures between 0° C. and 100° C.

In step 4, scheme 14 the obtained compounds of formula XLIV are converted into their corresponding alcohols of formula XLV, using methods well known to someone skilled in the art, e.g. fluoride mediated deprotection of silyl ethers. The reaction is typically carried out in solvents such as tetrahydrofuran, dioxane, and dichloromethane at temperatures between 0° C. and 100° C. Typically used reagents are tetrabutylammoniumn fluoride, potassium fluoride, hydrogen fluoride pyridine complex and silica supported tetrabutylammonium fluoride.

In step 5, scheme 14 the obtained compounds of formula XLV are converted into their corresponding aldehydes of formula XLVI, using methods well known to someone skilled in the art, e.g. oxidation of an alcohol. The reaction is typically carried out in solvents such as N,N-dimethylformamide, N-methylpyrrolidinone, dimethyl sulfoxide, tetrahydrofuran, dioxane, and dichloromethane at temperatures between 0° C. and 100° C. Typically used reagents are pyridine-sulfur trioxide complex, Dess-Martin periodinane (DMP) or 2-Iodoxybenzoic acid (IBX).

In step 6, scheme 14 the obtained compounds of formula XLVI are converted into their corresponding carboxylic acids of formula XLVII, using methods well known to someone skilled in the art, e.g. oxidation of carboxaldehyde. The reaction is typically carried out in solvents such as dichloromethane, tetrahydrofuran, water and mixtures thereof at temperatures between 0° C. and 40° C. Typically used reagents are sodium chlorite, using buffering reagents such as sulfamic acid and phosphoric acid and radical trapping reagents such as isobutene.

In step 7, scheme 14 the obtained compounds of formula XLVII are converted into their corresponding carboxamides of formula XLVIII, using methods well known to someone skilled in the art, e.g. amide formation by acid-amine coupling. The reaction is typically carried out in solvents such as tetrahydrofuran, dichloromethane, N,N-dimethylformamide, N-methylpyrrolidinone and mixtures thereof at temperatures between 0° C. and 80° C. Typically used reagents are dicyclohexylcarbodiimide, N-(3-dimethylaminopropyl)-N'-ethylcarbodiimide, O-benzotriazol-1-yl-N,N,N',N'-tetramethyluronium tetrafluoroborate, bromotripyrrolidinophosphonium hexafluorophophate, and (7-azabenzotriazol-1-yloxy)tripyrrolidinophosphonium hexafluorophophate, with or without a base such as triethylamine, N,N-diisopropyl ethylamine and pyridine.

In step 8, scheme 14 the obtained compounds of formula XLVIII are converted into compounds of formula I-m, using methods well known to someone skilled in the art, e.g. acid-mediated deprotection of carbamates. The reaction is typically carried out in solvents such as tetrahydrofuran, dichloromethane, diethyl ether and dioxane and mixtures thereof at temperatures between 0° C. and 50° C. Typically used reagents are trifluoroacetic acid, hydrogen chloride, sulfuric acid and trifluoromethane sulfonic acid.

Scheme 15

A preferred method for the synthesis of the derivatives of formula I, wherein n is 1 and Y is -alkylene-C(O)— or -alkylene-CH(OH)—, is described in scheme 15. The derivatives of formula I, wherein n is 1 and Y is -alkylene-C(O)— are named I-n and the derivatives of formula I, wherein n is 1 and Y is -alkylene-CH(OH)— are named I-o in scheme 15.

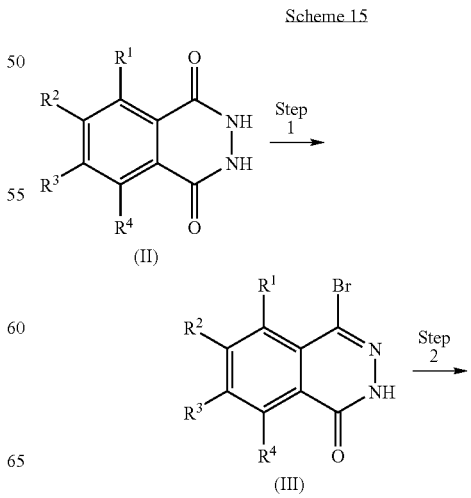

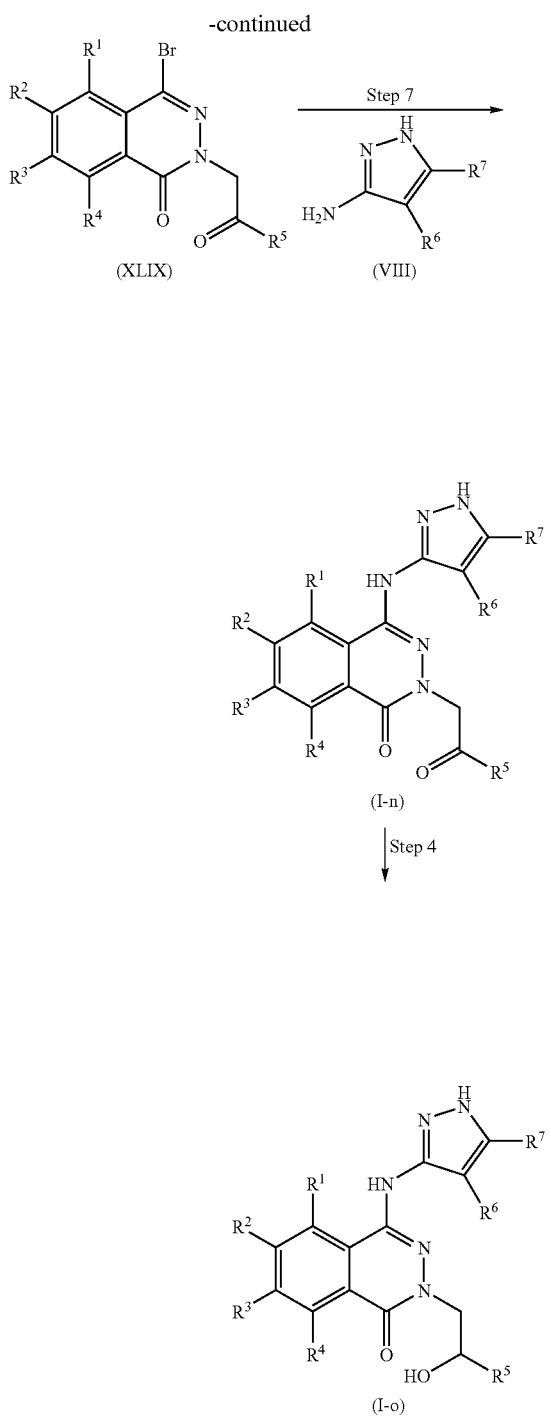

(XLIX) (VIII)

(I-n)

Step 4

(I-o)

A preferred method for the synthesis of the compounds of formula I-n and I-o starts from the corresponding Phthalazine diones of formula II. Step 1 of the reaction sequence (scheme 15) is a two step process in which a dibromination is followed by a monohydrolysis, yielding the 4-bromophthalazinone derivatives of formula III. The first step (dibromination) is typically carried out without solvent, or in solvents like dichloromethane, dichloroethane, anisole, and mixtures thereof, at temperatures between 30° C. and 150° C. Typically used brominating reagents are phosphorus oxybromide, phosphorus pentabromide and phosphorus tribromide. The second step (monohydrolysis of the dibromide) is typically carried out in aqueous or anhydrous conditions in solvents such as water, aqueous lithium hydroxide, aqueous sodium hydroxide, aqueous potassium hydroxide, aqueous sodium hydrogen carbonate, aqueous sodium carbonate, aqueous potassium hydrogen carbonate, aqueous potassium carbonate, aqueous methanol, glacial acetic acid at temperatures between 20° C. and 110° C.

In step 2, scheme 15 the obtained compounds of formula III are converted into their corresponding tertiary amides of formula XLIX, using methods well known to someone skilled in the art, e.g. alkylation under basic conditions. The reaction is typically carried out in aproticsolvents such as tetrahydrofuran, N,N-dimethylformamide, dimethyl sulfoxide, N-methylpyrrolidinone and mixtures thereof at temperatures between −78° C. and 100° C. Typically used bases are sodium hydride, potassium hydride, sodium methoxide, potassium tert-butoxide, lithium hexamethyldisilazide, sodium hexamethyldisilazide, potassium hexamethyldisilazide.

In step 3, scheme 14 the obtained compounds of formula XLIX are converted into their corresponding amino pyrazoles of formula I-n, using methods well known to someone skilled in the art, e.g. palladium-mediated amination of imminobromides, vinylbromides or aryl bromides. The reaction is typically carried out in solvents such as tetrahydrofuran, toluene, alkanols such as methanol, ethanol, isopropanol, and mixtures thereof at temperatures between 40° C. and 110° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, palladium tetrakis-triphenylphosphine, bis-triphenylphosphinepalladium dichloride in conjunction with phosphine based ligands such as 2,2′-bi(phenylphosphino)-1,1′-binaphthyl, 4,5-Bis(diphenylphosphino)-9,9 dimethylxanthene and 2-(di-tert-butylphosphino)biphenyl.

In step 4, scheme 15 the obtained compounds of formula I-n are converted into their corresponding alcohols of formula I-o, using methods well known to someone skilled in the art, e.g. reduction of ketones to form alcohols. The reaction is typically carried out in solvents like tetrahydrofuran, dioxane, dichloromethane and mixtures thereof, at temperatures between 0° C. and 100° C. Typically used reducing reagents are lithium borohydride and other reducing agents.

Scheme 16

A preferred method for the synthesis of the derivatives of formula I, wherein $R^5$ is phenyl which is substituted at the para- or meta-position with or —N(alkyl)-R' and R' is —C(O)-aryl, —C(O)-cycloalkyl, —C(O)-alkyl, —C(O)-alkoxyalkyl, —C(O)-alkoxy, —S(O)$_2$-aryl, —S(O)$_2$-alkyl, is described in scheme 16. The derivatives of formula I, wherein $R^5$ is phenyl which is substituted at the para- or meta-position with or —N(alkyl)-R' and R' is —C(O)-aryl, —C(O)-cycloalkyl, —C(O)-alkyl, —C(O)-alkoxyalkyl, —C(O)-alkoxy, —S(O)$_2$-aryl, —S(O)$_2$-alkyl, are named I-p in scheme 16.

Scheme 16

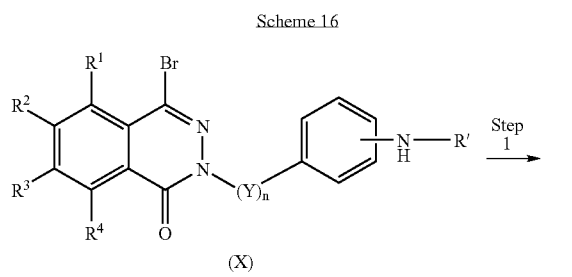

(X)

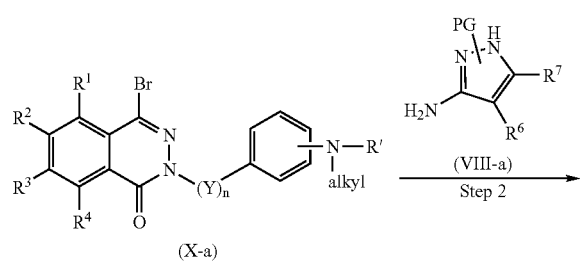

(X-a)

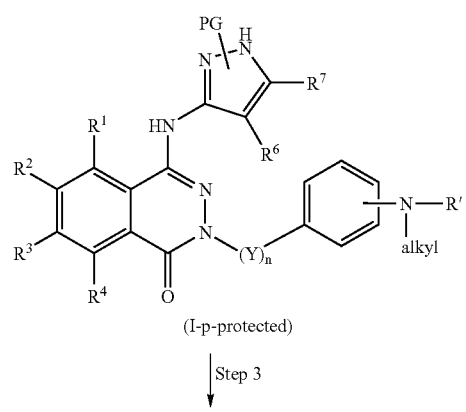

(I-p-protected)

Step 3

-continued

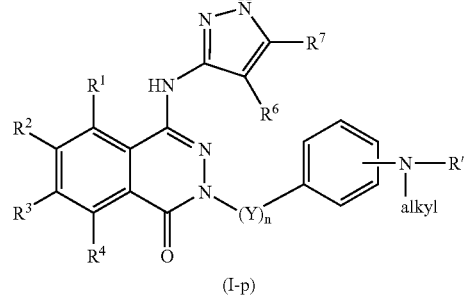

(I-p)

Step 1, scheme 16, is the alkylation of compounds of formula X (see scheme 2) by standard methods known to those skilled in the art, e.g. by alkylation with an alkyl bromide or iodide or tosylate or mesylate, in the presence of a base like sodium hydride, potassium tert.-butoxide, or di-isopropyl ethyl amine to yield the compounds of formula X-a. Suitable inert solvents are for instance N,N-dimethylformamide, dimethyl sulfoxide, N-methylpyrrolidinone, or tetrahydrofuran, and the reaction is carried out in a temperature range from −20° C. to 100° C.

Step 2, scheme 16, is the Buchwald coupling of the bromo-phthalazinones of formula X-a with an protected aminopyrazole of formula VIII-a as described in scheme 1, step 7b yielding the protected phthalazinone-aminopyrazole derivatives of formula I-p-protected Step 3, scheme 16, is the cleavage of the protecting group as described in scheme 1, step 8.

Scheme 17

Certain derivatives of formula I wherein R$^5$ is phenyl which is substituted at the para- or meta-position with a substituent R″″, R″″ being an aryl group or a nitrogen containing heterocyclyl attached via N, a NH-alkyl, a NH-aryl or an alkylsulfanyl or an arylsulfanyl group, are preferably synthesized according to scheme 17. Such derivatives of formula I are named I-q in scheme 17.

Scheme 17

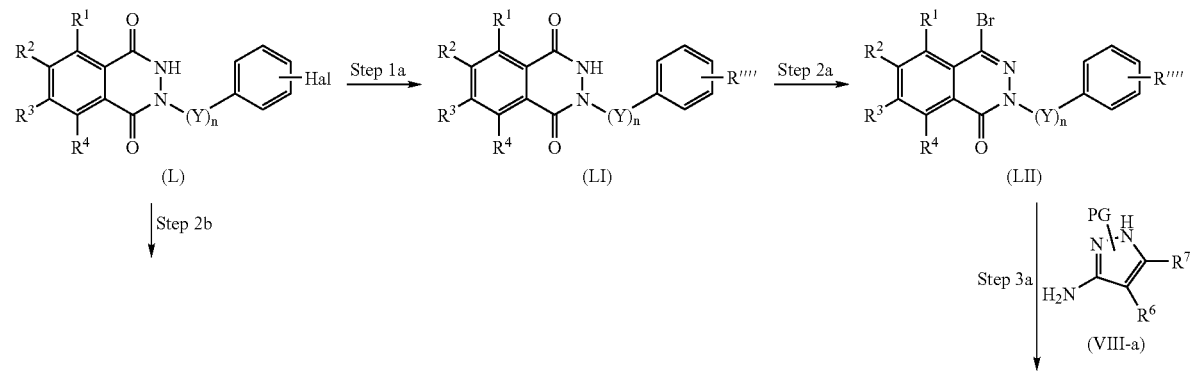

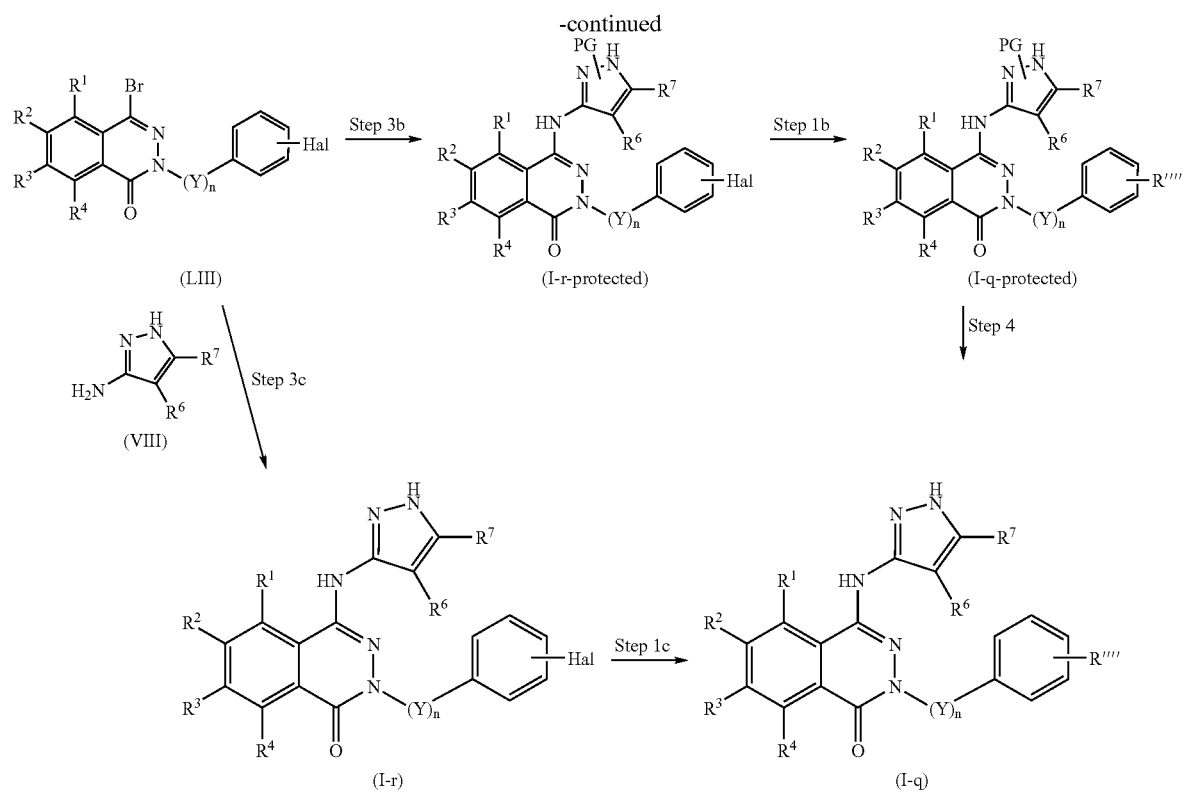

(LIII) (I-r-protected) (I-q-protected)

(VIII)

(I-r) (I-q)

In step 1a, scheme 17, halogen-substituted phthalazinones L, with Hal being iodo or bromo or chloro or fluoro, are converted to compounds of formula LI by a substitution reaction of the aromatic halogen by a group R''''. This can be carried out directly under basic conditions, if the group R'''' comprises a strong nucleophile and the halogen is a fluorine. More preferably, Hal is iodo, bromo or chloro and R'''' is introduced under transition metal catalysis by methods known to the skilled chemist. Typical reactions for this purpose are the Buchwald reaction if R''' is a nitrogen containing heterocyclyl attached via N, a NH-alkyl, a NH-aryl, or an alkylsulfanyl or an arylsulfanyl group. The conditions for such a Buchwald reaction are the same as described for scheme 1, step 7a. If R'''' is an alkylsulfanyl or an arylsulfanyl group, the substitution reaction can also be carried out under Ullman conditions, e.g. in the presence of a Cu catalyst like copper iodide or copper powder in solvents like quinoline, N-methylpyrrolidinone or ethylene glycol, optionally in the presence of e a base like pyridine. The Ullman reaction is carried out at elevated temperatures from 60° C. to 200° C. If R'''' is an aryl group, it is introduced best under the conditions of a Suzuki coupling. In a Suzuki coupling, a boronic acid derivative of R'''' is reacted with L under palladium catalysis by palladium black or a palladium phosphine complex like tetrakis-triphenylphosphino-palladium(0), in the presence of a base like sodium carbonate or potassium fluoride. Suitable solvents are toluene, water, dioxane, tetrahydrofuran, methanol, ethanol, or mixtures thereof, and the Suzuki coupling is run at temperatures from room temperature to 150° C.

Step 2a, scheme 17 is the bromination of a phthalazinedione derivative of formula LI to give a 4-bromophthalazinone derivative of formula LII. The same conditions apply as described for scheme 1, step 6.

Step 3a, scheme 17, is the Buchwald coupling of a bromophthalazinone derivative LII with a protected aminopyrazole VIII-a to give the final products in protected form, I-q-protected. The same methods and conditions apply as described for scheme 1, step 7b.

Step 4, scheme 17, is the deprotection of derivatives I-q-protected to give the final aminopyrazole derivatives I-q. The same conditions apply as described for scheme 1, step 8.

Step 1b, scheme 17, is the substitution reaction of the halogen atom in a protected aminopyrazole derivative of formula I-r-protected. It is carried out with the same methods and conditions as described for step 1a.

Step 2b, scheme 17, is the bromination of phthalazinedione L to give LIII and is carried out as described for scheme 1, step 6.

Step 3b, scheme 17, is the Buchwald coupling of a bromophthalazinone derivative LIII with a protected aminopyrazole VIII-a to give the aminopyrazole derivatives I-r-protected, in protected form. The same methods and conditions apply as described for scheme 1, step 7b. For this step it is preferred that Hal is chloro in order to achieve a selective replacement of only the bromo atom in LIII during the Buchwald reaction.

Step 1c, scheme 17, is the substitution reaction of the halogen atom in an unprotected aminopyrazole derivative of formula I-r. It is carried out with the same methods and conditions as described for step 1a.

Step 3c, scheme 17, is the Buchwald coupling of a bromophthalazinone derivative LIII with a aminopyrazole VIII to give the aminopyrazole derivatives I-r. The same methods and conditions apply as described for scheme 1, step 7a. For this step it is preferred that Hal is chloro in order to achieve a selective replacement of only the bromo atom in LIII during the Buchwald reaction.

If the substituent R'''' is alkylsulfanyl and arylsulfanyl group, these sulfanyl groups can subsequently be oxidized to substituents —S(O)alkyl, —SO$_2$alkyl and —S(O)aryl, —SO$_2$aryl by well known reagents like meta-chloroperbenzoic acid (MCPBA) or Oxone. Such an oxidation step can optionally be carried out at a later stage of the sequence, e.g. after step 2a or after step 3a or after step 1b.

Scheme 18

Another method for the synthesis of the derivatives of formula I, wherein one of $R^1$ to $R^4$ is NH$_2$ or NO$_2$ or $R^8$—$X^{II}$—, with $X^{II}$ being —C(O)NH—, —NHC(O)NH— or —S(O)$_2$NH—, one of $R^1$ to $R^4$ is R''', with R''' being defined as $R^1$ to $R^4$ above for formula I and the remaining two of $R^1$ to $R^4$ are hydrogen, is described in scheme 18. The derivatives of formula I, wherein one of $R^1$ to $R^4$ is $R^8$—$X^{II}$—, with $X^{11}$ being —C(O)NH—, —NHC(O)NH— or —S(O)$_2$NH—, one of $R^1$ to $R^4$ is R''', with R''' being defined as $R^1$ to $R^4$ above for formula I and the remaining two of $R^1$ to $R^4$ are hydrogen, are named I-d in scheme 18. The derivatives of formula I, wherein one of $R^1$ to $R^4$ is NO$_2$, one of $R^1$ to $R^4$ is R''', with R''' being defined as $R^1$ to $R^4$ above for formula I and the remaining two of $R^1$ to $R^4$ are hydrogen, are named I-s in scheme 18. The derivatives of formula I, wherein one of $R^1$ to $R^4$ is NH$_2$, one of $R^1$ to $R^4$ is R''', with R''' being defined as $R^1$ to $R^4$ above for formula I and the remaining two of $R^1$ to $R^4$ are hydrogen, are named I-t in scheme 18.

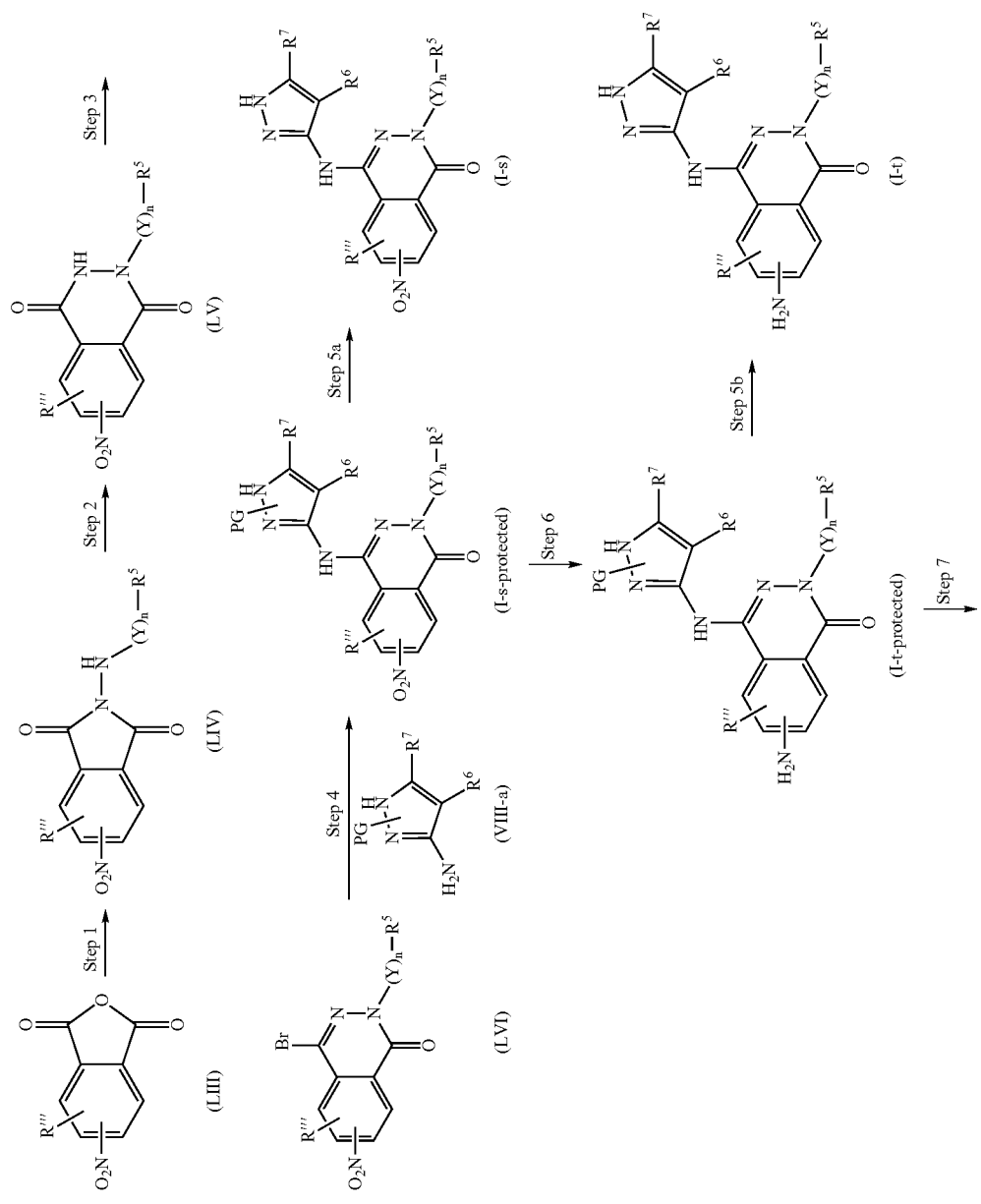

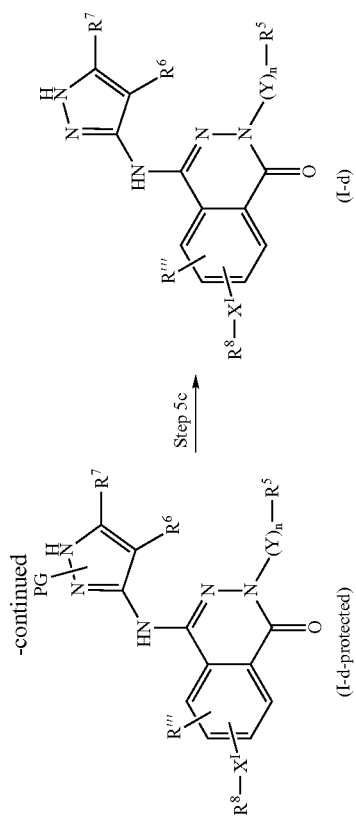

Step 1, scheme 18, is the reaction of a nitro-substituted phthalic anhydride of formula LIII with a substituted hydrazine to give compounds of formula LIV. Step 1 is carried out as described for scheme 1, step 4.

Step 2, scheme 18, is the rearrangement of compounds of formula LIV into phthalazindiones of formula LV and is carried out as described for scheme 1, step 5.

Step 3, scheme 18, is the bromination of phthalazindiones LV to give the 4-bromophthalazinones LVI, and is carried out as described for scheme 1, step 6.

Step 4, scheme 18, is the Buchwald reaction of bromophthalazinones LVI with a protected aminopyrazole derivative VIII-a to yield derivatives of formula I-s-protected and is carried out as described in scheme 1, step 7b.

Step 5a, scheme 18, is the deprotection of derivatives I-s-protected to give the nitro-substituted derivatives I-s and is carried out as described for scheme 1, step 8.

In step 6, scheme 18, the obtained compounds of formula I-s-protected are converted into their corresponding anilines of formula I-t-protected, using methods well known to someone skilled in the art, e.g. aniline formation by the reduction of nitrobenzenes. The reaction is typically carried out in solvents like N,N-dimethylformamide, N-methylpyrrolidinone, acetonitrile, acetic acid, ethanol and methanol, and mixtures thereof, at temperatures between 20° C. and 100° C. Typically used reducing reagents are tin(II) chloride, tin(II) chloride monohydrate, iron trichloride. Alternatively, the nitro group can be reduced by catalytic hydrogenation with palladium on charcoal as the catalyst in solvents like methanol or tetrahydrofuran, at temperatures between 20° C. and 100° C.

In step 7 scheme 18, the obtained aniline compounds of formula I-t-protected are converted into their corresponding amides, sulfonamides or ureas of formula I-d-protected, using methods well known to someone skilled in the art, e.g. sulfonylation, acylation or aminocarboxylation of anilines. The reaction is typically carried out in aprotic solvents such as dichloromethane, ethyl acetate, tetrahydrofuran, N,N-dimethylformamide, dimethyl sulfoxide, N-methylpyrrolidinone and mixtures thereof at temperatures between 0° C. and 80° C. Typically used bases are triethylamine, N,N-diisopropyl ethylamine, pyridine, potassium carbonate and 4-(dimethylamino)pyridine.

Step 5b, scheme 18, is the deprotection of derivatives I-t-protected to give the amino-substituted derivatives I-t and is carried out as described for scheme 1, step 8.

Step 5c, scheme 18, is the deprotection of derivatives I-d-protected to give the substituted derivatives I-d and is carried out as described for scheme 1, step 8.

For a few special cases the different reaction sequences can alternatively involve the step of generating a monochloro derivative of the phthalazinedione instead of the usual monobromo derivative, followed directly or after some intermediary steps by a Buchwald reaction with the appropriate aminopyrazoles (see e.g. Scheme 19).

Scheme 19

Another method for the synthesis of the derivatives of formula I, wherein one of $R^1$ to $R^4$ is $NO_2$, the remaining two of $R^1$ to $R^4$ are hydrogen, $R^5$ is hydrogen and n is 0, is described in scheme 19. The derivatives of formula I, wherein one of $R^1$ to $R^4$ is $NO_2$, the remaining two of $R^1$ to $R^4$ are hydrogen, $R^5$ is hydrogen and n is 0, are named I-u in scheme 19.

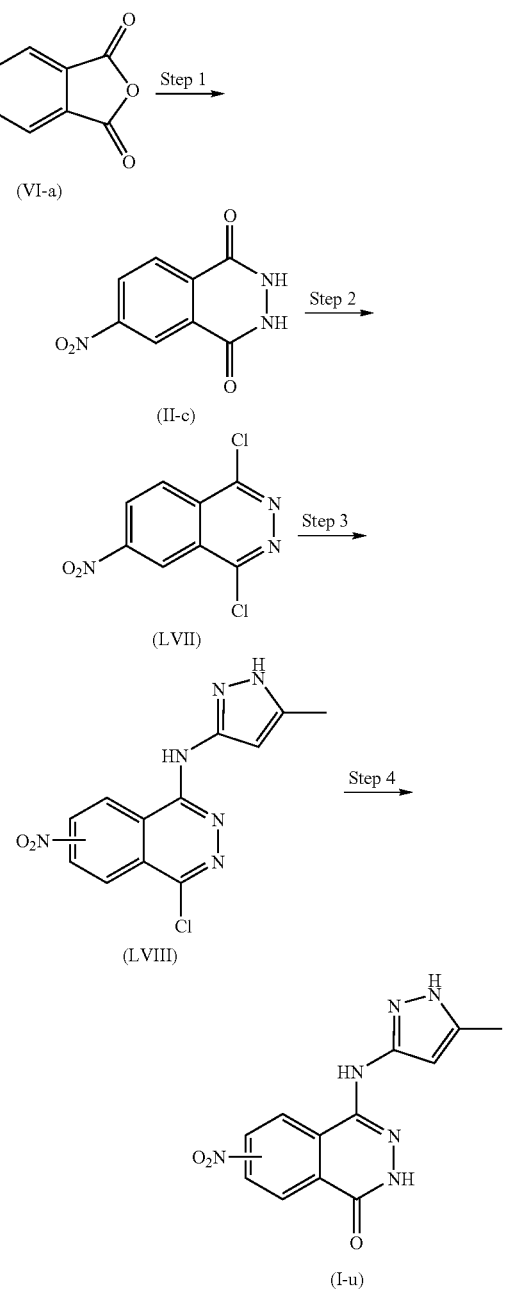

In step 1, scheme 19 the substituted phthalic anhydrides [compounds of formula (VI-a)] are converted into their corresponding Phthalazinones of formula (II-c), using methods well known to someone skilled in the art, e.g. hydrazine mediated ring expansion of phthalic anhydrides. The reaction is typically carried out in aprotic solvents such as tetrahydrofuran, N,N-dimethylformamide, N-methylpyrrolidinone or protic solvents such as acetic acid, ethanol, methanol and isopropanol and mixtures thereof at temperatures between 0° C. and 120° C. Typically used reagents are hydrazine, hydrazine hydrate and hydrazine hydrochloride. (This method can also be used to obtain phthalazinones of formula I wherein $R^5$ is not hydrogen, when N-substituted hydrazine, hydrazine hydrate and hydrazine hydrochloride instead and the next steps were accordingly).

In step 2, scheme 19 the obtained compounds of formula (II-c) are converted into their corresponding dichlorophthalazines of formula (LVII), using methods well known to someone skilled in the art, e.g. iminochloride formation from secondary amides. The reaction is typically carried out without solvent, or in solvents like dichloromethane, dichloroethane and anisole, and mixtures thereof, at temperatures between 30° C. and 150° C. Typically used chlorinating reagents are phosphorus oxychloride, phosphorus pentachloride and phosphorus trichloride, in the presence or absence of bases such as pyridine, triethylamine and N,N-diisopropylethylamine.

In step 3, scheme 19 the obtained compounds of formula (LVII) are converted into their corresponding aminopyrazole (LVIII), using methods well known to someone skilled in the art, e.g. aromatic substitution displacements of iminochlorides with amines. The reaction is typically carried out in solvents such as tetrahydrofuran, pyridine, toluene, alkanols such as isopropanol or tert-butanol, and mixtures thereof at temperatures between 40° C. and 150° C.

In step 4, scheme 19 the iminochlorides of formula (LVIII) are converted into their corresponding amide (I-u), using methods well known to someone skilled in the art, e.g., monohydrolysis of the iminochloride. The reaction is typically carried out under aqueous or anhydrous conditions in solvents such as water, aqueous lithium hydroxide, aqueous potassium hydroxide, aqueous sodium carbonate, aqueous potassium hydrogen carbonate, aqueous potassium carbonate, aqueous methanol, glacial acetic acid at temperatures between 20° C. and 110° C.

In the above schemes 1 to 19, certain substituents on the groups $R^1$ to $R^4$ and $R^5$ may not be inert to the conditions of the synthesis sequences described above and may require protection by standard protecting groups known in the art. For instance, an amino or hydroxyl group may be protected as an acetyl or tert.-butoxycarbonyl derivative. Alternatively, some substituents may be derived from others at the end of the reaction sequence. For instance, a compound of formula I may be synthesized bearing a nitro-, an ethoxycarbonyl, a sulfonic acid substituent on the group $R^1$ to $R^4$ and $R^5$, which substituents are finally converted to an amino-, alkylamino-, dialkylamino-, acylamino-, alkylsulfonylamino, arylsulfonylamino substituent, or to a carboxamide substituent, or to a sulfonamide substituent by standard procedures.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic bases or from organic or inorganic acids. Examples of base-addition salts include those derived from sodium, potassium, ammonium, quaternary ammonium hydroxides (such as for example, tetramethylammonium hydroxide). Examples of acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, naphthalenesulfonic acid, naphthalenedisulfonic acid, methanesulfonic acid, ethanesulfonic acid and the like. The chemical modification of a pharmaceutical compound (i.e. a drug) into a salt is a technique well known to pharmaceutical chemists to obtain improved physical and chemical stability, hygroscopicity, flowability and solubility of compounds. See, e.g. Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427–435.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

Pharmacological Activity

The compounds of formula I and their pharmaceutically acceptable salts possess valuable pharmacological properties. It has been found that said compounds show activity as inhibitors of the Aurora kinase family and also show antiproliferative activity. Consequently the compounds of the present invention are useful in the therapy and/or prevention of illnesses with known over-expression of kinases of the Aurora family preferably Aurora A, especially in the therapy and/or prevention of illnesses mentioned above. The activity of the present compounds as inhibitors of the Aurora kinase family is demonstrated by the following biological assay:

$IC_{50}$ Determination for Inhibitors of Aurora A (96 MTP-ELISA)

Assay Principle

Aurora A is a serine threonine kinase involved in spindle assembly and chromosome segregation.

The assay is a typically ELISA-type assay where biotinylated substrate (PKB-GSK2) is phosphorylated. Phosphorylation is detected by peroxidase (POD) labelled polyclonal antibody (PAK<M-Ig>S-IgG-POD) and phosphopeptide monoclonal antibody (Mab) (MAK<P-GSK>M-27E5-IgG). The assay is validated for $IC_{50}$-determination.

Materials

Assay plates 96-well polystyrene plates, streptavidin-coated

Samples 10 mM in dimethylsulfoxide (DMSO)

Aurora A-His-4 C-terminally Histidine$_4$ (His$_4$)-tagged Aurora A full-length protein, stock solution 0.7 mg/ml, final conc.: 250 ng/ml PKB-GSK2 biotinylated peptide derived from human GSK3α sequence (Biotin-SGRARTSSFAEPGG-CONH$_2$), stock solution 600 µM, final conc.: 200 nM.

PAK<M-Ig>S-IgG-POD Anti-mouse IgG, HRP-linked Antibody, diluted in 3% BSA/PBS-T (1:10000), (Cell Signaling, Cat. No.: 7076)

MAK<P-GSK>M-27E5-IgG Phospho-GSK-3α (Ser 21) (27E5) Monoclonal Antibody, stock solution 1.85 mg/ml, diluted in 3% BSA/PBS-T (1:6000), final conc.: 0.31 µg/ml, (Cell Signaling, Cat. No.: 9337B)

ATP Adenosine-5'-triphosphate 1 mM, diluted in kinase buffer, (, Cat. No.: 127531-001), final conc.: 4 µM TRIS 2-Amino-2-hydroxymethyl-1,3-propoanediol ("tris-(hydroxymethyl)-aminomethane") (MERCK, Cat. No.: 108382.2500)

BSA Bovine Serum Albumin Fraction V, fatty acid free (Roche Diagnostics GmbH, Cat. No. 9100221)

EDTA Titriplex III (di-Sodium-EDTA di-Hydrate), 120 mM, (MERCK, Cat. No.: 1.08418.1000)

ABTS buffer ABTS (2,2'-azino-bis(3-ethylbenzthiazoline-6-sulfonic acid))16.7 mg/ml (Roche Diagnostics GmbH, Cat. No.: 1204530)
ABTS tablets dissolve one ABTS tablet in 50 ml of working solution (ABTS buffer) (Roche Diagnostics GmbH, Cat. No.: 1112422)
Tween 20 Polysorbat 20 (Roche Diagnostics GmbH, Cat. No.: 10006394-001)
DTT 1,4-Dithiothreitol (Roche Diagnostics GmbH, Cat. No.: 197777)
$MgCl_2 \times 6H_2O$ MERCK, Cat. No.: 105833.1000
Kinase buffer 50 mM TRIS, 10 mM $MgCl_2$, 1 mM DTT, 0,1% Tween 20, pH 7.8
PBS-T (=Wash buffer) (PBS-T) 10 g/l PBS(Phosphate buffered saline) with 0.033%
Tween 20
3% BSA/PBS-T 3% BSA dissolved in PBS-T
Method
This assay is performed in 96-well format for $IC_{50}$ determination with 5 samples (each with 8 concentrations by twofold testing), 100 μl incubation volume and the following plate layout:

|   | 1  | 2   | 3   | 4   | 5   | 6   | 7   | 8  | 9   | 10  | 11  | 12  |
|---|----|-----|-----|-----|-----|-----|-----|----|-----|-----|-----|-----|
| A | NC | RS a | RS a | S1a | S1a | S2a | S2a | NC | S3a | S3a | S4a | S4a |
| B | NC | RS b | RS b | S1b | S1b | S2b | S2b | NC | S3b | S3b | S4b | S4b |
| C | NC | RS c | RS c | S1c | S1c | S2c | S2c | NC | S3c | S3c | S4c | S4c |
| D | NC | RS d | RS d | S1d | S1d | S2d | S2d | NC | S3d | S3d | S4d | S4d |
| E | PC | RS e | RS e | S1e | S1e | S2e | S2e | PC | S3e | S3e | S4e | S4e |
| F | PC | RS f | RS f | S1f | S1f | S2f | S2f | PC | S3f | S4f | S4f | S4f |
| G | PC | RS g | RS g | S1g | S1g | S2g | S2g | PC | S3g | S4g | S4g | S4g |
| H | PC | RS h | RS h | S1h | S1h | S2h | S2h | PC | S3h | S4h | S4h | S4h |

NC negative control, without ATP, 1% DMSO
PC positive control, with ATP, 1% DMSO
S samples, with ATP, 1% DMSO, final conc.: a = 100 μM, b = 20 μM, c = 4 μM, d = 0.8 μM, e = 0.16 μM, f = 0.032 μM, g = 0.0064 μM, h = 0.00128 μM Step/Action Sample preparation: add 24 μl per well samples (descending sequence) diluted in kinase buffer to assay plate (final conc. for DMSO 1%).

Add directly 16 μl Aurora-A-his-4 diluted in kinase buffer to assay plate.

Add directly 40 μl per well PKB_GSK2/ATP mixture to assay plate, (final conc.: Aurora A=250 ng/ml, GSK2=200 nM, ATP=4 μM).

Negative control: without ATP.

Incubate assay plate for exactly 90 min at room temperature.

Stop reaction by adding 20 μl EDTA in all wells.

Wash assay plate 3× with 200 μl washing buffer per well.

Add 100 μl MAK<P-GSK>M27E5-IgG (1:10000) and PAK<M-Ig>S-IgG-POD (1:6000) dissolved in 3% BSA/PBS-T to assay plate per well.

Incubate assay plate for 60 min at room temperature.

Wash assay plate 3× with 200 μl washing buffer per well

Add 100 μl ABTS solution to assay plate per well, incubate for approx. 4 min at RT on MTP shaker.

Measure absorption at 405/492 nm.
Calculate % inhibition as:

$$(1-(E_{sample}-E_{NC})/(E_{PC}-E_{NC})) \times 100$$

Calculate $IC_{50}$ using a non-linear curve fit (XLfit software (ID Business Solution Ltd., Guilford, Surrey, UK))

Results: Table 1

| Examples | IC50 Aurora A kinase inhibition [nM] |
|---|---|
| G-5 | 7 |
| A-1 | 31 |
| A-2 | 65 |
| D-2 | 555 |
| A-5, A-7, A-9, A-11, A-12, A-14, A-18, A-20, A-22, A-23, A-24, A-25, C-1, B-2, D-1, E-2, E-4, E-5, E-9, F-1, F-3, F-4, F-5, F-6, F-8, F-9, G-1, G-2, G-4, G-7, G-8, G-9, H-1, H-2, I-1, I-2, I-3, I-4, I-5, I-6, I-11, I-12, I-13, I-14, K-1, K-2, | 1–100 |

-continued

Results: Table 1

| Examples | IC50 Aurora A kinase inhibition [nM] |
|---|---|
| L-1, L-2, M-1, M-2, M-3, M-4, M-7, M-8, M-9, N-1, P-1, P-2, Q-2, R-1, R-3, R-4, T-5, U-1, U-2, W-2, W-3, V-1, X-2, Y-2, ZA-1, ZB-1, ZB-3, A-3, A-8, A-10, A-16, B-3, E-6, E-7, E-13, F-7, K-3, M-10, O-1, O-2, S-1, T-1, T-3, T-4, W-1, X-1, Z-1 | 100–1000 |

Antiproliferative Activity

The activity of the present compounds as antiproliferative agents is demonstrated by the following biological assay:

CellTiter-Glo™ Assay in HCT 116 Cells

The CellTiter-Glo™ Luminescent Cell Viability Assay (Promega) is a homogeneous method of determining the number of viable cells in culture based on quantitation of the ATP present, which signals the presence of metabolically active cells.

HCT 116 cells (human colon carcinoma, ATCC-No. CCl-247) were cultivated in RPMI 1640 medium with GlutaMAX™ I (Invitrogen, Cat-No. 61870-010), 2.5% Fetal Calf Serum (FCS, Sigma Cat-No. F4135 (FBS)); 100 Units/ml penicillin/100 µg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the CellTiter-Glo™ assay was done according to the instructions of the manufacturer (CellTiter-Glo™ Luminescent Cell Viability Assay, from Promega). In brief: the cell-plate was equilibrated to room temperature for approximately 30 minutes and than the CellTiter-Glo™ reagent was added. The contents were carefully mixed for 15 minutes to induce cell lysis. After 45 minutes the luminescent signal was measured in Victor 2, (scanning multiwell spectrophotometer, Wallac).

Details:
1st. Day:
Medium: RPMI 1640 with GlutaMAX™ I (Invitrogen, Cat-Nr. 61870), 5% FCS (Sigma Cat.-No. F4135), Pen/Strep (Invitrogen, Cat No. 15140).
HCT116 (ATCC-No. CCl-247): 1000 cells in 60 µl per well of 384 well plate (Greiner 781098, µClear-plate white)
After seeding incubate plates 24 h at 37° C., 5% $CO_2$
2nd. Day: Induction (Treatment with Compounds, 10 Concentrations):
In order to achieve a final concentration of 30 µM as highest concentration 3.5 µl of 10 mM compound stock solution were added directly to 163 µl media. Then step e) of the dilution procedure described below, was followed.
In order to achieve the second highest to the lowest concentrations, a serial dilution with dilution steps of 1:3 was followed according to the procedure (a-e) as described here below:
a) for the second highest concentration add 10 µl of 10 mM stock solution of compound to 20 µl dimethylsulfoxide (DMSO)
b) dilute 8×1:3 (always 10 µl to 20 µl DMSO) in this DMSO dilution row (results in 9 wells with concentrations from 3333.3 µM to 0.51 µM)
c) dilute each concentration 1:47.6 (3.5 µl compound dilution to 163 µl media)
e) add 10 µl of every concentration to 60 µl media in the cell plate resulting in final concentration of DMSO: 0.3% in every well and resulting in 10 final concentration of compounds ranging from 30 µM to 0.0015 µM.
Each compound is tested in triplicate.
Incubate 120 h (5 days) at 37° C., 5% $CO_2$ Analysis:
Add 30 µl CellTiter-Glo™ Reagent (prepared from CellTiter-Glo™ Buffer and CellTiter-Glo™ Substrate (lyophilized) purchased from Promega) per well,
shake 15 minutes at room temperature
incubate further 45 minutes at room temperature without shaking Measurement:
Victor 2 scanning multiwell spectrophotometer (Walac), Luminescence mode (0.5 sec/read, 477 nm)
Determine IC50 using a non-linear curve fit (XLfit software (ID Business Solution Ltd., Guilford, Surrey, UK))
With all compounds a significant inhibition of HCT 116 cell viability was detected, which is exemplified by the compounds shown in Table 2.

Results: Table 2

| Examples | IC50 HCT 116 [µM] |
| --- | --- |
| A-1 | 1.66 |
| B-2 | 0.78 |
| D-1 | 4.19 |
| F-8 | 0.42 |
| A-2, A-3, A-4, A-5, A-8, A-12, A-13, A-15, A-16, A-20, A-22, A-25, B-1, B-3, C-1, C-2, E-2, E-3, E-5, E-7, E-9, E-10, E-11, E-12, F-1, F-2, F-3, F-4, F-5, F-9, G-1, G-2, G-4, G-5, G-7, G-9, H-1, H-3, I-1, I-3, I-4, I-6, I-7, I-10, I-13, I-14, J-2, K-1, K-2, L-2, M-2, M-3, M-5, M-8, M-9, M-10, N-1, P-1, R-1, R-4, S-1, T-2, T-3, T-4, U-1, U-2, U-3, V-1, W-2, X-1, Y-1, Y-3, Z-1, ZA-1, ZA-2, ZB-1, ZB-2, ZB-3, ZB-6 | 0.1–10.0 |
| E-6, E-13, M-7, O,-1, P-2, Q-1, W-3 | 10.0–100 |

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or it's salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical compositions comprise e.g. the following:
Tablet Formulation (Wet Granulation):

| Item | Ingredients | mg/tablet | | | |
| --- | --- | --- | --- | --- | --- |
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
Mix items 1, 2, 3 and 4 and granulate with purified water.
Dry the granules at 50° C.
Pass the granules through suitable milling equipment.
Add item 5 and mix for three minutes; compress on a suitable press.

Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
Mix items 1, 2 and 3 in a suitable mixer for 30 minutes.
Add items 4 and 5 and mix for 3 minutes.
Fill into a suitable capsule.

Micro Suspension

Weigh 4.0 g glass beads in custom made tube GL 25.4 cm (the beads fill half of the tube).
Add 50 mg compound, disperse with spatulum and vortex.
Add 2 ml gelatin solution (weight beads: gelatin solution=2:1) and vortex.
Cap and wrap in aluminum foil for light protection.
Prepare a counter balance for the mill.
Mill for 4 hours, 20/s in a Retsch mill (for some substances up to 24 hours at 30/s).
Extract suspension from beads with two layers of filter (100 μm) on a filter holder, coupled to a recipient vial by centrifugation at 400 g for 2 min.
Move extract to measuring cylinder.
Repeat washing with small volumes(here 1 ml steps) until final volume is reached or extract is clear.
Fill up to final volume with gelatin and homogenize.

The above described preparation yields micro-suspensions of the compounds of formula I with particle sizes between 1 and 10 μm. The suspensions are suitable for oral applications and can be used in vivo assays.

Medicaments containing a compound of the present invention or a pharmaceutically acceptable salt thereof and a therapeutically inert carrier are an object of the present invention, as is a process for their production, which comprises bringing one or more compounds of the present invention and/or pharmaceutically acceptable salts and, if desired, one or more other therapeutically valuable substances into a galenical administration form together with one or more therapeutically inert carriers.

In accordance with the invention the compounds of the present invention as well as their pharmaceutically acceptable salts are useful in the control or prevention of illnesses. Based on their Aurora tyrosine kinase inhibition and their antiproliferative activity, said compounds are useful for the treatment of diseases such as cancer in humans or animals and for the production of corresponding medicaments. The dosage depends on various factors such as manner of administration, species, age and/or individual state of health. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1000 mg, should be appropriate, although the upper limit may be exceeded when indicated. The daily dosage can be administered as a single dose or in divided doses, or for parenteral administration, it may be given as a continuous infusion.

Another embodiment of the invention is a medicament containing one or more compounds of formula I as active ingredients together with pharmaceutically acceptable adjuvants.

Another embodiment of the invention is a medicament containing one or more compounds of formula I as active ingredients together with pharmaceutically acceptable adjuvants for the treatment of diseases mediated by an inappropriate activation of Aurora A tyrosine kinase.

Another embodiment of the invention is a medicament containing one or more compounds of formula I as active ingredients together with pharmaceutically acceptable adjuvants for the treatment of cancer.

Another embodiment of the invention is a medicament containing one or more compounds of formula I as active ingredients together with pharmaceutically acceptable adjuvants for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is a medicament containing one or more compounds of formula I as active ingredients together with pharmaceutically acceptable adjuvants for the treatment of acute-myelogenous leukemia (AML, acute lymphocytic leukemia (ALL) and gastrointestinal stromal tumor (GIST).

Another embodiment of the invention is the use of one or more compounds of formula I for the manufacture of medicaments for the treatment of diseases mediated by an inappropriate activation of Aurora A tyrosine kinases.

Another embodiment of the invention is the use of one or more compounds of formula I for the manufacture of medicaments for the treatment of cancer Another embodiment of the invention is the use of the compounds of formula I as Aurora A tyrosine kinase inhibitors.

Another embodiment of the invention is the use of the compounds of formula I as anti-proliferating agents.

Another embodiment of the invention is the use of one or more compounds of formula I for the treatment of cancer.

The following examples and references are provided to aid the understanding of the present invention, the true scope of which is set forth in the appended claims. It is understood that modifications can be made in the procedures set forth without departing from the spirit of the invention.

EXAMPLES

Generic Experimental for the Synthesis of Phthalazinone Derivatives

Method A

Example A-1

4-(5-Methyl-2H-pyrazole-3-ylamino)-phenyl-2H-phthalazin-1-one

2-Phenyl-2,3-dihydro-phthalazine-1,4-dione
Phenyl hydrazine (59.4 g, 0.55 mol) was added in one portion to a stirred mixture of phthalic anhydride (74.0 g, 0.5 mmol), in acetic acid (500 ml) at room temperature. The reaction mixture was heated to 125° C. for 2 hours, and then allowed to cool to room temperature. The resultant suspension was poured into water (500 ml) and the solid was isolated by filtration. The solid was then stirred in 1M Na$_2$CO$_3$ (400 ml), and the remaining undissolved solid removed by filtration. This solid was washed with two further 400 ml portions of 1M Na$_2$CO$_3$.

The basic solutions were combined and acidified by dropwise addition of concentrated HCl until gas evolution ceased. The precipitate formed was isolated by filtration and dried for 18 hours in a vacuum oven (50° C.) to give the phthalazinone as a white solid (46.3 g, 39% yield). $^1$H-NMR: (400 MHz; D$_6$-DMSO); 11.7 (1H, br. s), 8.30 (1H, d), 8.03 (1H, d), 7.93 (2H, m), 7.67 (1H, d), 7.51 (1H, t), 7.4 (1H, t); MS (ESI$^+$)=(M+H)$^+$ 239

4-Bromo-2-phenyl-2H-phthalazin-1-one (Bromination)

Phosphorus oxybromide (3.13 g, 10.9 mmol) was added to a stirred suspension of 2-phenyl-2,3-dihydro-phthalazine-1,4-dione (1.30 g, 5.4 mmol) in 1,2 dichloroethane (15.0 ml). The reaction was heated to 100° C. for 18 hours and then cooled and poured into water.

The aqueous layer was made basic with 1M Na$_2$CO$_3$, then extracted into dichloromethane (DCM) (3×100 ml). The organic layers were combined, dried (MgSO$_4$) and concentrated under vacuum. The residue was purified by silica column chromatography (20% ethyl acetate:hexane) to give the bromophthalazinone as a white solid (0.770 g, 2.6 mmol, 48% yield). $^1$H-NMR: (400 MHz; D$_6$-DMSO); 8.20 (1H, dd), 7.91 (1H, td), 7.89 (1H, td), 7.35–7.55 (5H, m); MS (ESI$^+$)=(M+H)$^+$ 301, 303

4-(5-Methyl-2H-pyrazole-3-ylamino)-phenyl-2H-phthalazin-1-one (A-1)

(Typical Procedure for the Buchwald Reaction)

Degassed toluene (6 ml) and ethanol (3 ml) were added in one portion to a mixture of 4-bromo-2-phenyl-2H-phthalazin-1-one (0.750 g, 2.5 mmol), sodium t-butoxide (0.337 g, 3.5 mmol), 3-amino-5-methyl pyrazole (0.291 g, 3 mmol), tris-(dibenzylideneacetone)-dipalladium (0.115 g, 0.125 mmol) and 2-(di-t-butylphosphino)-biphenyl (0.075 g, 0.25 mmol) under nitrogen. The reaction mixture was heated to 100° C. for 20 hours with stirring and then cooled to room temperature. Diethyl ether (10 ml) was added and the precipitated solid was filtered to give the crude product as a grey solid (0.6 g, 76% yield). A 0.06 g portion of the crude product was triturated with acetonitrile (2 ml) and water (2 ml) to give the target compound (0.045 g, 58% yield based on recovered materials). $^1$H-NMR: (400 MHz, D$_6$-DMSO) 11.96 (1H, s), 9.33 (1H, s), 8.53 (1H, d), 8.38 (1H, d), 7.92–7.99 (2H, m), 7.88 (2H, d), 7.77 (2H, t) 7.34 (1H, t) 6.24 (1H, s) 2.18 (3H, s) MS (ESI$^+$)=(M+H)$^+$ 318.29.

Using the experimental conditions reported above (Method A) and the appropriate starting materials, the following derivatives were prepared:

| Example-No. | Systematic name | $^1$H-NMR | MS (ESI+, M+H) |
|---|---|---|---|
| A-2 | 2-Benzyl-4-(5-methyl-1H-pyrazol-3-ylamino)-2H-phthalazin-1-one | (400MHz, D$_6$-DMSO) 11.86(1H, s), 9.25(1H, s), 8.46(1H, d), 8.32(1H, d), 7.84–7.94(2H, m), 7.25–7.38(5H m), 6.10(1H, s), 5.24(2H, s) 2.17(3H, s) | 332.08 |
| A-3 | 2-Methyl-4-(5-methyl-1H-pyrazol-3-ylamino)-2H-phthalazin-1-one | (400MHz, D$_6$-DMSO) 11.70(1H, s), 9.00(1H, s), 8.23(1H, d), 8.10(1H d), 7.73–7.64(2H, m), 6.13(1H, S), 3.44(3H S), 2.04(3H, s) | 389.27 |
| A-4 | 2-Isobutyl-4-(5-methyl-1H-pyrazol-3-ylamino)-2H-phthalazin-1-one | (400MHz, D$_6$-DMSO) 11.76(1H, s), 9.00(1H, s), 8.2(1H, d), 8.15(1H d), 7.77–7.67(2H, m), 6.17(1H, S), 3.71(2H d), 2.10–2.07(4H, m), 0.75(6H, d) | 298.33 |
| A-5 | 4-(5-Methyl-1H-pyrazol-3-ylamino)-2-(2,2,2-trifluoro-ethyl)-2H-phthalazin-1-one | (400MHz, D$_6$-DMSO) 9.58(1H, s), 8.47(1H, d), 8.34(1H, d), 8.01–7.83(2H m), 6.34(1H, S), 4.93(2H q), 2.25(3H, s) | 323.10 |
| A-6 | 4-(5-Methyl-1H-pyrazol-3-ylamino)-2-p-tolyl-2H-phthalazin-1-one | (400MHz, D$_6$-DMSO) 11.70(1H s), 9.04(1H, s), 8.26(1H, d), 8.11(1H, d), 7.74–7.64(2H m), 7.34(2H, d), 7.05(2H d), 6.01(1H, s), 2.14(3H, s), 1.94(3H, s) | 332.34 |
| A-7 | 2-(4-Fluoro-phenyl)-4-(5-methyl-1H-pyrazol-3-ylamino)-2H-phthalazin-1-one | (400MHz, D$_6$-DMSO) 12.17(1H s), 9.51(1H, s), 8.73(1H, d), 8.59(1H, d), 8.20–8.10(2H m), 7.99–7.95(2H, m), 7.55(2H t), 6.45(1H, s), 2.40(3H, s) | 336.31 |
| A-8 | 2-(4-tert-Butyl-phenyl)-4-(5-methyl-1H-pyrazol-3-ylamino)-2H-phthalazin-1-one | (400MHz, D$_6$-DMSO) 9.36(1H, s), 8.46(1H, d), 8.38(1H, d), 8.00–7.89(2H m), 7.62(2H, d), 7.50(2H, d) 6.24(1H, s), 2.21(3H, s), 1.34(9H, s) | 374.40 |
| A-9 | 2-(4-Methoxy-phenyl)-4-(5-methyl-1H-pyrazol-3-ylamino)-2H-phthalazin-1-one | (400MHz, D$_6$-DMSO) 11.72(1H, s) 9.05(1H, s), 8.28(1H, d), 8.15(1H, d), 7.76–7.66(2H m), 7.40(2H, d), 6.84(2H, d) 6.03(1H, s), 3.61(3H, s), 1.97(3H, s) | 348.34 |
| A-10 | 4-(1H-Pyrazol-3-ylamino)-2-p-tolyl-2H-phthalazin-1-one | (400MHz, D$_6$-DMSO) 12.05(1H, s) 9.22(1H, s), 8.33(1H, d), 8.15(1H, d), 7.78–7.68(2H m), 7.39–7.37(3H, m), 7.09(2H, d) 6.29(1H, s), 2.16(3H, s) | 318.32 |
| A-11 | 2-(4-Methoxy-benzyl)-4-(5-methyl-1H-pyrazol-3-ylamino)-2H-phthalazin-1-one | (400MHz, D$_6$-DMSO) 11.91(1H, s), 9.28(1H, s), 8.47(1H, d), 8.36(1H, d), 7.97–7.89(2H, m), 7.37(2H, d), 6.18(1H, s), 5.21(2H, s), 3.76(3H, s), 2.24(3H, s) | 362.36 |
| A-12 | 2-(3-Methoxy-benzyl)-4-(5-methyl-1H-pyrazol-3-ylamino)-2H-phthalazin-1-one | (400MHz, D$_6$-DMSO) 11.88(1H, s), 9.23(1H, s), 8.44(1H, d), 8.32(1H, d), 7.92–7.86(2H, m), 7.24(1H, t), 6.96(1H, d), 6.93(1H, s), 6.84(1H, s), 6.15(1H, s), 5.21(2H, s), 3.72(3H, s), 2.18(3H, s) | 362.35 |
| A-13 | 2-(2,5-Difluoro-benzyl)-4-(5-methyl-1H- | (400MHz, D$_6$-DMSO) 11.88(1H, s), 9.25(1H, s), 8.32(1H, d), | 368.14 |

| Example-No. | Systematic name | ¹H-NMR | MS (ESI+, M+H) |
|---|---|---|---|
| | pyrazol-3-ylamino)-2H-phthalazin-1-one | 7.93–7.85(2H, m), 7.32–7.21(3H, m), 5.93(1H, s), 5.29(2H, s), 2.16(3H, s) | |
| A-14 | 2-(4-Methanesulfonyl-benzyl)-4-(5-methyl-2H-pyrazol-3-ylamino)-2H-phthalazin-1-one | (400MHz, D₆-DMSO) 9.20(1H, s), 8.35(1H, d), 8.25(1H, d), 7.89–7.79(4H, m), 7.53(2H, d), 6.00(1H, s), 5.30(2H, s), 3.08(3H, s), 2.12(3H, s) | 410.12 |
| A-15 | 2-(3,4-Difluoro-benzyl)-4-(5-methyl-1H-pyrazol-3-ylamino)-2H-phthalazin-1-one | (400MHz, D₆-DMSO) 9.51(1H, s), 8.34(1H, s), 8.24(1H, d), 7.91–7.80(2H, m), 7.41–7.29(2H, m), 7.16–7.13(1H, m), 6.04(1H, s), 5.21(2H, s), 2.16(3H, s) | 368.20 |
| A-16 | 4-(5-Methyl-1H-pyrazol-3-ylamino)-2-(2-methyl-thiazol-4-ylmethyl)-2H-phthalazin-1-one | (400MHz, D₆-DMSO) 9.82(1H, s), 8.39(1H, d), 8.33(1H, d), 7.99–7.88(2H, m), 7.36(1H, s), 6.16(1H, s), 5.34(2H, s), 2.64(3H, s), 2.26(3H, s) | 353.18 |
| A-17 | 4-(5-Methyl-2H-pyrazol-3-ylamino)-2-pyridin-4-ylmethyl-2H-phthalazin-1-one | (400MHz, D₆-DMSO) 9.38(1H, s), 8.70(2H, d), 8.44(1H, d), 8.31(1H, d), 7.98–7.86(2H, m), 7.69(2H, d), 6.06(1H, s), 5.46(2H, s), 2.17(3H, s) | 333.21 |
| A-18 | 4-(5-Methyl-2H-pyrazol-3-ylamino)-2-pyridin-3-ylmethyl-2H-phthalazin-1-one | (400MHz, D₆-DMSO) 9.38(1H, s), 8.68(2H, d), 8.54(2H, d), 8.29(2H, d), 8.17(2H, dd), 8.05(2H, d), 7.83–7.72(4H, m), 7.58(2H, dd), 5.95(2H, s), 5.27(3H, s), 2.07(4H, s) | 333.14 |
| A-19 | 2-(2-Fluoro-benzyl)-4-(5-methyl-1H-pyrazol-3-ylamino)-2H-phthalazin-1-one | (400MHz, D₆-DMSO) 9.45(1H, s), 8.42(1H, d), 8.31(1H, dd), 7.96–7.85(2H, m), 7.38–7.31(2H, m), 7.24–7.13(2H, m), 5.97(1H, s), 5.33(2H, s), 2.16(3H, s) | 350.11 |
| A-20 | 2-(4-Fluoro-benzyl)-4-(5-methyl-1H-pyrazol-3-ylamino)-2H-phthalazin-1-one | (400MHz, D₆-DMSO) 9.53(1H, s), 8.40(1H, d), 8.31(1H, dd), 7.96–7.85(2H, m), 7.41(2H, dd), 7.15(2H, t), 6.11(1H, s), 5.26(2H, s), 2.22(3H, s) | 350.11 |
| A-21 | 2-(3,5-Difluoro-benzyl)-4-(5-methyl-1H-pyrazol-3-ylamino)-2H-phthalazin-1-one | (400MHz, D₆-DMSO) 9.59(1H, s), 8.44(1H, d), 8.33(1H, dd), 7.99–7.88(2H, m), 7.17(2H, tt), 7.08(2H, dd), 6.12(1H, s), 5.32(2H, s), 2.23(3H, s) | 368.10 |
| A-22 | 4-(5-Methyl-2H-pyrazol-3-ylamino)-2-pyridin-2-ylmethyl-2H-phthalazin-1-one | (400MHz, D₆-DMSO) 9.23(1H, s), 8.54(1H, d), 8.47(1H, d), 8.31(1H, d), 7.97–7.85(2H, m), 7.76(1H, t), 7.32–7.24(2H, m), 5.95(1H, s), 5.36(2H, s), 2.13(3H, s) | 333.28 |
| A-23 | 2-Isopropyl-4-(5-methyl-1H-pyrazol-3-ylamino)-2H-phthalazin-1-one | (400MHz, D₆-DMSO) 11.73(1H, br s), 8.99(1H, br s), 8.25(1H, d), 8.10(1H, d), | 284.34 |
| | phthalazin-1-one | 7.71–7.62(2H, m), 6.16(1H, t), 5.10–5.03(1H, m), 2.05(3H, s), 1.13(6H, d) | |
| A-24 | 3-[4-(5-Methyl-1H-pyrazol-3-ylamino)-1-oxo-1H-phthalazin-2-ylmethyl]-benzoic acid | (400MHz, D₆-DMSO) 11.94–11.76(1H, m), 9.26(1H, br s), 8.46(1H, d), 8.31(1H, d), 7.92–7.82(3H, m), 7.75(1H, d), 7.33–7.22(2H, m), 6.08(1H, s), 5.23(2H, s), 2.14(3H, s) | 376.15 |
| A-25 | 4-(5-Methyl-1H-pyrazol-3-ylamino)-2-(4-trifluoromethyl-phenyl)-2H-phthalazin-1-one | (400MHz, DMSO) 9.28(1H, s), 8.41(1H, d), 8.27(1H, d), 7.96–7.73(6H, m), 6.13(1H, s), 2.05(3H, s) | 386.1 |

Example A-2 is composed as Example E-1 under Method E.

Method B

Example B-1

2-(4-Chloro-phenyl)-4-(5-methyl-1H-pyrazol-3-ylamino)-2H-phthalazin-1-one 2-(4-chlorophenyl)-2,3-dihydro-phthalazine-1,4-dione 4-Chlorophenyl hydrazine hydrochloride (5.00 g, 28 mmol) was added in one portion to a stirred mixture of phthalic anhydride (3.70 g, 25 mmol), in acetic acid (50 ml) at room temperature. The mixture was heated to 125° C. for 2 hours, and then allowed to cool to room temperature. The suspension was poured into water (100 ml) and the precipitate was filtered. The precipitate was stirred in 1M Na₂CO₃ (100 ml), and the remaining undissolved solid removed by filtration. This solid was washed with a further 100 ml portion of 1M Na₂CO₃.

The basic aqueous solutions were combined and acidified by dropwise addition of conc. HCl until gas evolution ceased. A white precipitate formed and was filtered and dried for 18 hours in a vacuum oven (50° C.) to give the phthalazine dione (270 mg, 4% yield).

The solid insoluble in 1M Na₂CO₃ was stirred in glycerol (50 ml) and heated to 150° C. for 10 hrs. The reaction mixture was then diluted with water (50 ml). 4M HCl was added dropwise until a precipitate formed. This was filtered, re-suspended in methanol (MeOH) (30 ml) and isolated by filtration. The product was dried under vacuum to give the desired phthalazine dione (3.6 g, 72% yield). ¹H-NMR: (400 MHz; D₆-DMSO); 12.1 (1H, br. s), 8.3 (1H, d), 7.9–8.0 (3H, m), 7.7 (2H, d), 7.6 (2H, d); MS (ESI⁺)=(M+H)⁺ 273,275

This material was then brominated with phosphorus oxybromide and used in the Buchwald reaction as described in Method A. to give the corresponding 2-(4-Chloro-phenyl)-4-(5-methyl-1H-pyrazol-3-ylamino)-2H-phthalazin-1-one (example B-1).

Using the experimental conditions reported above (Method B) and the appropriate starting materials, the following derivatives were prepared:

| Example-No. | Systematic name | ¹H-NMR | MS(ESI+, M+H) |
|---|---|---|---|
| B-1 | 2-(4-Chloro-phenyl)-4-(5-methyl-1H-pyrazol-3-ylamino)-2H-phthalazin-1-one | (400MHz, $D_6$-DMSO), 11.97(1H, s) 9.34(1H, s), 8.51(1H, d), 8.38(1H, d), 7.99–7.89(2H m), 7.80(2H, d), 7.58(2H, d) 6.24(1H, s), 2.20(3H, s) | 352.30 |
| B-2 | 4-(5-Methyl-1H-pyrazol-3-ylamino)-2-m-tolyl-2H-phthalazin-1-one | (400MHz, $D_6$-DMSO) 9.45(1H s), 8.49(1H, d), 8.38(1H, d), 7.98–7.91(2H, m), 7.54–7.50(1H m), 7.38(1H, t), 7.17(1H d), 6.26(1H, s), 2.38(3H, s), 2.20(3H, s) | 332.34 |
| B-3 | 4-(5-Methyl-1H-pyrazol-3-ylamino)-2-(4-nitro-benzyl)-2H-phthalazin-1-one | (400MHz, $D_6$-DMSO) 9.32(1H, s), 8.34(2H, d), 8.21(2H, d), 8.0(2H, d), 7.49–7.85(2H, m), 7.49(2H d), 5.93(1H, s), 5.29(2H, s), 2.04(3H, s) | 377.24 |

Method C

Example C-1

2-(4-Aminobenzyl)-4-(5-methyl-1H-pyrazol-3-ylamino)-2H-phthalazin-1-one

Tin (II) chloride dihydrate (1.3 g, 5.76 mmol) was added to a suspension of 4-(5-Methyl-1H-pyrazol-3-ylamino)-2-(4-nitro-benzyl)-2H-phthalazin-1-one (Example B-3) (600 mg, 1.6 mmol) in dimethylformamide (DMF) (10 ml). The reaction mixture was stirred at room temperature overnight. The DMF was evaporated under reduced pressure and the residue dissolved in dichloromethane (DCM). A saturated solution of potassium sodium tartrate tetrahydrate in water (20 ml) was added and the mixture stirred for 30 minutes (mins).

The phases were separated and the aqueous phase back-extracted with DCM (20 ml). The organic layers were combined, washed with brine, and evaporated under reduced pressure to give 2-(4-Aminobenzyl)-4-(5-methyl-1H-pyrazol-3-ylamino)-2H-phthalazin-1-one as an off-white solid (55 mg, 10% yield). ¹H-NMR: (400 MHz, $D_6$-DMSO) 9.37 (1H, s), 8.40 (2H, d), 8.28 (2H, d), 7.81–7.91 (2H, m), 7.32 (2H, d), 7.04 (2H d), 6.12 (1H, s), 5.18 (2H, s), 2.17 (3H, s), MS (ESI⁺)=(M+H)⁺ 347.31.

Using the experimental conditions reported above (Method C) and the appropriate starting material W-3, the following derivative was prepared:

| Example-No. | Systematic name | ¹H-NMR | MS(ESI+, M+H) |
|---|---|---|---|
| C-2 | 2-(4-Amino-phenyl)-4-(5-methyl-1H-pyrazol-3-ylamino)-2H-phthalazin-1-one | (400MHz, $D_6$-DMSO), 11.90(1H, s), 9.15(1H, s), 8.47(1H, d), 8.33(1H, d), 7.85–7.94(2H, m), 7.28(2H, d), 6.65(2H, d), 6.25(1H, s), 5.23(2H, s), 2.18(3H, s) | 333.3 |

Method D

Example D-1

N-{4-[4-(5-Methyl-1H-pyrazol-3-ylamino)-1-oxo-1H-phthalazin-2-ylmethyl]-phenyl}-acetamide 4-Bromo-2-(4-aminobenzyl)-2H-phthalazin-1-one Tin (II) chloride dihydrate (68 mg, 3.6 eq) was added to a suspension of 4-bromo-2-(4-nitrobenzyl)-2H-phthalazin-1-one (30 mg, 0.09 mmol) in dimethylformamide (DMF) (0.5 ml). The reaction mixture was stirred at room temperature overnight. The DMF was evaporated under reduced pressure and the residue dissolved in dichloromethane (DCM) (0.5 ml). A saturated solution of potassium sodium tartrate tetrahydrate in water (0.5 ml) was added and the mixture stirred for 30 mins.

The phases were separated and the aqueous phase back-extracted with DCM (0.5 ml). The organic layers were combined, washed with brine, and evaporated under reduced pressure to give the desired product as an off-white solid (23 mg, 87% yield) ¹H-NMR: (400 MHz; $C_6D_6$); 8.42 (1H, d), 7.91 (1H, d), 7.83 (2H, m), 7.33 (2H, d), 6.63 (2H, d), 5.25 (2H, s). MS (ESI⁺)=(M+H)⁺ 330.2, 332.2.

4-Bromo-2-(4-acetylaminobenzyl)-2H-phthalazin-1-one

Acetic anhydride (0.43 ml, 4.5 mmol) was added to a mixture of 4-bromo-2-(4-aminobenzyl)-2H-phthalazin-1-one (500 mg, 1.5 mmol) and pyridine (0.49 ml, 6 mmol) in acetonitrile (5 ml). The reaction mixture was stirred at room temperature overnight.

The solvent was removed under reduced pressure. 1M ammonia in methanol (2 ml) was added and the reaction mixture stirred for 1 hr. The solvent was removed under reduced pressure. The residue was triturated with DCM to give the product as an off-white solid (398 mg, 71% yield) MS (ESI⁺)=(M+H)⁺ 372.2, 374.2.

This material was then used in the Buchwald reaction as described in Method A. to give the corresponding N-{4-[4-(5-Methyl-1H-pyrazol-3-ylamino)-1-oxo-1H-phthalazin-2-ylmethyl]-phenyl}-acetamide (example D-1).

Using the experimental conditions reported above (Method D) and the appropriate starting materials, the following derivatives were prepared:

| Example-No. | Systematic name | ¹H-NMR | MS(ESI+, M+H) |
|---|---|---|---|
| D-1 | N-{4-[4-(5-Methyl-1H-pyrazol-3- | (400MHz, $D_6$-DMSO) 9.94(1H, s), 9.26(1H, s), | 389.27 |

| Example-No. | Systematic name | ¹H-NMR | MS(ESI+, M+H) |
|---|---|---|---|
| | ylamino)-1-oxo-1H-phthalazin-2-ylmethyl]-phenyl}-acetamide | 8.42(2H, d), 8.32(2H d), 7.85–7.94(2H, m), 7.52(2H, d), 7.31(2H d), 6.10(1H, s), 5.18(2H, s), 2.19(3H, s), 2.17(3H, s) | |
| D-2 | N-{4-[1-Oxo-4-(1H-pyrazol-3-ylamino)-1H-phthalazin-2-ylmethyl]-phenyl}-acetamide | (400MHz, D$_6$-DMSO) 12.16(1H, s) 9.84(1H, s), 8.38(1H, d), 8.25(1H, d), 7.87–7.78(2H m), 7.50(1H, d), 7.45(2H, d) 7.23(2H, d), 6.40(1H, s), 5.10(2H, s), 1.93(3H, s) | 375.29 |

Method E

Example E-1

2-Benzyl-4-(5-methyl-1H-pyrazol-3-ylamino)-2H-phthalazin-1-one

4-Bromo-2H-phthalazin-1-one 2,3-Dihydro-1,4-phthalazinedione (12.5 g, 78 mmol) was suspended in dichloroethane (200 ml) and phosphorous pentabromide (50.0 g, 116 mmol) was added in one portion and the reaction heated to reflux for 24 hours. A further portion of phosphorous pentabromide (20.0 g, 70 mol) was added and the reaction heated for a further 24 hours. The reaction was cooled to room temperature and poured into ice water. The resulting precipitate was filtered and washed with water to give a crude mixture of mono and dibrominated product (22.8 g).

This crude material was suspended in acetic acid (230.0 mL) and heated to 120° C. for 2 hrs. The reaction was cooled to room temperature and poured into ice water and the resulting precipitate filtered. The solid was washed with water and dried to give the title compound (10.4 g, 60% yield) as a white solid. ¹H-NMR: (400 MHz, D$_6$-DMSO), 12.95 (1H, s), 8.25 (1H, dd), 8.03 (1H, ddd), 7.96–7.90-(2H, m); MS (ESI$^+$)=(M+H)$^+$ 225 & 227

2-Benzyl-4-bromo-2H-phthalazin-1-one

4-Bromo-2H-phthalazin-1-one (10.38 g, 46 mmol) was dissolved in dimethylformamide (DMF) (60 ml). To this was added NaH (60%, 1.55 g, 46.2 mmol) as a DMF suspension (20 ml). The mixture was stirred at room temperature for 30 mins then benzyl bromide (13.82 g, 50.8 mmol) was added in one portion as a solution in DMF (20 ml). The reaction mixture was stirred for 2 hours then the DMF was removed under reduced pressure and the resulting crude material purified by column chromatography (gradient elution: 100% heptane to 20% ethyl acetate: heptane) to give the title compound (8.16 g, 56% yield) as a white solid. ¹H-NMR: (400 MHz, D$_6$-DMSO), 8.30 (1H, dd), 8.03 (1H, ddd), 7.97–7.91 (2H, m), 7.34–7.27 (5H, m), 5.31 (2H, s); MS (ESI$^+$)=(M+H)$^+$ 315 & 317

This material was then used in the Buchwald reaction as described in Method A. to give the corresponding 2-Benzyl-4-(5-methyl-1H-pyrazol-3-ylamino)-2H-phthalazin-1-one (example E-1).

Using the experimental conditions reported above (Method E) and the appropriate starting materials, the following derivatives were prepared:

| Example-No. | Systematic name | ¹H-NMR | MS (ESI+, M+H) |
|---|---|---|---|
| E-1 | 2-Benzyl-4-(5-methyl-1H-pyrazol-3-ylamino)-2H-phthalazin-1-one | (400MHz, D$_6$-DMSO) 11.86(1H, s), 9.25(1H, s), 8.46(1H, d), 8.32(1H, d), 7.84–7.94(2H, m), 7.25–7.38(5H m), 6.10(1H, s), 5.24(2H, s) 2.17(3H, s) | 332.08 |
| E-2 | 7-Fluoro-2-isopropyl-4-(5-methyl-1H-pyrazol-3-ylamino)-2H-phthalazin-1-one | (400MHz, D$_6$-DMSO) 9.35(1H, s), 8.53(1H, dd), 7.95(1H, dd), 7.82(1H, ddd), 6.35(1H, s), 5.27–5.19(1H, m), 2.26(3H, s), 1.32(6H, s) | 302.29 |
| E-3 | 6-Fluoro-2-isopropyl-4-(5-methyl-1H-pyrazol-3-ylamino)-2H-phthalazin-1-one | (400MHz, D$_6$-DMSO) 9.09(1H, s), 8.19–8.14(2H, m), 7.56–7.50(1H, m), 6.18(1H, s), 5.09–5.00(1H, m), 2.07(3H, s), 1.14(6H, d) | 302.29 |
| E-4 | 2-[2-(4-Methoxy-phenyl)-2-oxo-ethyl]-4-(5-methyl-1H-pyrazol-3-ylamino)-2H-phthalazin-1-one | (400MHz, D$_6$-DMSO) 9.43(1H, s), 8.40(1H, d), 8.22(1H, d), 8.00(1H, d), 7.93–7.81(2H, m), 7.04(2H, d), 6.12(1H, s), 5.54(2H, s), 3.80(3H, s), 2.11(3H, s) | 390.14 |
| E-5 | 2-[2-(3-Methoxy-phenyl)-2-oxo-ethyl]-4-(5-methyl-1H-pyrazol-3-ylamino)-2H-phthalazin-1-one | (400MHz, D$_6$-DMSO) 9.38(1H, s), 8.43(1H, d), 8.21(1H, d), 7.92–7.80(2H, m), 7.61(1H, d), 7.49–7.42(2H, m), 7.21(1H, d), 6.11(1H, s), 5.57(2H, s), 3.77(3H, s), 2.09(3H, s) | 390.15 |
| E-6 | 4-(5-Methyl-1H-pyrazol-3-ylamino)-2-[2-oxo-2-(4-trifluoromethoxy-phenyl)-ethyl]-2H-phthalazin-1-one | (400MHz, D$_6$-DMSO) 12.06(1H, br s), 9.41(1H, br s), 8.64(1H, d), 8.45–8.36(3H, m), 8.14–8.02(2H, m), 7.75(2H, d), 6.38(1H, s), 5.79(2H, s), 2.30(3H, s) | 444.23 |
| E-7 | 2-(2-Benzo[1,3]dioxol-5-yl-2-oxo-ethyl)-4-(5-methyl-1H-pyrazol-3-ylamino)-2H-phthalazin-1-one | (400MHz, D$_6$-DMSO) 9.26(1H, br s), 8.48(1H, d), 8.30(1H, d), 7.97–7.88(2H, m), 7.75(1H, d), 7.56(1H, s), 7.12(1H, d), 6.18(2H, s), | 404.18 |

-continued

| Example-No. | Systematic name | ¹H-NMR | MS (ESI+, M+H) |
|---|---|---|---|
| E-8 | 4-(5-Methyl-1H-pyrazol-3-ylamino)-2-[2-oxo-2-(4-trifluoromethyl-phenyl)-ethyl]-2H-phthalazin-1-one | (400MHz, $D_6$-DMSO) 11.84(1H, br s), 9.26(1H, br s), 8.42(1H, d), 8.22–8.20(3H, m), 7.91–7.80(4H, m), 6.12(1H, s), 5.61(2H, s), 5.55(2H, s), 2.16(3H, s) | 428.09 |
| E-9 | 4-(5-Methyl-1H-pyrazol-3-ylamino)-2-(2-oxo-2-phenyl-ethyl)-2H-phthalazin-1-one | (400MHz, DMSO) 11.91(1H, br s), 9.31(1H, br s), 8.48(1H, d), 8.30(1H, d), 8.09(2H, d), 7.98–7.87(2H, m), 7.74–7.70(1H, m), 7.62–7.58(2H, m), 6.21(1H, s), 5.63(2H, s), 2.15(3H, s) | 360.10 |
| E-10 | 2-Allyl-4-(5-methyl-1H-pyrazol-3-ylamino)-2H-phthalazin-1-one | (400MHz, $D_6$-DMSO) 11.90(1H, s), 9.20(1H, s), 8.45(1H, d,), 8.29(1H, d), 7.98–7.81(2H, m), 6.36(1H, s), 6.06–5.94(1H, m), 5.23–5.15(2H, m), 4.69–4.61(2H, m), 2.21(3H, s) | 282.09 |
| E-11 | 2-Cyclopropylmethyl-4-(5-methyl-1H-pyrazol-3-ylamino)-2H-phthalazin-1-one | (400MHz, $D_6$-DMSO) 11.91(1H, s), 9.16(1H, s), 8.44(1H, d), 8.29(1H, dd), 7.94–7.82(2H, m), 6.36(1H, s), 3.91(2H, d), 2.23(3H, s), 1.34–1.25(1H, m), 0.52–0.46(2H, m), 0.43–0.37(2H, m) Tr=1.54min, m/z(ES⁺)(M+H)⁺ 296.12 | |
| E-12 | 4-(5-Methyl-1H-pyrazol-3-ylamino)-2-(4-methylsulfanyl-benzyl)-2H-phthalazin-1-one | (400MHz, $D_6$-DMSO) 11.88(1H, s), 9.21(1H, s), 8.44(1H, d), 8.31(1H, dd), 7.94–7.84(2H, m), 7.34–7.30(2H, m), 7.25–7.21(2H, m), 6.11(1H, s), 5.19(2H, s), 2.43(3H, s), 2.19(3H, s) Tr=1.87min, m/z (ES⁺)(M+H)⁺ 378.08 | |

Example E-13

2-(2-Hydroxy-2-phenyl-ethyl)-4-(5-methyl-1H-pyrazol-3-ylamino)-2H-phthalazin-1-one Sodium borohydride (6 mg, 0.15 mmol) was added in one portion to a stirred solution of 4-(5-Methyl-1H-pyrazol-3-ylamino)-2-(2-oxo-2-phenyl-ethyl)-2H-phthalazin-1-one (17 mg, 0.05 mmol) (Example E-9) in tetrahydrofuran (THF) (1 ml). The reaction mixture was stirred at room temperature for two hours. After this time LC-MS indicated complete consumption of starting material, methanol (0.5 ml) was added and the reaction mixture was concentrated under vacuum. The resulting residue was purified by flash column chromatography (elution: 97% dichloromethane (DCM), 3% methanol (MeOH)) to give the title compound (2.2 mg, 12% yield) as a white solid. MS (ESI⁺)=(M+H)⁺ 361.98.

Method F

Example F-1

2-Isopropyl-4-(5-methyl-1H-pyrazol-3-ylamino)-7-morpholino-2H-phthalazin-1-one

7-Nitro-2,3-dihydro-phthalazine-1,4-dione

Hydrazine hydrate (26.6 g, 0.53 mol) was added in one portion to a stirred mixture of 4-nitrophthalic anhydride (100 g, 0.52 mol), in acetic acid (1.0 L) at room temperature. The mixture was heated to 120° C. for 2 hours and then allowed to cool to room temperature. The solid was filtered, washed with water (250 ml) and dried in the vacuum oven at 50° C. for 20 hours to give the nitrophthalazinone (95 g, 88% yield). MS (ESI⁺)=(M+H⁺) 208

7-Nitro-4-bromo-2H-phthalazin-1-one

7-Nitro-2,3-dihydro-phthalazine-1,4-dione (95.0 g, 0.46 mol) was suspended in dichloroethane (1.0 L) and phosphorus pentabromide (789.0 g, 1.83 mol) was added in three portions and the reaction heated to reflux for 24 hours. The reaction was cooled to room temperature and poured onto ice (2.5 kg) and the resulting precipitate filtered and washed with water to give the crude product (160 g).

This crude material was suspended in acetic acid (1.60 L) and heated to 125° C. for 2 hours. The reaction was cooled to room temperature and poured onto ice (1.5 kg) and the resulting precipitate filtered. The solid was washed with water and dried to give the title compound (84 g, 68% yield) as a yellow solid.

¹H-NMR: (400 MHz, $D_6$-DMSO), 13.29 (1H,), 8.83 (1H, d), 8.79 (1H, dd), 8.61 (1H, dd), 8.54 (1H, d), 8.46 (1H, d), 8.16 (d) MS (ESI⁺)=(M+H)⁺ 269 & 271

7-Nitro-2-Isopropyl-4-bromo-2H-phthalazin-1-one

7-Nitro-4-bromo-2H-phthalazin-1-one (84 g, 0.31 mol) was dissolved in dimethylformamide (DMF) (400 ml). To this was added NaH (60%, 7.5 g, 0.31 mol) as a DMF suspension (200 ml). The mixture was stirred at room temperature for 30 minutes then 2-bromo-propanol (7.7 g, 62 mmol) was added in one portion as a solution in DMF (250 ml). The reaction mixture was stirred for 24 hours whereupon LC-MS showed 40% starting material remaining. To this was added NaH (3.75 g 0.15 mol) and the reaction stirred for a further 24 hours. The DMF was removed under vacuum and the resulting crude material purified by successive column chromatography (elution: 92% heptane to 8% ethyl acetate) to give the title compound (38.8 g, 40% yield) as a light yellow solid.

¹H-NMR: (400 MHz, $D_6$-DMSO), 8.88 (1H, d), 8.87 (1H, dd), 8.16 (1H, d), 5.19 (1H, m), 1.13 (6H, d).

7-Amino-2-Isopropyl-4-bromo-2H-phthalazin-1-one

7-Nitro-2-Isopropyl-4-bromo-2H-phthalazin-1-one (4.6 g, 0.015 mol) was dissolved in a 5:1 mixture of ethanol and water (150 ml). To this solution was added iron powder (2.14 g, 0.039 mol) and concentrated hydrochloric acid (1 ml), the mixture was heated to 80° C. for three hours. After this time, the reaction mixture was cooled to room temperature and filtered through a pad of celite, the celite was washed with ethanol (100 ml), and the solution was concentrated under vacuum to give the title compound (4.2 g, 98% yield) as a white solid.

$^1$H-NMR: (400 MHz, D$_6$-DMSO), 7.56 (1H, d), 7.28 (1H, s), 7.13 (1H, d), 6.47 (2H, s), 5.24–5.09 (1H, m), 1.23 (6H, d); MS (ESI$^+$)=(M+H)$^+$ 282, 284

7-Morpholino-2-Isopropyl-4-bromo-2H-phthalazin-1-one

To a solution of 7-Amino-2-Isopropyl-4-bromo-2H-phthalazin-1-one (0.8 g, 0.0028 mol) in DMF (8 ml), was added potassium carbonate (2 g, 0.014 mol). After five minutes, bis (2-chloroethyl)ether (0.41 g, 0.0028 mol) was added and the solution was heated to 140° C. for 24 hours. After this time LC-MS indicated the complete consumption of starting material and the mixture was cooled, concentrated under vacuum and purified by flash column chromatography (elution: 70% heptane, 30% ethyl acetate) to give the title compound (0.2 g, 20% yield) as a white solid.

This material was then used in the Buchwald reaction as described in Method A. to give the corresponding 2-Isopropyl-4-(5-methyl-1H-pyrazol-3-ylamino)-7-morpholino-2H-phthalazin-1-one (example F-1)

Using the experimental conditions reported above (Method F) and the appropriate starting materials, the following derivatives were prepared:

| Example-No. | Systematic name | $^1$H-NMR | MS(ESI+, M+H) |
|---|---|---|---|
| F-1 | 2-Isopropyl-4-(5-methyl-1H-pyrazol-3-ylamino)-7-morpholino-2H-phthalazin-1-one | (400MHz, D$_6$-DMSO) 11.86(1H, s), 8.97(1H, s), 8.29(1H, d), 7.57(1H, d), 7.52(1H, d), 6.35(1H, br s), 5.28–5.20(1H, m), 3.79–3.74(4H, m), 3.21(4H, obscured), 2.23(3H, s), 1.30(6H, d) | 368.15 |
| F-2 | 2-Isopropyl-4-(5-methyl-1H-pyrazol-3-ylamino)-6-morpholino-2H-phthalazin-1-one | (400MHz, D$_6$-DMSO) 11.88(1H, s), 9.19(1H, s), 8.07(1H, d), 7.65(1H, s), 7.41(1H, dd), 6.37(1H, s), 5.25–5.16(1H, m), 3.80–3.73(4H, m), 3.44–3.35(4H, m), 1.28(6H, d) | 369.37 |
| F-3 | 2-Isopropyl-4-(5-methyl-1H-pyrazol-3-ylamino)-8-morpholino-2H-phthalazin-1-one | (400MHz, DMSO) 9.45(1H, br s), 8.35(1H, br s), 8.03(1H, br s), 6.33(1H, s), 5.31–5.17(1H, m), 3.96(4H, br s), 3.51(4H, br s), 2.26(3H, s), 1.35(6H, d) | 369.30 |
| F-4 | 2-Benzyl-4-(5-methyl-1H-pyrazol-3-ylamino)-7-morpholino-2H-phthalazin-1-one | (400MHz, D$_6$-DMSO) 9.50(1H, s), 8.10(1H, d), 7.61(1H, d), 7.46(1H, dd), 7.34–7.23(5H, m), 6.14(1H, s), 5.22(2H, s), 3.83–3.72(4H, m), 3.42–3.40(4H, m), 2.20(3H, s) | 417.30 |
| F-5 | 2-Isopropyl-7-(4-methyl-piperazin-1-yl)-4-(5-methyl-2H-pyrazol-3-ylamino)-2H-phthalazin-1-one | (400MHz, CDCl$_3$) 7.83(1H, d), 7.61(1H, d), 7.31(1H, dd), 7.15(1H, s), 6.33(1H, s), 5.49–5.41(1H, m), 3.46–3.41(4H, m), 2.61–2.55(4H, m), 2.37(3H, s), 2.35(3H, s), 1.43(6H, d) | 382.33 |
| F-6 | 2-Isopropyl-4-(5-methyl-1H-pyrazol-3-ylamino)-7-dimethylamino-2H-phthalazin-1-one | (400MHz, D$_6$-DMSO) 9.21(1H, s), 8.27(1H, d), 7.41(1H, d), 7.35(1H, dd), 6.42(1H, s), 5.36–5.29(1H, m), 3.16(6H, s), 2.34(3H, s), 1.39(6H, d) | 327.36 |
| F-7 | 2-Isopropyl-4-(5-methyl-1H-pyrazol-3-ylamino)-6-dimethylamino-2H-phthalazin-1-one | | 327.30 |
| F-8 | 2-Isopropyl-4-(5-methyl-1H-pyrazol-3-ylamino)-8-dimethylamino-2H-phthalazin-1-one | (400MHz, D$_6$-DMSO) 11.82(1H, br s), 8.77(1H, br s), 7.67–7.56(2H, m), 7.20(1H, d), 6.26(1H, br s), 5.26–5.15(1H, m), 2.84(6H, s), 2.22(3H, s), 1.27(6H, d) | 327.18 |
| F-9 | 4-(5-Cyclopropyl-2H-pyrazol-3-ylamino)-7-dimethylamino-2-isopropyl-2H-phthalazin-1-one | (400MHz, DMSO) 11.89(1H, br s), 8.90(1H, br s), 8.23(1H, br s), 7.32(1H, d), 7.24(1H, d), 6.25(1H, br s), 5.29–5.18(1H, m), 3.07(6H, s), 1.92–1.84(1H, m), 1.29(6H, d), 0.98–0.88(2H, m), 0.65(2H, dd) | 353.41 |
| F-10 | 2-Isopropyl-4-(5-methyl-1H-pyrazol-3-ylamino)-7-piperidin-1-yl-2H-phthalazin-1-one | (400MHz, DMSO) 9.04(1H, s), 8.32(1H, d), 7.63(1H, d), 7.57(1H, dd), 6.42(1H, s), 5.40–5.25(1H, m), 3.49(4H, s), 2.32(3H, s), | 367.22 |

-continued

| Example-No. | Systematic name | $^1$H-NMR | MS(ESI+, M+H) |
|---|---|---|---|
| F-11 | 2-Isopropyl-4-(5-methyl-1H-pyrazol-3-ylamino)-7-pyrrolidin-1-yl-2H-phthalazin-1-one | (250MHz, DMSO) 8.88(1H, s), 8.23(1H, d), 7.18(1H, d), 7.11–7.03(1H, m), 6.35(1H, s), 5.33–5.18(1H, m), 3.39(4H, br s), 2.24(3H, s), 2.02(4H, br s), 1.31(6H, d), 1.70(6H, br s), 1.39(6H, d) | 353.18 |

Method G

Example G-1

2-Isopropyl-4-(5-methyl-1H-pyrazol-3-ylamino)-7-methoxy-2H-phthalazin-1-one

7-Hydroxy-2-Isopropyl-4-bromo-2H-phthalazin-1-one

Concentrated sulfuric acid (17 ml) was added slowly to a solution of 7-Amino-2-Isopropyl-4-bromo-2H-phthalazin-1-one (4.6 g, 0.016 mol) in acetic acid (50 ml). The reaction mixture was cooled to 0° C. and a solution of $NaNO_2$ (1.52 g, 0.022 mol) in water (10 ml) was added dropwise. The reaction mixture was stirred for a further 20 minutes at 0° C. prior to the addition of urea (0.55 g, 0.009 mol) and cold water (50 ml). The reaction mixture was then added carefully to a refluxing mixture of sulfuric acid (28 ml) in water (115 ml) and the reaction was stirred for a further 10 minutes at reflux before being allowed to cool to room temperature. Upon standing, an orange precipitate was observed, which was collected by filtration and washed with water to give the title compound (4.22 g, 93% yield) as an orange powder.

7-Methoxy-2-Isopropyl-4-bromo-2H-phthalazin-1-one

To a stirred solution of 7-Hydroxy-2-Isopropyl-4-bromo-2H-phthalazin-1-one (0.4 g, 1.4 mmol) in tetrahydrofuran (THF) (5 ml) were added successively, $K_2CO_3$ (0.59 g, 4.3 mmol) and methyl iodide (0.22 g, 1.55 mmol) and the mixture was heated to reflux for 24 hours. After this time, LC-MS indicated complete consumption of starting material, and the reaction mixture was concentrated under vacuum. The residue was re-dissolved in ethyl acetate (50 ml) and washed with water (2×30 ml), the organic layer was dried ($MgSO_4$), filtered and concentrated under vacuum to give the title compound (0.32 g, 76% yield) as an orange powder.

This material was then used in the Buchwald reaction as described in Method A. to give the corresponding 2-Isopropyl-4-(5-methyl-1H-pyrazol-3-ylamino)-7-methoxy-2H-phthalazin-1-one (example G-1)

Using the experimental conditions reported above (Method G) and the appropriate starting materials, the following derivatives were prepared:

| Example-No. | Systematic name | $^1$H-NMR | MS(ESI+, M+H) |
|---|---|---|---|
| G-1 | 2-Isopropyl-4-(5-methyl-1H-pyrazol-3-ylamino)-7-methoxy-2H-phthalazin-1-one | (400MHz, D$_6$-DMSO) 12.07(1H, s), 9.27(1H, s), 8.56(1H, d), 7.85(1H, s), 7.63(1H, d), 6.52(1H, s), 5.46–5.39(1H, m), 4.10(3H, s), 2.86(3H, s), 1.50(6H, d) | 314.32 |
| G-2 | 2-Isopropyl-4-(5-methyl-1H-pyrazol-3-ylamino)-7-(pyridin-2-ylmethoxy)-2H-phthalazin-1-one | (250MHz, D$_6$-DMSO) 9.12(1H, br s), 8.62–8.58(1H, m), 8.40(1H, d), 7.89–7.81(1H, m), 7.74(1H, d), 7.59–7.52(2H, m), 7.40–7.33(1H, m), 6.32(1H, s), 5.38(2H, s), 5.29–5.13(1H, m), 2.23(3H, s), 1.31(6H, d) | 391 |
| G-3 | 2-Isopropyl-4-(5-methyl-1H-pyrazol-3-ylamino)-7-(pyridin-3-ylmethoxy)-2H-phthalazin-1-one | (250MHz, D$_6$-DMSO) 9.13(1H, br s), 8.73(1H, d), 8.57(1H, dd), 8.41(1H, d), 7.96–7.89(1H, m), 7.80(1H, d), 7.55(1H, dd), 7.49–7.41(1H, m), 6.33(1H, s), 5.36(2H, s), 5.31–5.19(1H, m), 2.24(3H, s), 1.32(6H, d) | 391 |
| G-4 | 2-Isopropyl-4-(5-methyl-1H-pyrazol-3-ylamino)-7-(pyridin-4-ylmethoxy)-2H-phthalazin-1-one | (250MHz, D$_6$-DMSO) 9.13(1H, br s), 8.64–8.58(2H, m), 8.42(1H, d), 7.76(1H, d), 7.58(1H, dd), 7.52–7.46(2H, m), 6.34(1H, s), 5.41(2H, s), 5.32–5.18(1H, m), 2.24(3H, s), 1.32(6H, d) | 391.21 |
| G-5 | 2-Isopropyl-4-(5-methyl-1H-pyrazol-3-ylamino)-7-(2-morpholin-4-yl-ethoxy)-2H-phthalazin-1-one | (250MHz, D$_6$-DMSO) 9.09(1H, br s), 8.38(1H, d), 7.69(1H, d), 7.46(1H, dd), 6.33(1H, s), 5.31–5.17(1H, m), 4.27(2H, t), 3.62–3.55(4H, m), 3.41(4H, obscured), 2.75(2H, t), 2.24(3H, s), 1.32(6H, d) | 413.28 |
| G-6 | 7-Hydroxy-2-isopropyl-4-(5-methyl-1H-pyrazol-3-ylamino)-2H-phthalazin-1-one | (400MHz, D$_6$-DMSO) 11.84(1H, s), 10.59(1H, s), 8.99(1H, s), 8.27(1H, d), 7.58(1H, d), 7.25(1H, dd), 6.32(1H, s), 5.28–5.16(1H, m), 2.23(3H, s), 1.30(6H, d) | 300.33 |
| G-7 | 7-Difluoromethoxy-2-isopropyl-4-(5-methyl-1H-pyrazol-3-ylamino)-2H-phthalazin-1-one | (400MHz, DMSO), 12.03(1H, br s), 9.31(1H, br s), 8.61(1H, d), 7.62–7.49(1H, m), 7.43(1H, s), 6.41(1H, s), 5.37–5.22(1H, m), 2.29(3H, s), 1.40(6H, d) | 350.13 |
| G-8 | 2-Benzyl-7-methoxy-4-(5- | (400MHz, DMSO) 9.46(1H, | 362.30 |

| | | | |
|---|---|---|---|
| | methyl-1H-pyrazol-3-ylamino)-2H-phthalazin-1-one | s), 8.35(1H, d), 7.84(1H, s), 7.55–7.38(5H, m), 6.24(1H, s), 5.35(2H, s), 4.08(3H, s), 5.85(3H, s) | |
| G-9 | 2-Isopropyl-6-methoxy-4-(5-methyl-1H-pyrazol-3-ylamino)-2H-phthalazin-1-one | (400MHz, DMSO) 11.97(1H, br s), 9.16(1H, s), 8.24(1H, d), 7.96(1H, s), 7.42(1H, d), 6.39(1H, s), 5.34–5.28(1H, m), 3.98(3H, s), 2.30(3H, s), 1.37(6H, d) | 314.20 |

Method H

Example H-1

2-Isopropyl-4-(5-methyl-1H-pyrazol-3-ylamino)-7-methylsulfanyl-2H-phthalazin-1-one 7-Mercapto-2-isopropyl-4-bromo-2H-phthalazin-1-one Concentrated sulfuric acid (5 ml) was added dropwise to a solution of 7-Amino-2-Isopropyl-4-bromo-2H-phthalazin-1-one (1.5 g, 5.3 mmol) in acetic acid (15 ml) and the solution was cooled to 0° C. A solution of $NaNO_2$ (0.5 g, 7.4 mmol) in water (2.5 ml) was added dropwise and the reaction mixture was stirred at 0° C. for twenty minutes, after which time urea (0.17 g, 2.8 mmol) was added in one portion. The reaction mixture was then added dropwise to a solution of potassium ethyl xanthate (6 g, 37.7 mmol) in water (7.5 ml) and the mixture was heated to 80° C. for 30 minutes. After this time, the reaction mixture was cooled to room temperature and dichloromethane (DCM) (100 ml) was added. The organic layer was separated, dried ($MgSO_4$), filtered and concentrated under vacuum.

The residue was taken up in THF (10 ml), NaOH (4.95 g, 0.12 mmol) was added in one portion and the mixture was heated to reflux for 24 hours. The mixture was then cooled to room temperature and the suspension was acidified to pH 2 with concentrated HCl. DCM (100 ml) was added, the organic layer was separated and was subsequently washed with HCl (1M, 20 ml) and water (20 ml). The organic layer was extracted with NaOH (1M, 200 ml), the aqueous layer was separated and acidified to pH 1 with concentrated HCl. The mixture was extracted with DCM (2×50 ml), the organic layers were combined, dried ($MgSO_4$), filtered and concentrated under vacuum to give the title compound (0.77 g, 48% yield) as a light brown solid which was taken on directly without further purification.

7-Methylsulfanyl-2-isopropyl-4-bromo-2H-phthalazin-1-one

To a solution of 7-Mercapto-2-isopropyl-4-bromo-2H-phthalazin-1-one (0.77 g, 2.6 mmol) in tetrahydrofuran (THF) (8 ml), was added NaH (60%, 0.13 g, 3.1 mmol) portion-wise. After stirring for five minutes, methyl iodide (0.44 g, 3.1 mmol) was added dropwise and stirring was continued for four hours. The mixture was concentrated under vacuum and the residue was subjected to flash column chromatography (elution: 90% heptane, 10% ethyl acetate) to give the title compound (0.44 g, 54% yield) as a white solid.

$^1$H-NMR: (400 MHz, $D_6$-DMSO), 8.02 (1H, d), 7.88 (1H, d), 7.75 (1H, d), 5.26–5.15 (1H, m), 2.59 (3H, s), 1.35 (6H, d).

This material was then used in the Buchwald reaction as described in Method A to give the corresponding 2-Isopropyl-4-(5-methyl-1H-pyrazol-3-ylamino)-7-methylsulfanyl-2H-phthalazin-1-one (Example H-1).

$^1$H-NMR: (400 MHz, $D_6$-DMSO), 11.92 (1H, s), 9.16 (1H, s), 8.36 (1H, d), 8.01 (1H, d), 7.75 (1H, d), 6.35 (1H, s), 5.29–5.19 (1H, m), 2.62 (3H, s), 2.25 (2H, s), 1.32 (6H, d) MS ($ESI^+$)=$(M+H)^+$ 330.26.

Example H-2

2-Isopropyl-7-methanesulfonyl-4-(5-methyl-1H-pyrazol-3-ylamino)-2H-phthalazin-1-one 2-Isopropyl-7-methanesulfonyl-4-(5-methyl-1H-pyrazol-3-ylamino)-2H-phthalazin-1-one Oxone (0.88 g, 1.4 mmol) was added in one portion to a stirred solution of 2-isopropyl-4-(5-methyl-1H-pyrazol-3-ylamino)-7-methylsulfanyl-2H-phthalazin-1-one (0.12 g, 0.36 mmol) in a 4:1 mixture of dioxane/water (1.2 ml) and the reaction mixture was stirred at room temperature for one hour. The reaction mixture was diluted with water (5 ml) and the solution was extracted with ethyl acetate (3×75 ml), the organic layers were combined, dried ($MgSO_4$), filtered and concentrated under vacuum to give a dark brown solid. Flash column chromatography (elution: 96% DCM, 4% methanol) gave the title compound (0.032 g, 25% yield) as a light yellow solid (Example H-2).

$^1$H-NMR: (400 MHz, $D_6$-DMSO) 11.99 (1H, br s), 9.44 (1H, s), 8.76–8.68 (2H, m), 8.39 (1H, d), 6.36 (1H, s), 5.32–5.18 (1H, m), 3.36 (3H, s), 2.25 (3H, s), 1.34 (6H, d) MS ($ESI^+$)=$(M+H)^+$ 362.16.

Using the experimental conditions reported above (Method H, Example H-1 or H-2) and the appropriate starting materials, the following derivatives were prepared:

| Example-No. | Systematic name | $^1$H-NMR | MS(ESI+, M+H) |
|---|---|---|---|
| H-3 | 2-Isopropyl-4-(5-methyl-1H-pyrazol-3-ylamino)-7-(2-morpholin-4-yl-ethylsulfanyl)-2H-phthalazin-1-one | (250MHz, $D_6$-DMSO) 9.15(1H, s), 8.35(1H, d), 8.08(1H, d), 7.79(1H, dd), 6.34(1H, s), 5.31–5.16(1H, m), 3.61–3.54(4H, m), 3.33–3.24(2H, m), 2.62(2H, t), 2.48–2.40(4H, m), 2.24(3H, s), 1.32(6H, d) | 429.16 |

Method I

Example I-1

2-Isopropyl-7-[methyl-(2-morpholin-4-yl-ethyl)-amino]-4-(5-methyl-1H-pyrazol-3-ylamino)-2H-phthalazin-1-one Bromo-3-isopropyl-4-oxo-3,4-dihydro-phthalazin-6-yl)-carbamic acid tert-butyl ester 7-Amino-2-Isopropyl-4-bromo-2H-phthalazin-1-one (1.88 g, 6.7 mmol) was dissolved in dimethylformamide (DMF) (20 ml). To this was added NaH (60%, 0.8 g, 20.1 mmol) as a suspension in DMF (5 ml). The mixture was stirred at room temperature for 30 minutes then di-tert-butyl dicarbonate (Boc$_2$O) (4.36 g, 20.1 mmol) was added in one portion as a solution in DMF (5 ml) and the reaction mixture was heated at 70° C. for 3 hours. After this time, the reaction mixture was cooled to room temperature and water (20 ml) was added cautiously, the mixture was extracted with ethyl acetate (3×50 ml), the organic layers were combined, dried (MgSO$_4$), filtered and concentrated under vacuum.

The residue was dissolved in a 1:1 mixture of tetrahydrofuran (THF)/ethanol (10 ml) and aqueous NaOH (50% by weight solution, 10 ml) was added in one portion, the reaction mixture was stirred vigorously for 30 minutes. After this time, the mixture was partitioned between water (20 ml) and ethyl acetate (50 ml). The organic layer was dried (MgSO$_4$), filtered and concentrated to give the title compound (2.2 g, 88% yield) as a light brown solid.

$^1$H-NMR: (400 MHz, D$_6$-DMSO), 8.32 (1H, d), 8.19 (1H, s), 7.88 (1H, d), 7.41 (1H, s), 5.46–5.31 (1H, m), 1.52 (9H, s), 1.41 (6H, d) MS (ESI$^+$)=(M+H)$^+$ 382.22.

4-Bromo-2-isopropyl-7-methylamino-2H-phthalazin-1-one

Bromo-3-isopropyl-4-oxo-3,4-dihydro-phthalazin-6-yl)-carbamic acid tert-butyl ester (2.2 g, 5.7 mmol) was dissolved in THF (10 ml). To this was added NaH (60%, 0.34 g, 8.6 mmol) as a suspension in THF (5 ml). The mixture was stirred at room temperature for 30 minutes then methyl iodide (1.4 ml, 23.0 mmol) was added in one portion as a solution in THF (5 ml) and the reaction mixture was stirred at room temperature for 3 hours. After this time, the reaction mixture was cooled to room temperature and water (20 ml) was added cautiously, the mixture was extracted with ethyl acetate (3×50 ml), the organic layers were combined, dried (MgSO$_4$), filtered and concentrated under vacuum.

The residue was dissolved in a 20% trifluoroacetic acid (TFA)/dichloromethane (DCM) solution (10 ml) and the reaction mixture was stirred at room temperature for 2 hours. After this time, the reaction mixture was concentrated under vacuum to afford a brown oil. Heptane (20 ml) was added, and the mixture was concentrated under vacuum. Diethyl ether (10 ml) was added to the residue and the resulting precipitate was filtered and dried under vacuum to afford the title compound (1.14 g, 68% yield) as a light brown solid MS (ESI$^+$)=(M+H)$^+$ 296.16.

4-Bromo-2-isopropyl-7-[methyl-(2-morpholin-4-yl-ethyl)-amino]-2H-phthalazin-1-one 4-Bromo-2-isopropyl-7-methylamino-2H-phthalazin-1-one (0.13 g, 0.44 mmol) was dissolved in dimethylformamide (DMF) (5 ml). To this was added NaH (60%, 0.053 g, 1.3 mmol) as a suspension in DMF (2 ml). The mixture was stirred at room temperature for 30 minutes then 4-(2-Chloro-ethyl)-morpholine (0.12 g, 0.66 mmol) was added in one portion as a solution in DMF (1 ml) and the reaction mixture was heated to 70° C. for 24 hours. After this time, the reaction mixture was cooled to room temperature and water (10 ml) was added cautiously, the mixture was extracted with ethyl acetate (3×10 ml), the organic layers were combined, dried (MgSO$_4$), filtered and concentrated under vacuum. Flash column chromatography (elution: 95% ethyl acetate, 5% methanol) gave the title compound (0.051 g, 30% yield) as a white solid.

$^1$H-NMR: (400 MHz, CDCl$_3$), 7.72 (1H, d), 7.49 (1H, s), 7.16 (1H, d), 5.42–5.29 (1H, m), 3.73–3.67 (4H, m), 3.66–3.59 (2H, t), 3.15 (3H, s), 2.61–2.54 (2H, m), 2.53–2.46 (4H, m), 1.41 (6H, d).

This material was then used in the Buchwald reaction as described in Method A to give the corresponding 2-Isopropyl-7-[methyl-(2-morpholin-4-yl-ethyl)-amino]-4-(5-methyl-1H-pyrazol-3-ylamino)-2H-phthalazin-1-one (example I-1).

Using the experimental conditions reported above (Method I) and the appropriate starting materials, the following derivatives were prepared:

| Example-No. | Systematic name | $^1$H-NMR | MS(ESI+, M+H) |
|---|---|---|---|
| I-1 | 2-Isopropyl-7-[methyl-(2-morpholin-4-yl-ethyl)-amino]-4-(5-methyl-1H-pyrazol-3-ylamino)-2H-phthalazin-1-one | (400MHz, D$_6$-DMSO), 11.81(1H, br s), 8.89(1H, br s), 8.19(1H, d), 7.33(1H, d), 7.23(1H, dd), 6.31(1H, s), 5.28–5.19(1H, m), 3.61(2H, t), 3.57–3.53(4H, m), 3.05(3H, s), 2.48–2.45(2H, m), 2.44–240(4H, m), 2.22(3H, s), 1.29(6H, d) | 426.24 |
| I-2 | 2-Isopropyl-4-(5-methyl-1H-pyrazol-3-ylamino)-7-(methyl-pyridin-4-ylmethyl-amino)-2H-phthalazin-1-one | (250MHz, CD$_3$OD), 8.46(2H, d), 7.96(1H, d), 7.51(1H, d), 7.34–7.22(4H, m), 6.32(1H, s), 5.43–5.23(1H, m), 4.83(2H, s), 3.28(3H, s), 2.29(3H, s), 1.40(6H, d) | 404.28 |
| I-3 | 2-Isopropyl-4-(5-methyl-1H-pyrazol-3-ylamino)-7-(methyl-pyridin-3-ylmethyl-amino)-2H-phthalazin-1-one | (400MHz, D$_6$-DMSO), 9.29(1H, br s), 8.73–8.67(2H, m), 8.18(1H, d), 8.10(1H, d), 7.78(1H, dd), 7.41–7.33(2H, m), 6.36(1H, s), 5.27–5.16(1H, m), 4.95(2H, s), 3.24(3H, s), 2.26(3H, s), 1.30(6H, d) | 404.33 |

-continued

| Example-No. | Systematic name | ¹H-NMR | MS(ESI+, M+H) |
|---|---|---|---|
| I-4 | 2-Isopropyl-4-(5-methyl-1H-pyrazol-3-ylamino)-7-(methyl-pyridin-2-ylmethyl-amino)-2H-phthalazin-1-one | (400MHz, $D_6$-DMSO), 9.24(1H, br s), 8.63(1H, d), 8.15(1H, d), 7.91(1H, t), 7.46–7.40(1H, m), 7.36(1H, d), 7.34–7.28(2H, m), 6.35(1H, s), 5.25–5.15(1H, m), 4.92(2H, s), 3.26(3H, s), 2.26(3H, s), 1.29(6H, d) | 404.32 |
| I-5 | N-[3-Isopropyl-1-(5-methyl-1H-pyrazol-3-ylamino)-4-oxo-3,4-dihydro-phthalazin-6-yl]-N-methyl-acetamide | (400MHz, $D_6$-DMSO), 11.92(1H, s), 9.23(1H, s), 8.48(1H, d), 8.13(1H, d), 7.87(1H, dd), 6.35(1H, s), 5.31–5.16(1H, m), 3.28(3H, s), 2.24(3H, s), 1.94(3H, s), 1.32(6H, d) | 355.33 |
| I-6 | 3-Isopropyl-1-[3-isopropyl-1-(5-methyl-1H-pyrazol-3-ylamino)-4-oxo-3,4-dihydro-phthalazin-6-yl]-1-methyl-urea | (400MHz, $D_6$-DMSO), 11.88(1H, br s), 9.15(1H, s), 8.36(1H, d), 8.03(1H, d), 7.78(1H, dd), 6.48(1H, d), 6.34(1H, s), 5.32–5.18(1H, m), 3.91–3.76(1H, m), 3.28(3H, s), 2.24(3H, s), 1.32(6H, d), 1.10(6H, d) | 398.34 |
| I-7 | [3-Isopropyl-1-(5-methyl-1H-pyrazol-3-ylamino)-4-oxo-3,4-dihydro-phthalazin-6-yl]-methyl-carbamic acid ethyl ester | (400MHz, $D_6$-DMSO) 12.16–11.60(1H, m), 9.23(1H, s), 8.49(1H, d), 8.23(1H, s), 7.95(1H, d), 6.43(1H, s), 5.48–5.13(1H, m), 4.21(2H, q), 3.42(3H, s), 2.31(3H, s), 1.39(6H, d), 1.27(3H, t) | 385.13 |
| I-8 | N-[3-Isopropyl-1-(5-methyl-1H-pyrazol-3-ylamino)-4-oxo-3,4-dihydro-phthalazin-6-yl]-acetamide | (250MHz, $D_6$-DMSO) 10.50(1H, s), 9.11(1H, s), 8.51(1H, d), 8.37(1H, d), 8.06(1H, dd), 6.34(1H, s), 5.32–5.17(1H, m), 2.25(3H, s), 2.13(3H, s), 1.32(6H, d) | 341.41 |
| I-9 | 7-[(4-Fluoro-benzyl)-methyl-amino]-2-isopropyl-4-(5-methyl-1H-pyrazol-3-ylamino)-2H-phthalazin-1-one | (400MHz, $D_6$-DMSO) 8.99(1H, s), 8.18(1H, d), 7.35(1H, d), 7.28(1H, dd), 7.26–7.20(2H, m), 7.19–7.11(2H, m), 6.32(1H, s), 5.28–5.16(1H, m), 4.76(2H, s), 3.18(3H, s), 2.23(3H, s), 1.29(6H, d) | 421.40 |
| I-10 | N-[3-Isopropyl-1-(5-methyl-1H-pyrazol-3-ylamino)-4-oxo-3,4-dihydro-phthalazin-6-yl]-N-methyl-methanesulfonamide | (400MHz, DMSO) 11.94(1H, br. s.), 9.23(1H, br. s.), 8.48(1H, d), 8.23(1H, d), 7.91(1H, dd), 6.36(1H, s), 5.30–5.21(1H, m), 3.38(3H, s), 3.03(3H, s), 2.25(3H, s), 1.32(6H, d) | 391.35 |
| I-11 | 2-Isopropyl-4-(5-methyl-1H-pyrazol-3-ylamino)-7-(2-morpholin-4-yl-ethylamino)-2H-phthalazin-1-one | (250MHz, $D_6$-DMSO), 9.64(1H, br s), 8.91(1H, s), 8.09(1H, d), 7.27(1H, d), 7.07(1H, d), 6.71(1H, br s), 6.25(1H, s), 5.20–5.13(1H, m), 3.95–3.92(2H, m), 3.29–3.27(4H, m), 3.11–3.08(2H, m), 2.17(3H, s), 1.23(6H, d) | 412.37 |
| I-12 | 2-Isopropyl-7-methylamino-4-(5-methyl-1H-pyrazol-3- | (400MHz, $D_6$-DMSO), 9.04(1H, br s), 8.08(1H, d), 7.19(1H, d), 7.06(1H, dd), 6.33(1H, | 313.18 |

-continued

| Example-No. | Systematic name | ¹H-NMR | MS(ESI+, M+H) |
|---|---|---|---|
| | ylamino)-2H-phthalazin-1-one | d), 5.29–5.19(1H, m), 2.80(3H, s), 2.26(3H, s), 1.30(6H, d) | |
| I-13 | 1-[3-Isopropyl-1-(5-methyl-1H-pyrazol-3-ylamino)-4-oxo-3,4-dihydro-phthalazin-6-yl]-3-methyl-urea | (400MHz, $D_6$-DMSO), 8.98(1H, s), 8.91(1H, s), 8.06(1H, s), 8.03(1H, s), 7.71(1H, d), 6.12(1H, s), 6.05(1H, s), 5.05–4.97(1H, m), 2.45(3H, s), 2.03(3H, s), 1.10(6H, d) | |
| I-14 | [3-Isopropyl-1-(5-methyl-2H-pyrazol-3-ylamino)-4-oxo-3,4-dihydro-phthalazin-6-yl]-methyl-carbamic acid tert-butyl ester | (250MHz, DMSO), 9.31(1H, br s), 8.37(1H, d), 8.15(1H, d), 7.87(1H, dd), 6.36(1H, s), 5.31–5.15(1H, m), 3.32(3H, s), 2.26(3H, s), 1.44(9H, s), 1.32(6H, d) | 413.18 |

Example I-13 is composed as Example J-1 under Method J.

Method J

Example J-1

1-[3-Isopropyl-1-(5-methyl-1H-pyrazol-3-ylamino)-4-oxo-3,4-dihydro-phthalazin-6-yl]-3-methyl-urea 1-(1-Bromo-3-isopropyl-4-oxo-3,4-dihydro-phthalazin-6-yl)-3-methyl-urea 7-Amino-2-Isopropyl-4-bromo-2H-phthalazin-1-one (0.5 g, 1.77 mmol) was dissolved in tetrahydrofuran (THF) (5 ml). To this was added NaH (60%, 0.14 g, 3.54 mmol) as a suspension in THF (2 ml) and the reaction mixture was stirred for 5 minutes. After this time methyl isocyanate (0.2 g, 3.55 mmol) was added in one portion and the reaction mixture was stirred at room temperature for a further 48 hours. After this time, the reaction mixture was partitioned between ethyl acetate (50 ml) and water (50 ml), the organic layer was separated, dried (MgSO₄), filtered and concentrated under vacuum to give the title compound (0.47 g, 78% yield) as a light brown solid.

This material was then used in the Buchwald reaction as described in Method A to give the corresponding 1-[3-Isopropyl-1-(5-methyl-1H-pyrazol-3-ylamino)-4-oxo-3,4-dihydro-phthalazin-6-yl]-3-methyl-urea (example J-1).

Using the experimental conditions reported above (Method J) and the appropriate starting materials, the following derivatives were prepared:

| Example-No. | Systematic name | ¹H-NMR | MS(ESI+, M+H) |
|---|---|---|---|
| J-1 | 1-[3-Isopropyl-1-(5-methyl-1H-pyrazol-3-ylamino)-4-oxo-3,4-dihydro-phthalazin-6-yl]-3-methyl-urea | (400MHz, $D_6$-DMSO), 8.98(1H, s), 8.91(1H, s), 8.04(1H, d), 7.70(1H, dd), 6.12(1H, s), 6.04(1H, s), 5.05–4.97(1H, m), 2.47(3H, d), 2.03(3H, s), 1.09(6H, d) | |
| J-2 | N-[3-Isopropyl-1-(5-methyl-1H-pyrazol-3-ylamino)-4-oxo-3,4-dihydro-phthalazin-6-yl]-methanesulfonamide | (400MHz, $D_6$-DMSO), 10.49(1H, br s), 9.34(1H, s), 8.43(1H, d), 8.11(1H, s), 6.36(1H, s), 5.32–5.19(1H, m), 3.15(3H, s), 2.25(3H, s), 1.33(6H, d) | 377.24 |

Method K

Example K-1

2-Isopropyl-7-methoxymethyl-4-(5-methyl-1H-pyrazol-3-ylamino)-2H-phthalazin-1-one 1,4-Dioxo-1,2,3,4-tetrahydro-phthalazine-6-carboxylic acid Hydrazine hydrate (26 g, 0.52 mol) was added in one portion to a stirred mixture of 1,2,4-benzenetricarboxylic anhydride (10 g, 0.52 mol), in acetic acid (1.0 L) at room temperature. The mixture was heated to 120° C. for 2 hours and then allowed to cool to room temperature. The solid was filtered, washed with water (250 ml) and dried in the vacuum oven at 50° C. for 20 hours to give the title compound (91 g, 85% yield).

Bromo-4-oxo-3,4-dihydro-phthalazine-6-carboxylic acid 1,4-Dioxo-1,2,3,4-tetrahydro-phthalazine-6-carboxylic acid (91.0 g, 0.44 mol) was suspended in dichloroethane (1.0 L) and phosphorus pentabromide (761.0 g, 1.77 mol) was added in three portions and the reaction heated to reflux for 24 hours. The reaction was cooled to room temperature and poured onto ice (2.50 kg) and the resulting precipitate filtered and washed with water to give the crude product (130 g).

This crude material was suspended in acetic acid (1.60 L) and heated to 125° C. for 2 hours. The reaction was cooled to room temperature and poured onto ice (1.5 kg) and the resulting precipitate filtered. The solid was washed with water and dried to give the title compound (85 g, 73% yield) as a yellow solid. MS (ESI⁺)=(M+H)⁺ 310 & 312

Bromo-4-oxo-3,4-dihydro-phthalazine-6-carboxylic acid ethyl ester

Concentrated sulfuric acid (40 ml) was added to a stirred solution of 1-Bromo-4-oxo-3,4-dihydro-phthalazine-6-carboxylic acid (85 g, 0.32 mol) in ethanol (500 ml) and the mixture was heated to reflux for 48 hours. After this time, the reaction mixture was cooled and the resulting precipitate was filtered. The precipitate was partitioned between ethyl acetate (1 L) and saturated NaHCO₃ (500 ml), the organic layer was separated and washed with water (500 ml) before being dried (MgSO₄), filtered and concentrated under vacuum to give the title compound (30 g, 31% yield) as a white solid. MS (ESI⁺)=(M+H)⁺ 297 & 299

Bromo-3-isopropyl-4-oxo-3,4-dihydro-phthalazine-6-carboxylic acid ethyl ester

Bromo-4-oxo-3,4-dihydro-phthalazine-6-carboxylic acid ethyl ester (6 g, 0.02 mol) was dissolved in dimethylformamide (DMF) (60 ml). To this was added NaH (60%, 0.97 g, 0.024 mol) as a DMF suspension (5 ml). The mixture was stirred at room temperature for 30 minutes then 2-bromopropanol (3.7 g, 0.03 mol) was added in one portion as a solution in DMF (5 ml). The reaction mixture was stirred for 48 hours whereupon LC-MS showed complete consumption of starting material. The DMF was removed under vacuum and the resulting residue was partitioned between DCM (100 ml) and water (100 ml), the organic layer was dried (MgSO₄), filtered and concentrated under vacuum. The resulting yellow oil was recrystallised from methanol to give the title compound (2.3 g, 34% yield) as a white solid. MS (ESI⁺)=(M+H)⁺ 339 & 341

4-Bromo-7-hydroxymethyl-2-isopropyl-2H-phthalazin-1-one

Bromo-3-isopropyl-4-oxo-3,4-dihydro-phthalazine-6-carboxylic acid ethyl ester (2.3 g, 6.8 mmol) was suspended in tetrahydrofuran (THF) (50 ml) and cooled to 0° C. To the suspension was added LiBH₄ (5.1 ml of a 2M solution in THF, 10.2 mmol) dropwise, the suspension was allowed to warm to room temperature and stirred for 24 hours. After this time, LC-MS showed 50% starting material remained. To this was added LiBH₄ (1.7 ml of a 2M solution in THF, 3.4 mmol) and the reaction mixture was stirred for a further 3 hours. The reaction was cooled to 0° C., saturated NH₄Cl (40 ml) was added and the reaction mixture was then partitioned between water (50 ml) and dichloromethane (DCM) (150 ml). The organic layer was separated, dried (MgSO₄), filtered and concentrated under vacuum. The resulting residue was then purified by flash column chromatography (elution: 50% toluene, 30% ethyl acetate, 20% DCM) to give the title compound (0.9 g, 43% yield) as a white solid.

¹H-NMR: (400 MHz, D₆-DMSO), 8.28 (1H, s), 7.96 (1H, d), 7.88 (1H, d), 5.64 (1H, t), 5.31–5.18 (1H, m), 4.78 (2H, d), 1.35 (6H, d); MS (ESI⁺)=(M+H)⁺ 297 & 299

4-Bromo-2-isopropyl-7-methoxymethyl-2H-phthalazin-1-one

4-Bromo-7-hydroxymethyl-2-isopropyl-2H-phthalazin-1-one (0.11 g, 0.37 mmol) was dissolved in THF (2 ml). To this was added NaH (60%, 0.019 g, 0.44 mmol) as a THF suspension (2 ml). To this was added methyl iodide (0.063 g, 0.48 mmol) and the reaction mixture was stirred for 20 hours. The reaction mixture was concentrated under vacuum and the residue was purified by flash column chromatography (elution: 80% heptane, 20% ethyl acetate) to give the title compound (0.08 g, 69% yield) as a white solid.

This material was then used in the Buchwald reaction as described in Method A to give the corresponding 2-Isopropyl-7-methoxymethyl-4-(5-methyl-1H-pyrazol-3-ylamino)-2H-phthalazin-1-one (example K-1).

Using the experimental conditions reported above (Method K) and the appropriate starting materials, the following derivatives were prepared:

| Example-No. | Systematic name | ¹H-NMR | MS(ESI+, M+H) |
|---|---|---|---|
| K-1 | 2-Isopropyl-7-methoxymethyl-4-(5-methyl-1H-pyrazol-3-ylamino)-2H-phthalazin-1-one | (400MHz, DMSO), 11.88(1H, br s), 9.18(1H, br s), 8.42(1H, d), 8.23(1H, br s), 7.80(1H, d), 6.35(1H, s), 5.30–5.20(1H, m), 4.62(2H, s), 2.24(3H, s), 1.32(6H, d) | 328.31 |
| K-2 | Isopropyl-6-methoxymethyl-4-(5-methyl-2H-pyrazol-3-ylamino)-2H-phthalazin-1-one | | 376.30 |
| K-3 | 2-Benzyl-7-methoxymethyl-4-(5-methyl-1H-pyrazol-3-ylamino)-2H-phthalazin-1-one | (400MHz, DMSO), 11.93(1H, s), 9.19(1H, s), 8.43(1H, s), 8.27(1H, d), 7.79(1H, d), 6.37(1H, s), 5.30–5.20(1H, m), 4.61(2H, s), 3.37(3H, s), 2.25(3H, s), 1.33(6H, d) | 328.31 |

Method L

Example L-1

2-Isopropyl-7-(4-methyl-piperazin-1-ylmethyl)-4-(5-methyl-1H-pyrazol-3-ylamino)-2H-phthalazin-1-one 4-Bromo-7-bromomethyl-2-isopropyl-2H-phthalazin-1-one A solution of 4-Bromo-7-hydroxymethyl-2-isopropyl-2H-phthalazin-1-one (0.74 g, 2.5 mmol) in acetonitrile (5 ml) was added dropwise to a stirred suspension of trimethylsilyl bromide (TMSBr) (0.9 g, 6.3 mmol) and LiBr (0.41 g, 5 mmol) in acetonitrile (15 ml). The reaction mixture was heated to 80° C. for 24 hours, after which time the reaction mixture was cooled to room temperature and the solvent removed under vacuum. The resulting residue was purified by flash column chromatography (elution: 85% heptane, 15% ethyl acetate) to give the title compound (0.4 g, 44% yield) as a white solid.

¹H-NMR: (250 MHz, D₆-DMSO), 8.37 (1H, s), 8.03 (1H, d), 7.94 (1H, d), 5.26–5.09 (1H, m), 4.93 (2H, s), 1.35 (6H, d).

4-Bromo-2-isopropyl-7-(4-methyl-piperazin-1-ylmethyl)-2H-phthalazin-1-one

4-Bromo-7-bromomethyl-2-isopropyl-2H-phthalazin-1-one (0.2 g, 0.56 mmol) was dissolved in tetrahydrofuran (THF) (1 ml), to this was added N-Methyl piperazine (0.14 g, 1.4 mmol) as a solution in THF (1 ml) and the reaction mixture was stirred for 1 hour. Whereupon LC-MS indicated complete consumption of starting material, the solvent was removed under vacuum and the residue was purified by flash column chromatography (elution: 90% ethyl acetate, 10% methanol) to give the title compound (0.17 g, 84% yield) as a light yellow solid.

This material was then used in the Buchwald reaction as described in Method A to give the corresponding 2-Isopropyl-7-(4-methyl-piperazin-1-ylmethyl)-4-(5-methyl-1H-pyrazol-3-ylamino)-2H-phthalazin-1-one (example L-1).

Using the experimental conditions reported above (Method L) and the appropriate starting materials, the following derivatives were prepared:

| Example-No. | Systematic name | $^1$H-NMR | MS(ESI+, M+H) |
|---|---|---|---|
| L-1 | 2-Isopropyl-7-(4-methyl-piperazin-1-ylmethyl)-4-(5-methyl-1H-pyrazol-3-ylamino)-2H-phthalazin-1-one | (250MHz, D$_6$-DMSO), 9.16(1H, br s), 8.40(1H, d), 8.20(1H, d), 7.80(1H, d), 6.36(1H, s), 5.32–5.21(1H, m), 3.65(2H, s), 2.45–2.28(8H, m), 2.25(3H, s), 2.16(3H, s), 1.32(6H, d) | 396.33 |
| L-2 | 2-Isopropyl-4-(5-methyl-1H-pyrazol-3-ylamino)-7-morpholin-4-ylmethyl-2H-phthalazin-1-one | (250MHz, D$_6$-DMSO), 9.20(1H, br s), 8.41(1H, d), 8.23–8.19(1H, m), 7.81(1H, dd), 6.34(1H, s), 5.33–5.17(1H, m), 3.66(2H, s), 3.62–3.54(4H, m), 2.43–2.34(4H, m), 2.24(3H, s), 1.32(6H, d) | 383.31 |

Method M

Example M-1

3-Isopropyl-1-(5-methyl-1H-pyrazol-3-ylamino)-4-oxo-3,4-dihydro-phthalazine-6-carboxylic acid 3-{tert-Butoxycarbonyl-[6-(tert-butyl-dimethyl-silanyloxymethyl)-3-isopropyl-4-oxo-3,4-dihydro-phthalazin-1-yl]-amino}-5-methyl-pyrazole-1-carboxylic acid tert-butyl ester 7-(tert-Butyl-dimethyl-silanyloxymethyl)-2-isopropyl-4-(5-methyl-1H-pyrazol-3-ylamino)-2H-phthalazin-1-one (0.68 g, 1.59 mmol) was dissolved in dimethylformamide (DMF) (20 ml). To this was added NaH (60%, 0.22 g, 5.56 mmol) as a suspension in DMF (2 ml). The mixture was stirred at room temperature for 15 minutes then di-tert-butyl dicarbonate (Boc$_2$O) (1.05 g, 5.56 mmol) in DMF (2 ml) was added in one portion and the reaction mixture was stirred at room temperature for 3 hours. After this time, the reaction mixture was concentrated under vacuum and the resulting residue was purified by flash column chromatography (elution: 50% heptane, 50% ethyl acetate) to give the title compound (0.78 g, 78% yield) as a brown oil. MS (ESI$^+$)=(M+H)$^+$ 628.51.

3-[tert-Butoxycarbonyl-(6-hydroxymethyl-3-isopropyl-4-oxo-3,4-dihydro-phthalazin-1-yl)-amino]-5-methyl-pyrazole-1-carboxylic acid tert-butyl ester 3-{tert-Butoxycarbonyl-[6-(tert-butyl-dimethyl-silanyloxymethyl)-3-isopropyl-4-oxo-3,4-dihydro-phthalazin-1-yl]-amino}-5-methyl-pyrazole-1-carboxylic acid tert-butyl ester (0.78, 1.25 mmol) was dissolved in tetrahydrofuran (THF) (3 ml), to this was added a 1M solution of tetrabutylammonium fluoride (TBAF) in THF (1.87 ml, 1.87 mmol) and the mixture was stirred at room temperature for 24 hours. After this time the reaction mixture was concentrated under vacuum and the residue was purified by flash column chromatography (elution: 50% heptane, 50% ethyl acetate) to give the title compound (0.39 g, 45% yield) as a brown solid MS (ESI$^+$)=(M+H)$^+$ 514.43.

1-[tert-Butoxycarbonyl-(1-tert-butoxycarbonyl-5-methyl-1H-pyrazol-3-yl)-amino]-3-isopropyl-4-oxo-3,4-dihydro-phthalazine-6-carboxylic acid 3-[tert-Butoxycarbonyl-(6-hydroxymethyl-3-isopropyl-4-oxo-3,4-dihydro-phthalazin-1-yl)-amino]-5-methyl-pyrazole-1-carboxylic acid tert-butyl ester (0.2 g, 0.39 mmol) was dissolved in dimethylsulfoxide (DMSO) (3 ml). To this was added 2-iodoxybenzoic acid (IBX) (0.22 g, 0.78 mmol) in one portion and the reaction mixture was stirred at room temperature for 24 hours. After this time, the reaction mixture was partitioned between ethyl acetate (20 ml) and water (20 ml), the organic layer was separated and washed with water (3×20 ml) before being dried (MgSO$_4$), filtered and concentrated under vacuum.

The resulting orange oil (0.197 g, 0.38 mmol) was dissolved in dichloromethane (DCM) (3 ml) and water (3 ml). To this was added sulfamic acid (0.037 g, 0.38 mmol) and the reaction mixture was stirred vigorously at 0° C. After 5 minutes, sodium chlorite (0.034 g, 0.38 mmol) was added in one portion and the mixture stirred for a further hour. After this time, the reaction mixture was diluted with DCM (20 ml) and washed with water (10 ml). The organic layer was separated, dried (MgSO$_4$), filtered and concentrated under vacuum. The resulting residue was purified by flash column chromatography (elution: 50% heptane, 50% ethyl acetate to 100% ethyl acetate) to give the title compound (0.088 g, 44% yield) as a white solid. MS (ESI$^+$)=(M+H)$^+$ 528.41.

Isopropyl-1-(5-methyl-1H-pyrazol-3-ylamino)-4-oxo-3,4-dihydro-phthalazine-6-carboxylic acid 1-[tert-Butoxycarbonyl-(1-tert-butoxycarbonyl-5-methyl-1H-pyrazol-3-yl)-amino]-3-isopropyl-4-oxo-3,4-dihydro-phthalazine-6-carboxylic acid (13.0 mg, 0.02 mmol) was dissolved in a 20% trifluoroacetic acid (TFA)/DCM solution (2 ml) and the reaction mixture was stirred for 48 hours. After this time, the reaction mixture was concentrated and the resulting residue was triturated with diethyl ether to give the title compound (Example M-1) as a white solid.

$^1$H-NMR: (400 MHz, D$_6$-DMSO), 9.34(1H, s), 8.73 (1H, s), 8.47 (1H, d), 8.26 (1H, d), 6.28 (1H, s), 5.20–5.17 (1H, m), 2.19 (3H, s), 1.26 (6H, d) MS (ESI$^+$)=(M+H)$^+$ 328.31.

Example M-2

2-Isopropyl-4-(5-methyl-1H-pyrazol-3-ylamino)-7-(morpholine-4-carbonyl)-2H-phthalazin-1-one Isopropyl-4-(5-methyl-1H-pyrazol-3-ylamino)-7-(morpholine-4-carbonyl)-2H-phthalazin-1-one 1-[tert-Butoxycarbonyl-(1-tert-butoxycarbonyl-5-methyl-1H-pyrazol-3-yl)-amino]-3-isopropyl-4-oxo-3,4-dihydrophthalazine-6-carboxylic acid (13 mg, 0.025 mmol) was dissolved in DMF (2 ml). To this was added morpholine (6.4 mg, 0.075 mmol) and the reaction mixture was cooled to 0° C., 2-(1H-Benzotriazole-1-yl)-1,1,3,3-tetramethyluronium tetrafluoroborate (TBTU) (15 mg, 0.03 mmol) and triethylamine (0.014 ml, 0.1 mmol) were added consecutively and the reaction mixture stirred at room temperature for 24 hours. After this time, the reaction mixture was partitioned between ethyl acetate (10 ml) and water (10 ml). The organic layer was separated, dried (MgSO$_4$), filtered and concentrated under vacuum.

The resulting residue (13.0 mg, 0.02 mmol) was dissolved in a 20% TFA/DCM solution (2 ml) and the reaction mixture was stirred for 48 hours. After this time, the reaction mixture was concentrated and the resulting residue was triturated with diethyl ether to give the corresponding 2-Isopropyl-4-(5-methyl-1H-pyrazol-3-ylamino)-7-(morpholine-4-carbonyl)-2H-phthalazin-1-one (Example M-2).

$^1$H-NMR: (400 MHz, D$_6$-DMSO) 9.40 (1H, s), 8.50 (1H, d), 8.23 (1H, s), 7.91 (1H, d), 6.36 (1H, s), 5.28–5.21 (1H, m), 4.12–3.30 (8H, obscured) 2.26 (3H, s), 1.33 (6H, d) MS (ESI$^+$)=(M+H)$^+$ 397.21.

Using the experimental conditions reported above (Method M, Example M-2) and the appropriate starting materials, the following derivatives were prepared:

| Example No. | Systematic name | $^1$H-NMR | MS(ESI+, M+H) |
|---|---|---|---|
| M-3 | 3-Isopropyl-1-(5-methyl-1H-pyrazol-3-ylamino)-4-oxo-3,4-dihydro-phthalazine-6-carboxylic acid diethylamide | (400MHz, D$_6$-DMSO), 9.46(1H, s), 8.46(1H, d), 8.17(1H, s), 7.88(1H, d), 6.37(1H, s), 5.26–5.23(1H, m), 3.48–3.47(2H, m), 3.18–3.16(2H, m), 2.27(3H, s), 1.34(6H, d), 1.18–1.15(3H, m), 1.08–1.01(3H, m) | 383.16 |
| M-4 | 3-Isopropyl-1-(5-methyl-1H-pyrazol-3-ylamino)-4-oxo-3,4-dihydro-phthalazine-6-carboxylic acid methoxy-amide | (400MHz, D$_6$-DMSO), 12.16(1H, br s), 9.39(1H, s), 8.66(1H, s), 8.51(1H, d), 8.21(1H, d), 6.36(1H, s), 5.28–5.22(1H, m), 3.75(3H, s), 2.26(3H, s), 1.33(6H, d) | 357.12 |
| M-5 | 3-Isopropyl-1-(5-methyl-1H-pyrazol-3-ylamino)-4-oxo-3,4-dihydro-phthalazine-6-carboxylic acid isopropylamide | (400MHz, D$_6$-DMSO) 9.43(1H, br. s.), 8.76(1H, d), 8.70(1H, d), 8.49(1H, d), 8.31(1H, dd), 6.38(1H, s), 5.31–5.22(1H, m), 4.21–4.09(1H, m), 2.27(3H, s), 1.34(6H, d), 1.20(6H, d) | 369.37 |
| M-6 | 3-Isopropyl-1-(5-methyl-1H-pyrazol-3-ylamino)-4-oxo-3,4-dihydro-phthalazine-6-carboxylic acid cyclopropylmethyl ester | (400MHz, D$_6$-DMSO) 9.36(1H, s), 8.83(1H, d), 8.60(1H, d), 8.36(1H, dd), 6.35(1H, s), 5.33–5.16(1H, m), 4.21(2H, d), 2.25(3H, s), 1.33(6H, d), 1.25–1.21(1H, m), 0.65–0.56(2H, m), 0.45–0.34(2H, m) | 382.36 |
| M-7 | 7-(4-Acetyl-piperazine-1-carbonyl)-2-isopropyl-4-(5-methyl-1H-pyrazol-3-ylamino)-2H-phthalazin-1-one | (400MHz, D$_6$-DMSO) 9.30(1H, s), 8.51(1H, d), 8.25(1H, d), 7.90(1H, dd), 6.34(1H, s), 5.32–5.16(1H, m), 2.24(3H, s), 2.01(3H, d), 1.32(6H, d) | 438.40 |

Example M-8

3-Isopropyl-1-(5-methyl-1H-pyrazol-3-ylamino)-4-oxo-3,4-dihydro-phthalazine-6-carboxylic acid methyl ester 1-[tert-Butoxycarbonyl-(1-tert-butoxycarbonyl-5-methyl-1H-pyrazol-3-yl)-amino]-3-isopropyl-4-oxo-3,4-dihydro-phthalazine-6-carboxylic acid (10 mg, 0.019 mmol) (Intermediate of Example M-1) was dissolved in dichloromethane (DCM) (1 ml). To this was added K$_2$CO$_3$ (3.1 mg, 0.028 mmol) followed by methyl iodide (3.3 mg, 0.028 mmol) and the reaction mixture was stirred at room temperature for 30 minutes. After this time the reaction mixture was partitioned between ethyl acetate (10 ml) and water (10 ml). The organic layer was separated, dried (MgSO$_4$), filtered and concentrated under vacuum.

The resulting residue was dissolved in a 20% trifluoroacetic acid (TFA)/DCM solution (2 ml) and the reaction mixture was stirred for 48 hours. After this time, the reaction mixture was concentrated and the resulting residue was triturated with diethyl ether to give the title compound as a white solid.

$^1$H-NMR: (400 MHz, D$_6$-DMSO), 12.16 (1H, br s), 9.39 (1H, s), 8.66 (1H, s), 8.51 (1H, d), 8.21 (1H, d), 6.36 (1H, s), 5.28–5.22 (1H, m), 3.75 (3H, s), 2.26 (3H, s), 1.33 (6H, d) MS (ESI$^+$)=(M+H)$^+$ 357.12.

Example M-9

7-Hydroxymethyl-2-isopropyl-4-(5-methyl-1H-pyrazol-3-ylamino)-2H-phthalazin-1-one Bromo-7-hydroxymethyl-2-isopropyl-2H-phthalazin-1-one (2.0 g, 6.73 mmol) was dissolved in DCM (15 ml). To this was added, triethylamine (1.4 ml, 10.09 mmol) and 4-(Dimethylamino)pyridine (DMAP) (5 mg). The mixture was stirred at room temperature for 5 minutes, after which time a solution of tert-butyldimethylsilyl chloride (TBSCl) (1.22 g, 8.07 mmol) in DCM (5 ml) was added dropwise and the reaction mixture was stirred at room temperature for 24 hours. The reaction mixture was partitioned between DCM (100 ml) and water (50 ml), the organic layer was separated, dried (MgSO$_4$), filtered and concentrated under vacuum. The resulting residue was purified by flash column chromatography to give 4-Bromo-7-(tert-butyl-dimethyl-silanyloxymethyl)-2-isopropyl-2H-phthalazin-1-one (2.54 g, 92% yield) as a white solid. MS (ESI$^+$)=(M+H)$^+$ 412 & 414

This material was then used in the Buchwald reaction as described in Method A and the residue was dissolved in a 1:1 tetrahydrofuran (THF)/DCM solution (6 ml). TBAF on silica (0.35 g, 0.35 mmol) was added and the mixture was stirred at room temperature for 24 hours. After this time the reaction mixture was filtered and the silica washed with DCM (20 ml). The solvent was removed under vacuum to give the corresponding 7-Hydroxymethyl-2-isopropyl-4-(5-methyl-1H-pyrazol-3-ylamino)-2H-phthalazin-1-one (Example M-9).

$^1$H-NMR: (400 MHz, D$_6$-DMSO), 9.12 (1H, s), 8.40 (1H, d), 8.26 (1H, s), 7.79 (1H, d), 6.37 (1H, s), 5.51 (1H, t), 5.30–5.21 (1H, m), 4.69 (2H, d), 2.24 (3H, s), 1.32 (6H, d) MS (ESI$^+$)=(M+H)$^+$ 314.16.

Using the experimental conditions reported above (Method M, Example M-9) and the appropriate starting materials, the following derivatives were prepared:

| Example-No. | Systematic name | $^1$H-NMR | MS(ESI+, M+H) |
|---|---|---|---|
| M-10 | 6-Hydroxymethyl-2-isopropyl-4-(5-methyl-1H-pyrazol-3-ylamino)-2H-phthalazin-1-one | (400MHz, D$_6$-DMSO), 9.44(1H, br s), 8.32(1H, s), 8.26(1H, d), 7.82(1H, d), 6.38(1H, s), 5.29–5.19(1H, m), 4.71(2H, s), 2.28(3H, s), 1.33(6H, d) | 314.24 |

Method N

Example N-1

3-Isopropyl-1-(5-methyl-1H-pyrazol-3-ylamino)-4-oxo-3,4-dihydro-phthalazine-6-carboxylic acid amide Bromo-3-isopropyl-4-oxo-3,4-dihydro-phthalazine-6-carbonitrile Concentrated HCl (0.82 ml) was added slowly to a suspension of 7-Amino-2-Isopropyl-4-bromo-2H-phthalazin-1-one (1.0 g, 3.55 mmol) in water (4 ml). The reaction mixture was cooled to 0° C. and a solution of NaNO$_2$ (0.3 g, 4.30 mmol) in water (1 ml) was added dropwise. The mixture was cooled to −20° C., toluene (4 ml) was added, and the mixture was neutralised with saturated NaHCO$_3$ (5 ml).

At the same time, a solution of KCN (1.5 g, 23.4 mmol) in water (3 ml) was added dropwise to a suspension of Cu(I)Cl in water (4 ml), the mixture was cooled to 0° C. and stirred for 1 hour. After this time, ethyl acetate (8 ml) was added, followed portionwise by the diazonium species prepared above and the mixture was stirred for a further hour before being cooled and filtered through celite. The filtrate was washed with water (5 ml), saturated NaHCO$_3$ (5 ml) and brine (5 ml). The organic layer was dried (MgSO$_4$), filtered and concentrated under vacuum. The resulting residue was purified by flash column chromatography (elution: 80% heptane, 20% ethyl acetate) to give the title compound (0.077 g, 8% yield) as an orange solid. MS (ESI$^+$)=(M+H)$^+$ 292 & 294.

This material was then used in the Buchwald reaction as described in Method A to give the corresponding 3-Isopropyl-1-(5-methyl-1H-pyrazol-3-ylamino)-4-oxo-3,4-dihydro-phthalazine-6-carboxylic acid amide (example N-1).

Example N-1

3-Isopropyl-1-(5-methyl-1H-pyrazol-3-ylamino)-4-oxo-3,4-dihydro-phthalazine-6-carboxylic acid amide $^1$H-NMR: (400 MHz, D$_6$-DMSO), 11.79 (1H, s), 9.12 (1H, s), 8.63 (1H, s), 8.37 (1H, d), 8.22 (1H, s), 8.16 (1H, d), 7.52 (1H, s), 6.20 (1H, s), 5.21–4.95 (1H, m), 2.10 (3H, s), 1.18 (6H, d); MS (ESI$^+$)=(M+H)$^+$ 327.30.

Method O

Example O-1

2-(2-Methoxyethyl)-4-(5-methyl-2H-pyrazol-3-ylamino)-2H-phthalazin-1-one

4-Bromo-2-(2-methoxyethyl)-4-bromo-2H-phthalazin-1-one

4-Bromo-2H-phthalazin-1-one (see Method E, 2.25 g, 10 mmol) was dissolved in dimethylformamide (DMF) (30 ml). To this was added NaH (60%, 0.27 g, 11 mmol) as a DMF suspension (10 ml). The mixture was stirred at 5° C. for 30 min then 1-bromo-2methoxyethane (1.67 g, 12 mmol) was added in one portion as a solution in DMF (10 ml). The reaction mixture was stirred for 24 hours at room temperature, before it was poured into H$_2$O (200 ml). Extraction with ethyl acetate, subsequent drying of the combined organic phases over Na$_2$SO$_4$, filtration of the solid and stirring of the collected precipitate in diethyl ether:heptane (1:1) gave the title compound (2.4 g, 85% yield) as a white solid. $^1$H-NMR: (400 MHz, D$_6$-DMSO) 8.30 (1H, d), 8.03–8.30 (1H, m), 7.94–7.99 (2H, m), 4.30 (2H, t), 3.71 (2H, t), 3.25 (3H, s).

Typical procedure for the Buchwald reaction with 1-(tert-butyl)-3-methyl-1H-pyrazol-5-ylamine:

4-(2-tert-Butyl-5-methyl-2H-pyrazol-3-ylamino)-2-(2-methoxy-ethyl)-2H-phthalazin-1-one 4-Bromo-2-(2-methoxyethyl)-4-bromo-2H-phthalazin-1-one (0.57 g, 2.0 mmol), 1-(tert-butyl)-3-methyl-1H-pyrazol-5-ylamine (0.46 g, 3.0 mmol), Cs$_2$CO$_3$ (0.98 mg, 3.0 mmol), tris(dibenzylideneacetone)-dipalladium (0) (0.092 g, 0.1 mmol) and 4,5-bis(diphenylphosphino)-9,9-dimethylxanthene (0.17 mg, 0.3 mmol) were dissolved in degassed dioxane (10 ml). The reaction mixture was heated with stirring to 130° C. for 8 hours and then cooled to room temperature. H$_2$O (100 ml) was added and the precipitated solid was filtered and washed with ethyl acetate and H$_2$O. The raw product was purified over silica gel (ethyl acetate: heptane 0%-60% ethyl acetate) to give the title compound (0.46 g, 65% yield). $^1$H-NMR: (400 MHz, D$_6$-DMSO) 8.22–8.31 (3H, m), 7.95 (1H, t), 7.86 (1H, t), 5.91 (1H, s), 4.05 (1H, t), 3.55 (1H, t), 3.17 (3H, s), 2.14 (3H, s), 1.54 (9H, s); MS (ESI$^+$)=356.3 (M+H)$^+$.

Typical procedure for the deprotection of tert-butyl protected pyrazoles:

2-(2-Methoxyethyl)-4-(5-methyl-2H-pyrazol-3-ylamino)-2H-phthalazin-1-one 4-(2-tert-Butyl-5-methyl-2H-pyrazol-3-ylamino)-2-(2-methoxy-ethyl)-2H-phthalazin-1-one (0.36 g, 1.0 mmol) was dissolved in formic acid (20 ml) and heated at reflux for 4 h. The resulting raw product was dissolved in $H_2O$ and dichloromethane, after evaporation of formic acid. Addition of $NaHCO_3$ resulted in precipitation of a solid, which was collected by filtration. Subsequent washing with $H_2O$, dichloromethane and diethyl ether and drying in vacuum at 40° C. yielded the desired product 2-(2-Methoxyethyl)-4-(5-methyl-2H-pyrazol-3-ylamino)-2H-phthalazin-1-one (example O-1) (0.28 g, 94%). $^1$H-NMR: (400 MHz, $D_6$-DMSO) 9.21 (1H, s), 8.43 (1H, d), 8.29 (1H, d), 8.14 (1H, s), 7.84–7.94 (2H, m), 6.28 (1H, s), 4.23 (2H, t), 3.73 (2H, t), 3.33 (3H, s), 2.23 (3H, s); MS (ESI$^+$)=300.3 (M+H)$^+$ Using the experimental conditions reported above (Method O) and the appropriate starting materials, the following derivatives were prepared:

| Example-No. | Systematic name | $^1$H-NMR | MS(API+, M+H$^+$) |
|---|---|---|---|
| O-2 | 2-(2-Methoxy-1-methyl-ethyl)-4-(5-methyl-2H-pyrazol-3-ylamino)-2H-phthalazin-1-one | (400MHz, $D_6$-DMSO) 11.96(1H, s), 9.18(1H, s), 8.43(1H, d), 8.29(1H, d), 7.83–7.91(2H, m), 6.27(1H, s), 5.35(1H, m), 3.76(1H, t), 3.48(1H, m), 3.23(3H, s), 2.25(3H, s), 1.26(3H, d) | 314.1 |

Example O-3 cis-2-(4-tert-Butyl-cyclohexyl)-4-(5-methyl-2H-pyrazol-3-ylamino)-2H-phthalazin-1-one cis-4-Bromo-2-(4-tert-butyl-cyclohexyl)-2H-phthalazin-1-one 450 mg 4-Bromo-2H-phthalazin-1-one (see Method E), 469 mg trans-4-tert.-butylcyclohexanol and 787 mg triphenylphosphine were dissolved in 50 ml toluene. At 5 C, 1.306 g diethyl azodicarboxylate were added dropwise in 30 min. Stirring was continued for 24 hrs at room temperature. 50 ml water and 50 ml ethyl acetate were added and the organic phase separated and washed with water and sodium chloride solution. After drying and evaporating, the residue was chromatographed on silica eluting with a gradient of heptane to heptane /ethyl acetate 1:1. Yield 435 mg of the title product.

The 4-bromo-phthalazinone obtained above was coupled with 1-(tert-butyl)-3-methyl-1H-pyrazol-5-ylamine and subsequently deprotected by formic acid treatment as described for O-1, to give cis-2-(4-tert-Butyl-cyclohexyl)-4-(5-methyl-2H-pyrazol-3-ylamino)-2H-phthalazin-1-one (example O-3). MS (ESI, M–H) 378.2.

Method P

Example P-1

2-(4-Isopropyl-phenyl)-4-(5-methyl-2H-pyrazol-3-ylamino)-2H-phthalazin-1-one

4-Hydroxy-2-(4-isopropylphenyl)-2H-phthalazin-1-one
4-Isopropyl phenyl hydrazine hydrochloride (2.77 g, 14.6 mmol) was added in one portion to a stirred mixture of phthalic anhydride (2.0 g, 13 mmol) in acetic acid (25 ml) at room temperature. The reaction mixture was heated to 125° C. for 2 hours, and then allowed to cool to room temperature. The resultant suspension was poured into $H_2O$ (100 ml), $NaHCO_3$ solution (1M) was added and the resulting solid was removed by filtration. The mother liquor was acidified with conc. HCl The resulting solid was collected by filtration and dried in vacuum to give the title compound (1.62 g, 45% yield) as a white solid. $^1$H-NMR: (400 MHz, $D_6$-DMSO) 11.80 (1H, s), 8.30 (1H, d), 7.92–8.01 (3H, m), 7.92 (2H, d), 7.35 (2H, d), 2.96 (1H, m), 1.25 (6H, d); MS (ESI$^+$)=345.12 (M+H)$^+$.

4-Bromo-2-(4-isopropylphenyl)-2H-phthalazin-1-one
4-Hydroxy-2-(4-isopropylphenyl)-2H-phthalazin-1-one (0.10 g, 0.36 mmol), phosphorus oxybromide (0.41 g, 1.4 mmol) and 2,6-di-tert-butyl-4-methylphenol (0.02 g, 0.09 mmol) were stirred at 150° C. for 30 min. $H_2O$ (100 ml) was added after cooling to room temperature. Extraction with dichloromethane, drying of the combined organic phases over $Na_2SO_4$ and evaporation of the solvent yielded the desired compound (0.05 g, 41%) which was used without any further characterization.

This material was then used in the Buchwald reaction with 1-(tert-butyl)-3-methyl-1H-pyrazol-5-ylamine followed by acid catalyzed deprotection of the tert-butyl group as described in Method O to give the corresponding 2-(4-Isopropyl-phenyl)-4-(5-methyl-2H-pyrazol-3-ylamino)-2H-phthalazin-1-one (example P-1).

2-(4-Isopropyl-phenyl)-4-(5-methyl-2H-pyrazol-3-ylamino)-2H-phthalazin-1-one
Yield (0.004 g, 21%); $^1$H-NMR: (400 MHz, CDCl$_3$/MeOD), 8.50 (1H, d), 8.22 (1H, d), 7.97 (1H, t), 7.91 (1H, t), 7.63 (2H, d), 7.38 (2H, d), 6.25 (1H, s), 3.01 (1H, m), 2.26 (3H, s), 1.28 (6H, d).

Using the experimental conditions reported above (Method P) and the appropriate starting materials, the following derivatives were prepared:

| Example-No. | Systematic name | $^1$H-NMR | MS(API+, M+H$^+$) |
|---|---|---|---|
| P-2 | 2-(4-sec-Butyl-phenyl)-4-(5-methyl-2H-pyrazol-3-ylamino)-2H-phthalazin-1-one | (400MHz, $D_6$-DMSO) 9.29(1H, s), 8.50(1H, d), 8.36(1H, d), 7.89–7.98(2H, m), 7.64(2H, d), 7.32(2H, d), 6.22(1H, s), 2.67(1H, m), 2.19(3H, s), 1.62(2H, m), 1.24(3H, d), 0.84(3H, t) | 374.13 |

Method Q—Suzuki Coupling with 2-(iodophenyl)-phthalazinones

Example Q-1

2-Biphenyl-4-yl-4-(5-methyl-1H-pyrazol-3-ylamino)-2H-phthalazin-1-one

4-Hydroxy-2-(4-iodophenyl)-2H-phthalazin-1-one
4-Iodo phenyl hydrazine (8.97 g, 36.4 mmol) was added in one portion to a stirred mixture of phthalic anhydride (5.0 g, 33 mmol) in acetic acid (40 ml) at room temperature. The reaction mixture was heated to 125° C. for 2 hours, and then allowed to cool to room temperature. The suspension was poured into H₂O (100 ml) and the resulting solid was removed by filtration. The mother liquor was acidified with conc. HCl. The resulting solid was collected by filtration and dried in vacuum to give the title compound (1.0 g, 8% yield) as a white solid. $^1$H-NMR: (400 MHz, D$_6$-DMSO) 11.91 (1H, br. s), 8.30 (1H, d), 7.91–8.03 (3H, m), 7.83 (2H, d), 7.51 (2H, d); MS (ESI$^+$)=365.0 (M+H)$^+$.

2-Biphenyl-4-yl-4-hydroxy-2H-phtalazin-1-one

4-Hydroxy-2-(4-iodophenyl)-2H-phthalazin-1-one (0.1 g, 0.3 mmol), phenyl boronic acid (0.04 g, 3 mmol), palladium black (0.02 g, 0.2 mmol) and KF (0.1 g, 18 mmol) were dissolved in MeOH (2 ml) and heated at reflux for 7 h. Removal of supernatant palladium by filtration, extraction with H₂O and subsequent filtration of the precipitated solid yielded the desired title compound (0.07 g, 78% yield) as a white solid. $^1$H-NMR: (400 MHz, D$_6$-DMSO) 11.88 (1H, s), 8.33 (1H, d), 7.89–8.03 (3H, m), 7.78–7.86 (6H, m), 7.50 (2H, t), 7.39 (1H, t),; MS (ESI$^+$)=315.3 (M+H)$^+$.

This material was then brominated with neat phosphorus oxybromide as described in Method R and subsequently used in the Buchwald reaction as described in Method A to give the corresponding 2-Biphenyl-4-yl-4-(5-methyl-1H-pyrazol-3-ylamino)-2H-phthalazin-1-one (example Q-1).

2-Biphenyl-4-yl-4-(5-methyl-1H-pyrazol-3-ylamino)-2H-phthalazin-1-one

Yield (0.03 g, 29%); $^1$H-NMR: (400 MHz, D$_6$-DMSO), 9.36 (1H, s), 8.58 (1H, d), 8.45 (1H, d), 7.95 (3H, m), 7.87–7.92 (6H, m), 7.56 (2H, t), 7.46 (1H, t) 6.35 (1H, s), 2.26 (3H, s); MS (ESI$^+$)=394.6 (M+H)$^+$.

Example Q-2

2-(2'-Methyl-biphenyl-4-yl)-4-(5-methyl-1H-pyrazol-3-ylamino)-2H-phtalazin-1-one 4-(1-tert-Butyl-5-methyl-1H-pyrazol-3-ylamino)-2-(2'-methyl-biphenyl-4-yl)-2H-phtalazin-1-one 4-Bromo-2-(2'-methyl-biphenyl-4-yl)-2H-phtalazin-1-one (prepared from the appropriate starting materials in analogy to Method Q-1) was coupled with 1-tert-butyl-5-methyl-1H-pyrazol-3-ylamine in a Buchwald reaction as described in Method O to give the title compound (0.049 g, 31% yield). $^1$H-NMR: (400 MHz, D$_6$-DMSO) 8.44 (1H, s), 8.40 (1H, d), 8.33 (1H, d), 8.05 (1H, t), 7.97 (1H, t), 7.62 (2H, d), 7.40 (2H, d), 7.30 (2H, d), 7.24 (2H, d), 6.00 (1H, s), 2.28 (3H, s), 2.12 (3H, s), 1.57 (9H, s); MS (ESI+)= 464.36 (M+H)$^+$.

2-(2'-Methyl-biphenyl-4-yl)-4-(5-methyl-1H-pyrazol-3-ylamino)-2H-phthalazin-1-one 4-(1-tert-Butyl-5-methyl-1H-pyrazol-3-ylamino)-2-(2'-methyl-biphenyl-4-yl)-2H-phtalazin-1-one was deprotected with formic acid as described in Method O to give the title compound (0.036 g, 83% yield). $^1$H-NMR: (400 MHz, D$_6$-DMSO) 9.29 (1H, s), 8.52 (1H, d), 8.40 (1H, d), 8.17 (1H, s), 7.97 (1H, t), 7.93 (1H, t), 7.82 (2H, d), 7.48 (2H, d), 7.30 (4H, m), 6.29 (1H, s), 2.33 (3H, s), 2.20 (3H, s); MS (ESI$^+$)=408.16 (M+H)$^+$.

Method R—Bromination in Neat POBr3

Example R-1

4-(5-Methyl-1H-pyrazol-3-ylamino)-2-(3-trifluoromethyl-phenyl)-2H-phthalazin-1-one 4-Hydroxy-2-(3-trifluoromethylphenyl)-2H-phthalazin-1-one 4-Hydroxy-2-(3-trifluoromethylphenyl)-2H-phthalazin-1-one was prepared from 3-trifluoromethyl phenyl hydrazine as described in method B. $^1$H-NMR: (400 MHz, D$_6$-DMSO) 11.95 (1H, s), 8.31 (1H, d), 7.91–8.10 (5H, m), 7.74 (2H, d); MS (ESI$^+$)=307.14 (M+H)$^+$.

4-Bromo-2-(3-trifluoromethylphenyl)-2H-phthalazin-1-one

4-Hydroxy-2-(3-trifluoromethylphenyl)-2H-phthalazin-1-one (0.50 g, 1.6 mmol) and phosphorus oxybromide (1.9 g, 6.5 mmol) were stirred at 150° C. for 2 h. H₂O (100 ml) was added after cooling to room temperature. The precipitated solid was collected by filtration and washed with H₂O. Drying of the solid in vacuum gave the title compound (0.4 g, 66% yield). $^1$H-NMR: (400 MHz, D$_6$-DMSO) 8.39 (1H, d), 7.95–8.12 (5H, m), 7.79–7.99 (2H, m); MS (ESI$^+$)= 370.98 (M+H)$^+$.

This material was then used in the Buchwald reaction as described in Method A to give the corresponding 4-(5-Methyl-1H-pyrazol-3-ylamino)-2-(3-trifluoromethyl-phenyl)-2H-phthalazin-1-one (example R-1).

4-(5-Methyl-1H-pyrazol-3-ylamino)-2-(3-trifluoromethyl-phenyl)-2H-phthalazin-1-one Yield (0.078 g, 19%); $^1$H-NMR: (400 MHz, D$_6$-DMSO) 11.95 (1H, s), 9.38 (1H, s), 8.53 (1H, d), 8.41 (1H, d), 8.20 (2H, s), 7.98 (2H, t), 7.94 (2H, t), 7.69–7.74 (2H, m), 6.27 (1H, s), 2.19 (3H, s).

Using the experimental conditions reported above (Method R and Buchwald reaction as in method A) and the appropriate starting materials, the following derivatives were prepared:

| Example-No. | Systematic name | $^1$H-NMR | MS(ESI+, M+H) |
|---|---|---|---|
| R-2 | 4-(5-Methyl-1H-pyrazol-3-ylamino)-2-(4-phenoxy-phenyl)-2H-phthalazin-1-one | (400MHz, D$_6$-DMSO) 11.95(1H, s), 9.26(1H, s), 8.50(1H, d), 7.98(1H, d), 7.88–7.99(2H, m), 7.73(2H, d), 7.44(2H, t), 7.19(1H, t), 7.11(4H, d), 6.24(1H, s), 2.19(3H, s) | 410.17 |
| R-3 | 4-(5-Methyl-1H-pyrazol-3-ylamino)-2-naphthalen-2-yl-2H-phthalazin-1-one | (400MHz, D$_6$-DMSO) 11.96(1H, s), 9.33(1H, s), 8.55(1H, d), 8.41(1H, d), 8.30(1H, s), 7.87–8.05(6H, m), 7.58(2H, m), 6.31(1H, s), 2.17(3H, s) | 368.3 |
| R-4 | 2-(2-Chloro-phenyl)-4-(5-methyl-1H-pyrazol-3-ylamino)-2H-phthalazin-1-one | (400MHz, D$_6$-DMSO) 11.98(1H, s), 9.27(1H, s), 8.51(1H, d), 8.33(1H, d), 7.99(1H, t), 7.91(1H, t), 7.61–7.68(2H, m), 7.50–7.53(2H, m), 6.06(1H, s), 2.13(3H, s) | 352.3 |

Method S

Example S-1

N-Methyl-4-[4-(5-methyl-1H-pyrazol-3-ylamino)-1-oxo-1H-phthalazin-2-yl]-benzamide 4-(4-Bromo-1-oxo-1H-phthalazin-2-yl)benzoic acid The title compound was obtained from the appropriate starting materials using the experimental conditions reported above (Method R).Yield (0.65 g, 33%); $^1$H-NMR: (400 MHz, D$_6$-DMSO) 13.10 (1H, s), 8.39 (1H, d), 8.01–8.12 (5H, m), 7.80 (2H, d); MS (ESI$^+$)=345.13 (M+H)$^+$.

4-(4-Bromo-1-oxo-1H-phthalazin-2-yl)-N-methyl-benzamide 4-(4-Bromo-1-oxo-1H-phthalazin-2-yl)benzoic acid (0.15 g, 0.43 mmol) and 1,1'-carbonyldiimidazol (0.10 g, 0.65 mmol) were dissolved in DMF (10 ml) at room temperature. Methyl amine (0.33 ml of a 2M solution in THF, 0.65 mmol) were added and stirring was continued for 4 h. Evaporation of the solvent under reduced pressure, dilution with dichloromethane, extraction with a saturated aqueous NaHCO$_3$ solution and evaporation of the solvent in vacuum gave the title compound (0.12 g, 77% yield) $^1$H-NMR: (400 MHz, D$_6$-DMSO) 8.55 (1H, d), 8.38 (1H, d), 8.10 (1H, t), 8.03 (2H, d), 8.02 (2H, d), 7.73 (2H, d), 2.82 (3H, d).

This material was then used in the Buchwald reaction as described in Method A to give the corresponding N-Methyl-4-[4-(5-methyl-1H-pyrazol-3-ylamino)-1-oxo-1H-phthalazin-2-yl]-benzamide (example S-1).

N-Methyl-4-[4-(5-methyl-1H-pyrazol-3-ylamino)-1-oxo-1H-phthalazin-2-yl]-benzamide Yield (0.005 g, 10%); $^1$H-NMR: (400 MHz, D$_6$-DMSO) 11.95 (1H, s), 9.33 (1H, s), 8.52 (2H, d), 8.50 (1H, d), 7.84–8.03 (6H, m), 6.27 (1H, s), 2.74 (3H, s), 2.20 (3H, s).

Method T

Example T-1

N-{4-[4-(5-Methyl-1H-pyrazol-3-ylamino)-1-oxo-1H-phthalazin-2-yl]-phenyl}-acetamide 2-(4-Amino-phenyl)-4-(5-methyl-1H-pyrazol-3-ylamino)-2H-phthalazin-1-one (C-2, 0.050 g, 0.15 mmol) was dissolved in pyridine (1 ml) at 0° C. Acetylchloride (0.024 ml, 0.33 mmol) was added and stirring was continued for 30 min at 0° C. before the mixture was allowed to warm to room temperature. The solvent was evaporated after 2 h stirring at room temperature. The residue was diluted in MeOH (1 ml) and treated with conc. NH$_3$ (1 ml). The title compound was obtained after stirring at room temperature for 24 h and evaporation of the solvents in vacuum (0.016 g, 29%). $^1$H-NMR: (400 MHz, D$_6$-DMSO) 11.93 (1H, s), 10.08 (1H, s), 9.26 (1H, s), 8.49 (1H, d), 8.36 (1H, d), 7.88–7.98 (2H, m), 7.61–7.69 (4H, m), 6.24 (1H, s), 2.19 (3H, s), 2.08 (3H, s); MS (API$^+$)=375 (M+H)$^+$.

Using the experimental conditions reported above and the appropriate starting materials, the following derivatives were prepared:

| Example-No. | Systematic name | $^1$H-NMR | MS(ESI+, M+H) |
|---|---|---|---|
| T-2 | 2-Methoxy-N-{4-[4-(5-methyl-1H-pyrazol-3-ylamino)-1-oxo-1H-phthalazin-2-yl]-phenyl}-acetamide | (400MHz, D$_6$-DMSO) 11.93(1H, s), 9.90(1H, s), 9.26(1H, s), 8.50(1H, d), 8.36(1H, d), 7.88–7.98(2H, m), 7.77(2H, d), 7.64(2H, d), 6.24(1H, s), 4.04(2H, s), 3.41(3H, s), 2.19(3H, s) | 405.35 |
| T-3 | 2,2-Dimethyl-N-{4-[4-(5-methyl-1H-pyrazol-3-ylamino)-1-oxo-1H-phthalazin-2-yl]-phenyl}-propionamide | (400MHz, D$_6$-DMSO) 9.33(1H, s), 9.27(1H, s), 8.55(1H, d), 8.36(1H, d), 7.87–8.01(2H, m), 7.75(2H, d), 7.63(2H, d), 6.28(1H, s), 2.21(3H, s), 1.26(9H, s) | 417.4 |
| T-4 | N-{4-[4-(5-Methyl-1H-pyrazol-3-ylamino)-1-oxo-1H-phthalazin-2-yl]-phenyl}-benzamide | (400MHz, D$_6$-DMSO) 10.40(1H, d), 9.28(1H, s), 8.53(1H, d), 8.37(1H, t), 7.30–8.10(12H, m), 6.27(1H, s), 2.21(3H, s) | 437.55 |
| T-5 | N-{4-[4-(5-Methyl-1H-pyrazol-3-ylamino)-1-oxo-1H-phthalazin-2-yl]-phenyl}-methanesulfonamide | (400MHz, D$_6$-DMSO) 9.85(1H, d), 9.25(1H, s), 8.50(1H, d), 8.36(1H, d), 7.92–7.99(2H, m), 7.68(2H, d), 7.31(2H, d), 6.23(1H, s), 3.07(3H, s), 2.19(3H, s) | 411.19 |

Method U

Example U-1

4-(5-Methyl-1H-pyrazol-3-ylamino)-2-(4-phenylamino-phenyl)-2H-phthalazin-1-one 2-(4-Chloro-phenyl)-4-(5-methyl-1H-pyrazol-3-ylamino)-2H-phthalazin-1-one (B-1, 0.10 g, 0.28 mmol), aniline (0.034 g, 0.37 mmol), NaOtBu (0.041 g, 0.43 mmol), tris-(dibenzylideneacetone)-dipalladium (0.026 g, 0.028 mmol) and 2-(di-t-butylphosphino)-biphenyl (0.017 g, 0.057 mmol) under argon were heated to 100° C. for 17 hours, and then allowed to cool to room temperature. The solvent was evaporated in vacuum, the residue was diluted in H$_2$O (50 ml) and the resulting solid was collected by filtration. Purification of the raw product by chromatography over silica gel with dichloromethane:MeOH (20:1) gave the title compound (0.002 g, 2% yield) as a white solid (example U-1). $^1$H-NMR: (400 MHz, D$_6$-DMSO) 12.0 (1H, s), 9.23 (1H, s), 8.49 (1H, d), 8.33–8.37 (2H, m), 7.88–7.97 (2H, m), 7.54 (2H, d), 7.28 (2H, t), 7.15 (4H, m), 6.86 (1H, t), 6.25 (1H, s), 2.19 (3H, s); MS (API$^+$)=409.0 (M+H)$^+$.

Using the experimental conditions reported above (Method U) and the appropriate starting materials, the following derivatives were prepared:

| Example-No. | Systematic name | ¹H-NMR | MS(API+, M+H⁺) |
|---|---|---|---|
| U-2 | 4-(5-Methyl-1H-pyrazol-3-ylamino)-2-(4-morpholin-4-yl-phenyl)-2H-phthalazin-1-one | (400MHz, $D_6$-DMSO) 9.21(1H, s), 8.49(1H, d), 8.35(1H, d), 7.82–7.96(2H, m), 7.55(2H, d), 7.04(2H, d), 6.26(1H, s), 3.77(4H, t), 3.18(4H, t), 2.19(3H, s) | 403.54 |
| U-3 | 4-(5-Methyl-1H-pyrazol-3-ylamino)-2-(4-pyrrolidin-1-yl-phenyl)-2H-phthalazin-1-one | (400MHz, $D_6$-DMSO) 9.21(1H, s), 8.47(1H, d), 8.33(1H, d), 7.82–7.99(2H, m), 7.45(2H, d), 6.61(2H, d), 6.21(1H, s), 3.28(4H, s), 2.17(3H, s), 1.98(4H, s) | 387.54 |

Method V

Example V-1

4-(5-Methyl-2H-pyrazol-3-ylamino)-2-(4-piperidin-1-yl-phenyl)-2H-phthalazin-1-one 4-(2-tert-Butyl-5-methyl-2H-pyrazol-3-ylamino)-2-(4-chloro-phenyl)-2H-phthalazin-1-one 200 mg 4-Bromo-2-(4-chloro-phenyl)-2H-phthalazin-1-one (prepared as described in Method R), 91 mg 1-tert.-butyl-3-methyl-1H-pyrazol-5-ylamine, 310 mg cesium carbonate, 21 mg 4,5-bis(diphenylphosphino)-9,9-dimethylxanthene and 16.4 mg tris-(dibenzylideneacetone)-dipalladium in 2 ml dry dioxane were stirred under nitrogen at 100 C for 18 hrs. The solvent was removed under vacuum and the residue stirred with 50 ml water. The crude product was isolated by filtration, washed with water and purified by chromatography on silica, eluting sequentially with heptane, dichloromethane and finally dichloromethane/methanol 60:1. Yield 180 mg (74%) of the title product.

4-(2-tert-Butyl-5-methyl-2H-pyrazol-3-ylamino)-2-(4-piperidin-1-yl-phenyl)-2H-phthalazin-1-one 4-(2-tert-Butyl-5-methyl-2H-pyrazol-3-ylamino)-2-(4-chlorophenyl)-2H-phthalazin-1-one (0.10 g, 0.25 mmol), piperidine (0.025 g, 0.29 mmol), NaOtBu (0.033 g, 0.34 mmol), tris-(dibenzylideneacetone)-dipalladium (0.06 g, 0.008 mmol) and 2-(di-t-butylphosphino)-biphenyl (0.004 g, 0.014 mmol) under argon were heated to 100° C. for 19 hours, and then allowed to cool to room temperature. The solvent was evaporated in vacuum, the residue was diluted in $H_2O$ (30 ml) and the resulting solid was collected by filtration. Purification of the raw product by preparative HPLC gave the title compound (0.014 g, 13% yield). ¹H-NMR: (400 MHz, $D_6$-DMSO) 8.35 (1H, d), superimposed by 8.34 (1H, s), 8.29 (1H, d), 8.01 (1H, t), 7.92 (1H, t), 7.31 (2H, d), 6.92 (2H, d), 5.94 (1H, s), 3.16 (4H, m), 1.61 (4H, m), 1.55 (9H, s), superimposes 1.54 (2H, m); MS (ESI⁺)=457.16 (M+H)⁺.

4-(5-Methyl-2H-pyrazol-3-ylamino)-2-(4-piperidin-1-yl-phenyl)-2H-phthalazin-1-one 4-(2-tert-Butyl-5-methyl-2H-pyrazol-3-ylamino)-2-(4-piperidin-1-yl-phenyl)-2H-phthalazin-1-one (0.012 g, 0.026 mmol) was dissolved in formic acid (1 ml) and heated at 95° C. for 4 h. The resulting raw product was dissolved in dichloromethane, after evaporation of formic acid. Extraction with a saturated aqueous $NaHCO_3$ solution, combining of the organic phases, evaporation of the solvent in vacuum and purification by chromatography over silica gel with dichloromethane:MeOH (20:1) yielded the title compound (0.006 g, 57%). ¹H-NMR: (400 MHz, $D_6$-DMSO) 11.81 (1H, s), 9.21 (1H, s), 8.48 (1H, d), 8.35 (1H, d), 7.87–7.96 (2H, m), 7.50 (2H, d), 7.01 (2H, d), 6.25 (1H, s), 3.21 (4H, m), 2.19 (3H, s), 1.64 (4H, m), 1.60 (2H, m); MS (ESI⁺)=401.29 (M+H)⁺.

Method W—Buchwald Coupling with Boc-protected Aminopyrazole

Example W-1

2-(2-Chloro-4-trifluoromethyl-phenyl)-4-(5-methyl-1H-pyrazol-3-ylamino)-2H-phthalazin-1-one 2-(2-Chloro-4-trifluoromethyl-phenyl)-2,3-dihydro-phthalazine-1,4-dione 1.74 g 2-(2-Chloro-4-trifluoromethyl-phenylamino)-isoindole-1,3-dione (prepared from 2-chloro-4-trifluoromethyl-phenylhydrazine analogously to method A) in 80 ml dry ethanol were treated with 347 mg sodium ethoxide and the mixture was stirred at 85 C for 2 hrs. After cooling, the mixture was evaporated and dissolved in water. Precipitate was filtered off and washed several times with water. The combined filtrates was acidified by addition of conc. HCl whereupon the product precipitated. It was isolated by filtration and purified by chromatography on silica eluting with a gradient from heptane/ethyl acetate (50:50) to pure ethyl acetate. Yield 250 mg (14%)

3-Amino-5-methyl-pyrazole-1-carboxylic acid tert-butyl ester

NaH (95%, 0.57 g, 22.7 mmol) was added slowly to a 0° C. solution of 3-Amino-5-methylpyrazole (2.0 g, 20.6 mmol) in THF (40 ml). $Boc_2O$ (4.94 g, 22.7 mmol) was added after 30 min and the mixture was allowed to warm to room temperature. After stirring for 2 h at room temperature, the mixture was poured into a saturated aqueous solution of $NaHCO_3$. The aqueous phase was extracted with $CHCl_3$. The combined organic phases were dried over $Na_2SO_4$. Removal of the solvent in vacuum gave a crude mixture of the title compound and its 2-carboxylic acid tert.-butyl ester isomer, which were separated by chromatography on silica in ethyl acetate/heptane 2:1. Yield 2.4 g, 59%. ¹H-NMR: (400 MHz, $D_6$-DMSO) 5.60 (1H, s), 5.27 (2H, s), 2.34 (3H, s), 1.51 (9H, s); MS (ESI⁺)=198.26 (M+H)⁺.

Typical procedure for the Buchwald reaction with tert-butoxycarbonyl protected pyrazole:

2-(2-Chloro-4-trifluoromethyl-phenyl)-4-(5-methyl-1H-pyrazol-3-ylamino)-2H-phthalazin-1-one 4-Bromo-2-(2-chloro-4-trifluoromethyl-phenyl)-2H-phthalazin-1-one (obtained from the above phthalazine-1,4-dione by bromination with $POBr_3$ in analogy to Method R, as reported above) (0.15 g, 0.37 mmol), 3-amino-5-methyl-pyrazole-1-carboxylic acid tert-butyl ester (0.080 g, 0.41 mmol), Cs$_2$CO$_3$ (0.033 g, 0.34 mmol), tris-(dibenzylideneacetone)-dipalladium (0.017 g, 0.019 mmol) and 4,5-bis(diphenylphosphino)-9,9-dimethylxanthene (0.022 g, 0.037 mmol) in 2 ml dry dioxane under nitrogen were heated to 100° C. for 18 hours, and then allowed to cool to room temperature. H$_2$O was added and the solvent was evaporated in vacuum. The resulting solid was collected by filtration. Purification of the raw product by preparative HPLC gave the title compound (0.069 g, 44% yield). $^1$H-NMR: (400 MHz, D$_6$-DMSO) 11.92 (1H, s), 9.34 (1H, s), 8.54 (1H, d), 8.35 (1H, d), 8.14 (1H, s), 8.01 (1H, t), 7.92 (3H, m), 6.06 (1H, s), 2.14 (3H, s); MS (ESI$^+$)=420.23 (M+H)$^+$.

Analogously, 4-Bromo-2-(4-trifluoromethoxy-phenyl)-2H-phthalazin-1-one, 4-Bromo-2-(4-nitrophenyl)-2H-phthalazin-1-one and 4-Bromo-2-(4-cyclohexyl-phenyl)-2H-phthalazin-1-one (obtained from the corresponding phenyl hydrazines following method R) were coupled with 3-amino-5-methyl-pyrazole-1-carboxylic acid tert-butyl ester to give:

| Example-No. | Systematic name | $^1$H-NMR | MS(ESI+, M+H) |
|---|---|---|---|
| W-2 | 4-(5-Methyl-1H-pyrazol-3-ylamino)-2-(4-trifluoromethoxy-phenyl)-2H-phthalazin-1-one | (400MHz, D$_6$-DMSO) 11.97(1H, s), 9.30(1H, s), 8.53(1H, d), 8.38(1H, d), 8.01–7.88(m) and 7.90(d, together 4H), 7.51(2H, d), 6.25(1H, s), 2.20(3H, s). | 402.21 |
| W-3 | 4-(5-Methyl-1H-pyrazol-3-ylamino)-2-(4-nitro-phenyl)-2H-phthalazin-1-one | (400MHz, D$_6$-DMSO), 12.05(1H, s) 9.42(1H, s), 8.54(1H, d), 8.36–8.42(3H, m), 8.15–8.17(2H, m), 7.91–8.02(2H, m), 6.30(1H, s), 2.23(3H, s) | 363.3 |
| W-4 | 2-(4-Cyclohexyl-phenyl)-4-(5-methyl-1H-pyrazol-3-ylamino)-2H-phthalazin-1-one | (400MHz, D$_6$-DMSO), 9.22(1H, s), 8.50(1H, d), 8.35(1H, d), 8.03–7.84(2H, m), 7.62(2H, d), 7.35(2H, d), 6.24(1H, s), 2.59(1H, m), 2.19(3H, s), 1.90–1.78(4H, m), 1.78–1.61(1H, m), 1.55–1.20(5H, m). | 400.20 |

Method X—Buchwald Coupling with Aminopyrazole and 4,5-bis(diphenylphosphino)-9,9-dimethylxanthene (Xanthphos)

Example X-1

4-(5-Methyl-1H-pyrazol-3-ylamino)-2-pyridin-4-yl-2H-phthalazin-1-one

4-Bromo-2-pyridin-4-yl-2H-phthalazin-1-one (obtained from the appropriate starting materials in analogy to Method R, as reported above) (0.20 g, 0.66 mmol), 3-amino-5-methyl-pyrazole (0.093 g, 0.93 mmol), Cs$_2$CO$_3$ (0.30 g, 0.93 mmol), tris-(dibenzylideneacetone)-dipalladium (0.030 g, 0.033 mmol) and 4,5-bis(diphenylphosphino)-9,9-dimethylxanthene (Xanthphos) (0.039 g, 0.066 mmol) under nitrogen were heated to 100° C. for 20 hours, and then allowed to cool to room temperature. H$_2$O was added and the solvent was evaporated in vacuum. The resulting solid was collected by filtration. Purification of the raw product by chromatography over silica gel gave the title compound (0.015 g, 7% yield). $^1$H-NMR: (400 MHz, D$_6$-DMSO) 12.0 (1H, s), 9.38 (1H, s), 8.67 (2H, d), 8.53 (1H, d), 8.40 (1H, d), 7.91–8.02 (4H, m), 6.31 (1H, s), 2.24 (3H, s); MS (ESI$^+$)=319.2 (M+H)$^+$.

Example X-2

2-(3-tert-Butyl-phenyl)-4-(5-methyl-1H-pyrazol-3-ylamino)-2H-phthalazin-1-one

4-Bromo-2-(3-tert-butylphenyl)-2H-phthalazin-1-one (obtained from the appropriate starting materials in analogy to Method R, as reported above) (0.10 g, 0.28 mmol), 3-amino-5-methyl-pyrazole (0.038 g, 0.39 mmol), Cs$_2$CO$_3$ (0.13 g, 0.39 mmol), tris-(dibenzylideneacetone)-dipalladium (0.013 g, 0.014 mmol) and 4,5-bis(diphenylphosphino)-9,9-dimethylxanthene (0.016 g, 0.028 mmol) under nitrogen were heated to 100° C. for 10 hours, and then allowed to cool to room temperature. H$_2$O was added and the solvent was evaporated in vacuum. The resulting solid was collected by filtration. Purification of the raw product by chromatography over silica gel gave the title compound (0.020 g, 19% yield). $^1$H-NMR: (400 MHz, D$_6$-DMSO) 9.32 (1H, s), 8.50 (1H, d), 8.38 (1H, d), 7.95 (1H, t), 7.90 (1H, t), 7.78 (1H, s), 7.63 (1H, d), 7.37–7.40 (2H, m), 6.38 (1H, s), 2.18 (3H, s), 1.22 (9H, s); MS (ESI$^+$)=374.27 (M+H)$^+$.

Analogously to the examples described above, 4-Bromo-2-(4-tert-butyl-phenyl)-2H-phthalazin-1-one (obtained as in method R) was coupled with the appropriate amino-pyrazoles to give:

| Example-No. | Systematic name | $^1$H-NMR | MS(ESI+, M+H) |
|---|---|---|---|
| X-3 | 2-(4-tert-Butyl-phenyl)-4-(5-cyclopropyl-1H-pyrazol-3-ylamino)-2H-phthalazin-1-one | (400MHz, D$_6$-DMSO) 11.95(1H, s), 9.23(1H, s), 8.50(1H, d), 8.37(1H, d), 8.03–7.88(2H, m), 7.66(2H, d), 7.50(2H, d), 6.21(1H, s), 1.88(1H, m), 1.35(9H, s), 0.91(2H, m), 0.64(2H, m). | 400.21 |
| X-4 | 2-(4-tert-Butyl-phenyl)-4-(1H-pyrazol-3-ylamino)-2H-phthalazin-1-one | (400MHz, D$_6$-DMSO), 12.29(1H, s), 9.39(1H, s), 8.54(1H, d), 8.38(1H, d), 7.96(1H, m), 7.91(1H, m), 7.64(3H, m), 7.51(2H, d), 6.53(1H, s), 1.35(9H, s). | 360.19 |

Method Y

Example Y-1

N-Ethyl-N-{4-[4-(5-methyl-1H-pyrazol-3-ylamino)-1-oxo-1H-phthalazin-2-yl]-phenyl}-acetamide 2-(4-Amino-phenyl)-4-bromo-2H-phthalazin-1-one
4-Bromo-2-(4-nitro-phenyl)-2H-phthalazin-1-one (see Method B) (1.0 g, 2.9 mmol) and PtO$_2$ (0.13 g, 0.58 mmol) were dissolved in ethyl acetate (40 ml) at room temperature. The mixture was hydrogenated at ambient pressure for 2 h, before the catalyst was filtered off to yield title compound (0.61 g, 67% yield). $^1$H-NMR: (400 MHz, D$_6$-DMSO) 8.34 (1H, d), 8.07 (1H, t), 7.99 (2H, t), 7.18 (2H, d), 6.63 (2H, d), 5.35 (2H, s); MS (ESI$^+$)=318.42 (M+H)$^+$.

N-[4-(4-Bromo-1-oxo-1H-phthalazin-2-yl)-phenyl]acetamide

Acetyl chloride (0.15 g, 1.90 mmol) was added at room temperature to a stirred solution of 2-(4-amino-phenyl)-4-bromo-2H-phthalazin-1-one (0.30 g, 0.95 mmol) in pyridine (3 ml). Stirring was continued for 12 h before the solvent was evaporated in vacuum. The resulting raw product was dissolved in $H_2O$ and the title compound was collected by filtration (0.22 g, 65% yield). $^1$H-NMR: (400 MHz, $D_6$-DMSO) 10.16 (1H, s), 8.37 (1H, d), 8.08 (1H, t), 8.00–8.03 (2H, m), 7.72 (2H, d), 7.52 (2H, d), 2.05 (3H, s); MS (ESI$^+$)=358.15 (M+H)$^+$.

N-[4-(4-Bromo-1-oxo-1H-phthalazin-2-yl)-phenyl]-N-ethyl-acetamide

NaH (95%, 0.005 g, 0.21 mmol) was added slowly at room temperature to a solution of N-[4-(4-Bromo-1-oxo-1H-phthalazin-2-yl)-phenyl]acetamide (0.070 g, 0.20 mmol) in DMF (2 ml). Stirring was continued for 1 h before ethyl iodide (0.046 g, 0.29 mmol) was added. Stirring was continued for 12 h before the solvent was evaporated in vacuum. The resulting raw product was purified by chromatography over silica gel with heptane:ethyl acetate (3:1 up to 1:1) to give the title compound (0.010 g, 14% yield). MS (ESI$^+$)=388.22 (M+H)$^+$.

N-Ethyl-N-{4-[4-(5-methyl-1H-pyrazol-3-ylamino)-1-oxo-1H-phthalazin-2-yl]-phenyl}-acetamide N-[4-(4-Bromo-1-oxo-1H-phthalazin-2-yl)-phenyl]-N-ethyl-acetamide (0.10 g, 0.027 mmol), 3-amino-5-methyl-pyrazole-1-carboxylic acid tert-butyl ester (0.006 g, 0.03 mmol), $Cs_2CO_3$ (0.01 g, 0.03 mmol), tris-(dibenzylideneacetone)-dipalladium (0.001 g, 0.001 mmol) and 4,5-bis(diphenylphosphino)-9,9-dimethylxanthene (0.002 g, 0.003 mmol) under nitrogen were heated to 100° C. for 18 hours, and then allowed to cool to room temperature. $H_2O$ was added and the solvent was evaporated in vacuum. Purification via chromatography gave the title compound (0.003 g, 23% yield). $^1$H-NMR: (400 MHz, $D_6$-DMSO) 9.28 (1H, s), 8.51 (1H, d), 8.38 (1H, d), 7.99 (1H, t), 7.91 (1H, t), 7.87 (2H, d), 7.41 (2H, d), 6.25 (1H, s), 3.69 (2H, q), 2.20 (3H, s), 1.81 (3H, s), 1.07 (3H, t); MS (ESI$^+$)=403.34 (M+H)$^+$.

Analogous to example Y-1, 2-(4-amino-phenyl)-4-bromo-2H-phthalazin-1-one was acylated with appropriate chloroformates to yield the corresponding carbamates. These were used directly for coupling with Boc-protected amino-pyrazole under Buchwald conditions as described for Y-1, or were first alkylated and then used for the Buchwald coupling, as described for Y-1. Thus, the following analogs were obtained:

| Example-No. | Systematic name | $^1$H-NMR | MS(ESI+, M+H) |
|---|---|---|---|
| Y-2 | {4-[4-(5-Methyl-1H-pyrazol-3-ylamino)-1-oxo-1H-phthalazin-2-yl]-phenyl}-carbamic acid ethyl ester | (400MHz, $D_6$-DMSO) 9.76(1H, s), 9.25(1H, s), 8.49(1H, d), 8.36(1H, d), 7.97(1H, t), 7.89(1H, t), 7.58(4H, dd), 6.23(1H, s), 4.16(2H, q), 2.19(3H, s), 1.27(3H, t). | 405.36 |
| Y-3 | Methyl-{4-[4-(5-methyl-1H-pyrazol-3-ylamino)-1-oxo-1H-phthalazin-2-yl]-phenyl}-carbamic acid ethyl ester | (400MHz, $D_6$-DMSO) 11.95(1H, s), 9.22(1H, s), 8.50(1H, d), 8.34(1H, d), 7.98–7.91(2H, m), 7.73(2H, d), 7.43(2H, d), 6.23(1H, s), 4.12(2H, q), 2.20(3H, s), 1.21(3H, t). | |
| Y-4 | Methyl-{4-[4-(5-methyl-1H-pyrazol-3-ylammo)-1-oxo-1H-phthalazin-2-yl]-phenyl}-carbamic acid isopropyl ester | (400MHz, $D_6$-DMSO) 9.27(1H, s), 8.52(1H, d), 8.37(1H, d), 7.98–7.90(2H, m), 7.71(2H, d), 7.42(2H, d), 6.28(1H, s), 4.86(1H, m), 2.20(3H, s), 1.21(6H, d). | 433.33 |
| Y-5 | {4-[4-(5-Methyl-1H-pyrazol-3-ylamino)-1-oxo-1H-phthalazin-2-yl]-phenyl}-carbamic acid isopropyl ester | (400MHz, $D_6$-DMSO) 11.92(1H, br s), 9.70(1H, s), 9.26(1H, s), 8.49(1H, d), 8.35(1H, d), 8.01–7.85(2H, m), 7.59(4H, dd), 6.23(1H, s), 4.93(1H, hep), 2.18(3H, s), 1.28(6H, d). | 419.26 |

Method Z

According to an analogous procedure described under Method ZB, using the appropriate starting material, the following examples can be prepared.

| Example-No. | Systematic name | $^1$H-NMR | MS(ESI+, M+H) |
|---|---|---|---|
| Z-1 | 6-Ammo-4-(5-methyl-1H-pyrazol-3-ylamino)-2-phenyl-2H-phthalazin-1-one | | |

Method ZA—Sulfanyl Substituted 2-phenylphthalazinones from 2-(iodophenyl)phthalazinones Example ZA-1

2-[4-(2-Methyl-propane-2-sulfonyl)-phenyl]-4-(5-methyl-1H-pyrazol-3-ylamino)-2H-phthalazin-1-one 2-(4-tert-Butylsulfanyl-phenyl)-2,3-dihydro-phthalazine-1,4-dione 4-Hydroxy-2-(4-iodophenyl)-2H-phthalazin-1-one (see Method Q) (0.30 g, 0.8 mmol), sodium 2-methyl-propane-2-thiolate (0.094 g, 0.8 mmol), CuI (0.011 g, 0.06 mmol) and ethylene glycol (0.10 g, 1.6 mmol) were dissolved in N-methyl-pyrrolidinone (NMP) (0.5 ml) under argon and heated to 150° C. Stirring at this temperature was continued for 4 d before the mixture was allowed to warm to room temperature. $H_2O$ (50 ml) was added and the precipitated solid was collected by filtration. The title compound was obtained after purification of the raw product by chromatography over silica gel with dichloromethane (0.21 g, 78%). $^1$H-NMR: (400 MHz, $D_6$-DMSO) 12.35 (1H, s), 8.73 (1H, d), 8.33–8.41 (3H, m), 8.14 (2H, d), 8.01 (2H, d), 1.70 (9H, s); MS (ESI$^+$)=327.14 (M+H)$^+$.

2-[4-(2-Methyl-propane-2-sulfonyl)-phenyl]-2,3-dihydro-phthalazine-1,4-dione 2-(4-tert-Butylsulfanyl-phenyl)-2,3-dihydro-phthalazine-1,4-dione (0.20 g, 0.61 mmol) and MCPBA (0.28 g, 1.2 mmol) were stirred at room temperature in dichloromethane (3 ml) for 4 h. The title compound was obtained after evaporation of the solvent in vacuum and subsequent purification of the raw product by chromatography over silica gel with heptane:dichloromethane (1:1 until 0:1) (0.21 g, 98%). $^1$H-NMR: (400 MHz, D$_6$-DMSO) 13.30 (1H, s), 8.34 (1H, d), 7.85–8.12 (3H, m), 7.72 (2H, d), 7.55 (2H, t), 1.28 (9H, s); MS (ESI$^+$)=359.16 (M+H)$^+$.

4-Bromo-2-[4-(2-methyl-propane-2-sulfonyl)-phenyl]-2H-phthalazin-1-one

2-[4-(2-Methyl-propane-2-sulfonyl)-phenyl]-2,3-dihydro-phthalazine-1,4-dione (0.20 g, 0.56 mmol) and phosphorus oxybromide (0.48 g, 1.7 mmol) were stirred at 150° C. for 1 h. H$_2$O (50 ml) was added after cooling to room temperature. Extraction with dichloromethane, drying of the combined organic phases over Na$_2$SO$_4$, evaporation of the solvent and purification of the raw product by preparative HPLC yielded the desired compound (0.06 g, 18%). $^1$H-NMR: (400 MHz, D$_6$-DMSO) 8.41 (1H, d), 8.07 (1H, d), 8.03–8.10 (4H, m), 7.80 (2H, d), 1.30 (9H, s); MS (API$^+$)=423.0 (M+H)$^+$.

This material was then used in the Buchwald reaction as described in Method A to give the corresponding 2-[4-(2-Methyl-propane-2-sulfonyl)-phenyl]-4-(5-methyl-1H-pyrazol-3-ylamino)-2H-phthalazin-1-one (example ZA-1).

2-[4-(2-Methyl-propane-2-sulfonyl)-phenyl]-4-(5-methyl-1H-pyrazol-3-ylamino)-2H-phthalazin-1-one Yield (0.003 g, 8%); $^1$H-NMR: (400 MHz, D$_6$-DMSO) 9.40 (1H, s), 8.52 (1H, d), 8.39 (1H, d), 8.13 (2H, d), 7.99 (1H, t), 7.92 (2H, d), superimposes 7.91 (1H, t), 6.29 (1H, s), 1.30 (9H, s); MS (API$^+$)=438.3 (M+H)$^+$.

Example ZA-2

2-(4-Benzenesulfinyl-phenyl)-4-(5-methyl-1H-pyrazol-3-ylamino)-2H-phthalazin-1-one 2-(4-Phenylsulfanyl-phenyl)-2,3-dihydro-phthalazine-1,4-dione 4-Hydroxy-2-(4-iodophenyl)-2H-phthalazin-1-one (see Method Q) (0.20 g, 0.55 mmol), thiophenol (0.061 g, 0.55 mmol), CuI (0.006 g, 0.03 mmol) and ethylene glycol (0.070 g, 1.1 mmol) were dissolved in N-methyl-pyrrolidinone (NMP) (1 ml) under argon and heated to 90° C. Stirring at this temperature was continued for 26 h before the mixture was allowed to warm to room temperature. H$_2$O (50 ml) was added and the resulting solution was extracted with dichloromethane. The title compound was obtained after purification of the raw product by chromatography over silica gel with dichloromethane (0.10 g, 54%). $^1$H-NMR: (400 MHz, D$_6$-DMSO) 11.91 (1H, s), 8.30 (1H, s), 7.91–8.06 (3H, m), 7.69 (2H, d), 7.34–7.45 (7H, m); MS (ESI$^+$)=347.26 (M+H)$^+$.

4-Bromo-2-(4-phenylsulfanyl-phenyl)-2H-phthalazin-1-one
2-(4-Phenylsulfanyl-phenyl)-2,3-dihydro-phthalazine-1,4-dione (0.10 g, 0.29 mmol) and phosphorus oxybromide (0.33 g, 12 mmol) were stirred at 150° C. for 40 min. H$_2$O (50 ml) was added after cooling to room temperature. Extraction with dichloromethane, drying of the combined organic phases over Na$_2$SO$_4$, evaporation of the solvent and purification of the raw product by chromatography over silica gel with heptane:dichloromethane (2:1 to 0:1) gave the desired compound (0.10 g, 86%). $^1$H-NMR: (400 MHz, D$_6$-DMSO) 8.36 (1H, d), 8.11 (1H, d), 8.00 (2H, m), 7.65 (2H, d), 7.44 (7H, m); MS (ESI$^+$)=411.2 (M+H)$^+$.

2-(4-Benzensulfinyl-phenyl)-4-bromo-2H-phthalazin-1-one

4-Bromo-2-(4-phenylsulfanyl-phenyl)-2H-phthalazin-1-one (0.095 g, 0.23 mmol) and MCPBA (0.052 g, 0.23 mmol) were stirred at room temperature in dichloromethane (1 ml) for 1 h. The tide compound was obtained after evaporation of the solvent in vacuum and subsequent purification of the raw product by chromatography over silica gel with heptane:dichloromethane (1:1 until 0:1) (0.031 g, 31% yield). $^1$H-NMR: (400 MHz, CDCl$_3$) 8.49 (1H, d), 7.80–7.99 (5H, m), 7.76 (2H, d), 7.69 (2H, d), 7.48 (3H, m); MS (ESI$^+$)=427.22 (M+H)$^+$.

This material was then used in the Buchwald reaction as described in Method A to give the corresponding 2-(4-Benzenesulfinyl-phenyl)-4-(5-methyl-1H-pyrazol-3-ylamino)-2H-phthalazin-1-one (example ZA-2).

2-(4-Benzenesulfinyl-phenyl)-4-(5-methyl-1H-pyrazol-3-ylamino)-2H-phthalazin-1l-one Yield (0.003 g, 9%); $^1$H-NMR: (400 MHz, D$_6$-DMSO) 9.31 (1H, s), 8.50 (1H, d), 8.36 (1H, d), 7.89–8.00 (4H, m), 7.83 (2H, d), 7.80 (2H, d), 7.54 (3H, m), 6.22 (1H, s), 2.20 (3H, s); MS (ESI$^+$)=440.33 (M−H)$^+$.

Method ZB: 6- and 7-substituted 2-phenyl-4-pyrazolylamino-phthalazinones

Example ZB-1

N-[3-(4-tert-Butyl-phenyl)-1-(5-methyl-2H-pyrazol-3-ylamino)-4-oxo-3,4-dihydro-phthalazin-6-yl]-formamide 4-Bromo-2-(4-tert-butyl-phenyl)-6-nitro-2H-phthalazin-1-one and 4-Bromo-2-(4-tert-butyl-phenyl)-7-nitro-2H-phthalazin-1-one and 4,6-Dibromo-2-(4-tert-butyl-phenyl)-2H-phthalazin-1-one 4-Nitrophthalic anhydride and 4-tert.-butylphenylhydrazine were reacted analogous to method B and gave a 1:1 mixture of 2-(4-tert-Butyl-phenyl)-6-nitro-2,3-dihydro-phthalazine-1,4-dione and 2-(4-tert-Butyl-phenyl)-7-nitro-2,3-dihydro-phthalazine-1,4-dione. To 1.60 g of this mixture were added 6.47 g phosphorus oxybromide and it was heated to 150 C. with stirring. After 1 hr HPLC indicated complete conversion, and the mixture was cooled to room temperature, diluted with 100 ml water and stirred for 15 min. The crude product was isolated by filtration and purified by chromatography on silica, eluting first with heptane and subsequently with heptane/ethyl acetate 1:1. The first eluting material was 4,6-Dibromo-2-(4-tert-butyl-phenyl)-2H-phthalazin-1-one (121 mg), the second a 1:1 mixture of 4-Bromo-2-(4-tert-butyl-phenyl)-6-nitro-2H-phthalazin-1-one and 4-Bromo-2-(4-tert-butyl-phenyl)-7-nitro-2H-phthalazin-1-one (720 mg).

6-Nitro-4-(2-tert-butyl-5-methyl-2H-pyrazol-3-ylamino)-2-(4-tert-butyl-phenyl)-2H-phthalazin-1-one and 7-Nitro-4-(2-tert-butyl-5-methyl-2H-pyrazol-3-ylamino)-2-(4-tert-butyl-phenyl)-2H-phthalazin-1-one 4.56 g of a 1:1 mixture of 4-Bromo-2-(4-tert-butyl-phenyl)-6-nitro-2H-phthalazin-1-one and 4-Bromo-2-(4-tert-butyl-phenyl)-7-nitro-2H-phthalazin-1-one in 45 ml dry dioxane were reacted with 2.605 g 1-(tert. butyl)-3-methyl-1H-pyrazole-5-ylamine, 5.526 g cesium carbonate, 311 mg tris-(dibenzylideneacetone)-dipalladium and 393 mg 4,5-bis(diphenylphosphino)-9,9-dimethylxanthene under nitrogen at 80 C. After 2 hrs HPLC indicated complete conversion and the mixture was cooled to room temperature, diluted with 150 ml dichloromethane and washed twice with diluted HCl. The organic phase was dried and evaporated and the residue chromatographed on silica eluting first heptane and subsequently with heptane/ethyl acetate 8:2. The first eluting product was the 6-nitro isomer (1.82 g), the second eluting product was the 7-nitro isomer (2.05 g).

7-Amino-4-(2-tert-butyl-5-methyl-2H-pyrazol-3-ylamino)-2-(4-tert-butyl-phenyl)-2H-phthalazin-1-one 2.00 g of 7-Nitro-4-(2-tert-butyl-5-methyl-2H-pyrazol-3-ylamino)-2-(4-tert-butyl-phenyl)-2H-phthalazin-1-one were hydrogenated over palladium on charcoal in methanol/THF 1:1 at room temperature. After completion of the reaction the catalyst was filtered off and the filtrate evaporated. The residue was dissolved in 50 ml dichloromethane and extracted three times with a 3:1 mixture of water/conc. HCl. The combined aqueous phases were brought to pH 8 by addition of sodium bicarbonate and extracted with dichloromethane. Removal of the solvent yielded 1.25 g of the title product.

N-[3-(4-tert-Butyl-phenyl)-1-(5-methyl-2H-pyrazol-3-ylamino)-4-oxo-3,4-dihydro-phthalazin-6 6-yl]-formamide 15 mg of the above tert.-butyl protected pyrazole were heated in 1 ml formic acid to 90 C for 6 hrs. Excess formic acid was removed under vacuum and the residue dissolved in dichloromethane and washed with sodium bicarbonate solution. Evaporation of the dichloromethane yielded 12 mg of the title product. $^1$H-NMR: (400 MHz, D$_6$-DMSO) 12.00 (1H, s), 10.77 (1H, s), 9.17 (1H, s), 8.61 (1H, s), 8.50 (2H, m), 8.10 (1H, m), 7.63 (2H, d), 7.51 (2H, d), 6.22 (1H, s), 2.19 (3H, s), 1.35 (9H, s); MS (ESI$^+$)=417.25 (M+H)$^+$.

Example ZB-2

7-Amino-2-(4-tert-butyl-phenyl)-4-(5-methyl-2H-pyrazol-3-ylamino)-2H-phthalazin-1-one 9 mg of N-[3-(4-tert-Butyl-phenyl)-1-(5-methyl-2H-pyrazol-3-ylamino)-4-oxo-3,4-dihydro-phthalazin-6-yl]-formamide (ZB-1) in a mixture of 0,5 ml methanol and 0,5 ml conc. HCl were stirred at 50 C for 2 hrs. The mixture was evaporated under vacuum and the residue dissolved in dichloromethane. The dichloromethane solution was washed with sodium bicarbonate solution and evaporated to yield 4 mg of the title product. $^1$H-NMR: (400 MHz, D$_6$-DMSO) 11.8 (1H, br s), 8.81 (1H, s), 8.02 (1H, d), 7.52 (2H, d), 7.40 (2H, d), 7.34 (1H, d), 6.99 (1H, dd), 6.10 (br s, 2H), 2.10 (3H, s), 1.27 (9H, s); MS (ESI$^+$)=389.21 (M+H)$^+$.

Example ZB-3

2-(4-tert-Butyl-phenyl)-4-(5-methyl-2H-pyrazol-3-ylamino)-7-nitro-2H-phthalazin-1-one 15 mg 7-Nitro-4-(2-tert-butyl-5-methyl-2H-pyrazol-3-ylamino)-2-(4-tert-butyl-phenyl)-2H-phthalazin-1-one (preparation see ZB-1) were deprotected by heating in formic acid as described for ZA-1. Evaporation of excess formic acid and chromatography of the residue on silica, eluting with dichloromethane and then with dichloromethane/methanol 20:1 gave 7 mg of the title product. $^1$H-NMR: (400 MHz, D$_6$-DMSO) 11.9 (1H, br s), 9.53 (1H, br s), 8.98 (1H, s), 8.80 (1H, d), 8.71 (1H, d), 7.65 (2H, d), 7.54 (2H, d), 6.25 (1H, s), 2.20 (3H, s), 1.35 (9H, s); MS (ESI$^+$)=418.31 (M+H)$^+$.

Example ZB-4

2-(4-tert-Butyl-phenyl)-4-(5-methyl-2H-pyrazol-3-ylamino)-6-nitro-2H-phthalazin-1-one 12 mg 6-Nitro-4-(2-tert-butyl-5-methyl-2H-pyrazol-3-ylamino)-2-(4-tert-butyl-phenyl)-2H-phthalazin-1-one (preparation see ZB-1) were deprotected by heating in formic acid as described for ZB-1. Evaporation of excess formic acid and chromatography of the residue on silica, eluting with dichloromethane and then with dichloromethane/methanol 20:1 gave 5 mg of the title product. $^1$H-NMR: (400 MHz, D$_6$-DMSO) 11.9 (1H, br s), 9.78 (1H, s), 9.52 (1H, s), 8.65–8.56 (2H, m), 7.65 (2H, d), 7.53 (2H, d), 6.26 (1H, s), 2.20 (3H, s), 1.35 (9H, s); MS (ESI$^+$)=418.32 (M+H)$^+$.

Example ZB-5

6-Amino-2-(4-tert-butyl-phenyl)-4-(5-methyl-2H-pyrazol-3-ylamino)-2H-phthalazin-1-one 6-Amino-4-(2-tert-butyl-5-methyl-2H-pyrazol-3-ylamino)-2-(4-tert-butyl-phenyl)-2H-phthalazin-1-one 1.80 g 6-Nitro-4-(2-tert-butyl-5-methyl-2H-pyrazol-3-ylamino)-2-(4-tert-butyl-phenyl)-2H-phthalazin-1-one (preparation see ZB-1) were hydrogenated as described for the 7-nitro isomer under ZB-1, to give 1.11 g of the 6-aminophthalazinone.

6-Amino-2-(4-tert-butyl-phenyl)-4-(5-methyl-2H-pyrazol-3-ylamino)-2H-phthalazin-1-one 30 mg 6-Amino-4-(2-tert-butyl-5-methyl-2H-pyrazol-3-ylamino)-2-(4-tert-butyl-phenyl)-2H-phthalazin-1-one were dissolved in 0.5 ml methanol. 2 ml conc. HCl were added and the mixture was heated to 80° C. for 7 hrs. The mixture was evaporated under vacuum, the residue dissolved in dichloromethane and washed with sodium bicarbonate solution. Removal of the dichlormethane yielded 12 mg of the title product. $^1$H-NMR: (400 MHz, D$_6$-DMSO) 11.75 (1H, br s), 8.75 (1H, br s), 8.00 (1H, d), 7.59 (2H, d), 7.46 (2H, d), 7.27 (1H, s), 7.05 (1H, d), 6.16 (br s, 2H), 2.17 (3H, s), 1.33 (9H, s); MS (ESI$^+$)=389.22 (M+H)$^+$.

Example ZB-6

6-Bromo-2-(4-tert-butyl-phenyl)-4-(5-methyl-2H-pyrazol-3-ylamino)-2H-phthalazin-1-one 6-Bromo-4-(2-tert-butyl-5-methyl-2H-pyrazol-3-ylamino)-2-(4-tert-butyl-phenyl)-2H-phthalazin-1-one 11 mg 4,6-Dibromo-2-(4-tert-butyl-phenyl)-2H-phthalazin-1-one (preparation see ZA-1) were reacted with 39.0 mg 1-tert.-butyl-3-methyl-1H-pyrazol-5-ylamine, 132 mg cesium carbonate, 7.0 mg tris-(dibenzylideneacetone)-dipalladium and 8.8 mg 4,5-bis(diphenylphosphino)-9,9-dimethylxanthene were stirred under argon at 100° C. for 20 hrs until HPLC indicated complete conversion. The solvent was removed under vacuum, the residue was taken up in dichloromethane and washed dilute HCl. Removal of the dichloromethane and chromatography on silica in first heptane and then heptan/ethyl acetate 8:2 yielded 25 mg of the title product.

6-Bromo-2-(4-tert-butyl-phenyl)-4-(5-methyl-2H-pyrazol-3-ylamino)-2H-phthalazin-1-one 15 mg of 6-Bromo-4-(2-tert-butyl-5-methyl-2H-pyrazol-3-ylamino)-2-(4-tert-butyl-phenyl)-2H-phthalazin-1-one were heated in formic acid for 5 hrs at 90° C., then evaporated and chromatographed on silica (dichloromethane, then dichloromethane/methanol 40:1). Yield 10 mg. $^1$H-NMR: (400 MHz, D$_6$-DMSO) 9.33 (1H, br s), 8.86 (1H, br s), 8.26 (1H, d), 8.80 (1H, d) 7.62 (2H, d), 7.51 (2H, d), 6.26 (1H, s), 2.20 (3H, s), 1.35 (9H, s); MS (ESI$^+$) =452.35 (M+H)$^+$.

Method ZC

Example ZC-1

2-(4-tert-Butyl-2-chloro-phenyl)-4-(5-methyl-1H-pyrazol-3-ylamino)-2H-phthalazin-1-one 4-Bromo-2-(4-tert-butyl-2-chloro-phenyl)-2H-phthalazin-1-one 54 mg 4-Bromo-2-(4-tert-butyl-phenyl)-2H-phthalazin-1-one (prepared following method R) were dissolved in 5 ml methanol. At room temperature chlorine gas was bubbled through the solution for 2 min. Chlorine addition was stopped and the mixture was stirred for 3 days. 29 mg of the title product were isolated by filtration of the resulting suspension. From the filtrate another 11 mg were obtained after evaporation and preparative HPLC/MS chromatography.

2-(4-tert-Butyl-2-chloro-phenyl)-4-(5-methyl-1H-pyrazol-3-ylamino)-2H-phthalazin-1-one 2-(4-tert-Butyl-2-chloro-phenyl)-4-(5-methyl-1H-pyrazol-3-ylamino)-2H-phthalazin-1-one was obtained by Buchwald reaction of 4-Bromo-2-(4-tert-butyl-2-chloro-phenyl)-2H-phthalazin-1-one with 1-tert.-butyl-3-methyl-1H-pyrazol-5-ylamine and subsequent cleavage of the N-tert.-butyl group as described in method O. $^1$H-NMR: (400 MHz, CDCl$_3$/CD$_3$OD) 8.53 (1H, d), 8.13 (1H, d), 7.94 (1H, t), 7.88 (1H, t) 7.58 (1H, s), 7.46 (2H, s), 6.17 (1H, s), 2.24 (3H, s), 1.39 (9H, s); MS (ESI$^+$)=408.4 (M+H)$^+$.

The invention claimed is:
1. A compound of formula I

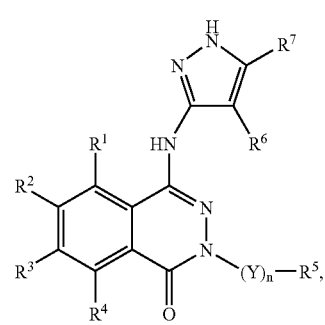

formula I wherein
$R^1$, $R^2$, $R^3$ and $R^4$ independently represent $R^8$—X—, cycloalkyl-$T^1$-, heterocyclyl-$T^2$-, hydrogen, halogen, nitro, cyano,
—OH, —NH$_2$, —NH—C(O)H, —C(O)OH, —C(O)NH$_2$, —S(O)$_2$NH$_2$,
—NHC(O)NH$_2$, —C(O)NH—O-alkyl,
—C(O)N(alkyl)-O-alkyl, —NHC(O)NH—O-alkyl,
—NHC(O)N(alkyl)-O-alkyl, —S(O)$_2$NH—O-alkyl,
—S(O)$_2$N(alkyl)-O-alkyl, or alkyl optionally substituted one or several times by halogen, hydroxy or alkoxy;
$R^8$ is cycloalkyl-$T^1$-,
heterocyclyl-$T^2$-,
aryl-$T^3$-,
heteroaryl-$T^4$-, or
alkyl optionally substituted one or several times by halogen;
x is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—NHS(O)$_2$—, —S(O)$_2$NH—, —S(O)$_2$N(alkyl)-,
—S(O)$_2$—, —S(O)—, —C(O)O—, —OC(O)—,
—C(O)—, —NH—,
—N(alkyl)-, —O— or —S—; and
$T^1$, $T^2$, $T^3$ and $T^4$ independently represent a single bond or alkylene optionally substituted one or two times by hydroxy;
$R^5$ is hydrogen,
alkyl being optionally substituted one or several times by halogen or alkoxy,
heteroaryl, or
phenyl, which is optionally substituted one or two times by halogen, —NO$_2$, —OH, —C(O)OH,
—C(O)NH-aryl, —C(O)NH$_2$,
—C(O)NH-alkyl, —C(O)N(alkyl)$_2$,
—C(O)-heterocyclyl, —NH$_2$, —NHC(O)-aryl,
—NHC(O)-cycloalkyl, —NHC(O)-alkyl,
—N(alkyl)C(O)-alkyl,
—NHC(O)O-alkyl, —N(alkyl)C(O)O-alkyl,
—NHC(O)-alkoxyalkyl, —NH—S(O)$_2$-aryl,
—NH—S(O)$_2$-alkyl, —C(O)NH—S(O)$_2$-aryl,
—C(O)NH—S(O)$_2$-alkyl, —S(O)$_2$-alkyl, —NH-aryl, —O-aryl,
—S(O)-aryl, aryl, heterocyclyl, cycloalkyl, alkyl, alkoxy or alkylsulfanyl, said alkyl, alkoxy and alkylsulfanyl groups being optionally substituted one or several times by halogen;

naphtyl,
1,3-Dihydro-isobenzofuranyl, benzo[1,3]dioxol-5-yl,
cycloalkyl or
alkenyl;
Y is alkylene, alkylene-C(O)— or alkylene-CH(OH)—;
n is 0 or 1;
$R^6$ is hydrogen, alkyl, cyano or halogen;
$R^7$ is hydrogen, alkyl or cycloalkyl;
and a pharmaceutically acceptable salt thereof.

2. The compound according to claim 1, wherein
X is —C(O)NH—, —C(O)N(alkyl)—,
—N(alkyl)C(O)—, —NHC(O)—,
—NHC(O)NH—, —NHC(O)N(alkyl)—
—NHS(O)$_2$—, —S(O)$_2$NH—, —S(O)$_2$N(alkyl)-,
—S(O)$_2$—, —S(O)—, —C(O)O—, —OC(O)—,
—C(O)—, —NH—,
—N(alkyl)-, —O— or —S—;
$R^5$ is hydrogen,
  alkyl being optionally substituted one or several times by halogen,
  heteroaryl, or
  phenyl, which is optionally substituted one or two times by
    halogen, —NO$_2$, —OH,
    —C(O)NH-aryl, —C(O)NH$_2$,
    —C(O)NH-alkyl, —C(O)N(alkyl)$_2$,
    —C(O)-heterocyclyl, —NH$_2$, —NHC(O)-aryl,
    —NHC(O)-cycloalkyl, —NHC(O)-alkyl,
    —NHC(O)-alkoxyalkyl, —NH—S(O)$_2$-aryl,
    —NH—S(O)$_2$-alkyl, —C(O)NH—S(O)$_2$-aryl,
    —C(O)NH—S(O)$_2$-alkyl, —S(O)$_2$-alkyl, alkyl, alkoxy or alkylsulfanyl, said alkyl, alkoxy and alkylsulfanyl groups being optionally substituted one or several times by halogen;
  or 1,3-Dihydro-isobenzofuranyl; and
Y is alkylene.

3. The compound according to claim 1, wherein
$R^1$, $R^2$, $R^3$ and $R^4$ independently represent $R^8$—X—,
heterocyclyl-$T^2$-, hydrogen, halogen,
  nitro, —OH, —NH$_2$, —NH—C(O)H, —C(O)OH,
  —C(O)NH$_2$, —C(O)NH—O-alkyl, or alkyl optionally substituted one or several times by hydroxy or alkoxy;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;
$T^1$, $T^2$, $T^3$ and $T^4$ independently represent a single bond or alkylene;
$R^5$ is hydrogen,
  alkyl being optionally substituted one or several times by halogen or alkoxy,
  heteroaryl, or
  phenyl, which is optionally substituted one or two times by halogen, —NO$_2$, —C(O)OH, —C(O)NH-alkyl, —NH$_2$,
    —NHC(O)-alkyl, —NHC(O)-alkoxyalkyl,
    —N(alkyl)C(O)-alkyl, —NHC(O)O-alkyl,
    —N(alkyl)C(O)O-alkyl, —NH—S(O)$_2$-alkyl,
    —S(O)$_2$-alkyl,
    —NHC(O)-aryl, —NH-aryl, —O-aryl, —S(O)-aryl, aryl, heterocyclyl, cycloalkyl, alkyl, alkoxy or alkylsulfanyl, said alkyl, alkoxy and alkylsulfanyl groups being optionally substituted one or several times by halogen;
naphtyl,
benzo[1,3]dioxol-5-yl,
cycloalkyl or
alkenyl; and
$R^6$ is hydrogen.

4. The compound according to claim 1, wherein
$R^1$ is hydrogen;
$R^2$, $R^3$ and $R^4$ independently represent $R^8$—X—, heterocyclyl-$T^2$-, hydrogen, halogen, nitro, —OH, —NH$_2$, —NH—C(O)H, —C(O)OH,
  —C(O)NH$_2$, —C(O)NH—O-alkyl, or alkyl optionally substituted one or several times by hydroxy or alkoxy;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;
$T^1$, $T^2$, $T^3$ and $T^4$ independently represent a single bond or alkylene;
$R^5$ is hydrogen,
  alkyl being optionally substituted one or several times by halogen or alkoxy,
  heteroaryl, or
  phenyl, which is optionally substituted one or two times by halogen, —NO$_2$, —C(O)OH, —C(O)NH-alkyl, —NH$_2$,
    —NHC(O)-alkyl, —NHC(O)-alkoxyalkyl,
    —N(alkyl)C(O)-alkyl, —NHC(O)O-alkyl,
    —N(alkyl)C(O)O-alkyl, —NH—S(O)$_2$-alkyl,
    —S(O)$_2$-alkyl,
    —NHC(O)-aryl, —NH-aryl, —O-aryl, —S(O)-aryl, aryl, heterocyclyl, cycloalkyl, alkyl, alkoxy or alkylsulfanyl, said alkyl, alkoxy and alkylsulfanyl groups being optionally substituted one or several times by halogen;
naphtyl,
benzo[1,3]dioxol-5-yl,
cycloalkyl or
alkenyl; and
$R^6$ is hydrogen.

5. The compound according to claim 1, wherein
$R^1$, $R^2$ and $R^4$ are hydrogen;
$R^3$ represents $R^8$—X—, heterocyclyl-$T^2$-, halogen, nitro, —OH, —NH$_2$, —C(O)OH,
  —C(O)NH$_2$, —C(O)NH—O-alkyl, or alkyl optionally substituted one or several times by hydroxy or alkoxy;
X is —C(O)NH—, —C(O)N(alkyl)-,
—N(alkyl)C(O)—, —NHC(O)—,
—NHC(O)NH—, —NHC(O)N(alkyl)-, —OC(O)N(alkyl)-,
—S(O)$_2$NH—, —S(O)$_2$N(alkyl)-,
—S(O)$_2$—, —OC(O)—, —C(O)—, —NH—,
—N(alkyl)-, —O— or —S—;
$T^1$, $T^2$, $T^3$ and $T^4$ independently represent a single bond or alkylene;
$R^5$ is alkyl or phenyl;
Y is alkylene;
n is 0 or 1;
$R^6$ is hydrogen; and
$R^7$ is hydrogen, alkyl or cycloalkyl.

6. The compound according to claim 1, wherein
$R^1$, $R^2$ and $R^4$ are hydrogen;
$R^3$ represents halogen, nitro, —OH, —NH$_2$, —C(O)OH, —C(O)NH$_2$, —C(O)NH—O-alkyl, or alkyl optionally substituted one or several times by hydroxy or alkoxy;
$R^5$ is alkyl or phenyl;
Y is alkylene;
n is 0 or 1;
$R^6$ is hydrogen; and
$R^7$ is hydrogen, alkyl or cycloalkyl.

7. A compound according to claim 6 which is selected from:
7-Fluoro-2-isopropyl-4-(5-methyl-1H-pyrazol-3-ylamino)-2H-phthalazin-1-one;
7-Hydroxy-2-isopropyl-4-(5-methyl-1H-pyrazol-3-ylamino)-2H-phthalazin-1-one;
2-Isopropyl-7-methoxymethyl-4-(5-methyl-1H-pyrazol-3-ylamino)-2H-phthalazin-1-one;
2-Benzyl-7-methoxymethyl-4-(5-methyl-1H-pyrazol-3-ylamino)-2H-phthalazin-1-one;
3-Isopropyl-1-(5-methyl-1H-pyrazol-3-ylamino)-4-oxo-3,4-dihydro-phthalazine-6-carboxylic acid;
3-Isopropyl-1-(5-methyl-1H-pyrazol-3-ylamino)-4-oxo-3,4-dihydro-phthalazine-6-carboxylic acid methoxy-amide;
7-Hydroxymethyl-2-isopropyl-4-(5-methyl-1H-pyrazol-3-ylamino)-2H-phthalazin-1-one; and
3-Isopropyl-1-(5-methyl-1H-pyrazol-3-ylamino)-4-oxo-3,4-dihydro-phthalazine-6-carboxylic acid amide.

8. The compound according to claim 1, wherein
$R^1$, $R^2$ and $R^4$ are hydrogen;
$R^3$ heterocyclyl-T$^2$-,
$T^2$ independently represent a single bond or alkylene;
$R^5$ is alkyl or phenyl;
Y is alkylene;
n is 0 or 1;
$R^6$ is hydrogen; and
$R^7$ is hydrogen, alkyl or cycloalkyl.

9. A compound according to claim 8 which is selected from:
2-Isopropyl-4-(5-methyl-1H-pyrazol-3-ylamino)-7-morpholino-2H-phthalazin-1-one;
2-Benzyl-4-(5-methyl-1H-pyrazol-3-ylamino)-7-morpholino-2H-phthalazin-1-one;
2-Isopropyl-7-(4-methyl-piperazin-1-yl)-4-(5-methyl-2H-pyrazol-3-ylamino)-2H-phthalazin-1-one;
2-Isopropyl-7-(4-methyl-piperazin-1-ylmethyl)-4-(5-methyl-1H-pyrazol-3-ylamino)-2H-phthalazin-1-one;
2-Isopropyl-4-(5-methyl-1H-pyrazol-3-ylamino)-7-morpholin-4-ylmethyl-2H-phthalazin-1-one;
2-Isopropyl-4-(5-methyl-1H-pyrazol-3-ylamino)-7-piperidin-1-yl-2H-phthalazin-1-one; and
2-Isopropyl-4-(5-methyl-1H-pyrazol-3-ylamino)-7-pyrrolidin-1-yl-2H-phthalazin-1-one.

10. The compound according to claim 1, wherein
$R^1$, $R^2$ and $R^4$ are hydrogen;
$R^3$ represents $R^8$—X—,
X is —O— or —S—;
$T^1$, $T^2$, $T^3$ and $T^4$ independently represent a single bond or alkylene;
$R^5$ is alkyl or phenyl;
Y is alkylene;
n is 0 or 1;
$R^6$ is hydrogen; and
$R^7$ is hydrogen, alkyl or cycloalkyl.

11. A compound according to claim 10 which is selected from:
2-Isopropyl-4-(5-methyl-1H-pyrazol-3-ylamino)-7-methoxy-2H-phthalazin-1-one;
2-Isopropyl-4-(5-methyl-1H-pyrazol-3-ylamino)-7-(pyridin-2-ylmethoxy)-2H-phthalazin-1-one;
2-Isopropyl-4-(5-methyl-1H-pyrazol-3-ylamino)-7-(pyridin-3-ylmethoxy)-2H-phthalazin-1-one;
2-Isopropyl-4-(5-methyl-1H-pyrazol-3-ylamino)-7-(pyridin-4-ylmethoxy)-2H-phthalazin-1-one;
2-Isopropyl-4-(5-methyl-1H-pyrazol-3-ylamino)-7-(2-morpholin-4-yl-ethoxy)-2H-phthalazin-1-one;
2-Benzyl-7-methoxy-4-(5-methyl-1H-pyrazol-3-ylamino)-2H-phthalazin-1-one;
7-Difluoromethoxy-2-isopropyl-4-(5-methyl-1H-pyrazol-3-ylamino)-2H-phthalazin-1-one;
2-Isopropyl-4-(5-methyl-1H-pyrazol-3-ylamino)-7-methylsulfanyl-2H-phthalazin-1-one; and
2-Isopropyl-4-(5-methyl-1H-pyrazol-3-ylamino)-7-(2-morpholin-4-yl-ethylsulfanyl)-2H-phthalazin-1-one.

12. The compound according to claim 1, wherein
$R^1$, $R^2$ and $R^4$ are hydrogen;
$R^3$ represents $R^8$—X—,
X is —NH—, or —N(alkyl)-;
$T^1$, $T^2$, $T^3$ and $T^4$ independently represent a single bond or alkylene;
$R^5$ is alkyl or phenyl;
Y is alkylene;
n is 0 or 1;
$R^6$ is hydrogen; and
$R^7$ is hydrogen, alkyl or cycloalkyl.

13. A compound according to claim 12 which is selected from:
2-Isopropyl-4-(5-methyl-1H-pyrazol-3-ylamino)-7-dimethylamino-2H-phthalazin-1-one;
2-Isopropyl-7-[methyl-(2-morpholin-4-yl-ethyl)-amino]-4-(5-methyl-1H-pyrazol-3-ylamino)-2H-phthalazin-1-one;
2-Isopropyl-4-(5-methyl-1H-pyrazol-3-ylamino)-7-(methyl-pyridin-4-ylmethyl-amino)-2H-phthalazin-1-one;
2-Isopropyl-4-(5-methyl-1H-pyrazol-3-ylamino)-7-(methyl-pyridin-3-ylmethyl-amino)-2H-phthalazin-1-one;
2-Isopropyl-4-(5-methyl-1H-pyrazol-3-ylamino)-7-(methyl-pyridin-2-ylmethyl-amino)-2H-phthalazin-1-one;
7-[(4-Fluoro-benzyl)-methyl-amino]-2-isopropyl-4-(5-methyl-1H-pyrazol-3-ylamino)-2H-phthalazin-1-one;
2-Isopropyl-4-(5-methyl-1H-pyrazol-3-ylamino)-7-(2-morpholin-4-yl-ethylamino)-2H-phthalazin-1-one;
2-Isopropyl-7-methylamino-4-(5-methyl-1H-pyrazol-3-ylamino)-2H-phthalazin-1-one; and
4-(5-Cyclopropyl-2H-pyrazol-3-ylamino)-7-dimethylamino-2-isopropyl-2H-phthalazin-1-one.

14. The compound according to claim 1, wherein
$R^1$, $R^2$ and $R^4$ are hydrogen;
$R^3$ represents $R^8$—X—;
X is —NHC(O)NH—, —NHC(O)N(alkyl)- or —OC(O)N(alkyl)-;
$T^1$, $T^2$, $T^3$ and $T^4$ independently represent a single bond or alkylene;
$R^5$ is alkyl or phenyl;
Y is alkylene;
n is 0 or 1;
$R^6$ is hydrogen; and
$R^7$ is hydrogen, alkyl or cycloalkyl.

15. A compound according to claim 14 which is selected from:
- [3-Isopropyl-1-(5-methyl-2H-pyrazol-3-ylamino)-4-oxo-3,4-dihydro-phthalazin-6-yl]-methyl-carbamic acid tert-butyl ester;
- 3-Isopropyl-1-[3-isopropyl-1-(5-methyl-1H-pyrazol-3-ylamino)-4-oxo-3,4-dihydro-phthalazin-6-yl]-1-methyl-urea;
- [3-Isopropyl-1-(5-methyl-1H-pyrazol-3-ylamino)-4-oxo-3,4-dihydro-phthalazin-6-yl]-methyl-carbamic acid ethyl ester; and
- 1-[3-Isopropyl-1-(5-methyl-1H-pyrazol-3-ylamino)-4-oxo-3,4-dihydro-phthalazin-6-yl]-3-methyl-urea.

16. The compound according to claim 1, wherein
$R^1$, $R^2$ and $R^4$ are hydrogen;
$R^3$ represents $R^8$—X—;
X is —S(O)$_2$NH—, —S(O)$_2$N(alkyl)- or —S(O)$_2$—;
$T^1$, $T^2$, $T^3$ and $T^4$ independently represent a single bond or alkylene;
$R^5$ is alkyl or phenyl;
Y is alkylene;
n is 0 or 1;
$R^6$ is hydrogen; and
$R^7$ is hydrogen, alkyl or cycloalkyl.

17. A compound according to claim 16 which is selected from:
- 2-Isopropyl-7-methanesulfonyl-4-(5-methyl-1H-pyrazol-3-ylamino)-2H-phthalazin-1-one;
- N-[3-Isopropyl-1-(5-methyl-1H-pyrazol-3-ylamino)-4-oxo-3,4-dihydro-phthalazin-6-yl]-N-methyl-methanesulfonamide; and
- N-[3-Isopropyl-1-(5-methyl-1H-pyrazol-3-ylamino)-4-oxo-3,4-dihydro-phthalazin-6-yl]-methanesulfonamide.

18. The compound according to claim 1, wherein
$R^1$, $R^2$ and $R^4$ are hydrogen;
$R^3$ represents $R^8$—X—;
X is —C(O)NH—, —C(O)N(alkyl)-, —N(alkyl)C(O)— or —NHC(O)—;
$T^1$, $T^2$, $T^3$ and $T^4$ independently represent a single bond or alkylene;
$R^5$ is alkyl or phenyl;
Y is alkylene;
n is 0 or 1;
$R^6$ is hydrogen; and
$R^7$ is hydrogen, alkyl or cycloalkyl.

19. A compound according to claim 18 which is selected from:
- N-[3-Isopropyl-1-(5-methyl-1H-pyrazol-3-ylamino)-4-oxo-3,4-dihydro-phthalazin-6-yl]-N-methyl-acetamide;
- N-[3-Isopropyl-1-(5-methyl-1H-pyrazol-3-ylamino)-4-oxo-3,4-dihydro-phthalazin-6-yl]-acetamide;
- 3-Isopropyl-1-(5-methyl-1H-pyrazol-3-ylamino)-4-oxo-3,4-dihydro-phthalazine-6-carboxylic acid diethylamide; and
- 3-Isopropyl-1-(5-methyl-1H-pyrazol-3-ylamino)-4-oxo-3,4-dihydro-phthalazine-6-carboxylic acid isopropylamide.

20. The compound according to claim 1, wherein
$R^1$, $R^2$ and $R^4$ are hydrogen;
$R^3$ represents $R^8$—X—;
X is —OC(O)— or —C(O)—;
$T^1$, $T^2$, $T^3$ and $T^4$ independently represent a single bond or alkylene;
$R^5$ is alkyl or phenyl;
Y is alkylene;
n is 0 or 1;
$R^6$ is hydrogen; and
$R^7$ is hydrogen, alkyl or cycloalkyl.

21. A compound according to claim 20 which is selected from:
- 2-Isopropyl-4-(5-methyl-1H-pyrazol-3-ylamino)-7-(morpholine-4-carbonyl)-2H-phthalazin-1-one;
- 3-Isopropyl-1-(5-methyl-1H-pyrazol-3-ylamino)-4-oxo-3,4-dihydro-phthalazine-6-carboxylic acid cyclopropylmethyl ester;
- 7-(4-Acetyl-piperazine-1-carbonyl)-2-isopropyl-4-(5-methyl-1H-pyrazol-3-ylamino)-2H-phthalazin-1-one; and
- 3-Isopropyl-1-(5-methyl-1H-pyrazol-3-ylamino)-4-oxo-3,4-dihydro-phthalazine-6-carboxylic acid methyl ester.

22. The compound according to claim 1, wherein
$R^1$, $R^2$ and $R^3$ are hydrogen;
$R^4$ represents $R^8$—X—, heterocyclyl-$T^2$-;
$R^8$ is alkyl;
X is —NH— or —N(alkyl)-;
$T^2$ represents a single bond or alkylene;
$R^5$ is alkyl;
n is 0; and
$R^6$ is hydrogen.

23. A compound according to claim 22 which is selected from:
- 2-Isopropyl-4-(5-methyl-1H-pyrazol-3-ylamino)-8-morpholino-2H-phthalazin-1-one; and
- 2-Isopropyl-4-(5-methyl-1H-pyrazol-3-ylamino)-8-dimethylamino-2H-phthalazin-1-one.

24. The compound according to claim 1, wherein
$R^1$, $R^3$ and $R^4$ are hydrogen;
$R^2$ represents $R^8$—X—, heterocyclyl-$T^2$-, halogen, nitro, —NH$_2$, or alkyl optionally substituted one or several times by hydroxy or alkoxy;
$R^8$ is alkyl;
X is —NH—, —N(alkyl)- or —O—;
$T^2$ represent a single bond or alkylene;
$R^5$ is alkyl or phenyl;
n is 0; and
$R^6$ is hydrogen.

25. A compound according to claim 24 which is selected from:
- 6-Fluoro-2-isopropyl-4-(5-methyl-1H-pyrazol-3-ylamino)-2H-phthalazin-1-one;
- 2-Isopropyl-4-(5-methyl-1H-pyrazol-3-ylamino)-6-morpholino-2H-phthalazin-1-one;
- 2-Isopropyl-4-(5-methyl-1H-pyrazol-3-ylamino)-6-dimethylamino-2H-phthalazin-1-one;
- 2-Isopropyl-6-methoxy-4-(5-methyl-1H-pyrazol-3-ylamino)-2H-phthalazin-1-one;
- 2-Isopropyl-6-methoxymethyl-4-(5-methyl-2H-pyrazol-3-ylamino)-2H-phthalazin-1-one;
- 6-Hydroxymethyl-2-isopropyl-4-(5-methyl-1H-pyrazol-3-ylamino)-2H-phthalazin-1-one; and
- 6-Amino-4-(5-methyl-1H-pyrazol-3-ylamino)-2-phenyl-2H-phthalazin-1-one.

26. The compound according to claim 1, wherein
$R^1$, $R^2$, $R^3$ and $R^4$ represent hydrogen;
$R^5$ is hydrogen,
alkyl being optionally substituted one or several times by halogen or alkoxy,
heteroaryl, or
phenyl, which is optionally substituted one or two times by halogen, —NO$_2$, —C(O)OH, —C(O)NH-alkyl, —NH$_2$, —NHC(O)-alkyl, —N(alkyl)C(O)-alkyl, —NHC(O)-alkoxyalkyl, —NHC(O)O-alkyl, —N(alkyl)C(O)O-alkyl, —NH—S(O)$_2$-alkyl, —S(O)$_2$-alkyl, —NHC(O)-aryl, —NH-aryl, —O-aryl, —S(O)-aryl, aryl, heterocyclyl, cycloalkyl, alkyl, alkoxy or alkylsulfanyl, said alkyl, alkoxy and alkylsulfanyl groups being optionally substituted one or several times by halogen;
naphtyl,
benzo[1,3]dioxol-5-yl,
cycloalkyl or
alkenyl; and
R$^6$ is hydrogen.

27. The compound according to claim 1, wherein
R$^1$, R$^2$, R$^3$ and R$^4$ represent hydrogen;
R$^5$ is hydrogen or alkyl being optionally substituted one or several times by halogen or alkoxy; and
R$^6$ is hydrogen.

28. A compound according to claim 27 which is selected from:
2-Methyl-4-(5-methyl-1H-pyrazol-3-ylamino)-2H-phthalazin-1-one;
2-Isobutyl-4-(5-methyl-1H-pyrazol-3-ylamino)-2H-phthalazin-1-one;
4-(5-Methyl-1H-pyrazol-3-ylamino)-2-(2,2,2-trifluoro-ethyl)-2H-phthalazin-1-one;
2-Isopropyl-4-(5-methyl-1H-pyrazol-3-ylamino)-2H-phthalazin-1-one;
2-(2-Methoxy-ethyl)-4-(5-methyl-2H-pyrazol-3-ylamino)-2H-phthalazin-1-one; and
2-(2-Methoxy-1-methyl-ethyl)-4-(5-methyl-2H-pyrazol-3-ylamino)-2H-phthalazin-1-one.

29. The compound according to claim 1, wherein
R$^1$, R$^2$, R$^3$ and R$^4$ represent hydrogen;
R$^5$ is phenyl, which is optionally substituted one or two times by halogen, —NO$_2$, —C(O)OH, —C(O)NH-alkyl, —NH$_2$, —NHC(O)-alkyl, —NHC(O)-alkoxy-alkyl, —N(alkyl)C(O)-alkyl, —NHC(O)O-alkyl, —N(alkyl)C(O)O-alkyl, —NH—S(O)$_2$-alkyl, —S(O)$_2$-alkyl, alkyl, alkoxy or alkylsulfanyl, said alkyl, alkoxy and alkylsulfanyl groups being optionally substituted one or several times by halogen;
R$^6$ is hydrogen; and
n is 0.

30. A compound according to claim 29 which is selected from:
4-(5-Methyl-1H-pyrazol-3-ylamino)-2-phenyl-2H-phthalazin-1-one;
4-(5-Methyl-1H-pyrazol-3-ylamino)-2-p-tolyl-2H-phthalazin-1-one;
2-(4-Fluoro-phenyl)-4-(5-methyl-1H-pyrazol-3-ylamino)-2H-phthalazin-1-one;
2-(4-tert-Butyl-phenyl)-4-(5-methyl-1H-pyrazol-3-ylamino)-2H-phthalazin-1-one;
2-(4-Methoxy-phenyl)-4-(5-methyl-1H-pyrazol-3-ylamino)-2H-phthalazin-1-one;
4-(1H-Pyrazol-3-ylamino)-2-p-tolyl-2H-phthalazin-1-one;
3-[4-(5-Methyl-1H-pyrazol-3-ylamino)-1-oxo-1H-phthalazin-2-ylmethyl]-benzoic acid;
4-(5-Methyl-1H-pyrazol-3-ylamino)-2-(4-trifluoromethyl-phenyl)-2H-phthalazin-1-one;
2-(4-Chloro-phenyl)-4-(5-methyl-1H-pyrazol-3-ylamino)-2H-phthalazin-1-one; and
4-(5-Methyl-1H-pyrazol-3-ylamino)-2-m-tolyl-2H-phthalazin-1-one-.

31. A compound according to claim 29 which is selected from:
N-{4-[4-(5-Methyl-1H-pyrazol-3-ylamino)-1-oxo-1H-phthalazin-2-yl]-phenyl}-methanesulfonamide;
N-Methyl-4-[4-(5-methyl-1H-pyrazol-3-ylamino)-1-oxo-1H-phthalazin-2-yl]-benzamide;
2-Methoxy-N-{4-[4-(5-methyl-1H-pyrazol-3-ylamino)-1-oxo-1H-phthalazin-2-yl]-phenyl}-acetamide;
{4-[4-(5-Methyl-1H-pyrazol-3-ylamino)-1-oxo-1H-phthalazin-2-yl]-phenyl}-carbamic acid ethyl ester;
Methyl-{4-[4-(5-methyl-1H-pyrazol-3-ylamino)-1-oxo-1H-phthalazin-2-yl]-phenyl}-carbamic acid ethyl ester;
Methyl-{4-[4-(5-methyl-1H-pyrazol-3-ylamino)-1-oxo-1H-phthalazin-2-yl]-phenyl}-carbamic acid isopropyl ester;
{4-[4-(5-Methyl-1H-pyrazol-3-ylamino)-1-oxo-1H-phthalazin-2-yl]-phenyl}-carbamic acid isopropyl ester;
2-(4-tert-Butyl-2-chloro-phenyl)-4-(5-methyl-1H-pyrazol-3-ylamino)-2H-phthalazin-1-one;
2-[4-(2-Methyl-propane-2-sulfonyl)-phenyl]-4-(5-methyl-1H-pyrazol-3-ylamino)-2H-phthalazin-1-one; and
N-Ethyl-N-{4-[4-(5-methyl-1H-pyrazol-3-ylamino)-1-oxo-1H-phthalazin-2-yl]-phenyl}-acetamide.

32. A compound according to claim 29 which is selected from:
4-(5-Methyl-1H-pyrazol-3-ylamino)-2-(4-nitro-phenyl)-2H-phthalazin-1-one;
2-(3-tert-Butyl-phenyl)-4-(5-methyl-1H-pyrazol-3-ylamino)-2H-phthalazin-1-one;
2-(4-Isopropyl-phenyl)-4-(5-methyl-2H-pyrazol-3-ylamino)-2H-phthalazin-1-one;
2-(4-sec-Butyl-phenyl)-4-(5-methyl-2H-pyrazol-3-ylamino)-2H-phthalazin-1-one
4-(5-Methyl-1H-pyrazol-3-ylamino)-2-(3-trifluoromethyl-phenyl)-2H-phthalazin-1-one;
2-(2-Chloro-phenyl)-4-(5-methyl-1H-pyrazol-3-ylamino)-2H-phthalazin-1-one;
N-{4-[4-(5-Methyl-1H-pyrazol-3-ylamino)-1-oxo-1H-phthalazin-2-yl]-phenyl}-acetamide;
2,2-Dimethyl-N-{4-[4-(5-methyl-1H-pyrazol-3-ylamino)-1-oxo-1H-phthalazin-2-yl]-phenyl}-propionamide;
2-(2-Chloro-4-trifluoromethyl-phenyl)-4-(5-methyl-1H-pyrazol-3-ylamino)-2H-phthalazin-1-one; and
2-(4-Amino-phenyl)-4-(5-methyl-1H-pyrazol-3-ylamino)-2H-phthalazin-1-one.

33. The compound according to claim 1, wherein
R$^1$, R$^2$, R$^3$ and R$^4$ represent hydrogen;
R$^5$ is phenyl, which is optionally substituted one or two times by —NHC(O)-aryl, —NH-aryl, —O-aryl, —S(O)-aryl, aryl, heterocyclyl, cycloalkyl; or naphtyl,
R$^6$ is hydrogen; and
n is 0.

34. A compound according to claim 33 which is selected from:
2-(4-Benzenesulfinyl-phenyl)-4-(5-methyl-1H-pyrazol-3-ylamino)-2H-phthalazin-1-one;
2-(4-Cyclohexyl-phenyl)-4-(5-methyl-1H-pyrazol-3-ylamino)-2H-phthalazin-1-one;
2-Biphenyl-4-yl-4-(5-methyl-1H-pyrazol-3-ylamino)-2H-phthalazin-1-one;
2-(2'-Methyl-biphenyl-4-yl)-4-(5-methyl-1H-pyrazol-3-ylamino)-2H-phthalazin-1-one;
phthalazin-1-one;
4-(5-Methyl-1H-pyrazol-3-ylamino)-2-(4-phenoxy-phenyl)-2H-phthalazin-1-one;

4-(5-Methyl-1H-pyrazol-3-ylamino)-2-naphthalen-2-yl-2H-phthalazin-1-one;
N-{4-[4-(5-Methyl-1H-pyrazol-3-ylamino)-1-oxo-1H-phthalazin-2-yl]-phenyl}-benzamide;
4-(5-Methyl-1H-pyrazol-3-ylamino)-2-(4-phenylamino-phenyl)-2H-phthalazin-1-one; and
4-(5-Methyl-1H-pyrazol-3-ylamino)-2-(4-morpholin-4-yl-phenyl)-2H-phthalazin-1-one.

35. The compound according to claim 1, wherein
$R^1$, $R^2$, $R^3$ and $R^4$ represent hydrogen;
$R^5$ is phenyl, which is optionally substituted one or two times by halogen, —$NO_2$, —C(O)OH, —$NH_2$, —NHC(O)-alkyl, —$S(O)_2$-alkyl, alkyl, alkoxy or alkylsulfanyl, said alkyl, alkoxy and alkylsulfanyl groups being optionally substituted one or several times by halogen;
$R^6$ is hydrogen;
Y is alkylene; and
n is 1.

36. A compound according to claim 35 which is selected from:
2-Benzyl-4-(5-methyl-1H-pyrazol-3-ylamino)-2H-phthalazin-1-one;
2-(4-Methoxy-benzyl)-4-(5-methyl-1H-pyrazol-3-ylamino)-2H-phthalazin-1-one;
2-(3-Methoxy-benzyl)-4-(5-methyl-1H-pyrazol-3-ylamino)-2H-phthalazin-1-one;
2-(2,5-Difluoro-benzyl)-4-(5-methyl-1H-pyrazol-3-ylamino)-2H-phthalazin-1-one;
2-(4-Methanesulfonyl-benzyl)-4-(5-methyl-2H-pyrazol-3-ylamino)-2H-phthalazin-1-one;
2-(3,4-Difluoro-benzyl)-4-(5-methyl-1H-pyrazol-3-ylamino)-2H-phthalazin-1-one;
2-(2-Fluoro-benzyl)-4-(5-methyl-1H-pyrazol-3-ylamino)-2H-phthalazin-1-one;
2-(4-Fluoro-benzyl)-4-(5-methyl-1H-pyrazol-3-ylamino)-2H-phthalazin-1-one;
2-(3,5-Difluoro-benzyl)-4-(5-methyl-1H-pyrazol-3-ylamino)-2H-phthalazin-1-one;
4-(5-Methyl-1H-pyrazol-3-ylamino)-2-(4-nitro-benzyl)-2H-phthalazin-1-one;
2-(4-Amino-benzyl)-4-(5-methyl-1H-pyrazol-3-ylamino)-2H-phthalazin-1-one;
N-{4-[4-(5-Methyl-1H-pyrazol-3-ylamino)-1-oxo-1H-phthalazin-2-ylmethyl]-phenyl}acetamide;
N-{4-[1-Oxo-4-(1H-pyrazol-3-ylamino)-1H-phthalazin-2-ylmethyl]-phenyl}-acetamide; and
4-(5-Methyl-1H-pyrazol-3-ylamino)-2-(4-methylsulfanyl-benzyl)-2H-phthalazin-1-one.

37. The compound according to claim 1, wherein
$R^1$, $R^2$, $R^3$ and $R^4$ represent hydrogen;
$R^5$ is phenyl, which is optionally substituted one or two times by alkyl or alkoxy, said alkyl or alkoxy groups being optionally substituted one or several times by halogen;
or benzo[1,3]dioxol-5-yl
$R^6$ is hydrogen;
Y is alkylene-C(O)— or alkylene-CH(OH)—; and
n is 1.

38. A compound according to claim 37 which is selected from:
2-[2-(4-Methoxy-phenyl)-2-oxo-ethyl]-4-(5-methyl-1H-pyrazol-3-ylamino)-2H-phthalazin-1-one;
2-[2-(3-Methoxy-phenyl)-2-oxo-ethyl]-4-(5-methyl-1H-pyrazol-3-ylamino)-2H-phthalazin-1-one;
4-(5-Methyl-1H-pyrazol-3-ylamino)-2-[2-oxo-2-(4-trifluoromethoxy-phenyl)-ethyl]-2H-phthalazin-1-one;
4-(5-Methyl-1H-pyrazol-3-ylamino)-2-[2-oxo-2-(4-trifluoromethyl-phenyl)-ethyl]-2H-phthalazin-1-one;
4-(5-Methyl-1H-pyrazol-3-ylamino)-2-(2-oxo-2-phenyl-ethyl)-2H-phthalazin-1-one;
2-(2-Hydroxy-2-phenyl-ethyl)-4-(5-methyl-1H-pyrazol-3-ylamino)-2H-phthalazin-1-one; and
2-(2-Benzo[1,3]dioxol-5-yl-2-oxo-ethyl)-4-(5-methyl-1H-pyrazol-3-ylamino)-2H-phthalazin-1-one.

39. The compound according to claim 1, wherein
$R^1$, $R^2$, $R^3$ and $R^4$ represent hydrogen;
$R^5$ is heteroaryl;
$R^6$ is hydrogen;
Y is alkylene; and
n is 0 or 1.

40. A compound according to claim 39 which is selected from:
4-(5-Methyl-1H-pyrazol-3-ylamino)-2-(2-methyl-thiazol-4-ylmethyl)-2H-phthalazin-1-one;
4-(5-Methyl-2H-pyrazol-3-ylamino)-2-pyridin-4-ylmethyl-2H-phthalazin-1-one;
4-(5-Methyl-2H-pyrazol-3-ylamino)-2-pyridin-3-ylmethyl-2H-phthalazin-1-one;
4-(5-Methyl-2H-pyrazol-3-ylamino)-2-pyridin-2-ylmethyl-2H-phthalazin-1-one; and
4-(5-Methyl-1H-pyrazol-3-ylamino)-2-pyridin-4-yl-2H-phthalazin-1-one.

41. The compound according to claim 1, wherein
$R^1$, $R^2$, $R^3$ and $R^4$ represent hydrogen;
$R^5$ is cycloalkyl or alkenyl; and
$R^6$ is hydrogen.

42. A compound according to claim 41 which is selected from:
2-Allyl-4-(5-methyl-1H-pyrazol-3-ylamino)-2H-phthalazin-1-one;
2-Cyclopropylmethyl-4-(5-methyl-1H-pyrazol-3-ylamino)-2H-phthalazin-1-one; and
2-(4-tert-Butyl-cyclohexyl)-4-(5-methyl-1H-pyrazol-3-ylamino)-2H-phthalazin-1-one.

43. The compound according to claim 1, wherein
$R^1$ and $R^4$ are hydrogen;
$R^2$ and $R^3$ independently represents hydrogen, $R^8$—X—, heterocyclyl-$T^2$-, halogen, nitro, —OH, —$NH_2$, —NH—C(O)H, —C(O)OH, —C(O)$NH_2$, —C(O)NH—O-alkyl, or alkyl optionally substituted one or several times by hydroxy or alkoxy;
X is —C(O)NH—, —C(O)N(alkyl)-, —N(alkyl)C(O)—, —NHC(O)—, —NHC(O)NH—, —NHC(O)N(alkyl)-, —OC(O)N(alkyl)-, —$S(O)_2$NH—, —$S(O)_2$N(alkyl)-, —$S(O)_2$-, —OC(O)—, —C(O)—, —NH—, —N(alkyl)-, —O— or —S—;
$T^1$, $T^2$, $T^3$ and $T^4$ independently represent a single bond or alkylene;
$R^5$ is phenyl which is substituted by alkyl or alkoxy said alkyl or alkoxy group being optionally substituted one or several times by halogen;
n is 0;
$R^6$ is hydrogen; and
$R^7$ is hydrogen, alkyl or cycloalkyl.

44. The compound according to claim 1, wherein
$R^1$ and $R^4$ are hydrogen;
$R^2$ and $R^3$ independently represents hydrogen, halogen, nitro, —$NH_2$, —NH—C(O)H;
$R^5$ is phenyl which is substituted at the para-position by tert-butyl, trifluoromethyl or trifluoromethoxy;

n is 0;

R⁶ is hydrogen; and

R⁷ is hydrogen, alkyl or cycloalkyl.

45. A compound according to claim 42 which is selected from:

N-[3-(4-tert-Butyl-phenyl)-1-(5-methyl-2H-pyrazol-3-ylamino)-4-oxo-3,4-dihydro-phthalazin-6-yl]-formamide;

7-Amino-2-(4-tert-butyl-phenyl)-4-(5-methyl-2H-pyrazol-3-ylamino)-2H-phthalazin-1-one;

2-(4-tert-Butyl-phenyl)-4-(5-methyl-2H-pyrazol-3-ylamino)-7-nitro-2H-phthalazin-1-one;

2-(4-tert-Butyl-phenyl)-4-(5-methyl-2H-pyrazol-3-ylamino)-6-nitro-2H-phthalazin-1-one;

6-Amino-2-(4-tert-butyl-phenyl)-4-(5-methyl-2H-pyrazol-3-ylamino)-2H-phthalazin-1-one;

6-Bromo-2-(4-tert-butyl-phenyl)-4-(5-methyl-2H-pyrazol-3-ylamino)-2H-phthalazin-1-one;

2-(4-tert-Butyl-phenyl)-4-(5-cyclopropyl-1H-pyrazol-3-ylamino)-2H-phthalazin-1-one;

2-(4-tert-Butyl-phenyl)-4-(1H-pyrazol-3-ylamino)-2H-phthalazin-1-one; and 4-(5-Methyl-1H-pyrazol-3-ylamino)-2-(4-trifluoromethoxy-phenyl)-2H-phthalazin-1-one.

46. A process for the manufacture of the compounds according to claim 1, wherein (a) a compound of formula VII

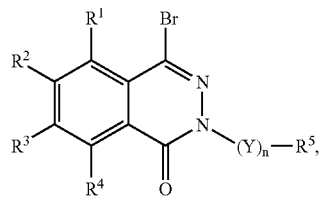

formula VII wherein R¹, R², R³, R⁴, R⁵ and Y have the significance as given in claim 1 above, is reacted with a compound of formula VIII

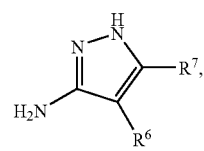

formula VIII wherein R⁶ and R⁷ have the significance given in claim 1 above, to give the respective compound of formula I.

47. The process of claim 46 further comprising isolating said compound of formula I from the reaction mixture.

48. The process of claim 47, further comprising converting the compound into a pharmaceutically acceptable salt.

49. A pharmaceutical composition comprising one or more compounds according to claim 1 together with pharmaceutically acceptable adjuvant.

\* \* \* \* \*